(12) United States Patent
Satyam

(10) Patent No.: US 8,357,723 B2
(45) Date of Patent: Jan. 22, 2013

(54) PRODRUGS CONTAINING NOVEL BIO-CLEAVABLE LINKERS

(75) Inventor: Apparao Satyam, Mumbai (IN)

(73) Assignee: Piramal Enterprises Limited and Apparao Satyam, Mumbai (IN)

( * ) Notice: Subject to any disclaimer, the term of this patent is extended or adjusted under 35 U.S.C. 154(b) by 0 days.

(21) Appl. No.: 12/977,929

(22) Filed: Dec. 23, 2010

(65) Prior Publication Data

US 2011/0269709 A1 Nov. 3, 2011

Related U.S. Application Data

(62) Division of application No. 11/213,396, filed on Aug. 26, 2005, now Pat. No. 7,932,294.

(60) Provisional application No. 60/604,632, filed on Aug. 26, 2004.

(30) Foreign Application Priority Data

Jan. 7, 2005 (IN) .......................... 779/MUM/2005

(51) Int. Cl.
*A61K 31/105* (2006.01)
*C07C 323/12* (2006.01)

(52) U.S. Cl. ......................................... 514/707; 568/22

(58) Field of Classification Search .................. 514/707; 568/22

See application file for complete search history.

(56) References Cited

U.S. PATENT DOCUMENTS

| | | | |
|---|---|---|---|
| 5,767,134 | A | 6/1998 | Li et al. |
| 5,807,847 | A | 9/1998 | Thatcher et al. |
| 5,883,122 | A | 3/1999 | Thatcher et al. |
| 6,369,071 | B1 | 4/2002 | Haj-Yehia |
| 6,566,509 | B1 | 5/2003 | Griffin et al. |
| 2003/0044845 | A1 | 3/2003 | Jenkins et al. |
| 2004/0147598 | A1 | 7/2004 | Haj-Yehia |
| 2005/0002942 | A1 | 1/2005 | Vlahov et al. |

FOREIGN PATENT DOCUMENTS

| | | |
|---|---|---|
| EP | 0317956 | 5/1989 |
| WO | 97/46521 | 12/1997 |
| WO | 98/42661 | 10/1998 |
| WO | 99/58152 | 11/1999 |
| WO | 00/54756 | 9/2000 |
| WO | 00/64483 | 11/2000 |
| WO | 01/13957 | 3/2001 |
| WO | 01/49275 A2 | 7/2001 |
| WO | 03/000643 A1 | 1/2003 |
| WO | 03/040104 | 5/2003 |
| WO | 2004/004648 A2 | 1/2004 |
| WO | 2004/012659 A2 | 2/2004 |
| WO | 2004/039771 | 5/2004 |
| WO | 2004/069159 | 8/2004 |
| WO | 2004/110432 A1 | 12/2004 |
| WO | 2005/030135 A2 | 4/2005 |

OTHER PUBLICATIONS

Lartia et al. "New reagent for the preparation of oligonucleotides involving a 5'-thiophosphate or a 5'-phosphate group" Tetrahedron Letters, 2004, pp. 5949-5952.*

"Nitric Oxide Donors and Cardiovascular Agents Modulating the Bioactivity of Nitric Oxide: An Overview" by Louis J. Ignarro, et al., Circulation Research, vol. 90, No. 1, pp. 21-22 (Jan. 11, 002).

"Bis[3-(4'-substituted phenyl)prop-2-ene]disulfides as a new class of antihyperlipidemic compounds" by Meenakshi Sharma, et al., Bioorganic and Medicinal Chemistry Leters, vol. 14, No. 21, pp. 5347-5350 (Nov. 1, 2004).

Abstract Onl y "Spectrophotometric determination of binary mixtures of pseudoephedrine with some histamine H1-receptor antagonists using derivative radio spectrum method" by H. Mahgouh, et al., J. Pham Biomed Anal, vol. 31, No. 4, pp. 801-809 Mar. 26, 2003.

Peter D. Senter et al., Development of Drug-Release Strategy Based on the Reductive Fragmentation pf Benzyl Carbamate Disulfides. Journal of Organic Chemistry, 1990, 55, 2975-2978. Published by American Chemical Society (USA).

Vivekananda M. Vrudhula et al., Reductively Activated Disulfide Prodrugs of Paclitaxel. Biorganic & Medicinal Chemistry Letters, 2002, 12, 3591-35-94, Published by Elsvier Sciences LTD. (USA).

Samuel Zalipsky et al., New Detachable Poly(ethylene glycol) Conjugates: Cysteinecleavable Lipopolymers Regenerating Natural Phospholipid, Diacyl Phosphatidylethanolamine. Bioconiugate Chemistry, Published by American Chemical Society (USA). 1999, vol. 10, No. 5, pp. 703-707.

Kexin Yang et al., Synthesis of novel organic nitrate esters: guanylate cyclase activation and tissue relaxation. Journal of Chemical Society, Perkin Transitions 1, 1996, 1073-1075, Publised by Royal Society of Chemistry (UK).

Sergei I. Zavorin et al., Nitrate Esters as Nitric Oxide Donors: SS-Nitrates. Organic Letters, 2001,3 (8), 1113-1116. Published by American Chemical Society (USA).

Abstract, Zhdanovich, E.S., et al. Zhumal Obshchei Khimii (1967), 37(2), 361-3.

Abstract, Oiry, Joel, et al. "Centre National de la Recherche Scientifique, Fr." Fr. Demande (1983) (FR 2528042).

Abstract, Joel, et al. "Centre National de la Recherche Scientifique, Fr" Eur. Patent Appln. 131500 (1885) 64 pp.

Abstract, Barcelo, Gerard, et al. (Soceite Nationale des Pourdes et Explosifs, Fr. Fr. Demande (1987), FR 2589860.

Abstract, Davidovich, Yu, et al. Izvestiya Akademii Nauk SSSR, Seriya Khimicheskaya (1989), (8), 1918-20.

Abstract, Vecsei, Laszlo, et al. Progress in Neuro-Psychopharmacology & Biological Psychiatry (1990), 14(6),835-62.

Abstract, Guetschow, Michael, et al. DD 293807 (Ger.(East)) (1991).

Abstract, Oiry, J. et al. European Journal of Medicinal Chemistry (1992), 27(8), 809-17.

Abstract, Thoene, Jess G., et al. WO 9306832 1993.

Smith et al. "Urethans of 2-Mercaptoethanol" Journal of the American Chemical Society, 1959, vol. 81, pp. 161-163.

* cited by examiner

*Primary Examiner* — Joseph Kosack
(74) *Attorney, Agent, or Firm* — Ladas & Parry LLP

(57) ABSTRACT

The invention provides the compounds of formula (I) or pharmaceutically acceptable salts thereof. The invention also provides pharmaceutical compositions comprising one or more compounds of formula I or intermediates thereof and one more of pharmaceutically acceptable carriers, vehicles or diluents. The invention further provides methods of preparation and methods of use of prodrugs including NO-releasing prodrugs, double prodrugs and mutual prodrugs comprising the compounds of formula I.

16 Claims, 1 Drawing Sheet

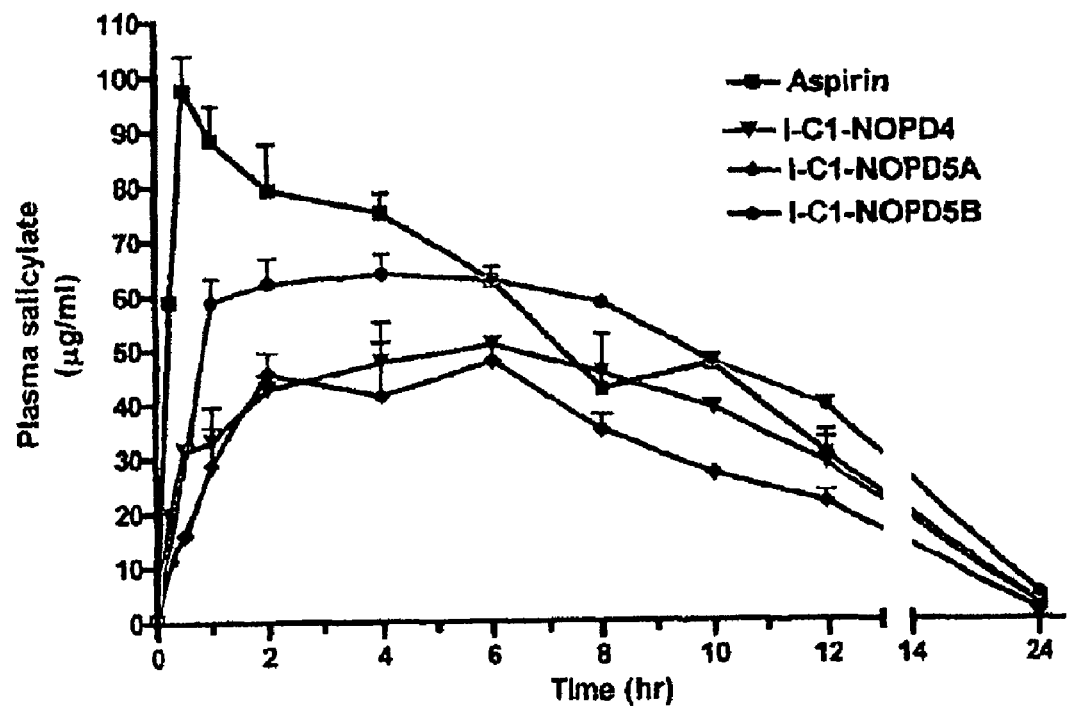

PRODRUGS CONTAINING NOVEL BIO-CLEAVABLE LINKERS

This is a divisional of application Ser. No. 11/213,396 filed on Aug. 26, 2005, now U.S. Pat. No. 7,932,294 claims the benefit thereof and incorporates the same by reference.

This application takes priority from US Provisional Application Ser. No. 60/604,632 filed 26 Aug. 2004 and Indian Provisional Application 779/MUM/2005 filed 1 Jul. 2005, which are herein incorporated in their entirety.

FIELD OF THE INVENTION

The present invention relates to compositions of prodrugs, including NO-releasing prodrugs, codrugs, double prodrugs and mutual prodrugs, containing bio-labile linkers and linkages, processes for their preparation and pharmaceutical compositions containing them and their use.

BACKGROUND OF THE INVENTION

A prodrug is an active drug chemically transformed into a per se inactive derivative which by virtue of chemical or enzymatic attack is converted to the parent drug within the body before or after reaching the site of action. The process of converting an active drug into inactive form is called drug latentiation. Prodrugs can be carrier-linked-prodrugs and bio-precursors. The carrier-linked prodrug results from a temporary linkage of the active molecule with a transport moiety. Such prodrugs are less active or inactive compared to the parent active drug. The transport moiety will be chosen for its non-toxicity and its ability to ensure the release of the active principle with efficient kinetics. Whereas the bioprecursors result from a molecular modification of the active principle itself by generation of a new molecule that is capable of being a substrate to the metabolizing enzymes releasing the active principle as a metabolite.

Prodrugs are prepared to alter the drug pharmacokinetics, improve stability and solubility, decrease toxicity, increase specificity, and increase duration of the pharmacological effect of the drug. By altering pharmacokinetics the drug bioavailability is increased by increasing absorption, distribution, biotransformation, and excretion of the drug. Limited intestinal absorption, distribution, fast metabolism, and toxicity are some of the causes of failure of drug candidates during development. Avoidance of the foreseeable or proven pharmacokinetic defects thus assumes considerable significance in drug research. Accordingly, prodrugs play a significant role in drug research as well.

In designing the prodrugs, it is important to consider the following factors: a) the linkage between the carrier and the drug is usually a covalent bond, b) the prodrug is inactive or less active than the active principle, c) the prodrug synthesis should not be expensive, d) the prodrug has to be reversible or bioreversible derivative of the drug, and e) the carrier moiety must be non-toxic and inactive when released.

Prodrugs are usually prepared by: a) formation of ester, hemiesters, carbonate esters, nitrate esters, amides, hydroxamic acids, carbamates, imines, mannich bases, and enamines of the active drug, b) functionalizing the drug with azo, glycoside, peptide, and ether functional groups, c) use of polymers, salts, complexes, phosphoramides, acetals, hemiacetals, and ketal forms of the drug. For example, see Andrejus Korolkovas's, "Essentials of Medicinal Chemistry", pp. 97-118.

The discovery and characterization of endothelium-derived nitric oxide (NO) was the subject of the 1998 Nobel Prize in Medicine and Physiology. NO is a major signaling molecule with important biological roles. See, for example, Kerwin, Jr., J. F. et al., J. Med. Chem. 1995, 38, 4343, and Williams. R. J. P., Chem. Soc. Rev., 1996, 77. The major biological functions of NO include controlling blood pressure, smoothing muscle tone and inhibition of platelet adherence and aggregation, assisting the immune system in destroying tumor cells and intracellular pathogens and participating in neuronal synaptic transmission. See, for example, Moncada, S. et al., Pharmacol. Rev. 1991, 43, 109; Bredt, D. S. et al., Anuu. Rev. Biochem., 1994, 63, 175; Schmidt, H. H. W. et al., Cell 1994, 78, 919; Feldman, P. L. et al., Chem. and Eng. News. 1993, 71 (20th December issue), 26; and Wilsonm E. K., Chem. and Eng. News. 2004 ($8^{th}$ March issue), 39. Endogenously, NO is produced from arginine by the catalytic action of nitric oxide synthase. See, for example, Nathan, C. et al., Cell 1994, 78, 915, and Marietta, M. A., Cell 1994, 78, 927.

NO is a free radical as well as a scavenger of free radicals. NO reacts quickly with ubiquitously generated reactive oxygen species (ROS) such as superoxide ($O_2^-$) to generate a nefarious peroxynitrite ($ONOO^-$) molecule, which is implicated in many human diseases such as diabetes, heart disease, Alzheimer's disease and multiple sclerosis. In this setting, NO is often viewed as pathogenic. However, the chemistry of NO can also be a significant factor in lessening the injury mediated by reactive oxygen species (ROS) and reactive nitrogen oxide species (RNOS). There is a relationship between NO and oxidation, nitrosation and nitration reactions. A number of factors determine whether NO promotes, abates or interconnects these chemistries. See, for example, Espay, et al., A chemical perspective on the interplay between NO, reactive oxygen species, and reactive nitrogen oxide species, Ann N.Y. Acad. Sci. 2002, 962, 195.

Thus, by being a free radical, along with the ability to scavenge other free radicals, NO is placed in a pivotal regulatory position. Insight into these pathophysiological processes and signaling are highly relevant to develop therapeutics.

NO deficiency has been implicated in the genesis and evolution of several disease states. In patients with cardiovascular problems, the production of superoxide is increased and level or location of NO synthesis is disrupted thereby causing cellular dysfunction as a result of vasoconstriction of blood vessels, which can lead to, if prolonged, cell damage or death. Agents that act to maintain the normal balance between NO and superoxide in vascular endothelial cells may prove particularly useful in this regard. See, for example, Stokes, K., et al., Free Radic. Bio. Med., 2002, 33, 1026-1036.

Nutritional and pharmacological therapies that enhance the bioactivity or production of NO have been shown to improve endothelium-dependent vasodilation, reduce symptoms, and slow the progression of atherosclerosis. Some of the strategies for NO modulation encompass anti-inflammatory, sexual dysfunction, and cardiovascular indications. Apart from newly developed drugs, several commonly used cardiovascular drugs exert their beneficial action, at least in part, by modulating the NO pathway. Pharmacological compounds that release NO have been useful tools for evaluating the pivotal role of NO in cardiovascular physiology and therapeutics.

NO-Donors:

There are a wide variety of structurally dissimilar organic compounds that act as NO donors and release NO in solution. Some NO donors, such as isoamyl nitrite, nitroglycerine (GTN) and sodium nitroprusside, have been used in cardiovascular medicine long before their biochemical mechanism was understood. The common mode of action for these drugs is liberation of NO, which evokes relaxation of smooth muscle through activation of guanylate cyclase with subsequent formation of cGMP. The relative importance of enzymatic versus non-enzymatic pathways for NO release, the identity of the actual NO-generating enzymes and the existence of competing metabolic events are additional important determinants of the different NO donor classes. Pharmacological compounds that release NO constitute two broad classes of compounds: those that release NO or one of its redox congeners spontaneously and those that require enzymatic metabolism to generate NO. See, for example, Ignarro, L. J. et al., Nitric oxide donors and cardiovascular agents modulating the bioactivity of nitric oxide: an overview, Circ. Res. 2002, 90, 21-28.

Nitroglycerine/glycerine trinitrate (GTN) and compounds referred to as nitrovasodilators or NO donors are frequently used in the treatment of ischemic heart disease. The common mode of action for these drugs is liberation of NO, which evokes relaxation of smooth muscle through activation of guanylate cyclase with subsequent formation of cGMP. However, early development of tolerance to nitrate therapy, particularly during acute myocardial infarction, has been the clinically significant drawback with GTN and some of the other available organic nitrates. This is a significant clinical problem and there exists a need for novel nitrate-based antianginal agents, which do not cause the problem of nitrate tolerance.

There are a number of new examples of organic nitrates in which an alkyl or aralkyl mononitrate is covalently linked to an existing drug molecule. Existing drugs from a large number of therapeutic areas such as anti-inflammatory, antiallergic, antibiotic, anticancer, antidiabetic, antiviral, antihypertensive, antianginal, anticonvulsant, analgesic, antiasthmatic, antidepressant, antidiarrheal, antiinfective, antimigraine, antipsychotic, antipyratic, antiulcerative, antithrombotic, etc., were made and evaluated. Some of Nicox's patents include: Synthesis and evaluation of nitrooxy derivatives of NSAIDs (WO 9412463, WO 0230867, WO 0292072, WO 0313499 and WO 0384550), aspirin (WO 9716405, WO 0044705 and WO 0112584), paracetamol (WO 0112584 and WO 0230866), antiepileptic agents (WO 0300642 and WO 0300643), COX-2 inhibitors (WO 0400781 and WO 0400300), statins (WO 04105754), ACE inhibitors (WO 04110432 and WO 04106300), and of known drugs used for the treatment of disease conditions resulting from oxidative stress and endothelial dysfunction (WO 0061537).

Most of these nitrate esters were shown to possess not only superior or equal efficacy when compared to the original drug but also exhibit much-reduced side effects. In fact, because of their superior efficacy combined with reduced toxicity, a few of such nitrate ester-containing drug conjugates are successfully passing through various stages of clinical trials. Some of Nicox's nitrooxy derivatives of drugs which are in clinical trials include: NCX 4016 (Phase II, peripheral vascular diseases), NCX 701 (Phase II, Acute pain), HCT 1026 (Phase I, Alzheimer's disease), HCT 3012 (Phase II, Osteoarthritis), NCX 285 (IND, Osteoarthritis), NCX 1022 (Phase IIa completed, Dermatitis), NCX 1020 (Phase I, Asthma/COPD), NCX 1000 (Phase I, Portal hypertension), and NCX 1510 (Phase II, Allergic rhinitis).

U.S. Pat. No. 5,767,134 and US20050002942A1 disclosed a few disulfide-containing prodrugs/folate-drug conjugates. WO 9842661, U.S. Pat. No. 5,807,847, WO 0054756 and WO 0149275 reported a few nitrooxy derivatives of organic molecules containing sulfahydryl or disulfide group which are called "SS-nitrates". These references are incorporated herein by reference.

Representative examples from WO 9842661 have shown superior vasorelaxant activity and no tolerance was observed to the cGMP-increasing effects of those compounds under the same experimental conditions used for the induction of in vivo tolerance. WO 0149275 reports drug conjugates where an anti-inflammatory drug is covalently linked to the beta-mercapto-nitrate via thioester bond. Biotransformation pathways proposed for NO release from GTN have largely been heme-dependent or sulfahydryl-dependent. See, for examples, Thatcher, G. R. J. et al., Chem. Soc. Rev. 1998, 27, 331 and reference cited therein, and Bennett, B M. et al., Trends Pharmacol, Sci. 1994, 15, 245. These references are incorporated herein by reference.

A mutual prodrug is the association in a unique molecule of two drugs, usually synergistic, attached to each other, one drug being the carrier for the other and vice versa. The embodiments of the invention also provide mutual prodrugs, which are prodrugs of two or three therapeutic agents currently used/potential for use in combination therapy utilizing novel bio-cleavable linkers, water-soluble prodrugs of insoluble/sparingly-soluble therapeutic agents using the same linker technology and water-soluble double and triple prodrugs of sparingly-soluble therapeutic agents or any of the prodrugs linked to NO-releasing agent using the same linker technology.

BRIEF DESCRIPTION OF THE FIGURE

FIG. 1 shows plasma salicylate profile of aspirin and its NO-releasing prodrugs.

SUMMARY OF THE INVENTION

Present invention relates to the compounds of formula (I) or pharmaceutically acceptable salts thereof:

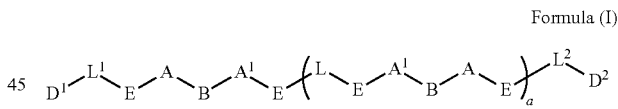

Formula (I)

wherein,
a is 0-2;
B independently represents a bond, $(CH_2)_b$, $(CH_2CH_2O)_c$, S—S, S—S=O, S—SO$_2$ or S—S=NH;
b is 1-6; c is 1-1000;
A and $A^1$ independently represent a bond, $(CH_2)_d$, 1,2-phenylene, 1,3-phenylene or 1,4-phenylene;
d is 1-8;
$D^1$ represents a therapeutic agent comprising one or more of the functional groups selected from the group consisting of —OH, —SH, —NHR$^1$, —CO$_2$H, —CONHR$^1$, —OC(=O)NHR$^1$, —SO$_2$NHR$^1$, —OSO$_2$NHR$^1$, —N(R$^1$)C(=O)NHR$^1$ and —N(R$^1$)SO$_2$NHR$^1$;
$D^2$ independently represents $D^1$, a peptide, protein, monoclonal antibody, vitamin, $R^2$, $R^3$, $R^4$, NO, NO$_2$, a linkable nitric oxide-releasing group comprising a NONOate, a group comprising one or more of water-solubilizing functional groups, or a polymer;
E independently represents CH$_2$ or a bond;

$L^1$ and $L^2$ independently represent a bond, O, S, $NR^1$, L, or a linkage selected from the group consisting of:

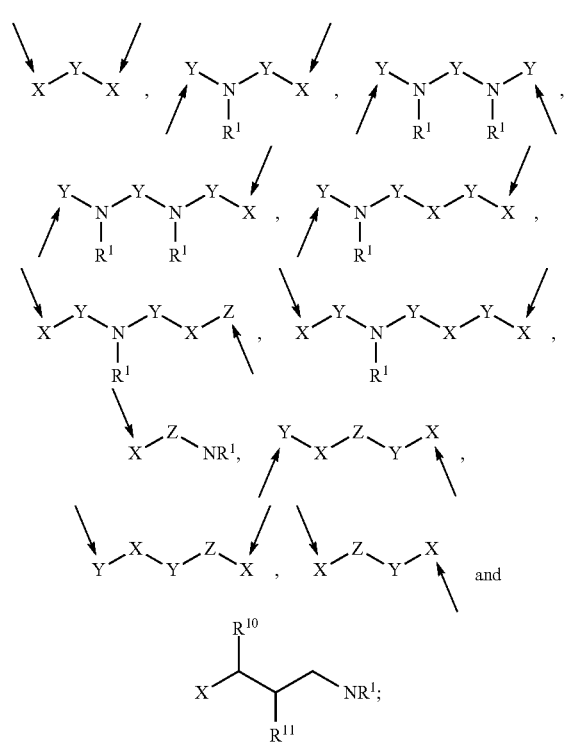

L is $R^{12}$ or a group with bonding in any direction, independently selected from the group consisting of:

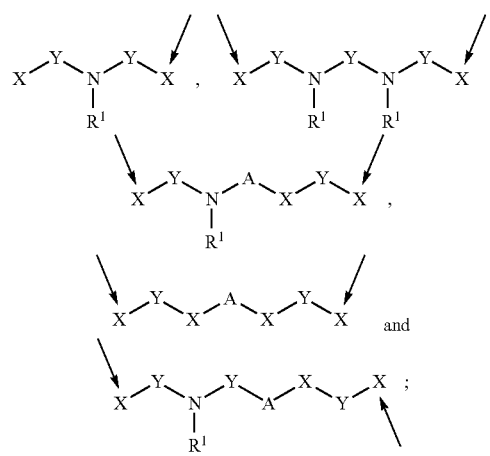

X independently represents a bond, C, O, S, or $NR^1$;

Y independently represents a bond, C=O, C=S, S=O, $SO_2$, P(=O)$XR^1$, or $(CH_2)_j$;

Z independently represents a bond, or $(CH_2)_3$; wherein, j is 1-4;

$R^1$ independently represents a bond, H, $(C_1-C_8)$alkyl, $(C_5-C_{14})$aryl, aralkyl or $M^{e+}$;

$R^2$ independently represents H, $NH_2$, or NHAc;

$R^3$ independently represents H, $CO_2R^5$, $CH_2CO_2R^5$, $R^4$ independently represents H, OH, O—$(C_1-C_8)$alkyl, $OM^{e+}$, or a group selected from the group consisting of:

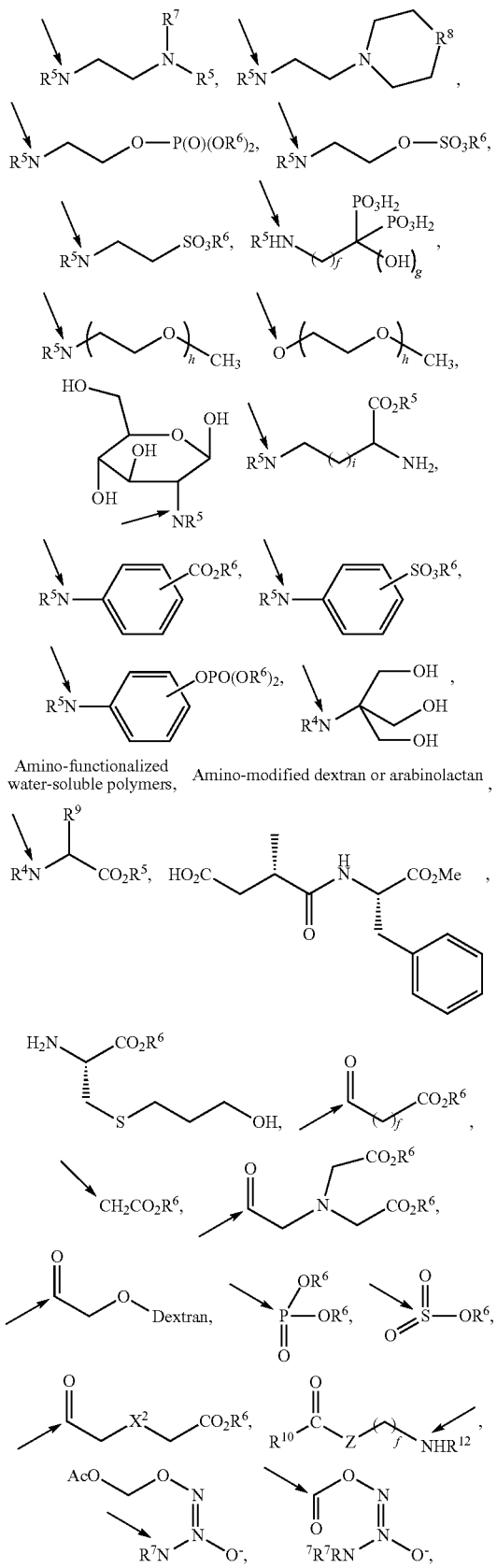

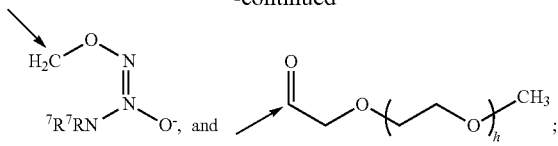

M independently represents Na, K or a pharmaceutically acceptable metal ion,
e=1-3,
$R^5$ independently represents at each occurrence H, $M^{e+}$, $(C_1-C_8)$alkyl, $(C_3-C_8)$cycloalkyl, substituted $(C_5-C_{14})$aryl, hetero $(C_2-C_{14})$aryl, $C(=O)(CH_2)_fCHR^9CO_2R^5$, $CH_2C(=O)OR^5$, $P(=O)(OR^5)_2$,

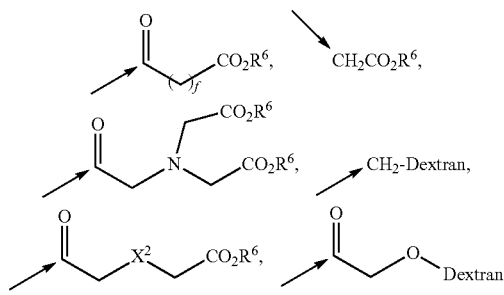

$X^2$ independently represents O, S, SO, $SO_2$, or $NR^5$;
$R^6$ independently represents H, $Na^+$, $K^+$, any other pharmaceutically acceptable metal ion, $(C_1-C_8)$alkyl, or $(C_3-C_8)$cycloalkyl,
$R^7$ independently represents at each occurrence same or different $R^5$;
$R^8$ independently represents $CH_2$, O, $NR^4$, S, S=O or O=S=O;
$R^9$ independently represents H, $(C_1-C_8)$alkyl or an amino acid;
f is 0-6;
g is 0-1;
h is 1-2000;
i is 1-4;
$R^{10}$ and $R^{11}$ independently represent H, $(C_1-C_8)$alkyl, $(C_3-C_8)$cycloalkyl, or a group selected from the group consisting of:

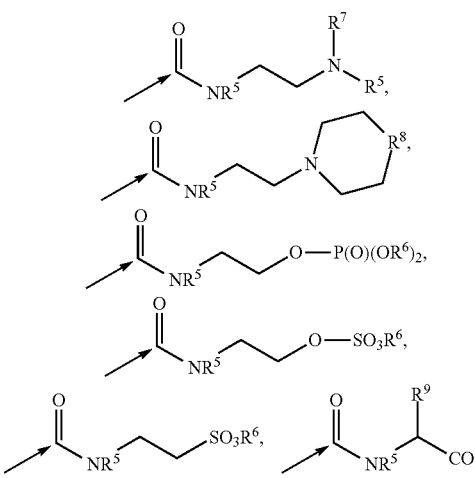

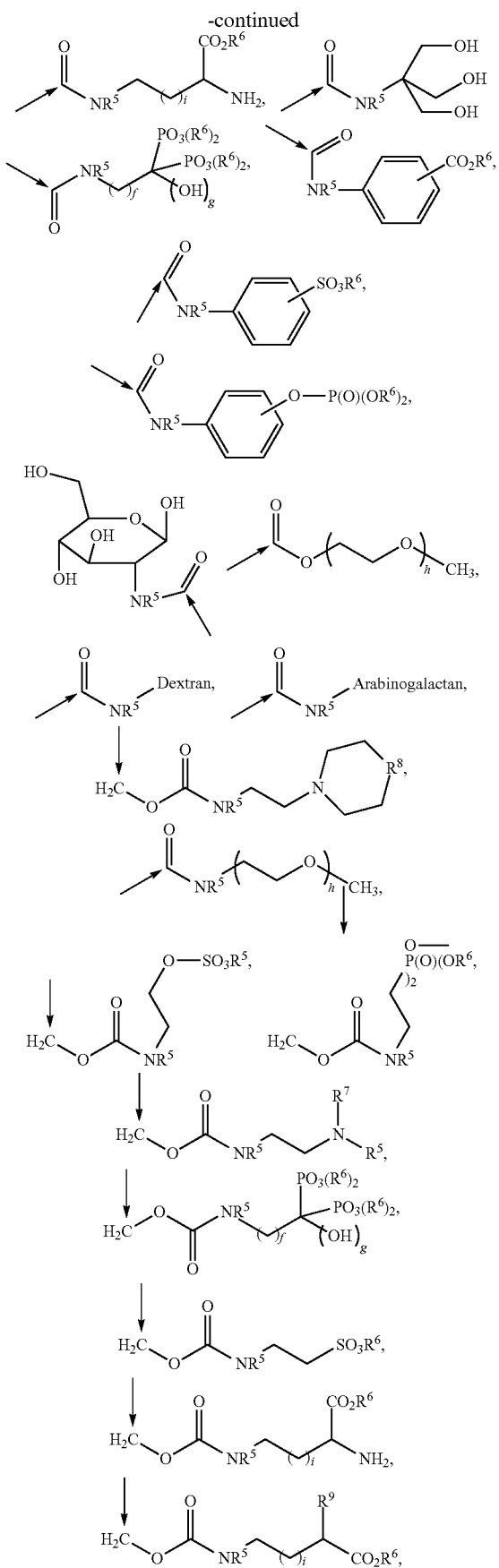

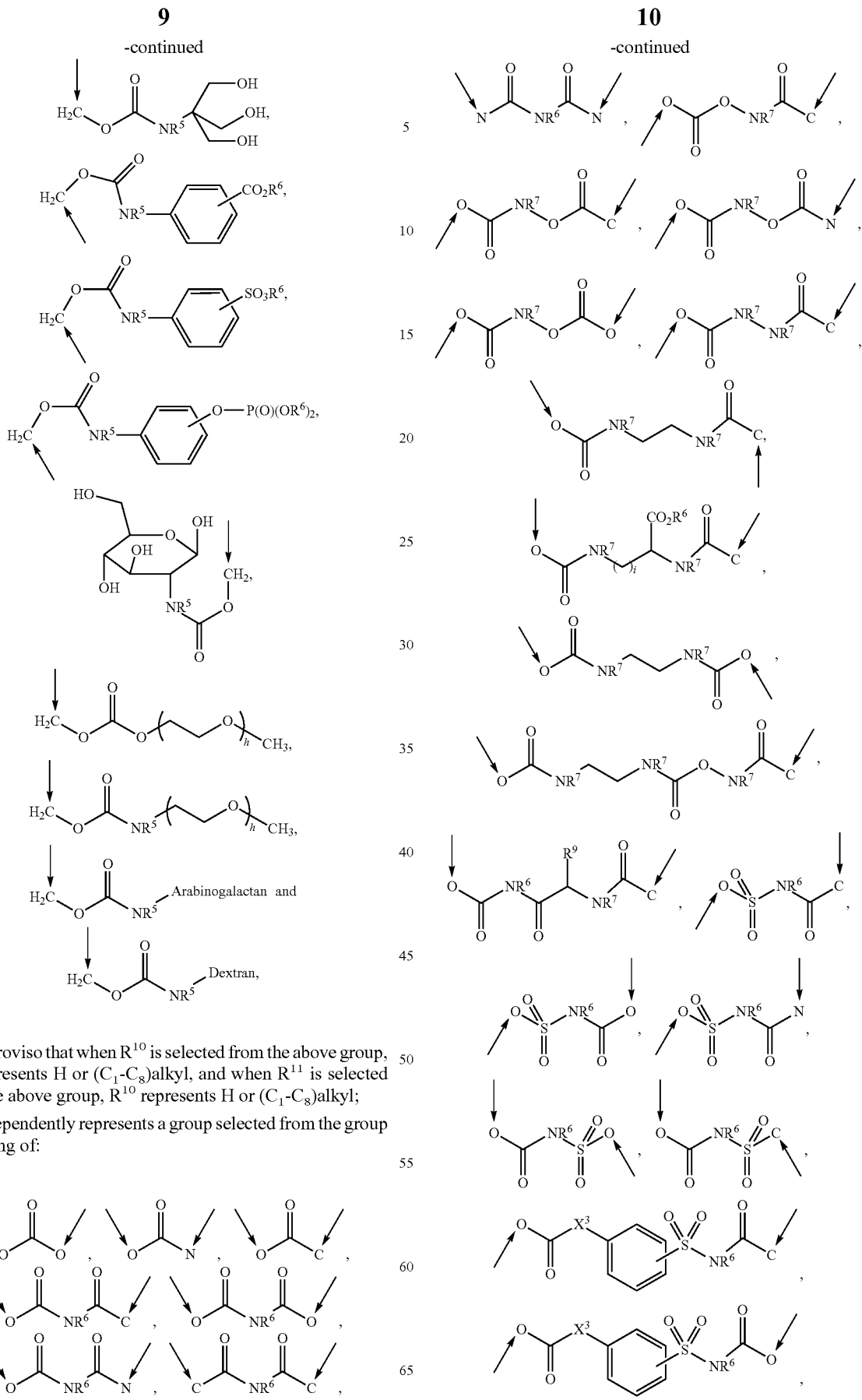
with a proviso that when $R^{10}$ is selected from the above group, $R^{11}$ represents H or $(C_1\text{-}C_8)$alkyl, and when $R^{11}$ is selected from the above group, $R^{10}$ represents H or $(C_1\text{-}C_8)$alkyl;
$R^{12}$ independently represents a group selected from the group consisting of:

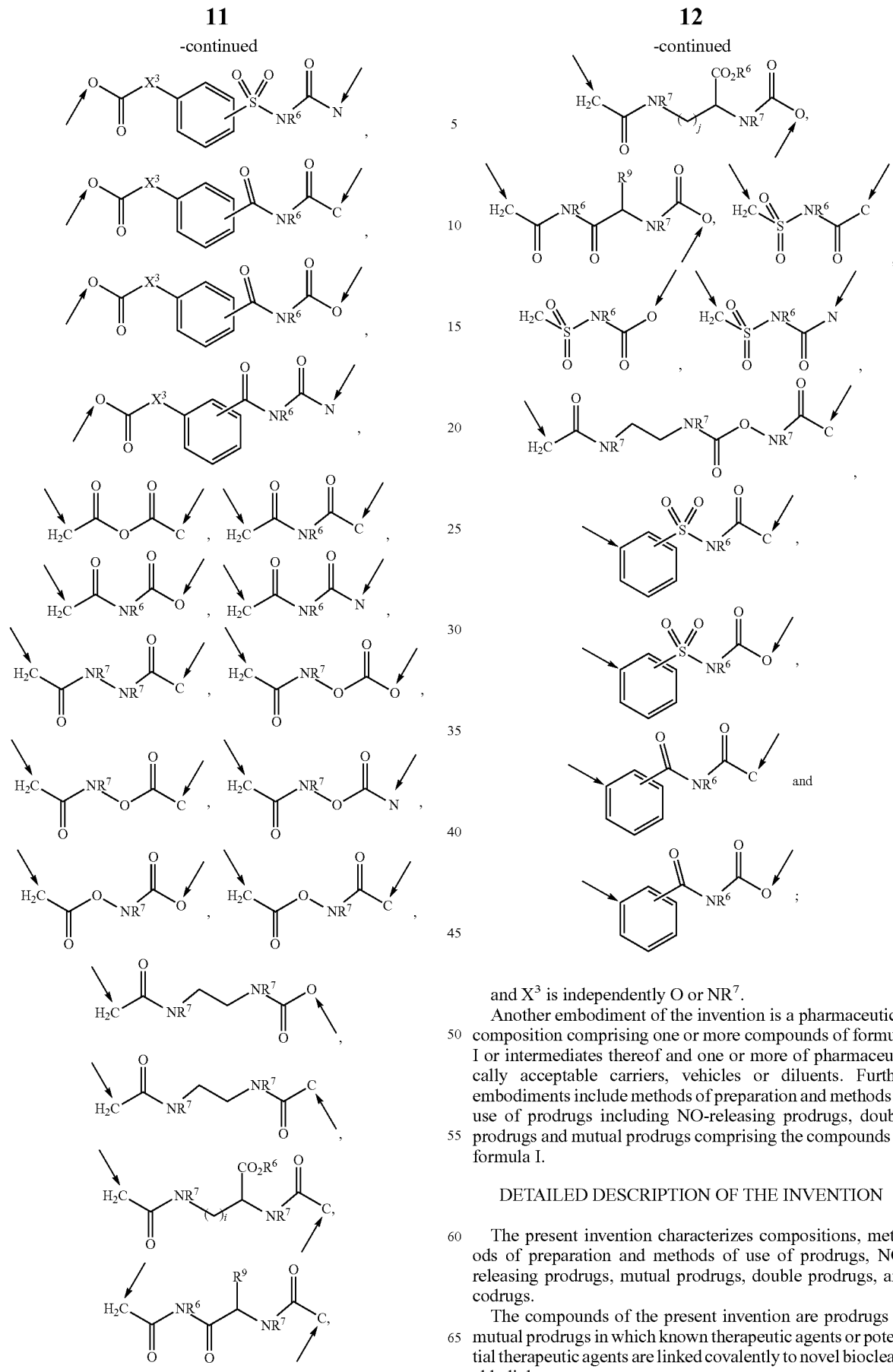

and X³ is independently O or NR⁷.

Another embodiment of the invention is a pharmaceutical composition comprising one or more compounds of formula I or intermediates thereof and one or more of pharmaceutically acceptable carriers, vehicles or diluents. Further embodiments include methods of preparation and methods of use of prodrugs including NO-releasing prodrugs, double prodrugs and mutual prodrugs comprising the compounds of formula I.

DETAILED DESCRIPTION OF THE INVENTION

The present invention characterizes compositions, methods of preparation and methods of use of prodrugs, NO-releasing prodrugs, mutual prodrugs, double prodrugs, and codrugs.

The compounds of the present invention are prodrugs or mutual prodrugs in which known therapeutic agents or potential therapeutic agents are linked covalently to novel biocleavable linkers.

The compounds of the present invention also include NO-releasing prodrugs in which a therapeutic agent is linked covalently to nitrooxy (nitrate ester) group via a novel biocleavable linker containing a strategically placed disulfide group at β-position to the nitrate ester. The present invention also characterizes composition of NO-releasing prodrugs (i.e., nitrooxy ester or nitrate ester prodrugs), processes for their preparation, pharmaceutical composition containing them and their use.

Unless otherwise defined, all technical and scientific terms used herein have the same meaning as commonly understood by one of ordinary skill in the art to which this invention belongs. Listed below are definitions of various terms used to describe the compounds of the present invention. These definitions apply to the term as they are used throughout the specification (unless they are otherwise limited in specific instances) either individually or part of a larger group.

The term "amino-containing" refers to drug/carrier molecule with NH functional groups such as amino (both primary and secondary), amide, urea, sulfonamide, carbamate, phosphoramadite, sulfamate, hydrazone, semicarbazone, thiosemicarbazone, hydrazide, carbazate and the like. This also includes NH-containing heterocylic compounds such as imidazoles, benzimidazoles, pyrazoles, benzpyrazols, pyrrols, indoles, triazoles, tetrazoles, benzotriazoles, benzotetrazoles and their derivatives. These NH-containing heterocyclic compounds can be sub-structures of more complex drug/carrier molecules. Amino group of the candidate drug can be primary or secondary (both acyclic and cyclic) which include amide-NH, sulfonamide-NH, carbamate-NH, sulfamate-NH, hydrazide-NH, hydrazone-NH, semicarbazone-NH, thiosemicarbazone-NH, urea-NH and also drugs containing indole, imidazole, benzimidazole, thiazole, oxazole, pyrrole, pyrazole, triazole, tetrazole, or similar NH-containing heterocylic sub-structures of a more complex drug molecule.

The term "hydroxyl-containing" refers to drug/carrier molecules with hydroxyl groups (primary, secondary, tertiary and phenolic) including hydroxyl groups of hydroxamic acids and ketoximes derived from keto-containing molecules. Hydroxyl group of drugs can be of primary, secondary, tertiary or phenolic in nature.

The term "sulfahydryl-containing" refers to drug/carrier with free sulfahydryl (SH) group.

The term "halo" refers to fluoro, chloro, bromo, and dodo.

The term "halide" refers to fluoride, chloride, bromide, and iodide.

The term "alkyl" refers to acyclic alkyl chains. For example, the term "$C_1$-$C_8$ alkyl" refers to methyl, ethyl, propyl, isopropyl, butyl, cyclobutyl, s-butyl, and t-butyl, pentyl, hexyl, heptyl, octyl, and the like.

The term "cycloalkyl" refers to cyclic alkyl chains, e.g., the term "$C_3$-$C_8$ cycloalkyl" refers to cyclopropyl, cyclooctyl, cyclopentyl, cyclohexyl, cycloheptyl, cyclooctyl and the like.

The term "aryl" refers to phenyl, naphthyl and the like.

The term "aralkyl" refers to benzyl, phenethyl and the like.

The term "alkoxy" refers to both acyclic and cyclic $C_1$-$C_8$ alkyloxy. For example, the term "$C_1$-$C_8$ alkyloxy" refers to methoxy, ethoxy, propoxy, isopropoxy, cyclopropoxy, butoxy, cyclobutoxy, s-butoxy, and t-butoxy, cyclopentyloxy, pentyloxy, hexyloxy, cyclohexyloxy, heptyloxy, cycloheptyloxy, octyloxy, cyclooctyloxy and the like.

The term "heterocyclic" and "heteroaryl" refers to both saturated and unsaturated 5- and 6-membered rings (including benzo-fused) containing from 1 to 4 heteroatoms selected from the group consisting of nitrogen, oxygen and sulfur. All of these rings may be substituted with up to three substituents independently selected from the group consisting of amino, halo, alkoxy, alkyl, cyano, nitro, hydroxyl, sulfahydryl, carboxyl and the like. Saturated rings include, for example, pyrrolidinyl, piperidinyl, piperazinyl, tetrahydrofuryl, oxazolidinyl, dioxanyl, pyranyl, and the like. Benzofused saturated rings include indolinyl, 1,2,3,4-tetrahydroquinolinyl, 1,2,3,4-tetrahydroisoquinolinyl and the like. Unsaturated rings include furyl, thienyl, pyridinyl, pyrrolyl, N-methylpyrrolyl, oxazolyl, isoxazolyl, pyrazolyl, imidazolyl, tetrazolyl, triazolyl, oxadiazolyl, thiadiazolyl, thiazolyl, pyrimidinyl, pyrazinyl, pyridazinyl, and the like. Benzofused unsaturated rings include isoquinolinyl, benzoxazolyl, benzthiazolyl, quinolinyl, benzofuranyl, thionaphthyl, indolyl and the like.

The term "substituted alkyl" refers to acylic and cyclic alkyl groups substituted with one or more of groups such as alkyl, aryl, hydroxy, alkoxy, cyano, carboxyl, sulfahydryl, alkylthio, amino, nitro, halo, carbonyl, carbamato, sulfamato, sulfonato, sulfato, and the like.

The term "substituted aryl" refers to aryl groups substituted (including fused) with one or more of groups such as alkyl, aryl, hydroxy, alkoxy, cyano, carboxyl, sulfahydryl, alkylthio, amino, nitro, halo, carbonyl, carbamato, sulfamato, sulfonato, sulfato, and the like.

The term "amino acid" refers to molecules containing one or more amino and carboxyl groups. Examples of alfa-amino acids (D-, L- and DL-amino acids)-include natural alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Other examples include beta-amino acids and known unnatural amino acids.

The term "amino acid ester" as used in this specification refers to an amino acid where the carboxyl group is substituted with a $C_1$-$C_8$ alkyl group. That is, the alkyl group when taken together with the carboxyl group forms a $C_1$-$C_6$ alkyl ester. It is appreciated that some amino acids (e.g., aspartic acid and glutamic acid) have two carboxyl groups these may form mono- and di-esters.

The term "protecting group" (PG) refers to an 'amino protecting group' or a 'hydroxyl protecting group' or a 'carboxyl protecting group' and the like.

The term "amino protecting group" refers to a group that selectively blocks or protects the amino functionality in presence of other functional groups on the molecule. Examples of such amino-protecting groups include the formyl group, the trityl group, the phthalimido group, the acetyl group, the trifluoroacetyl group, the chloroacetyl, bromoacetyl, and iodoacetyl groups, urethane-type blocking groups such as benzyloxycarbonyl ("CBZ"), 9-fluorenylmethoxycarbonyl ("FMOC"), tert-butoxycarbonyl ("BOC"), trichloroethylcarbonyl and the like. Additional examples of amino protecting groups are described by T. W. Greene, "Protective Groups in Organic Synthesis", John Wiley and Sons, New York, N.Y., 1991. Molecules with two or more amino groups may form mono-, di-, tri-, poly-, protected derivatives depending on the reaction conditions used.

The term "hydroxyl protecting group" refers to a group that selectively blocks or protects hydroxyl functionality in presence of other reactive functional groups on the molecule. Examples of such hydroxyl-protecting groups include, for example, ether groups including methyl and substituted methyl ether groups such as methyl ether, methoxymethyl ether, methylthiomethyl ether, tert-buylthiomethyl ether, triphenylmethyl, tetrahydropuranyl (THP), (phenyldimethylsilyl)methoxy-methyl ether, benzyloxymethyl ether, p-methoxybenzyloxy-methyl ether, and tert-butoxymethyl ether; substituted ethyl ether groups such as ethoxyethyl ether, 1-(2-chloroethoxy)-ethyl ether, 2,2,2-trichloroethoxymethyl ether, and 2-(trimethylsilyl)ethyl ether; isopropyl ether groups; phenyl and substituted phenyl ether groups such as phenyl ether, p-chlorophenyl ether, p-methoxyphenyl ether, and 2,4-dinitrophenyl ether; benzyl and substituted benzyl ether groups such as benzyl ether, p-methoxybenzyl ether, o-nitrobenzyl ether, and 2,6-dichlorobenzyl ether; and alkylsilyl ether groups such as trimethyl-, triethyl- and triisopropylsilyl ethers, mixed alkylsilyl ether groups such as dimethylisopropylsilyl ether, tert-butyldimethylsilyl ether and diethylisopropylsilyl ether; and ester protecting groups such as acetate ester, formate ester, benzylformate ester, mono-, di-, and trichloroacetate esters, pivalate ester, phenoxyacetate ester, and p-chlorophenoxyacetate, benzyloxycarbonate, 9-fluorenylmethoxycarbonate, tert-butoxycarbonate, trichloroethylcarbonate, carbamate, sulfamate and the like. Additional examples of hydroxyl protecting groups are described by T. W. Greene, "Protective Groups in Organic Synthesis", John Wiley and Sons, New York, N.Y., 1991. Molecules with two or more hydroxyl groups may form mono- and di-esters/ethers depending on the reaction condition.

The term "carboxyl protecting group" refers to a group that selectively blocks or protects carboxyl functionality in presence of other reactive functional groups on the molecule. Examples of such carboxyl-protecting groups include, for example (substituted) alkyl esters such methyl ester, ethyl ester, t-butyl ester, (substituted) benzyl ester, trichloroethyl ester, and the like. Additional examples of carboxylic acid protecting groups are described by T. W. Greene, "Protective Groups in Organic Synthesis", John Wiley and Sons, New York, N.Y., 1991. Molecules with two or more carboxylic acid groups may form mono-, di-, tri-, tetra-, poly-protected derivatives depending upon the reaction conditions used.

The term "carbonyl activating group" refers to leaving group ("LG") of a carboxyl derivative that is easily replaced by an incoming nucleophile. Such "LG" groups include, but are not limited to, (substituted) alkoxy, aryloxy, nitrogen containing unsaturated heterocycles such as N-oxybenzotriazole, imidazolyl, o/p-nitrophenoxy, pentachloro-phenoxy, N-oxysuccinimide, N,N'-dicyclohexylisoure-O-yl, N-hydroxy-N-methoxyamino, and the like; acetates, formates, sulfonates such as methanesulfonate, ethanesulfonate, benzenesulfonate, or p-toluenesulfonate, and the like; and halides especially fluoride, chloride, bromide, or iodide.

The term "carbonyl activating reagent" refers to a reagent that converts the carbonyl of a carboxylic acid group into one that is more susceptible to nucleophilic attack and includes, but is not limited to, such reagents as those found in "The Peptides", Gross and Meienhofer, Eds., Academic Press (1979), Ch. 2, and M. Bodanszky, "Principles of Peptide Synthesis", 2.sup.nd Ed., Springer-Verlag Berlin Heidelberg, 1993, hereafter referred to as "The Peptides" and "Peptide Synthesis" respectively. Carbonyl group (i.e., aldehyde or keto group) of candidate drugs may be converted first to aldoxime, ketoxime, hydrazone, semicarbazone and the like, before coupling to the linker. Specifically, carbonyl activating reagents include thionyl bromide, thionyl chloride, oxalyl chloride, and the like; esters of alcohols such as nitrophenol, pentachlorophenol, and the like; and compounds such as 1,1'-carbonyldiimidazole (CDI), benzotriazole, imidazole, N-hydroxysuccinimide, dicyclohexylcarbodiimide (DCC), EDC, phosgene or its equivalents, N,N-dimethylaminopyridine (DMAP) and the like.

The terms "phosgene or its equivalents" refer to phosgene or it equivalents such as diphosgene, triphosgene, CDI, DSC, BTBC, alkoxycarbonyl chlorides, o/p-nitrosubstituted phenoxycarbonyl chlorides, and the like.

In general, the term "pharmaceutical" when used as an adjective means substantially non-toxic to living organisms.

The terms "pharmaceutically acceptable metal ions or salts" refer to salts of the compounds of this invention, which are substantially non-toxic to living organisms. See, e.g., Berge, S. M. et al., "Pharmaceutical Salts", J. Pharm. Sci., 66:1, 1977. Typical pharmaceutical salts include those salts prepared by reaction of the compounds of this invention with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions. Examples of pharmaceutically acceptable salts are those with inorganic bases such as sodium, potassium, calcium, magnesium, and hydroxides, and the like, or with organic bases such as lysine, arginine, triethylamine, dibenzylamine, piperidine, and the like.

The term "suitable solvent" refers to a solvent that is inert to the ongoing reaction and sufficiently solubilizes the reactants to effect the desired reaction. Examples of suitable solvents include but are not limited to, dichloromethane, chloroform, 1,2-dichloroethane, diethyl ether, tert-butylmethyl ether, acetonitrile, ethyl acetate, 1,3-dimethyl-2-imidazolid-indne, tetrahydrofuran, dimethylformamide, benzene, toluene, xylene, N-dimethylacetamide, N-methylpyrrolidine, chlorobenzene, dimethylsulfoxide, dimethoxyethane, water, methanol, ethanol, isopropanol, pyridine, nitromethane, mixtures thereof, and the like.

The term "suitable base" refers to a base, which acts as a proton trap for any protons, which may be produced as a byproduct of the desired reaction, or to a base, which provides a reversible deprotonation of an acidic proton from the substrate and is reactive enough to effect the desired reaction without significantly effecting any undesired reactions. Examples of such bases include, but are not limited to, carbonates, bicarbonates, and hydroxides (e.g., lithium, sodium, potassium, magnesium, calcium and the like), sodium/potassium/calcium hydride, sodium/potassium alkoxide (i.e., methoxide, ethoxide, tert-butoxide and the like), triethylamine, diisopropylethylamine, N-methylpyrrolidine, N-methylmorpholine, tetramethylguinidine, or aromatic nitrogen containing heterocycles such pyridine, 4-(dimethylamino) pyridine (DMAP), and the like.

The term "NONOate" refers to a linkable nitric oxide-releasing group such as $AcOCH_2—O—N_2—N(O^-)R^7$, $OCHOCH_2—O—N_2—N(O^-)R^7R^7$, $CH_2—O—N_2—N(O^-)R^7R^7$ and the like.

The term "therapeutic agent" refers to biologically active molecules such as drugs, vitamins, and other molecules, agents or substances concerned with or contributing to the treatment and cure of illness or contributing to the general well being of a mammal or human. The therapeutic agents can be both known and investigational drugs compiled in drug databases such as the Merck Index, IDdb, Prous Science's Integrity®, Prous Science Drugs of the Future™, The Ensemble® and the like. The Merck Index is a one-volume encyclopedia of chemicals, drugs and biologicals that contains more than 10,000 monographs. Each monograph in this authoritative reference source is a concise description of a single substance or a small group of closely related compounds. Prous Science is an international health science publishing company, established in 1958 and headquartered in Barcelona, Spain. Prous Science Drugs of the Future™, produced by Prous Science Publishers, contains comprehensive drug monographs providing product information on new compounds, including the synthesis and corresponding schemes, pharmacological action, pharmacokinetics and metabolism, toxicity, clinical studies, manufacturer, and references. Information on compounds is continuously updated as advances in development status are disclosed worldwide. The Prous Science Integrity™ is a drug R&D portal where knowledge areas are coordinated to provide a harmonious and interrelated whole, which includes Drugs & Biologics, Targets, Organic Synthesis, Experimental Pharmacology, Pharmacokinetics and Metabolism, Clinical Studies, Disease Briefings, Companies & Markets, Literature and Patents. The Investigational Drugs database (IDdb), developed by Thomson Current Drugs, is a pharmaceutical competitor intelligence service. It covers all aspects of investigational drug development, from first patent to eventual launch or discontinuation. The Ensemble® on the Web provides essential information, including chemical structures, on more than 140,000 compounds with demonstrated biological activity in the drug research and development pipeline.

The term "vitamin" includes vitamin A, vitamin C, thiamine, folic acid, biotin, inositol, nicotinic acid, nicotinamide, riboflavin, pyridoxine, pyridoxal 5-phosphate, ergosterol, vitamin D2, vitamin D3, vitamin D4, vitamin E, menadoxime, menadiol, and vitamin K5.

The term "peptide" includes large and small peptides, including, but not limited to, targetable small peptides such as a dipeptide, tripeptide, tetrapeptide, etc.

The term "ligand" means a small molecule that binds to a larger macromolecule, whether or not the ligand actually binds at a metal site. Such ligands can be small peptides.

One aspect of the invention is to provide mutual prodrugs of two or three therapeutic agents currently used for use in combination therapy utilizing novel bio-cleavable linkers, water-soluble prodrugs of insoluble and sparingly-soluble therapeutic agents using the same linker technology, and water-soluble double and triple prodrugs of sparingly-soluble therapeutic agents using the same linker technology. The embodiments of the invention may also comprise vitamins and targetable small peptides in addition to or in place of a promoeity to yield targetable prodrugs.

The candidate drugs selected for mutual prodrug synthesis can be from one therapeutic category or from different therapeutic categories. Similarly, the constituent drugs of a mutual prodrug can act on the same biological target with similar mechanism of action or act on different biological targets with different mechanisms of action.

To be considered for prodrug synthesis, the candidate drugs should contain one or more of the essential functional groups such as amino, hydroxyl, keto, or carboxyl groups in their structure.

Amino group of the candidate drug can be primary or secondary (both acyclic and cyclic) which include amide-NH, sulfonamide-NH, carbamate-NH, sulfamate-NH, hydrazone-NH, semicarbazone-NH, thiosemicarbazone-NH and also drugs containing indole, imidazole, benzimidazole, thiazole, oxozole, pyrrole, pyrazole, triazole, tetrazole, or similar NH-containing heterocylic sub-structures of a more complex drug molecule. Similarly, hydroxyl group of drugs can be of primary, secondary, tertiary or phenolic in nature. Keto group of candidate drugs may be converted first to ketoxime, hydrazone, semicarbazone and the like, before coupling to the linker. Obviously, hydroxyl or amino functions thus generated will be used to form covalent bond between the drug and the linker.

The candidates for making mutual prodrugs can be the pairs of drugs that are currently used in combination therapy (including those combination studies at investigational stage) in various therapeutic areas provided each of those drugs possesses the requisite functional group(s). There are a number of therapeutic areas where such combination therapy is applied routinely and successfully.

On the basis of the proposed sulfahydryl-dependent mechanism of NO-release from GTN, we have designed the compounds and prodrugs of the present invention where a suitable drug molecule is linked covalently to a nitrooxy (nitrate ester) group via a bio-labile linker containing strategically located disulfide bond at beta-position to nitrate ester. In vivo, the disulfide bond in the prodrug is expected to be reduced by endogenous sulfahydryl-containing species such as glutathione (GSH) to generate a reactive thiolate anion (i.e., beta-mercapto-nitrate), which can trigger further breakdown of the linker moiety to release the free drug (via a mechanism as shown Scheme M1) and NO simultaneously at the same location. It is possible, as depicted in the mechanism Scheme M1, the release of NO can go via a hypothetical cyclic transient intermediate 'b'. Similar hypothetical mechanism was proposed for NO release from SS-nitrates, which were also designed on the basis of a sulfahydryl-dependent NO release from GTN. See, for example, Zavorin, S. I. et al., Organic Letters, 2001, 3, 1113, incorporated herein in its entirety. Mutual prodrugs can be made by linking covalently any two of the following: an amino-containing therapeutic agent to another amino-containing therapeutic agent; an amino-containing therapeutic agent to a hydroxyl-containing therapeutic agent; an amino-containing therapeutic agent to a carboxyl-containing therapeutic agent and its derivative; a hydroxyl-containing therapeutic agent to a carboxyl-containing therapeutic agent and its derivative; an amino-containing therapeutic agent to a carboxyl-containing therapeutic agent and its derivative; an amino-containing therapeutic agent to a keto-containing therapeutic agent or its hydrazone, semicarbazone or oxime derivative and the like; a hydroxyl-containing therapeutic agent to a keto-containing therapeutic agent via its hydrazone, semicarbazone, or oxime derivative and the like.

Another aspect of the present invention is to provide new nitrate ester (NO-releasing) prodrugs of many types of existing drugs using novel biocleavable linkers. Such prodrugs are expected to exhibit better efficacy and tolerability with reduced side effects compared to the corresponding original drugs.

An embodiment of present invention relates to the compounds of formula (I) or pharmaceutically acceptable salts thereof:

Formula (I)

wherein,
a is 0-2;
B independently represents a bond, $(CH_2)_b$, $(CH_2CH_2O)_c$, S—S, S—S=O, S—SO$_2$ or S—S=NH;
b is 1-6; c is 1-1000;
A and $A^1$ independently represent a bond, $(CH_2)_d$, 1,2-phenylene, 1,3-phenylene or 1,4-phenylene;
d is 1-8;
$D^1$ represents a therapeutic agent comprising one or more of the functional groups selected from the group consisting of —OH, —SH, —NHR$^1$, —CO$_2$H, —CONHR$^1$, —OC(=O)NHR$^1$, —SO$_2$NHR$^1$, —OSO$_2$NHR$^1$, —N(R$^1$)C(=O)NHR$^1$ and —N(R$^1$)SO$_2$NHR$^1$;

$D^2$ independently represents $D^1$, a peptide, protein, monoclonal antibody, vitamin, $R^2$, $R^3$, $R^4$, NO, $NO_2$, a linkable nitric oxide-releasing group comprising a NONOate, a group comprising one or more of water-solubilizing functional groups, or a polymer;

E independently represents $CH_2$ or a bond;

$L^1$ and $L^2$ independently represent a bond, O, S, $NR^1$, L, or a linkage selected from the group consisting of:

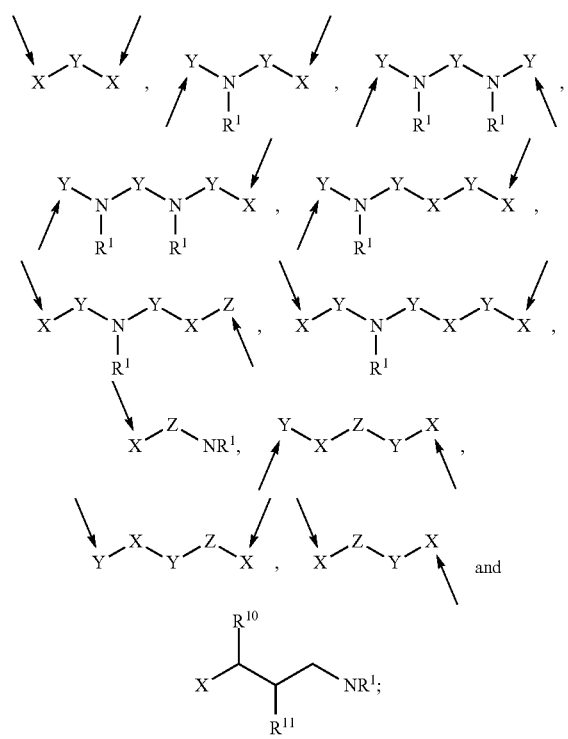

L is $R^{12}$ or a group with bonding in any direction, independently selected from the group consisting of:

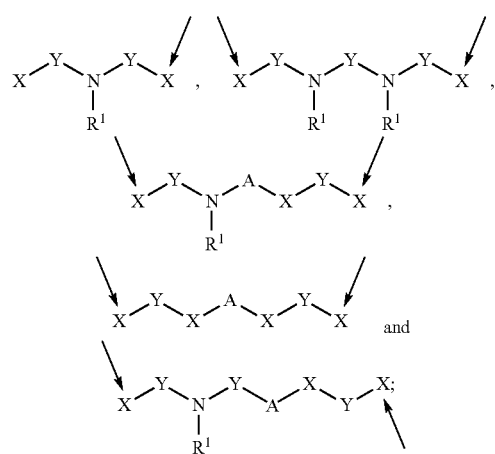

X independently represents a bond, C, O, S, or $NR^1$;
Y independently represents a bond, C=O, C=S, S=O, $SO_2$, $P(=O)XR^1$ or $(CH_2)_d$;
Z independently represents a bond, or $(CH_2)_j$; wherein, j is 1-4;

$R^1$ independently represents a bond, H, $(C_1-C_8)$alkyl, $(C_5-C_{14})$aryl, aralkyl or $M^{e+}$;

$R^2$ independently represents H, $NH_2$, or NHAc;

$R^3$ independently represents H, $CO_2R^5$, $CH_2CO_2R^5$, $R^4$ independently represents H, OH, O—$(C_1-C_8)$alkyl, $OM^{e+}$, or a group selected from the group consisting of:

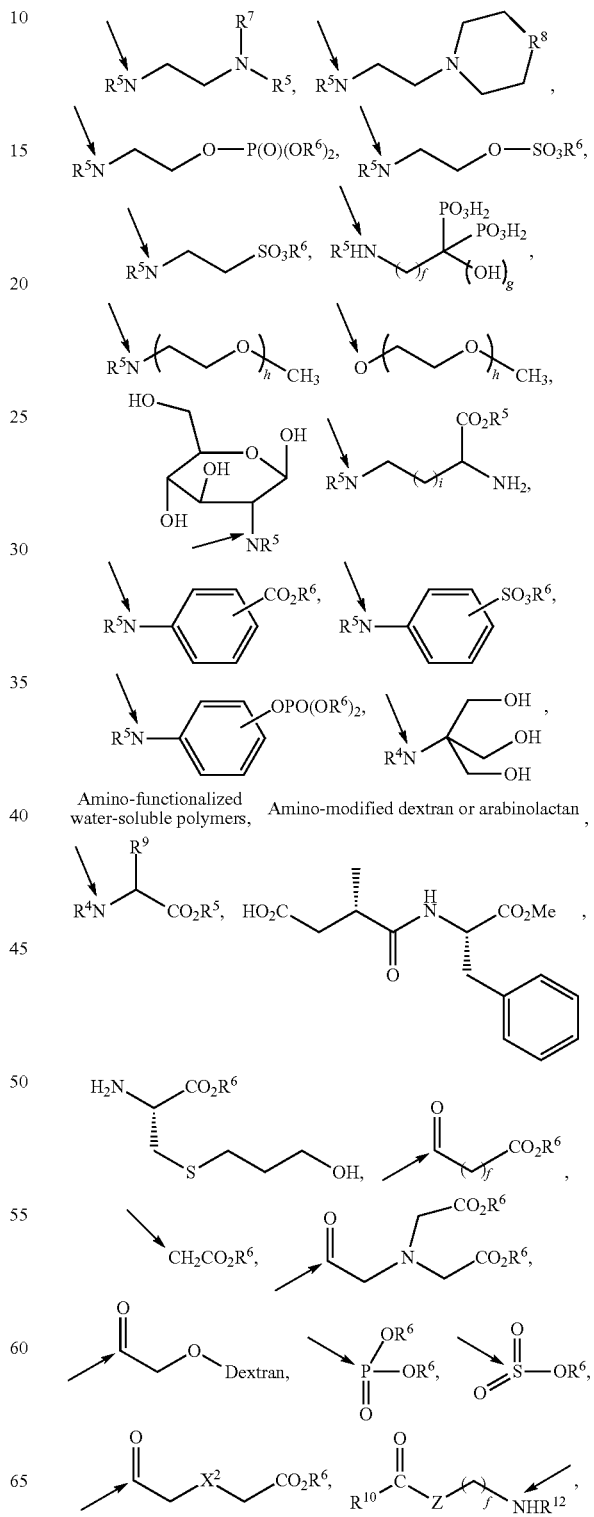

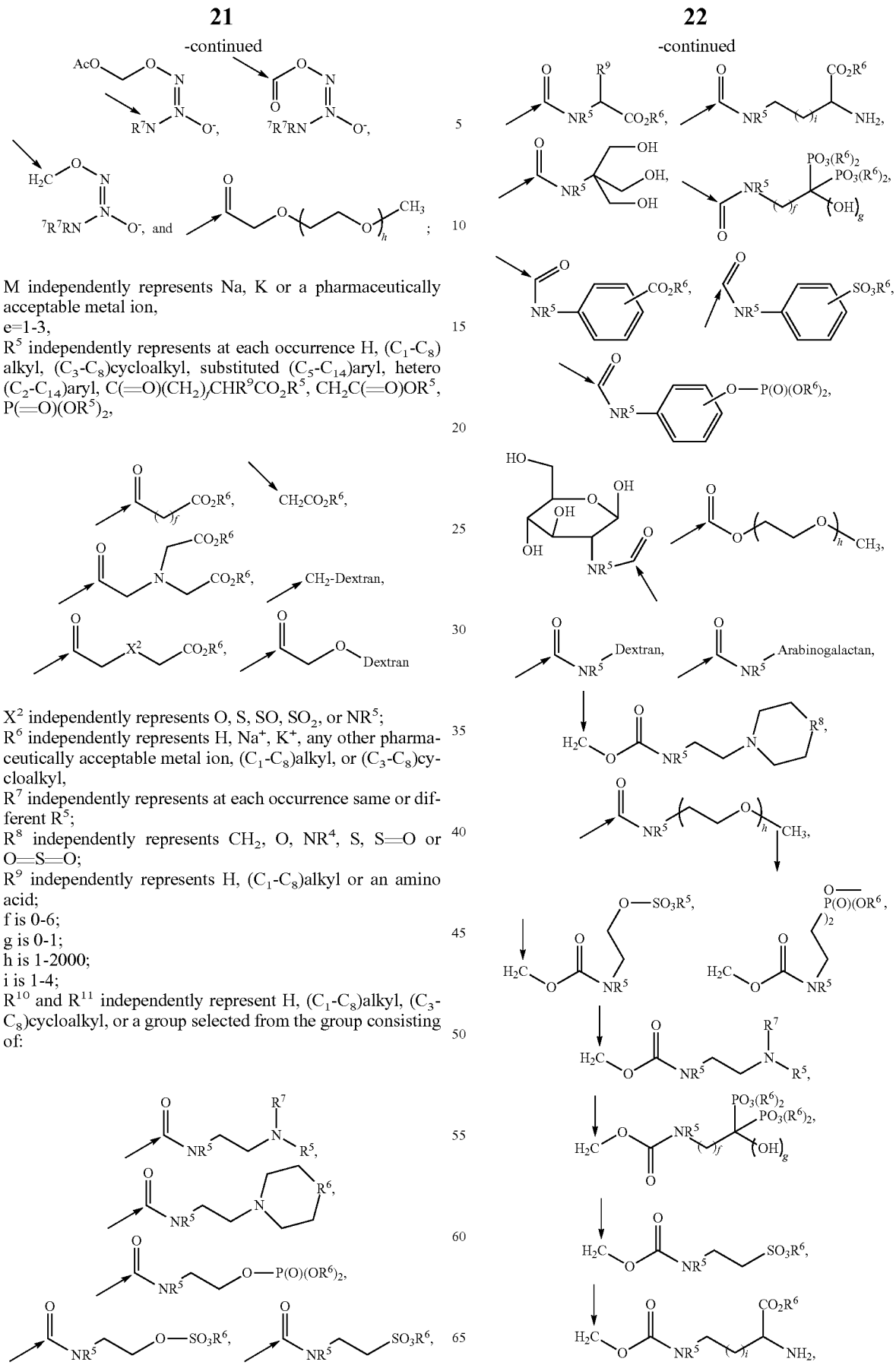

M independently represents Na, K or a pharmaceutically acceptable metal ion,
e=1-3,
$R^5$ independently represents at each occurrence H, $(C_1-C_8)$alkyl, $(C_3-C_8)$cycloalkyl, substituted $(C_5-C_{14})$aryl, hetero $(C_2-C_{14})$aryl, $C(=O)(CH_2)_f CHR^9 CO_2R^5$, $CH_2C(=O)OR^5$, $P(=O)(OR^5)_2$, $X^2$ independently represents O, S, SO, $SO_2$, or $NR^5$;
$R^6$ independently represents H, $Na^+$, $K^+$, any other pharmaceutically acceptable metal ion, $(C_1-C_8)$alkyl, or $(C_3-C_8)$cycloalkyl,
$R^7$ independently represents at each occurrence same or different $R^5$;
$R^8$ independently represents $CH_2$, O, $NR^4$, S, S=O or O=S=O;
$R^9$ independently represents H, $(C_1-C_8)$alkyl or an amino acid;
f is 0-6;
g is 0-1;
h is 1-2000;
i is 1-4;
$R^{10}$ and $R^{11}$ independently represent H, $(C_1-C_8)$alkyl, $(C_3-C_8)$cycloalkyl, or a group selected from the group consisting of:

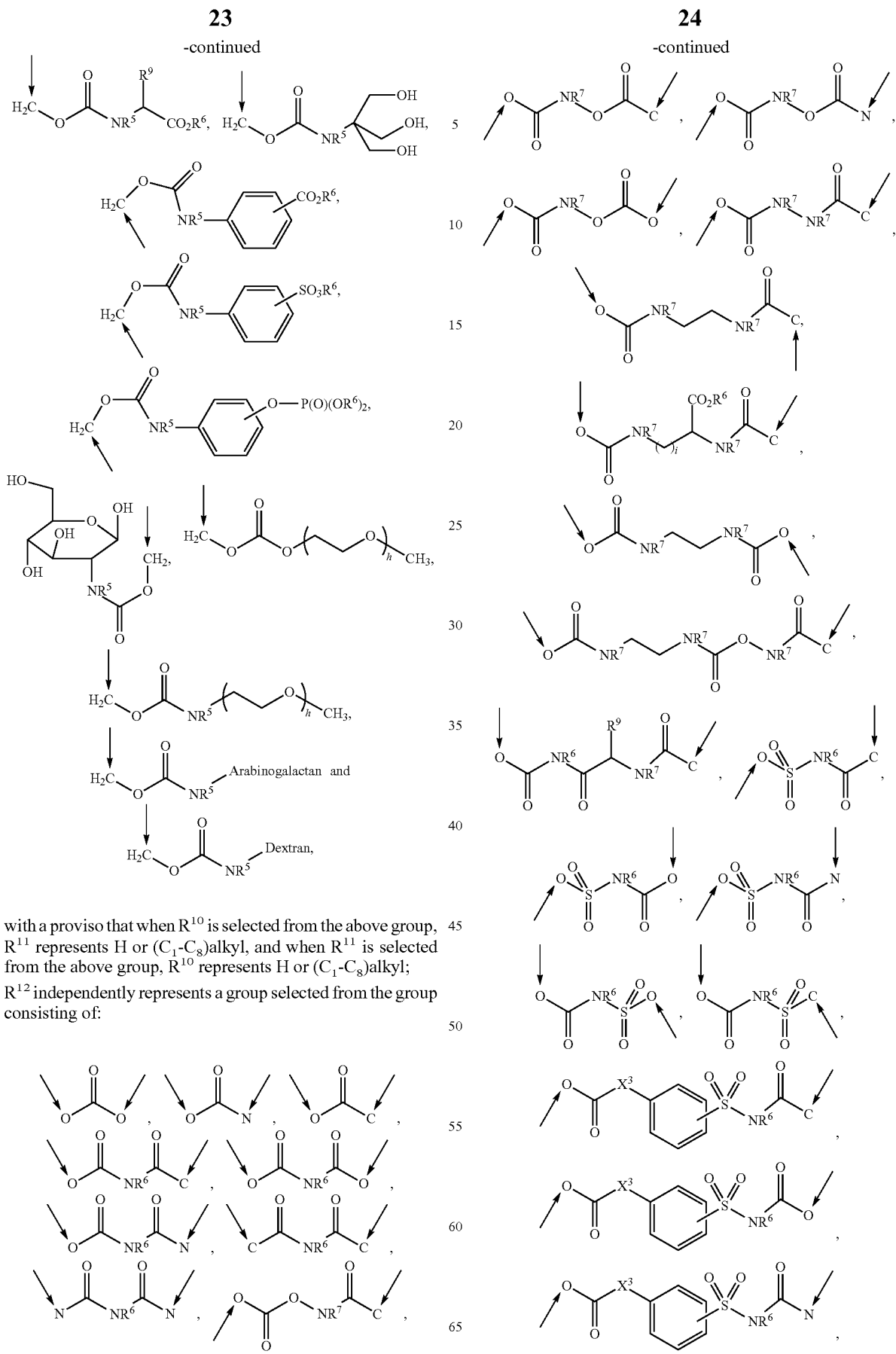

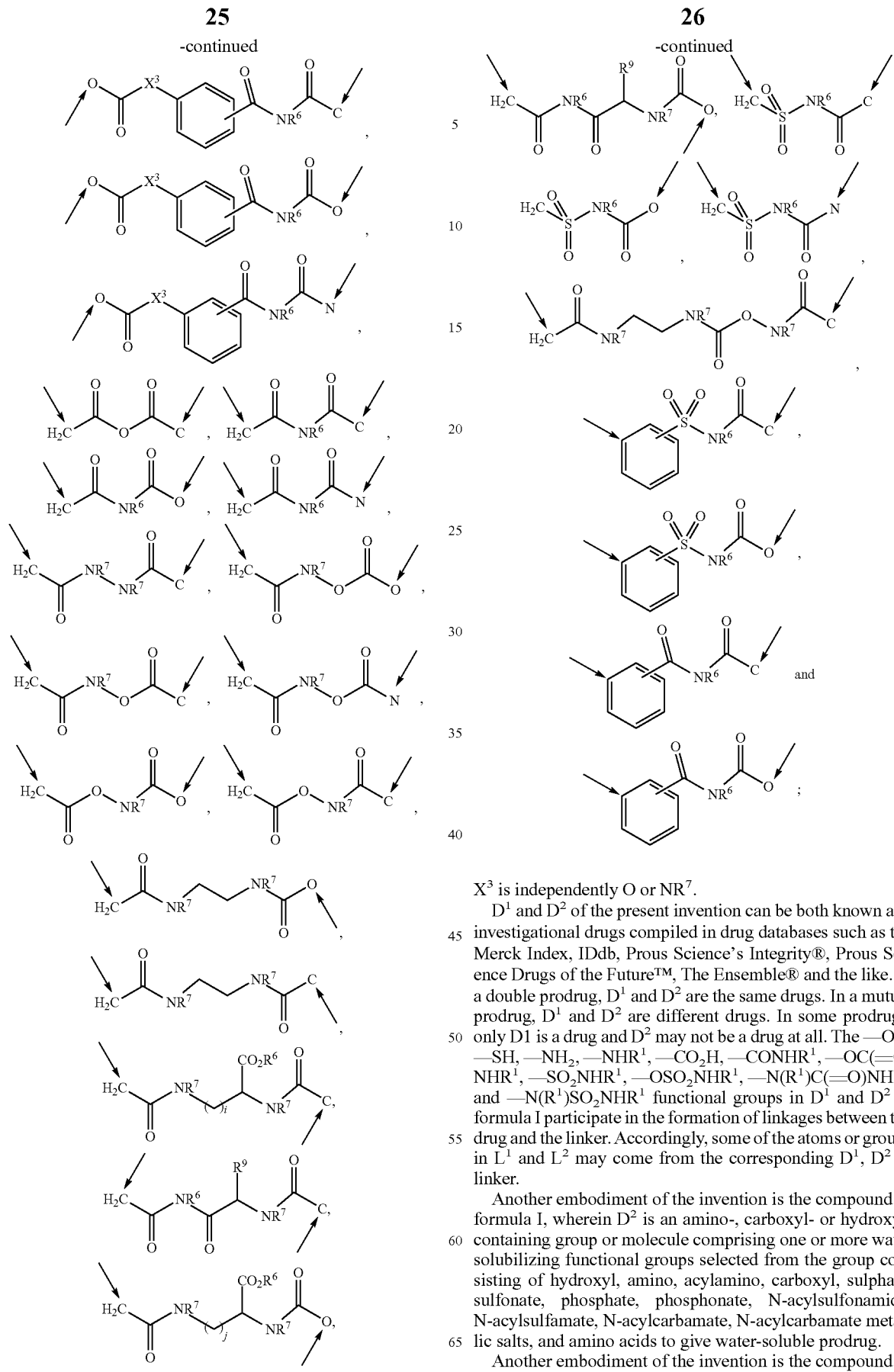

$X^3$ is independently O or $NR^7$.

$D^1$ and $D^2$ of the present invention can be both known and investigational drugs compiled in drug databases such as the Merck Index, IDdb, Prous Science's Integrity®, Prous Science Drugs of the Future™, The Ensemble® and the like. In a double prodrug, $D^1$ and $D^2$ are the same drugs. In a mutual prodrug, $D^1$ and $D^2$ are different drugs. In some prodrugs, only D1 is a drug and $D^2$ may not be a drug at all. The —OH, —SH, —$NH_2$, —$NHR^1$, —$CO_2H$, —$CONHR^1$, —OC(=O)$NHR^1$, —$SO_2NHR^1$, —$OSO_2NHR^1$, —$N(R^1)C(=O)NHR^1$ and —$N(R^1)SO_2NHR^1$ functional groups in $D^1$ and $D^2$ of formula I participate in the formation of linkages between the drug and the linker. Accordingly, some of the atoms or groups in $L^1$ and $L^2$ may come from the corresponding $D^1$, $D^2$ or linker.

Another embodiment of the invention is the compound of formula I, wherein $D^2$ is an amino-, carboxyl- or hydroxyl-containing group or molecule comprising one or more water solubilizing functional groups selected from the group consisting of hydroxyl, amino, acylamino, carboxyl, sulphate, sulfonate, phosphate, phosphonate, N-acylsulfonamide, N-acylsulfamate, N-acylcarbamate, N-acylcarbamate metallic salts, and amino acids to give water-soluble prodrug.

Another embodiment of the invention is the compound of formula I, wherein $D^2$ is selected from the group of D, L and DL amino acids consisting of Alanine, Arginine, Asparagine, Aspartic acid, Cysteine, Glutamine, Glutamic acid, Glycine, Histidine, Isoleucine, Leucine, Lysine, Methionine, Phenylalanine, Proline, Serine, Threonine, Tryptophan, Tyrosine, and Valine.

Another embodiment of the invention is the compound of formula I, wherein $D^2$ represents a polymer selected from the group consisting of arabinogalactan, polyamino acids, polyethylene glycol, polycaprolactone, polyglycolic acid, polylactic acid, polyacrylic acid, poly(2-hydroxyethyl 1-glutamine), dextran and modified dextrans such as dextran aldehyde, carboxymethyl dextran, arabinogalactane aldehyde, carboxymethyl arabinogalactane, and hyaluronic acid.

Yet another embodiment of the invention is the compound of formula I, wherein $D^2$ is a polyaminoacid selected from group consisting of poly(l-glutamic acid), poly(d-glutamic acid), poly(dl-glutamic acid), poly(l-aspartic acid), poly(d-aspartic acid), poly(dl-aspartic acid), copolymers of the polyaminoacids and polyethylene glycol.

Another embodiment of the invention is the compound of formula I, wherein the polymer has a molecular weight of about 5000 to about 100,000 Daltons. Yet another embodiment of the invention is the compound of formula I, wherein the polymer has a molecular weight of about 10,000 to about 50,000 Daltons.

In a further embodiment $D^2$ is a peptide, protein or monoclonal antibody for achieving targeted delivery of prodrugs and drugs. Another embodiment of the invention is the compound of formula I, wherein $D^2$ is a ligand or dipeptide or a dipeptide ligand. In a further embodiment $D^2$ is a dipeptide ligand that is a substrate for intestinal transporters for selective intestinal absorption of the corresponding prodrugs thereby increasing the bioavailability of the prodrugs. In a further embodiment $D^2$ is a targetable small peptide, i.e., dipeptide, tripeptide, tetrapeptide, etc.

Another embodiment of the invention is the compound of formula I, wherein $D^2$ is a vitamin. Such vitamin-conjugated prodrugs are expected to be taken up by the diseased cells via receptor-mediated endocytosis. In a further embodiment of the invention is a compound of formula I, wherein $D^2$ is selected from the group of vitamins consisting of vitamin A, vitamin C, thiamine, folic acid, biotin, inositol, nicotinic acid, nicotinamide, riboflavin, pyridoxine, pyridoxal 5-phosphate, ergosterol, vitamin D2, vitamin D3, vitamin D4, vitamin E, menadoxime, menadiol, and vitamin K5.

Another embodiment of the invention is the compound of formula I, wherein $D^1$ and $D^2$ represent the same therapeutic agent to give a symmetrical double prodrug. Another embodiment of the invention is the compound of formula I, wherein $D^1$ and $D^2$ represent different therapeutic agents to give a mutual prodrug. Another embodiment of the invention is the compound of formula (I), wherein $D^1$ and $D^2$ can be either from same or different therapeutic class. Another embodiment of the invention is the compound of formula (I), wherein $D^1$ and $D^2$ can be same or different therapeutic agents. Such therapeutic agents may have same or different mechanisms of action or they may work on different biological targets or work on different disease conditions.

Another embodiment of the invention is the compound of formula I, wherein $D^2$ is $R^2$, $R^3$ or $R^4$. Another embodiment of the invention is the compound of formula I, wherein a is 0, B is S—S, S—S=O, S—SO$_2$ or S—S=NH. Yet another embodiment of the invention is the compound of formula I, wherein a is 0, B is S—S or S—S=O, S—SO$_2$ and $D^2$ is $R^2$ or $R^3$ or $R^4$. A further embodiment of the invention is the compound of formula I, wherein B is S—S, A and $A^1$ are CH$_2$—CH$_2$, E is a bond and $D^2$ is $R^2$, $R^3$ or $R^4$.

Another embodiment of the invention is the compound of formula I, wherein a is 0; B is S—S or S—S=O, S—SO$_2$; A and $A^1$ are CH$_2$—CH, E is a bond and $D^2$ is $R^4$. Another embodiment of the invention is the compound of formula I, wherein a is 0; B is S—S; A and $A^1$ are CH$_2$—CH$_2$, E is a bond and $D^2$ is $R^4$.

Another embodiment of the invention is the compound of formula I, wherein a is 0, B is a bond, (CH$_2$)$_b$, or (CH$_2$CH$_2$O)$_c$; wherein b and c are as defined above. Another embodiment of the invention is the compound of formula I, wherein a is 0, B is a bond, (CH$_2$)$_b$ or (CH$_2$CH$_2$O)$_c$ and $D^2$ is $R^2$ or $R^3$ or $R^4$; wherein b and c are as defined above.

Yet another embodiment of the invention is the compound of formula I, wherein a is 0; B is S—S or S—S=O, S—SO$_2$; $D^1$ and $D^2$ are drug molecule or $R^2$ or $R^4$ containing carboxyl group; $L^1$ and $L^2$ are independently selected from the following linkages:

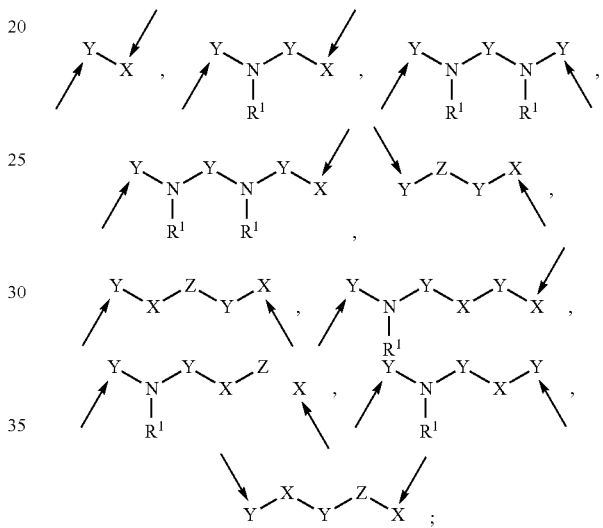

wherein, X, $R^1$, Z are as defined above; and Y is C=O. In another embodiment, A and $A^1$ are CH$_2$—CH$_2$ and E is a bond. In a further embodiment, A and $A^1$ are 1,2-phenylene, 1,3-phenylene or 1,4-phenylene and E is CH$_2$.

Yet another embodiment of the invention is the compound of formula I, wherein a is 0; B is S—S or S—S=O, S—SO$_2$; $D^1$ and $D^2$ are drug molecule or $R^2$ or $R^4$ containing amino- or hydroxyl group; $L^1$ and $L^2$ are independently selected from the following linkages:

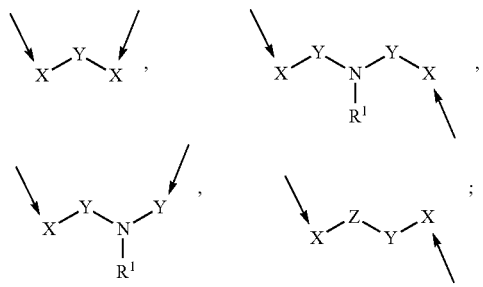

wherein, X, $R^1$, Z are as defined; and Y is C=O. In another embodiment, A and $A^1$ are CH$_2$—CH$_2$, and E is a bond. In a further embodiment, A and $A^1$ are 1,2-phenylene, 1,3-phenylene or 1,4-phenylene, and E is CH$_2$.

Yet another embodiment of the invention is the compound of formula I, wherein a is 0, B is S—S or S—S═O, S—SO$_2$ and D$^2$ is D$^1$. Another embodiment of the invention is the compound of formula I, wherein a is 0; B is S—S or S—S═O, S—SO$_2$; A and A$^1$ are CH$_2$—CH$_2$, E is a bond and D$^2$ is D$^1$. Another embodiment of the invention is the compound of formula I, wherein a is 0; B is S—S or S—S═O, S—SO$_2$; A and A$^1$ are 1,2-phenylene, 1,3-phenylene or 1,4-phenylene; E is CH$_2$ and D$^2$ is D$^1$ or R$^2$ or R$^3$ or R$^4$. Another embodiment of the invention is the compound of formula I, wherein a is 0; B is S—S; A and A$^1$ are 1,2-phenylene, 1,3-phenylene or 1,4-phenylene; E is CH$_2$ and D$^2$ is D$^1$ or R$^2$ or R$^3$ or R$^4$. A further embodiment of the invention is the compound of formula I, wherein B is S—S, A and A$^1$ are CH$_2$—CH$_2$, E is a bond and D$^2$ is D$^1$.

Yet another embodiment of the invention is the compound of formula I, wherein a is 0; B is S—S or S—S═O, S—SO$_2$; A and A$^1$ are CH$_2$—CH$_2$, E is a bond and D$^2$ is a dipeptide ligand. Yet another embodiment of the invention is the compound of formula I, wherein a is 0; B is S—S; A and A$^1$ are CH$_2$—CH$_2$, E is a bond and D$^2$ is a dipeptide ligand. The peptide ligands used in the invention can be substrates for intestinal transporters for selective intestinal absorption of the corresponding prodrugs thereby increasing the bioavailability of the prodrugs. An embodiment of the present invention is the compounds of formula (I), wherein D$^1$, L$^1$ and L$^2$ are as defined above; A and A$^1$ are CH$_2$; E is CH$_2$; B is a bond or (CH$_2$)$_b$; b is 1-6; a is 0; and D$^2$ is D$^1$ or R$^2$ or R$^4$.

Another embodiment of the present invention is the compound of formula (I), wherein E, D$^1$ and L$^1$ are as defined; L$^2$ is O; A and A$^1$ are independently (CH$_2$)$_d$, 1,2-phenylene, 1,3-phenylene, or 1,4-phenylene; d is 1-4; B is S—S, S—S═O, S—SO$_2$ or S—S═NH; a is 0; D$^2$ is NO, NO$_2$ or a nitric oxide releasing molecule such as NONOate. In a further embodiment, D$^2$ is a NONOate selected from the group consisting of:

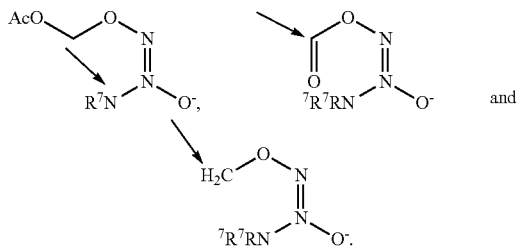

In yet another embodiment, when D$^2$ is one of the above NONOates, B is S—S.

Another embodiment of the present invention is the compound of formula (I), L$^2$ is O; A and A$^1$ are independently (CH$_2$)$_d$, 1,2-phenylene, 1,3-phenylene, or 1,4-phenylene; d is 1-4; B is S—S; a is 0; D$^2$ is NO$_2$. In a further embodiment, when A and A$^1$ CH$_2$—CH$_2$, E is a bond. In yet another embodiment, when E is CH$_2$, A and A$^1$ are independently 1,2-phenylene, 1,3-phenylene, or 1,4-phenylene.

Yet another embodiment of the present invention is the compound of formula (I), wherein D$^1$ is an amino containing drug molecule having the following reactive functional groups which are involved in the formation of L$^1$ linkages between the drug and the linker: —NH$_2$, —NHR$^1$, —CONHR$^1$, —O—C(═O)NHR$^1$, —SO$_2$NHR$^1$, —OSO$_2$NHR$^1$, —NR$^1$C(═O)NHR$^1$ or —N(R$^1$)SO$_2$NHR$^1$; L$^2$ is O; E is bond; L$^1$ is linkages selected from the group consisting of:

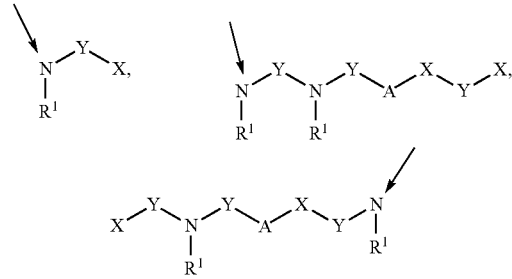

wherein, X is independently a bond, O or NR$^1$, Y is C═O or SO$_2$, A and A$^1$ are CH$_2$—CH$_2$, B is S—S, a is 0 and D$^2$ is NO$_2$.

An embodiment of the present invention is the compound of formula (I), wherein D$^1$ is a hydroxyl or sulfahydryl containing drug molecule such as Drug-OH or Drug-SH, wherein functional groups OH and SH are involved in the formation of L$^1$ linkages between the drug and the linker; L$^2$ is O; E is bond, L$^1$ is a linkage selected from the group consisting of:

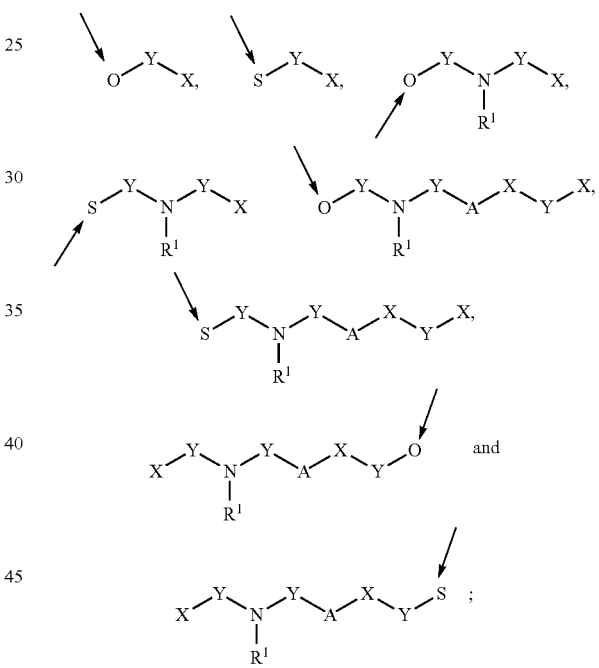

wherein, X is independently a bond, O or NR$^1$, R$^1$ is not a bond, Y is C═O or SO$_2$, A and A$^1$ are CH$_2$CH$_2$; B is S—S; a is 0; and D$^2$ is NO$_2$.

An embodiment of the present invention is the compound of formula (I), wherein D$^1$ is a drug molecule having carboxyl (—CO$_2$H) as a reactive functional group such as —CO$_2$H which is involved in the formation of L$^1$ linkages between the drug and the linker; L$^2$ is O; E is bond; L$^1$ is O or NR$^1$ or a linkage selected from the group consisting of:

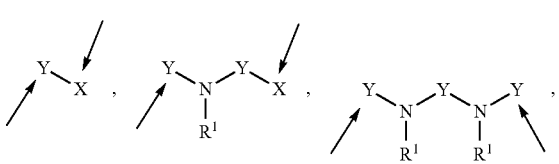

-continued

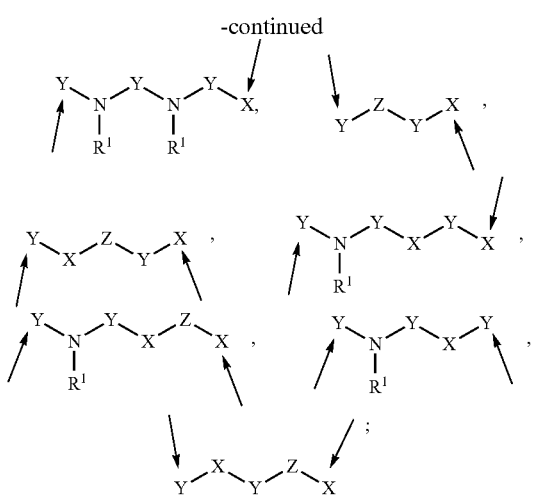

wherein, X is independently a bond, O or NR¹, R¹ is not a bond; Y is C=O or SO₂; A and A¹ are CH₂CH₂; B is S—S; a is 0 and D² is NO₂.

Another embodiment of the present invention is the compounds of formula (I), wherein D¹ is an antioxidant or free radical scavenger such as a hydroxyl-containing stable radical such a 4-hydroxy-2,2,6,6-tetramethylpiperidin-1-oxyl (4-hydroxy-TEMPO), 4-carboxy-2,2,6,6-tetramethylpiperidin-1-oxyl (4-carboxy-TEMPO) or any other amino-/carboxyl-/hydroxyl-containing antioxidants or radical/super oxide scavengers, and D² is NO₂. The amino-/carboxyl-/hydroxyl-containing antioxidants and radical/super oxide scavengers can be known or investigational.

An embodiment of the present invention is the compound of formula (I), wherein L¹ is

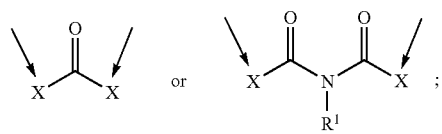

wherein, X is a bond, O, S or NR¹; L² is O, E is a bond; A and A¹ are CH₂CH₂; B is S—S; a is 0; and D² is NO₂.

An embodiment of the present invention is the compounds of formula (I), wherein D¹ and L¹ are as defined above; L² is O; A is 1,2-phenylene, 1,3-phenylene, or 1,4-phenylene; A¹ is CH₂; E is CH₂; B is S—S; a is 0 and D² is NO₂.

An embodiment of the present invention is the compounds of formula (I), wherein L² is O; A and A¹ are CH₂; E is CH₂; B is a bond or (CH₂)ᵦ; b is 1-6; a is 0; D² is NO₂ and L¹ is a group selected from

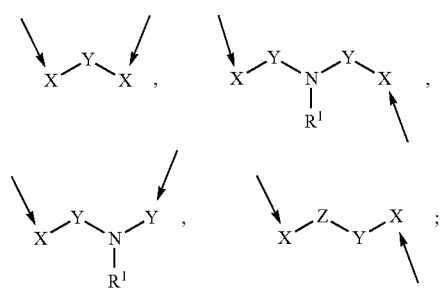

wherein, X is O, S or NR¹; R¹ is as defined.

An embodiment of the invention is the compound of formula I selected from the groups consisting of:

A. Prodrugs:
(a) From Carboxyl-Containing Drugs:

I-C1-PD1
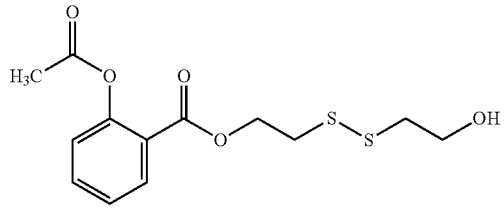

I-C1-PD2
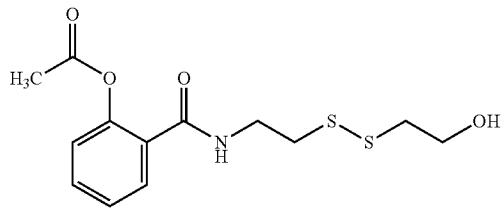

I-C1-PD3
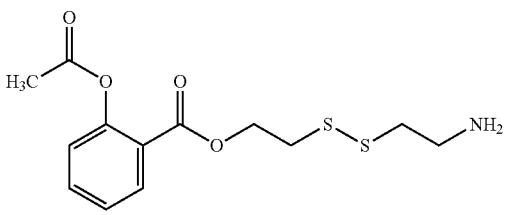

I-C1-PD4a
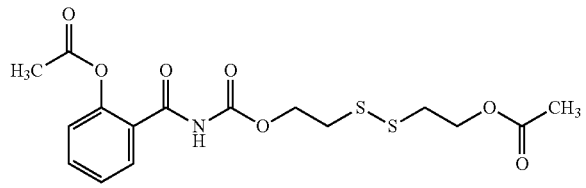

I-C1-PD4b
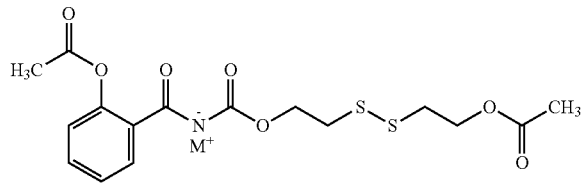

M⁺ = a metal ion

I-C1-PD5
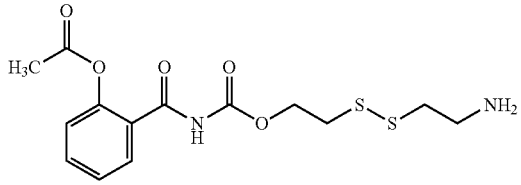

33
-continued
I-C1-PD6
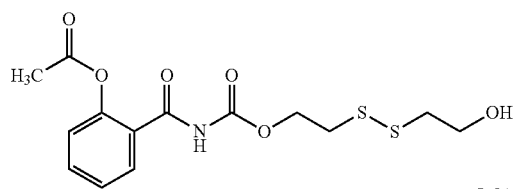
I-C1-PD7
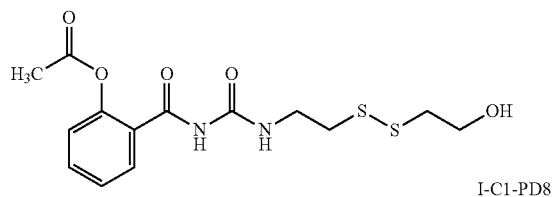
I-C1-PD8

I-C1-PD9
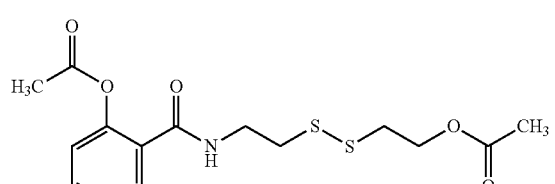
I-C1-PD10
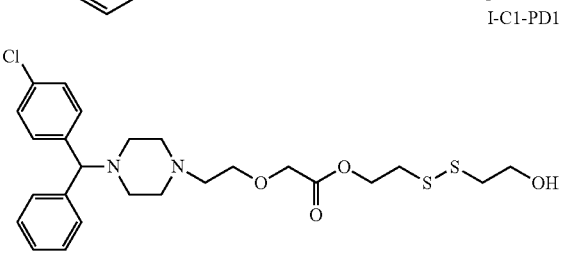
34
-continued
I-C1-PD11
I-C1-PD12
I-C1-PD13
I-C1-PD14
I-C1-PD15a
I-C1-PD15b
(b) From Amino-Containing Drugs:
I-A1-PD1
I-A1-PD2
I-A1-PD3

-continued
I-A1-PD4
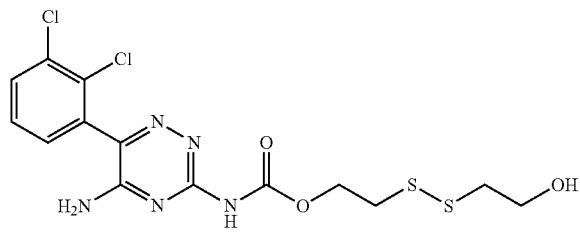
I-A1-PD5
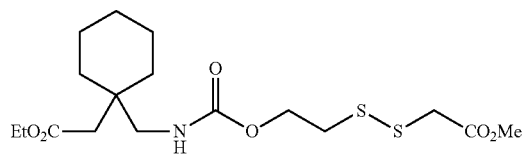
I-A1-PD6
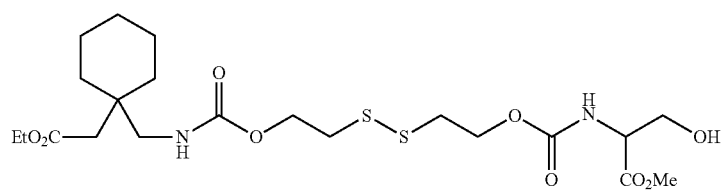
I-A1-PD7
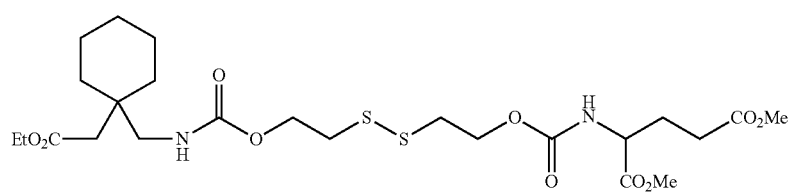
I-A1-PD8
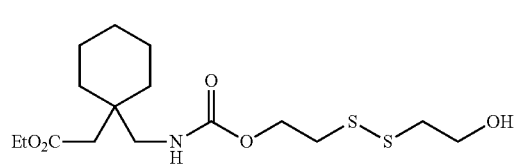
I-A1-PD9
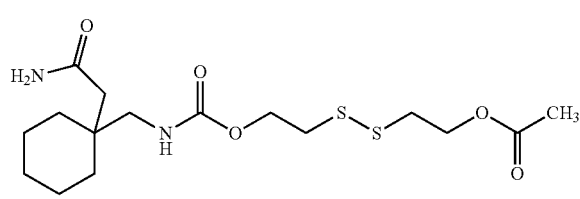
I-A1-PD10
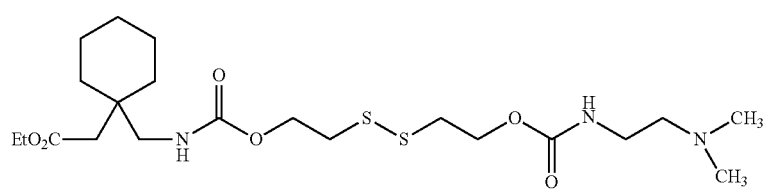
I-A1-PD11
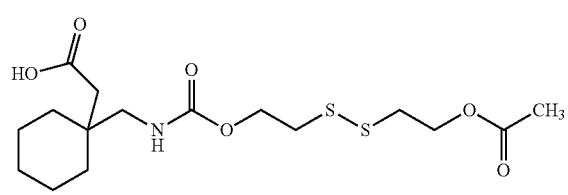
I-A1-PD12
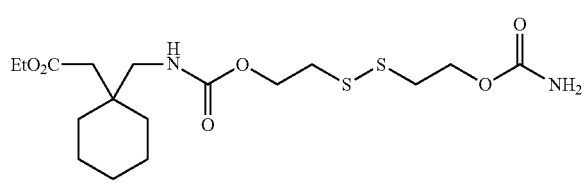
I-A1-PD13
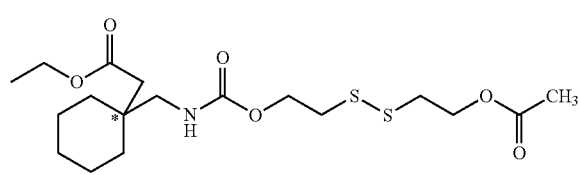
I-A1-PD14
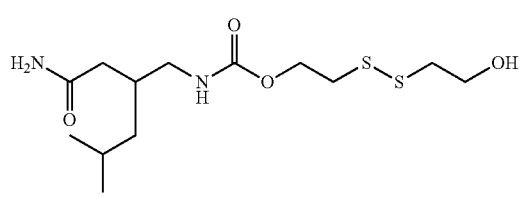

-continued
I-A1-PD15Aa
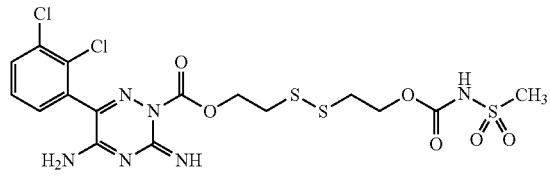
I-A1-PD15Ba
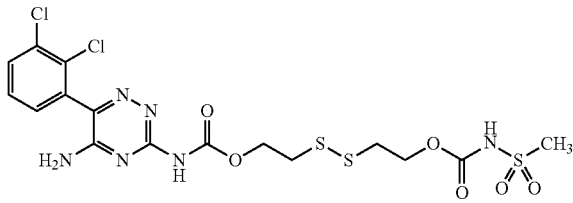
I-A1-PD15Ab
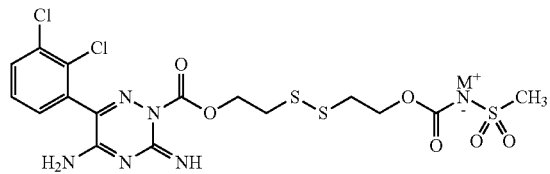
I-A1-PD15Bb
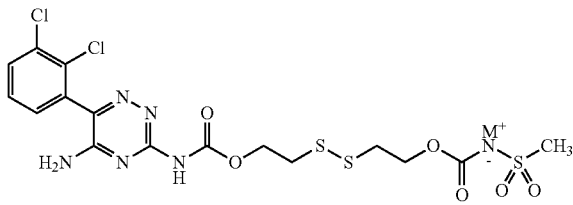
$M^+$ = a metal ion
I-A1-PD16
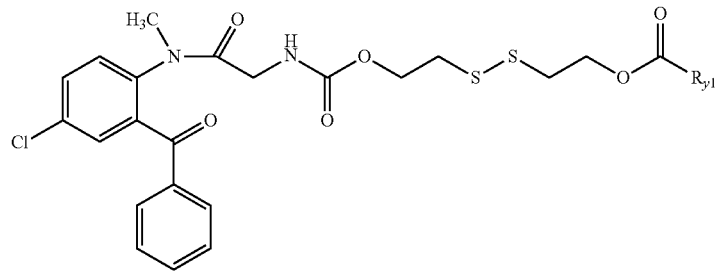
I-A1-PD17
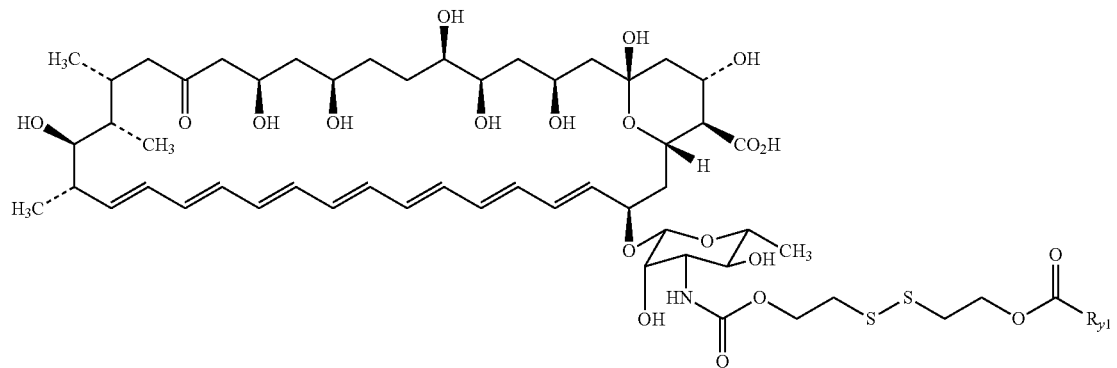
[$R_{y1}$ = $CH_2CH_2CO_2H$, $NHCH(R_{y2})CO_2H$ ($R_{y2}$ = side-chain groups of known amino acids) or any group or molecule containing water-solubilizing groups such as hydroxyl, amino, and carboxyl, phosphate, etc.]
I-A1-PD18
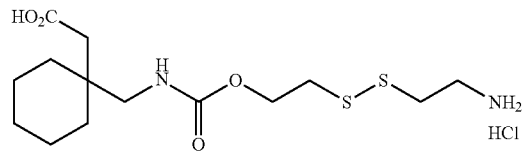
I-A2-PD1
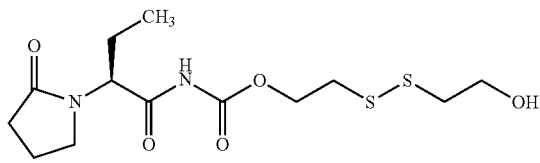

-continued
I-A2-PD2b
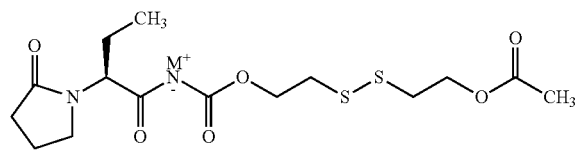
I-A2-PD3a
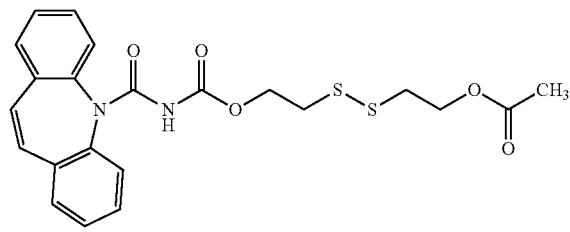
I-A2-PD3b
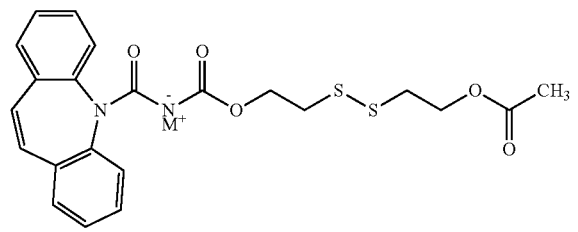
I-A2-PD4
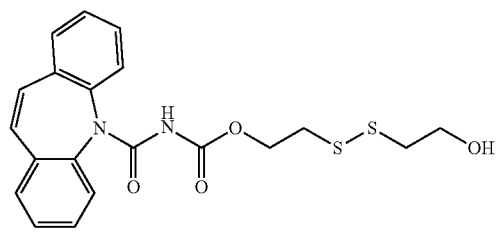
I-A2-PD5
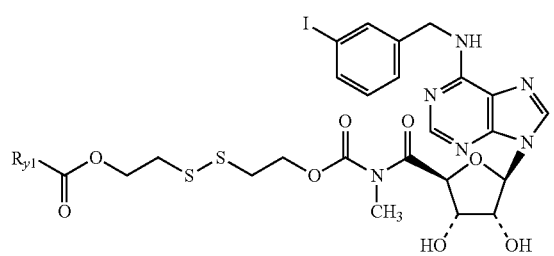
R_{y1} = An amino-, hydroxyl-containing molecule with water-solubilizing groups
I-A3-PD1
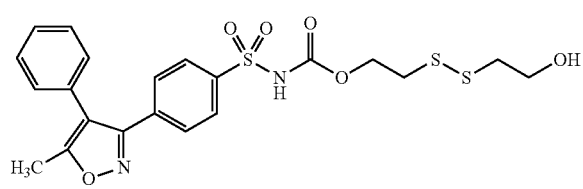
I-A3-PD2a
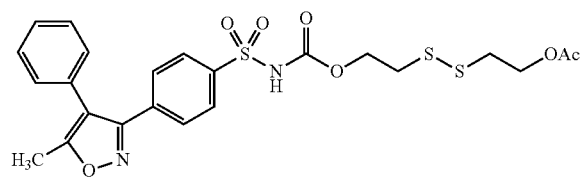
I-A3-PD2b
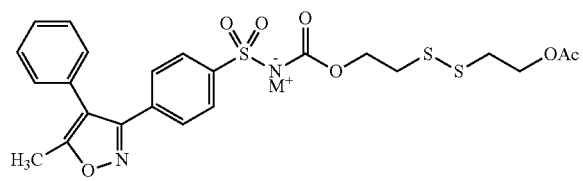
I-A3-PD3a
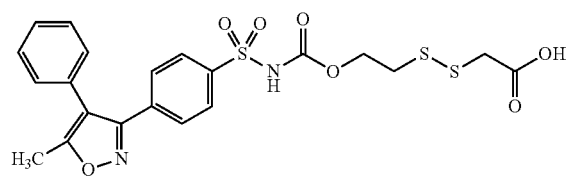
I-A3-PD3b
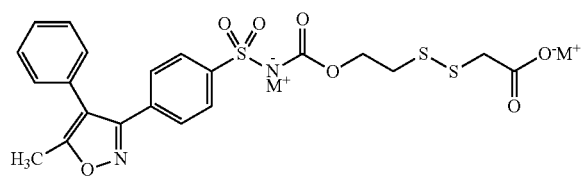
I-A3-PD4
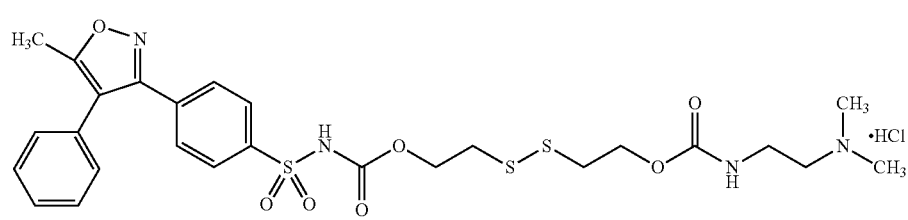

-continued
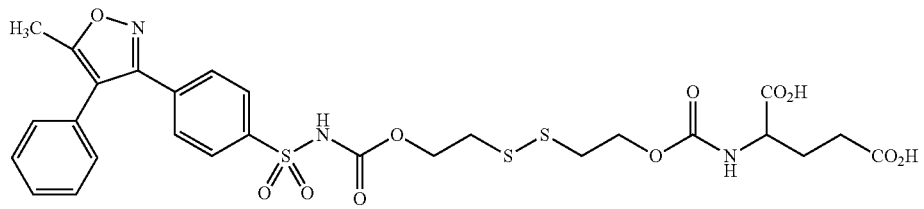
I-A3-PD5
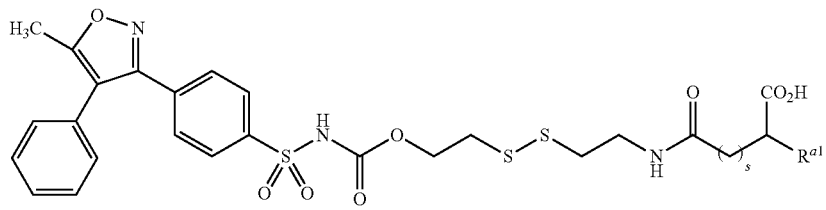
I-A3-PD6
s = 1, 2; $R^{a1}$ = H, OH, NH2, or a substituted amino group
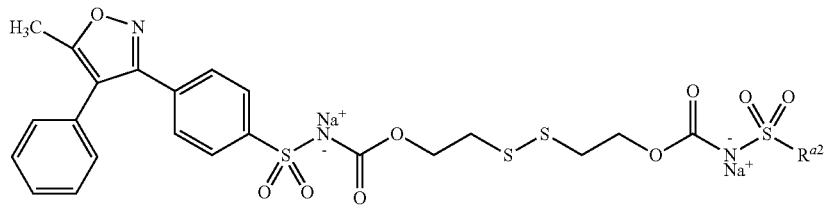
I-A3-PD7b
$R^{a2}$ = Me or any alkyl, aryl, aralkyl, or another sulfonamide containing drug such as valdecoxib, celecoxib, and the like.
(c) From Hydroxyl-Containing Drugs:
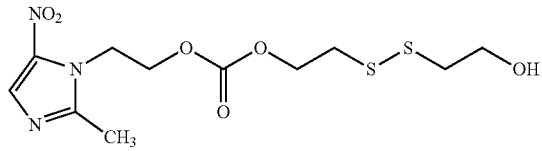
I-H1-PD1
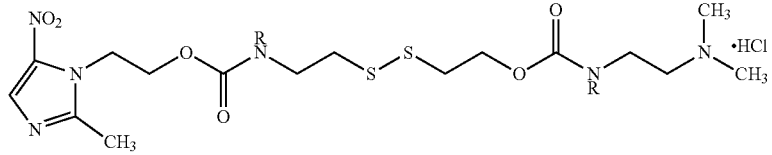
I-H1-PD2
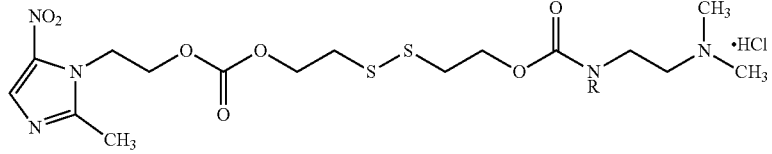
I-H1-PD3
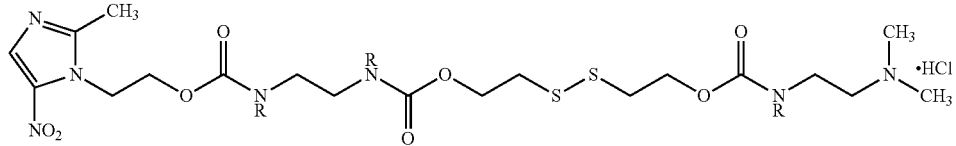
I-H1-PD4
R = H, lower alkyl, etc.

I-H1-PD5
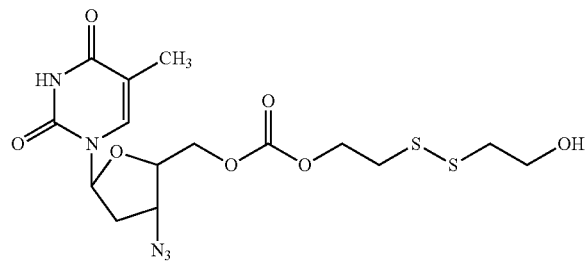
I-H1-PD6
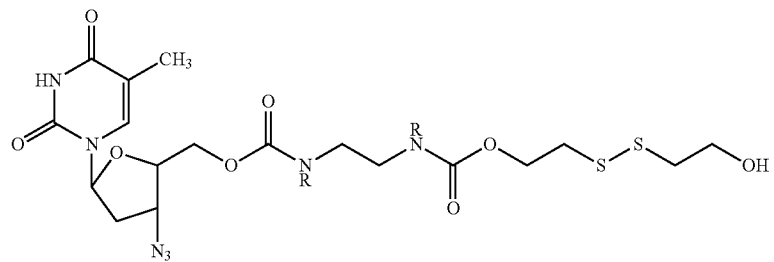
I-H1-PD7
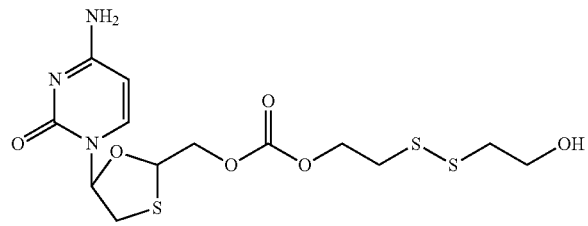
I-H1-PD8
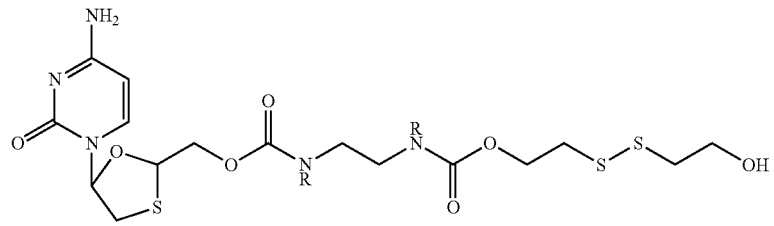
I-H1-PD9
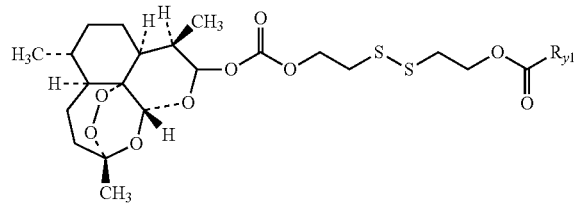
I-H1-PD10
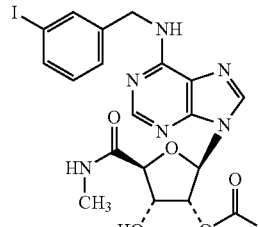
I-H1-PD11
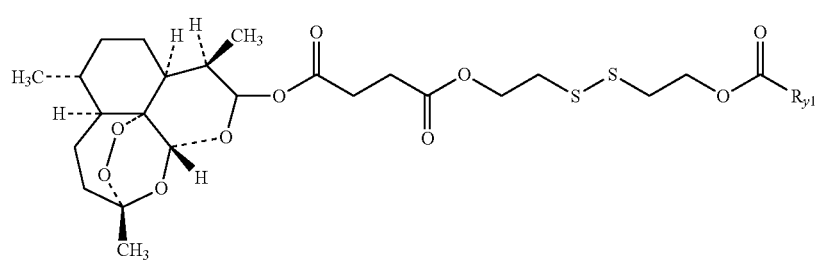

I-H1-PD12
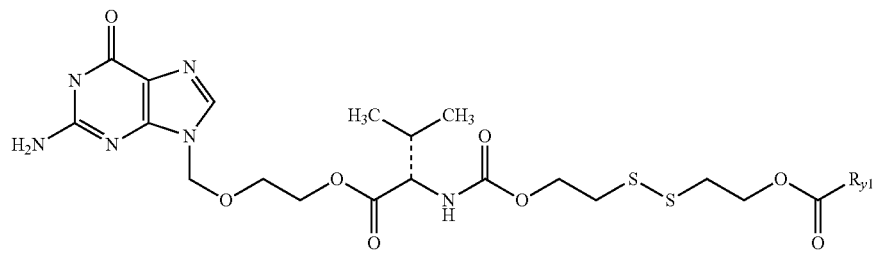
I-H1-PD13
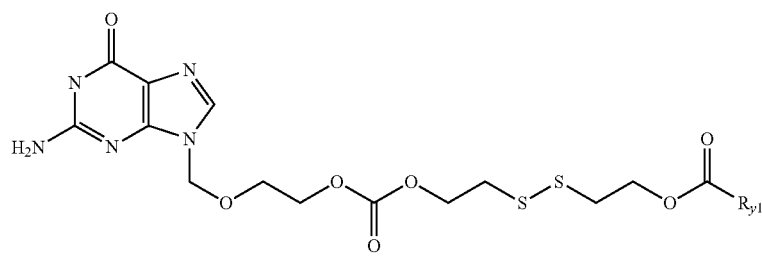
$R_{y1}$ = $CH_2CH_2CO_2H$, $NHCH(R_{y2})CO_2H$ ($R_{y2}$ = side-chain groups of amino acids) or any group or molecule containing water-solubilizing groups such as hydroxyl, amino, and carboxyl, phosphate, sulfate, etc.
I-H1-PD14
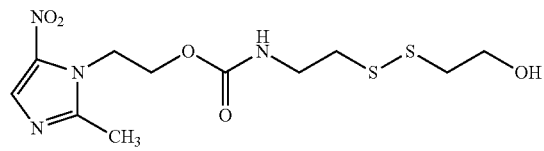
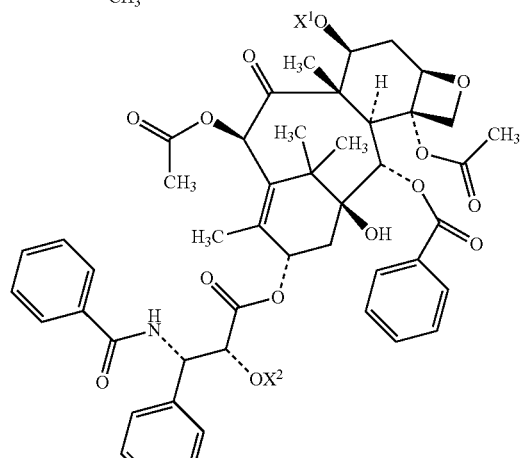
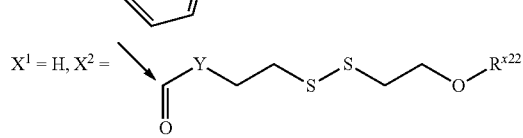
I-Taxol-PD1: $R^{x22}$ = H
I-Taxol-PD2: $R^{x22}$ = C(=O)CH$_2$CH$_2$CO$_2$H
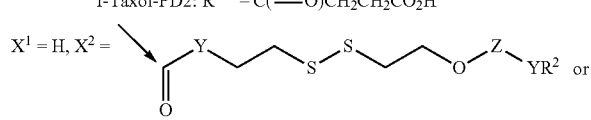
I-Taxol-PD3
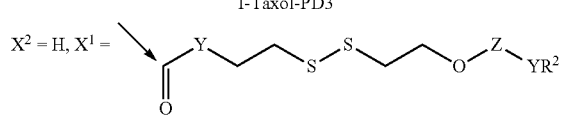
I-Taxol-PD4

$X^1 = H, X^2 =$

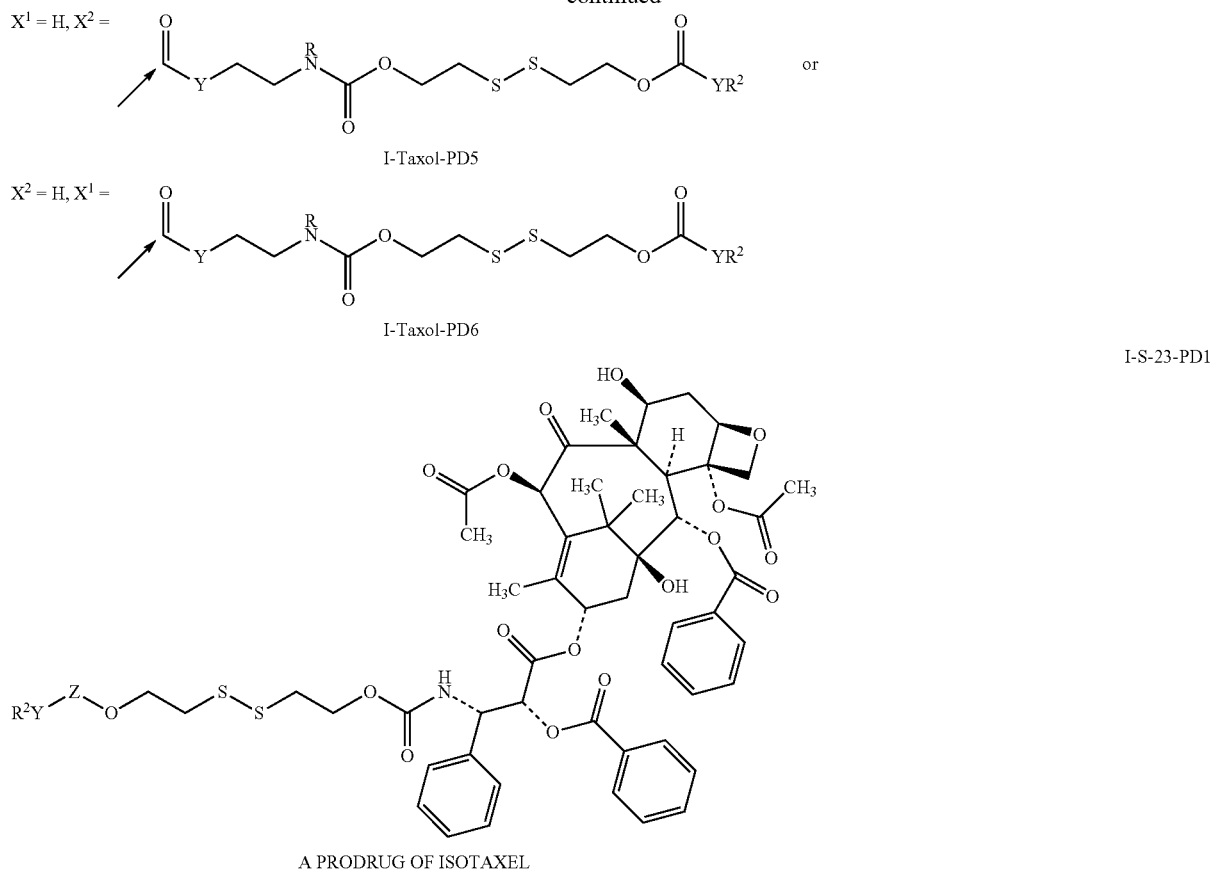

Y=O, NR$^1$ (R$^1$=H, Alkyl, Aralkyl, Cycloalkyl), (CH$_2$)$_n$C(=O) (n=1-6), (CH$_2$)$_n$CO$_2^-$ Z=C=O, SO$_2$, P(=O)YR$^3$ (R$^3$=H or a metal ion)

R$^2$=H, a bond, CH$_2$CH$_2$N(CH$_3$)$_2$, HCl, an Amino acid, or any molecule containing solubilizing groups such as carboxylic acid, sulphonic acid, hydroxyl, amino groups, polyethyleneglycol (PEG), a metal ion such a Na$^+$, Ca$^{2+}$, etc.

B. NO-Releasing Prodrugs (a) From Carboxyl-Containing Drugs

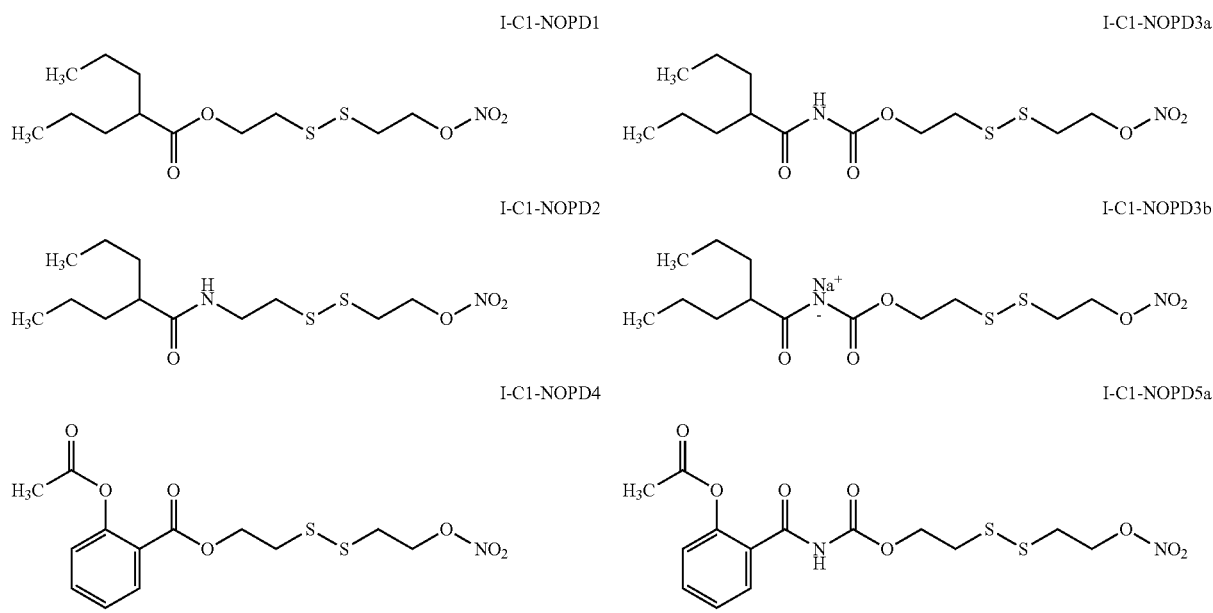

-continued
I-C1-NOPD6
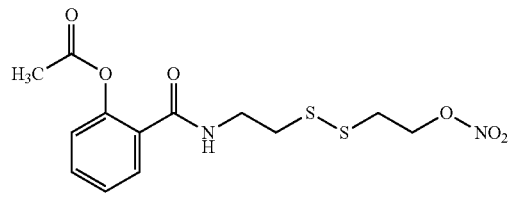
I-C1-NOPD7
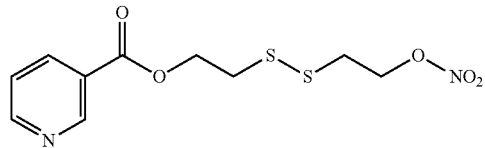
I-C1-NOPD9
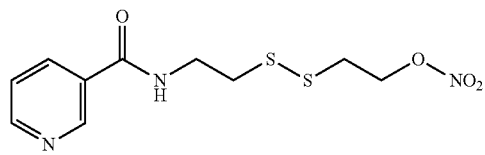
I-C1-NOPD10
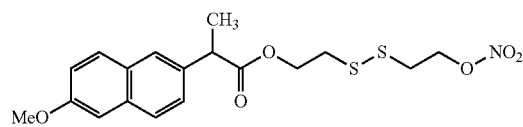
I-C1-NOPD12
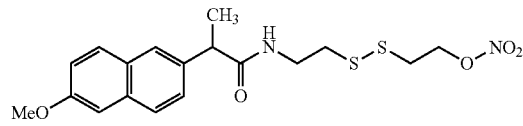
I-C1-NOPD13
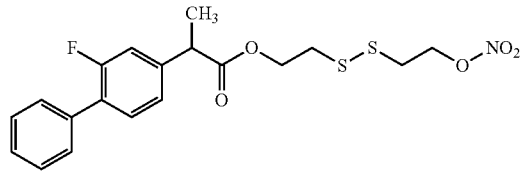
I-C1-NOPD15b
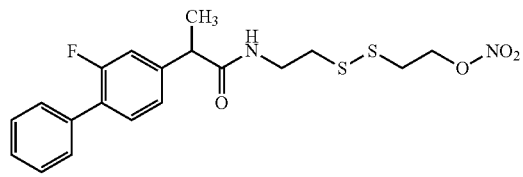
I-C1-NOPD16
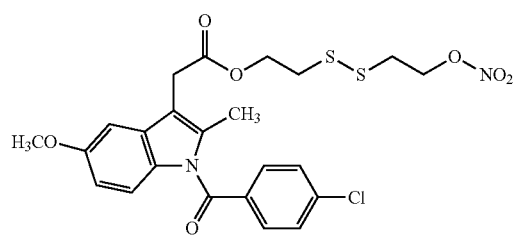
I-C1-NOPD5b
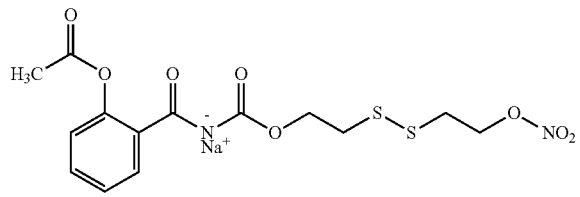
I-C1-NOPD8a
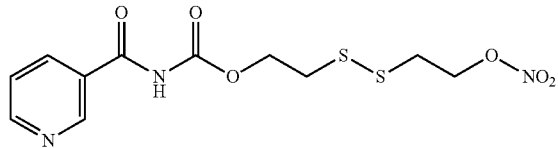
I-C1-NOPD8b
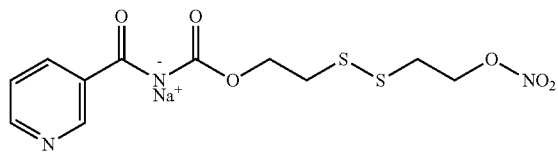
I-C1-NOPD11a
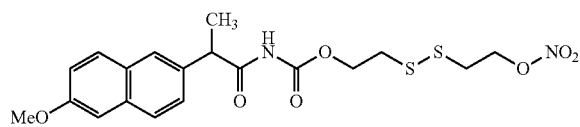
I-C1-NOPD11b
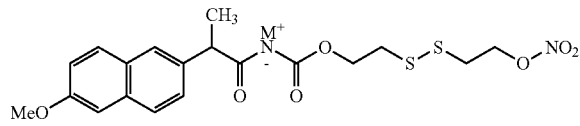
I-C1-NOPD14a
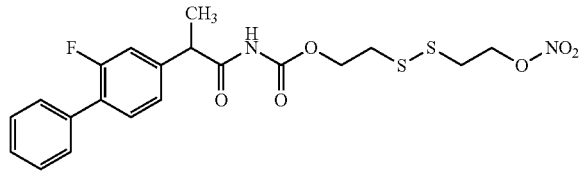
I-C1-NOPD14b
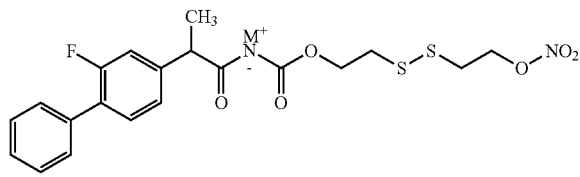
I-C1-NOPD17a
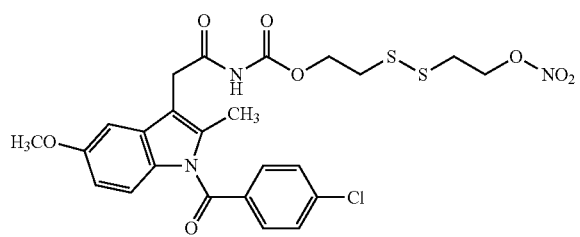

-continued
I-C1-NOPD18
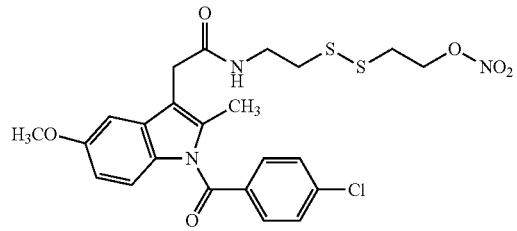
I-C1-NOPD17b
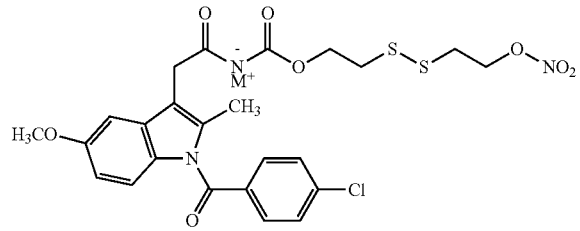
I-C1-NOPD19
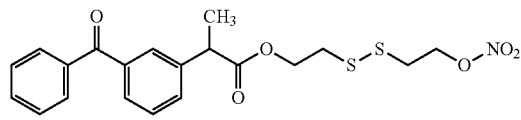
I-C1-NOPD20a
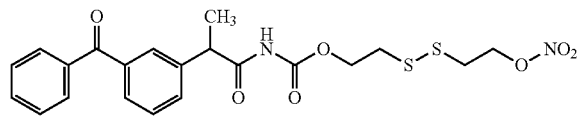
I-C1-NOPD21
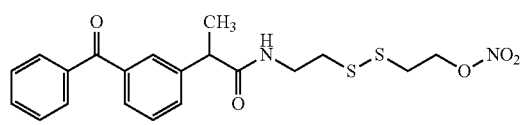
I-C1-NOPD20b
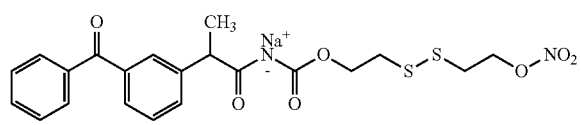
I-C1-NOPD22
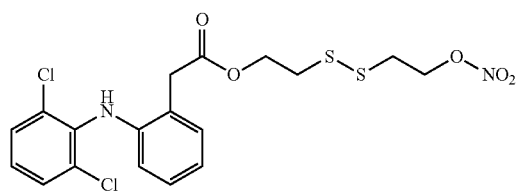
I-C1-NOPD23b
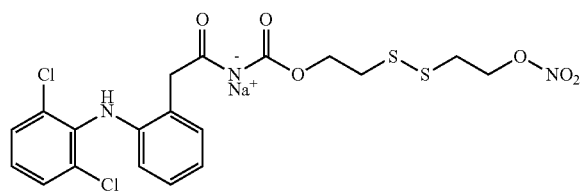
I-C1-NOPD24
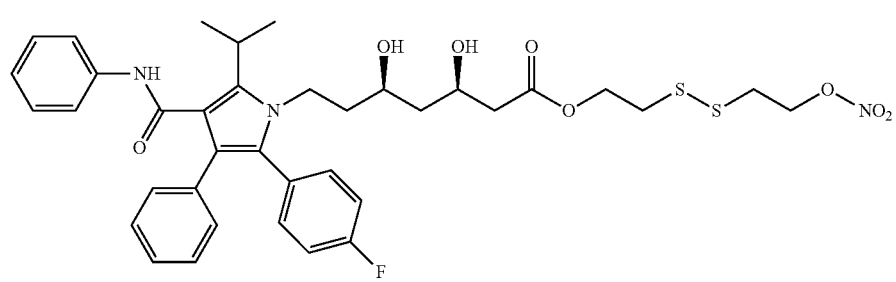
I-C1-NOPD25
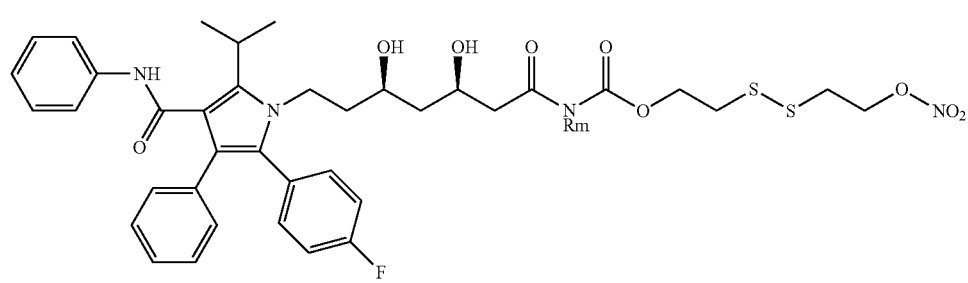
Rm = H, a metal ion such as $Na^+$, $Ca^{++}$, etc.
I-C1-NOPD26
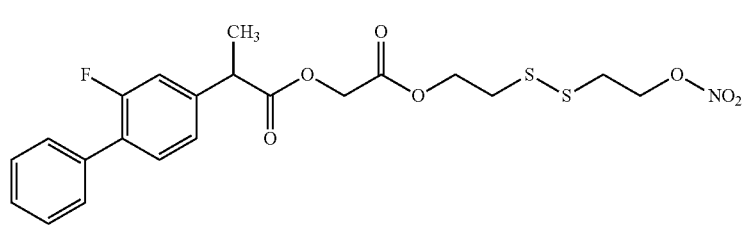

(b) From Amino-Containing Drugs
I-A1-NOPD1
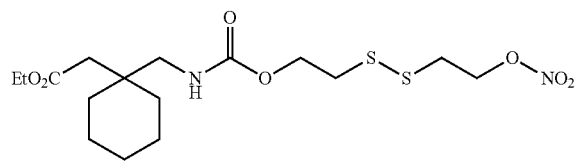
I-A1-NOPD2
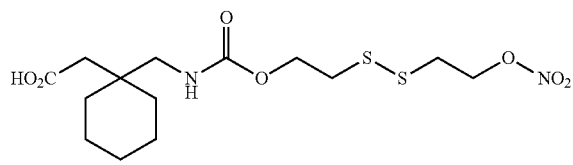
I-A1-NOPD3A
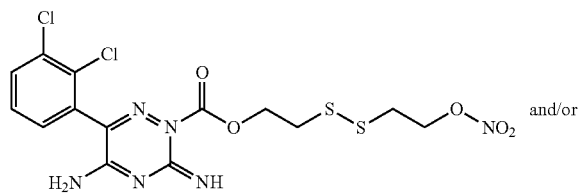
and/or
I-A1-NOPD3B
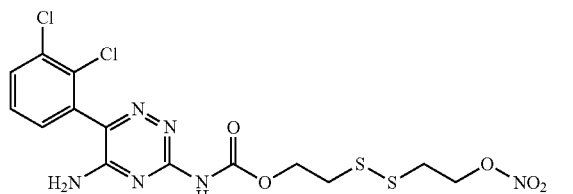
I-A1-NOPD5
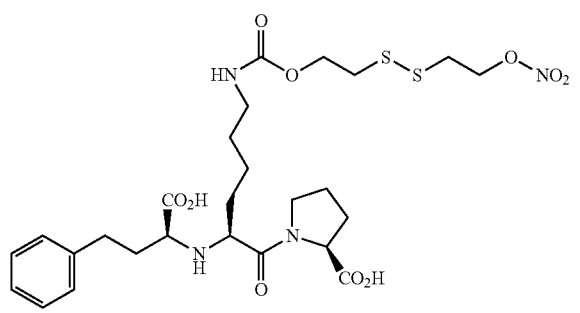
I-A1-NOPD4
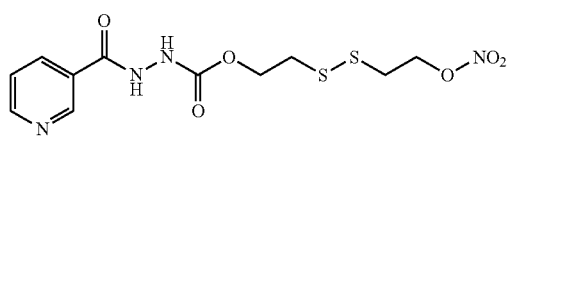
I-A1-NOPD6
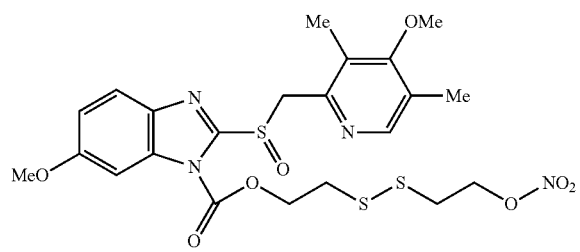
I-A1-NOPD8
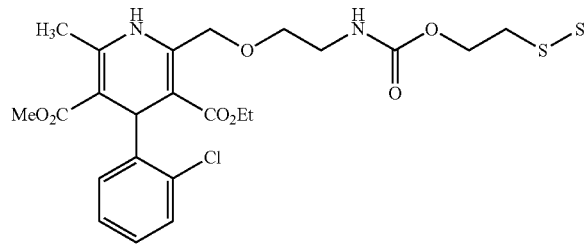
I-A1-NOPD7
I-A1-NOPD9
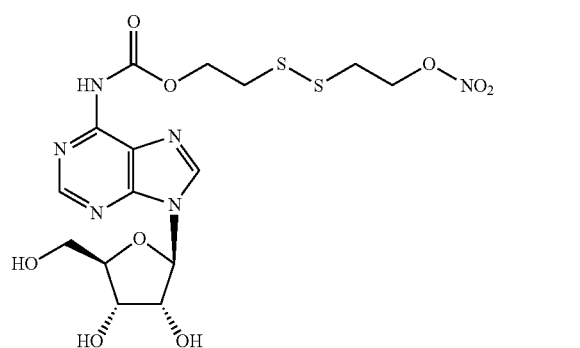
I-A1-NOPD10a
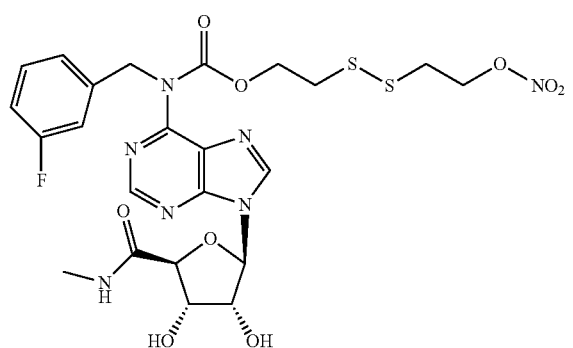

-continued
I-A1-NOPD10b
I-A2-NOPD1a
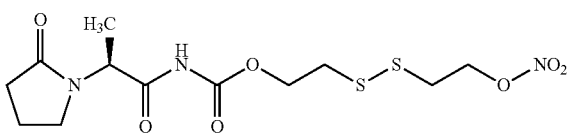
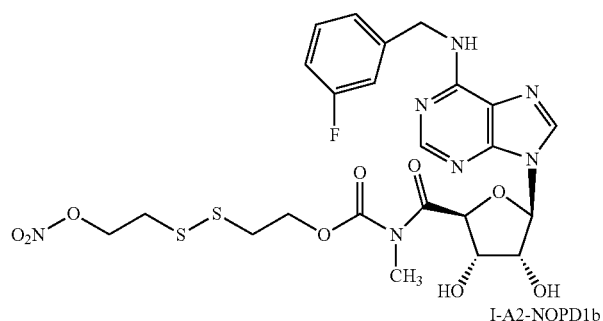
I-A2-NOPD1b
I-A2-NOPD2a
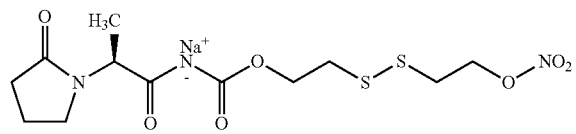
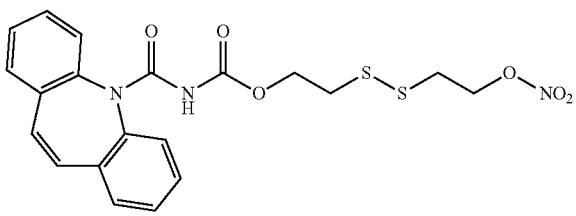
I-A2-NOPD2b
I-A3-NOPD1a
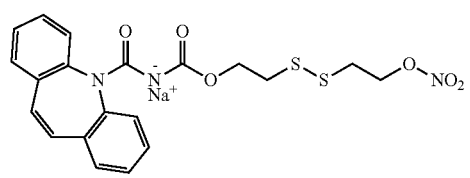
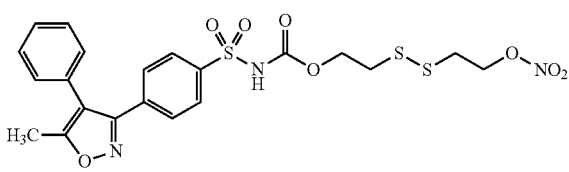
I-A3-NOPD1b
I-A3-NOPD2a
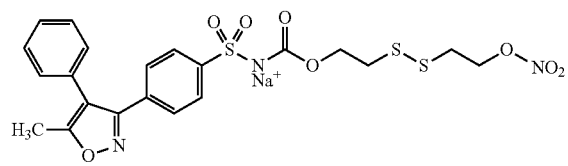
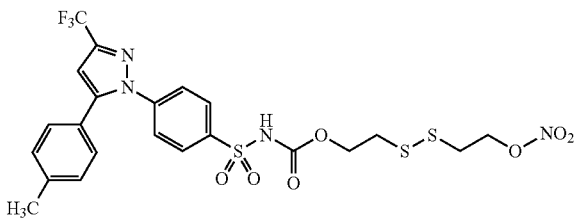
I-A3-NOPD2b
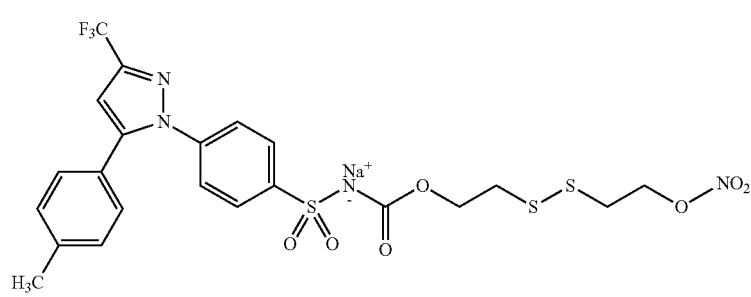
(c) From Hydroxyl-Containing Drugs
-continued
I-H1-NOPD1
I-H1-NOPD2a
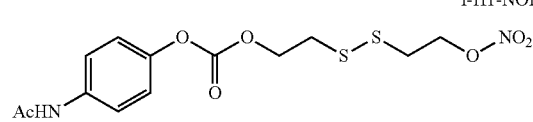
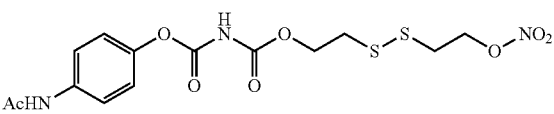

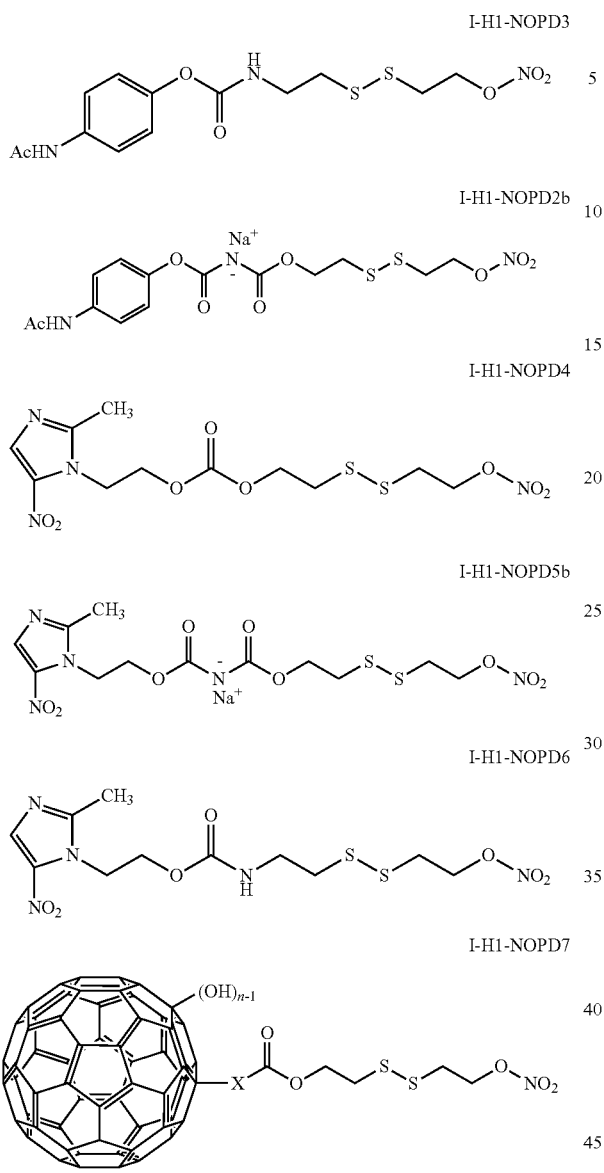
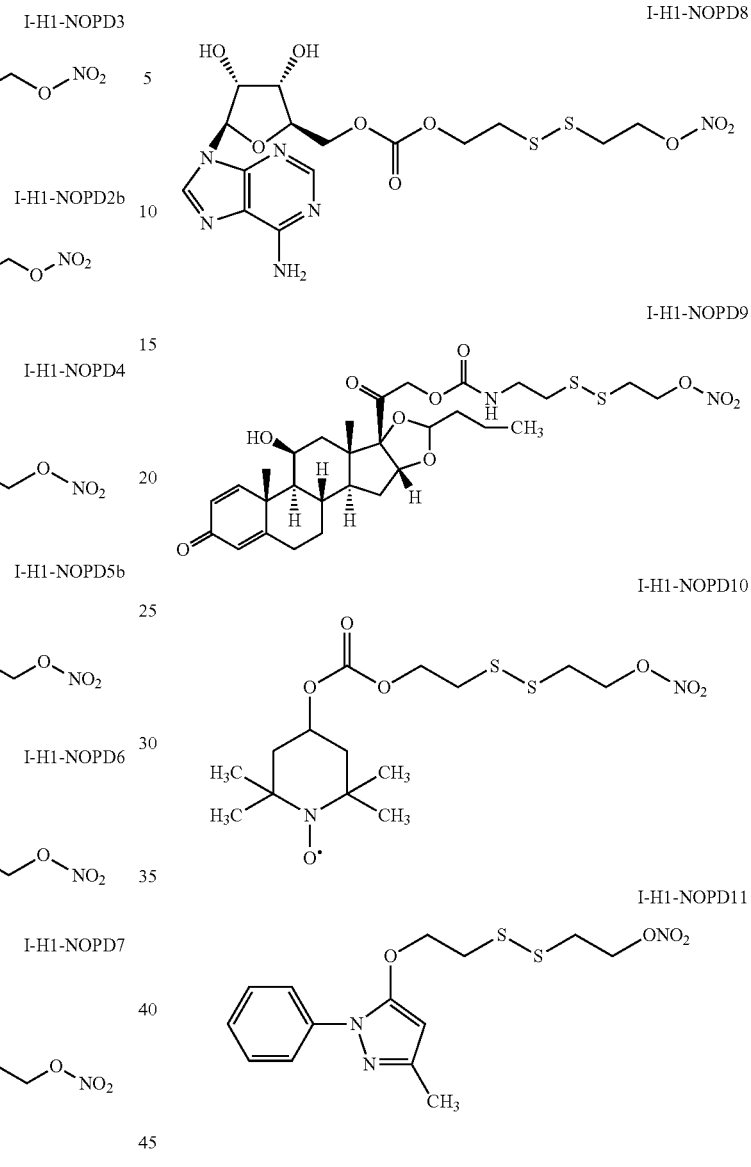
C. Mutual or Double Prodrugs
(a) From Two Amino-Containing Drugs
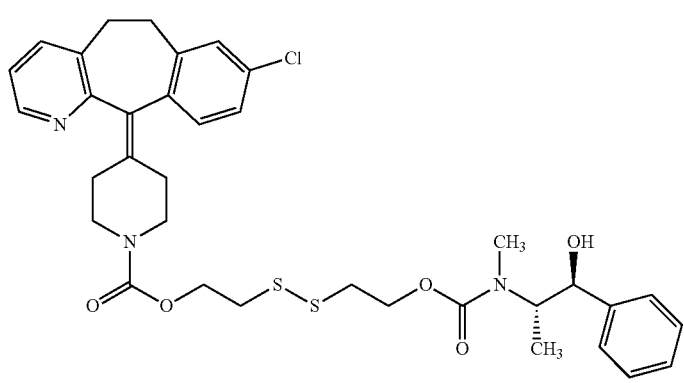

-continued
I-AA-MPD2
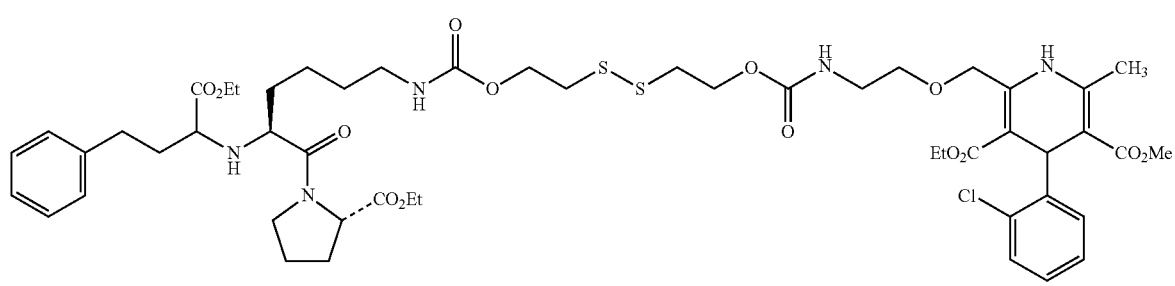
I-AA-MPD3a
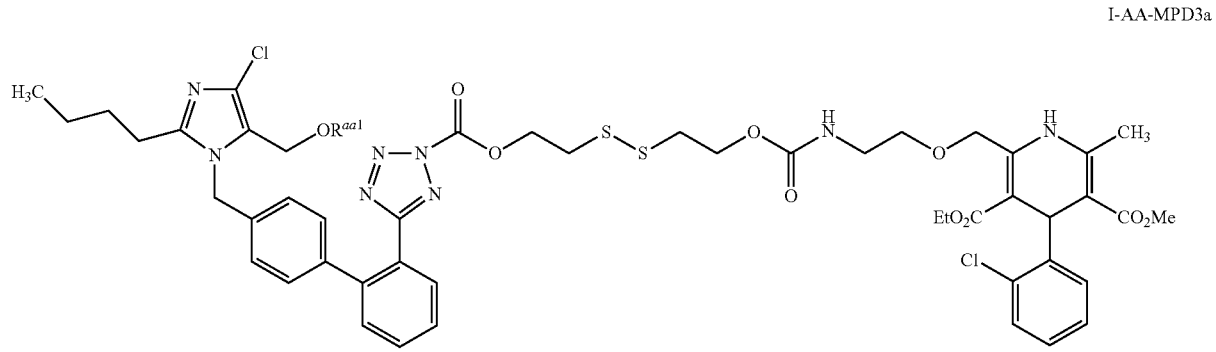
R$^{aa1}$ = H, PO$_3$H$_2$, C(O)NHCH$_2$CH$_2$NMe$_2$, C(O)CH2NR'2 (R' = H or Alkyl), C(O)OCH$_2$CH$_2$NMe$_2$, C(O)CH$_2$CH$_2$CO$_2$H, C(O)NHCH$_2$CH$_2$NHCOCH$_2$CH$_2$CO$_2$H, C(O)O(CH$_2$)$_2$NHCO(CH$_2$)$_2$CO$_2$H, and C(O)CH$_2$N(CH$_2$CO$_2$H)$_2$.
(R$^{aa1}$ = H)
I-AA-MPD4
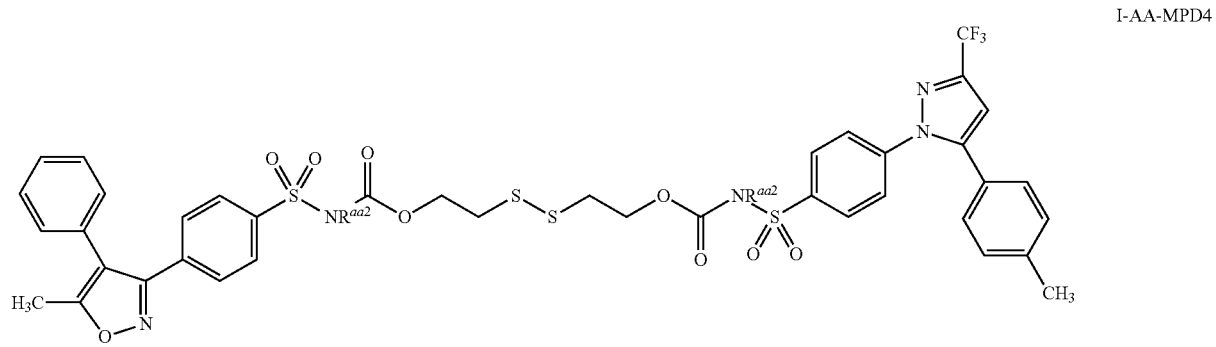
R$^{aa2}$ = H or a metal ion
I-AA-MPD5
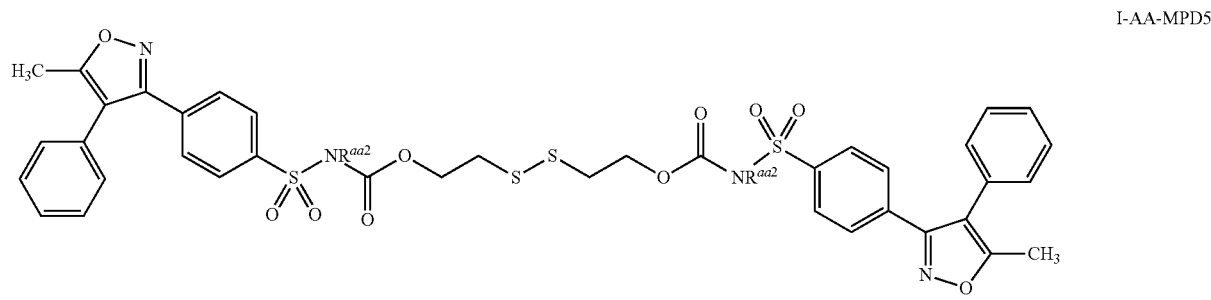
R$^{aa2}$ = H or a metal ion -continued
I-AA-MPD6
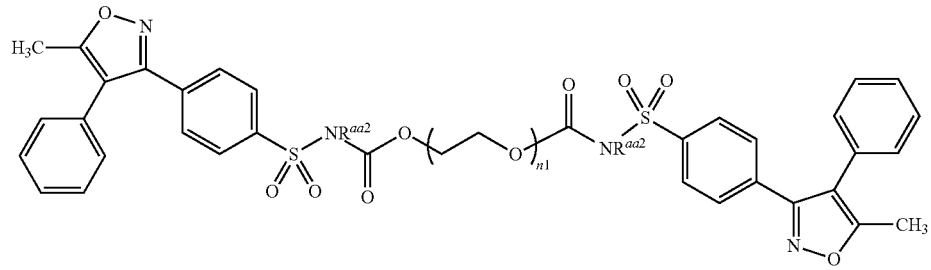
n1 = 1-1000; R<sup>aa2</sup> = H or a metal ion
I-AA-MPD7
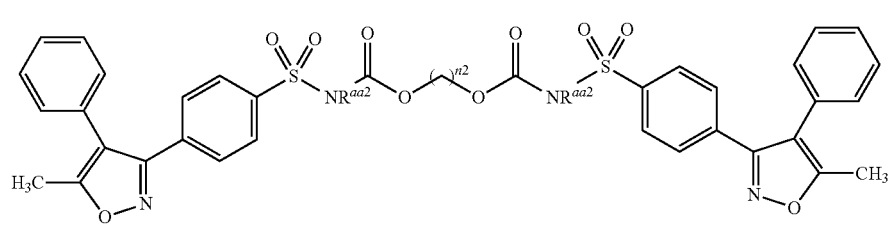
n2 = 1-6; R<sup>aa2</sup> = H or a metal ion
I-AA-MPD8
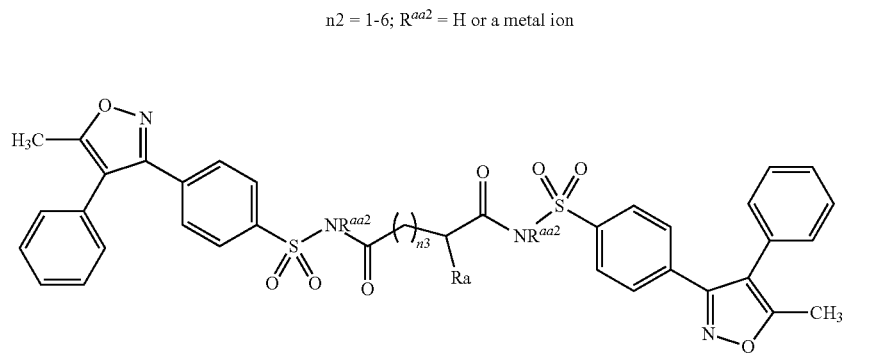
n3 = 0-6
R<sup>aa2</sup> = H or a metal ion; Ra = H, NH$_2$, acylamino groups
I-AA-MPD9
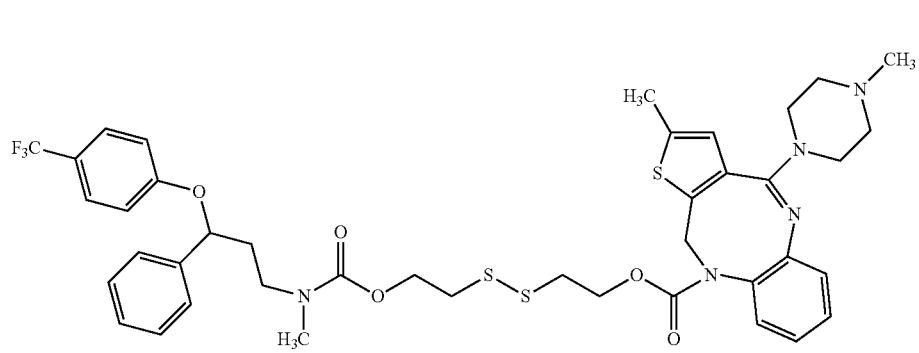
I-AA-MPD10
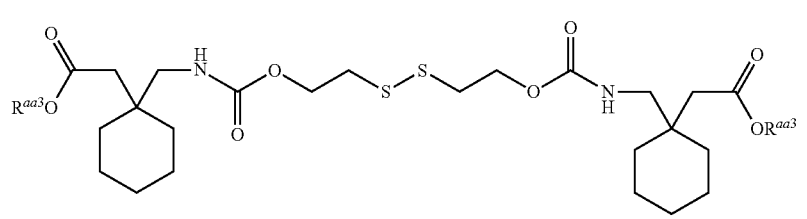
R<sup>aa3</sup> = H or alkyl -continued
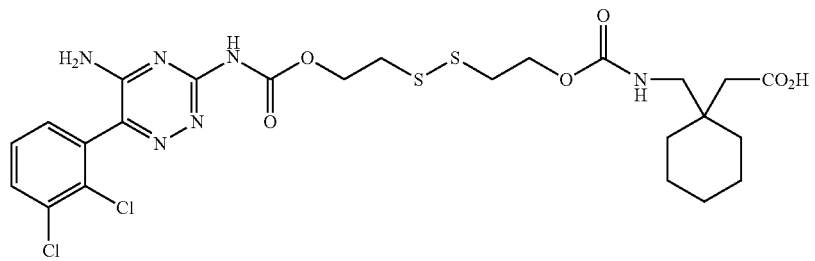
I-AA-MPD11
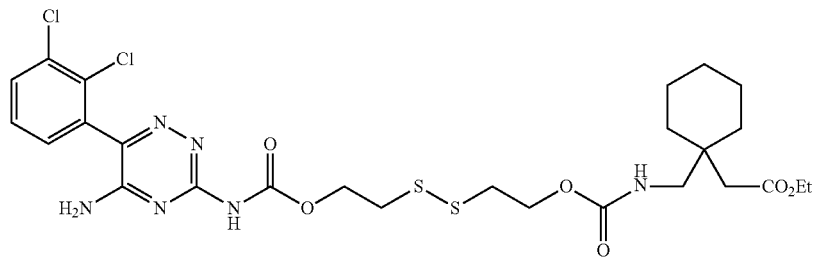
I-AA-MPD12
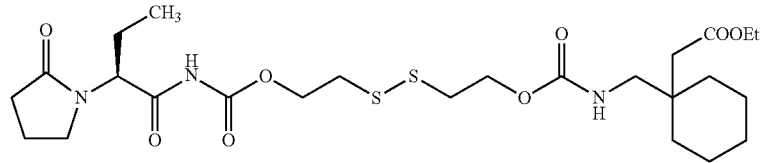
I-AA-MPD13
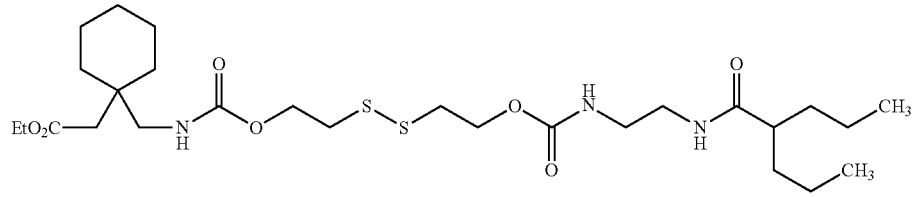
I-AA-MPD14
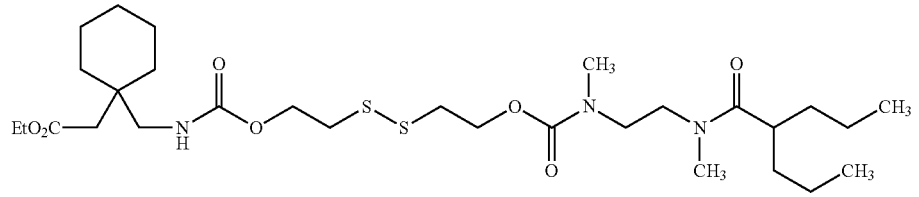
I-AA-MPD15
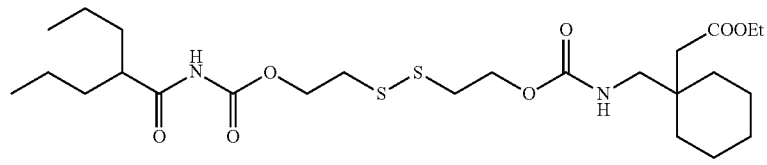
I-AA-MPD16
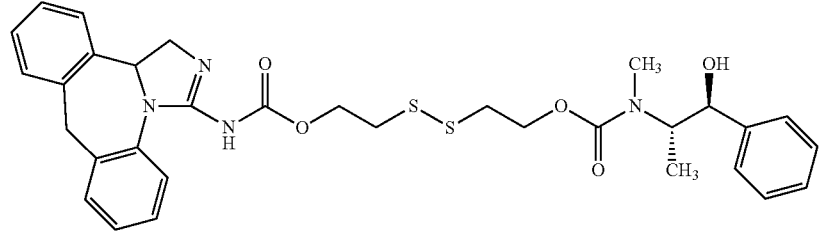
I-AA-MPD17

-continued
I-AA-MPD18
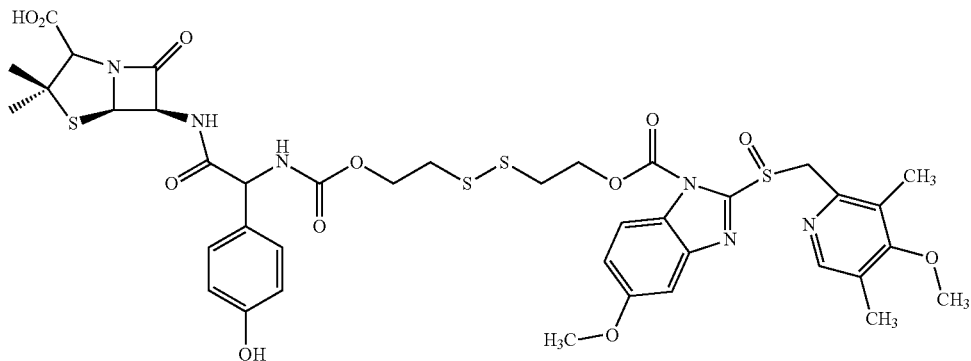
I-AA-MPD19
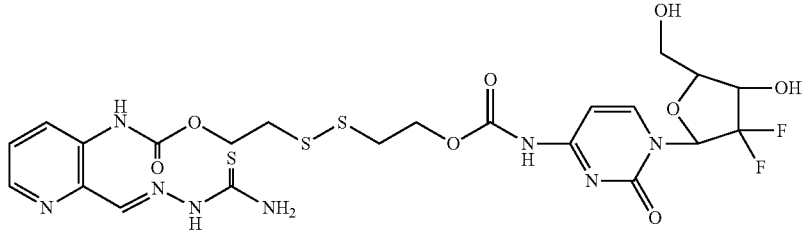
I-AA-MPD20
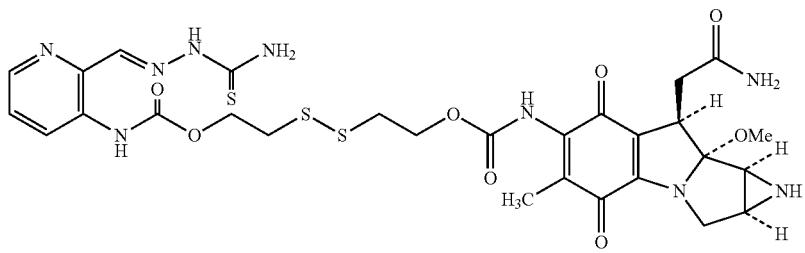
I-AA-MPD21
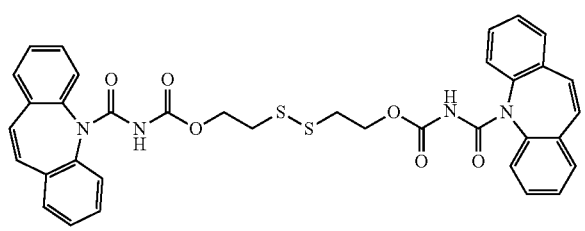
I-AA-MPD22
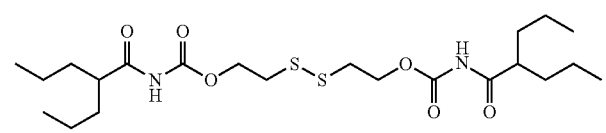
I-AA-MPD23
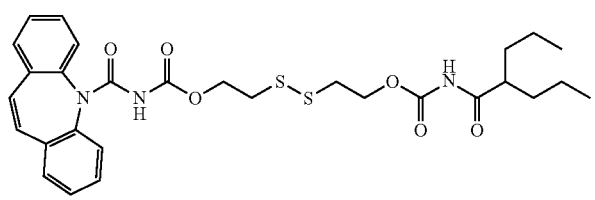
I-AA-MPD24
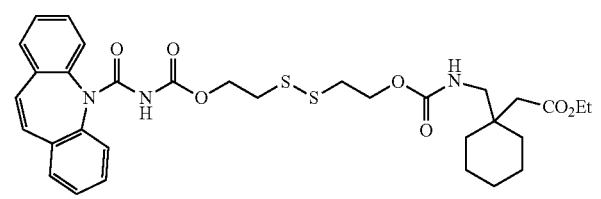
I-AA-MPD25
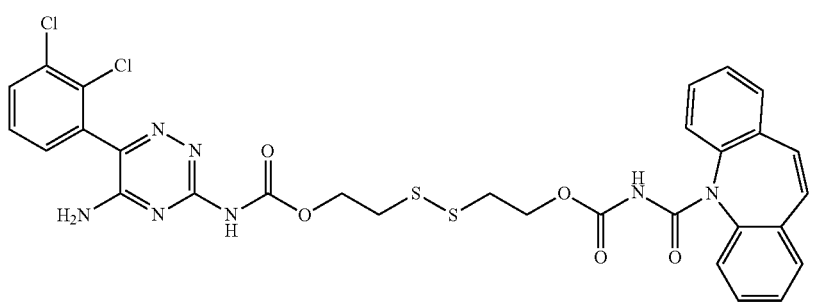

-continued
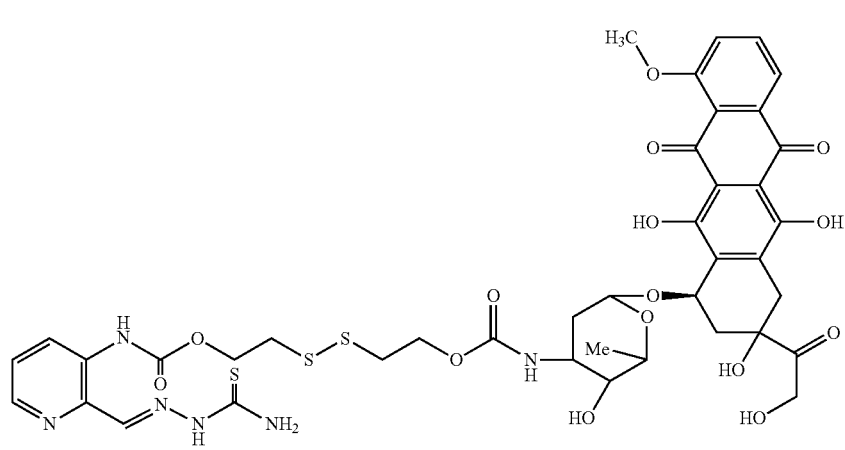
I-AA-MPD26
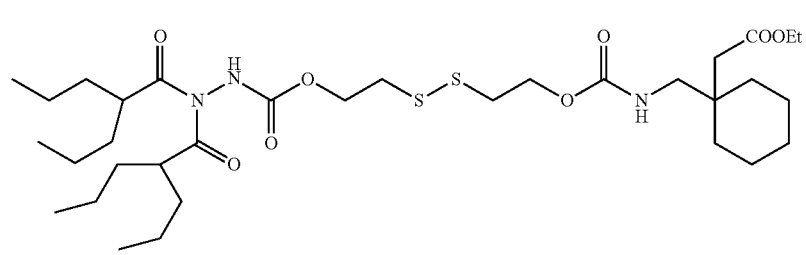
I-AA-MPD27
(b) From Two Carboxyl-Containing Drugs
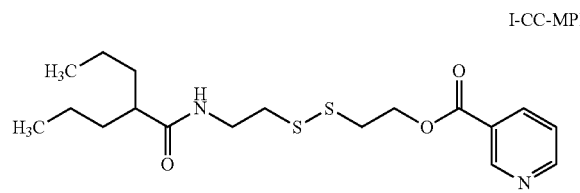
I-CC-MPD1
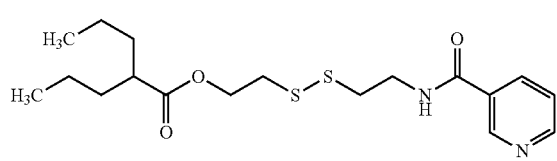
I-CC-MPD2
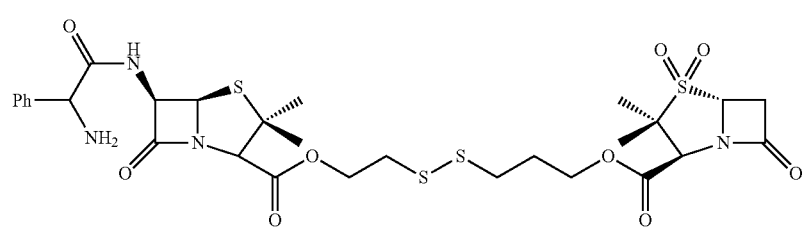
I-CC-MPD3
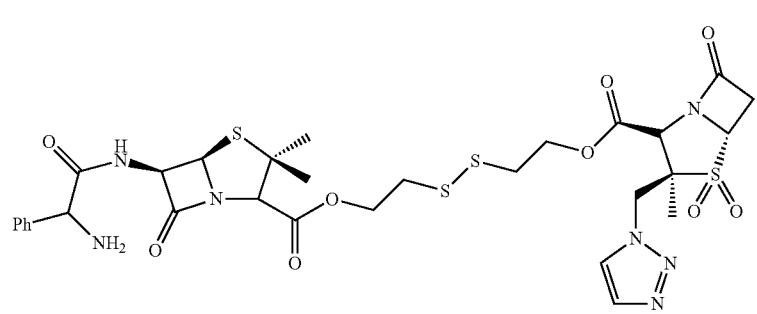
I-CC-MPD4

I-CC-MPD5
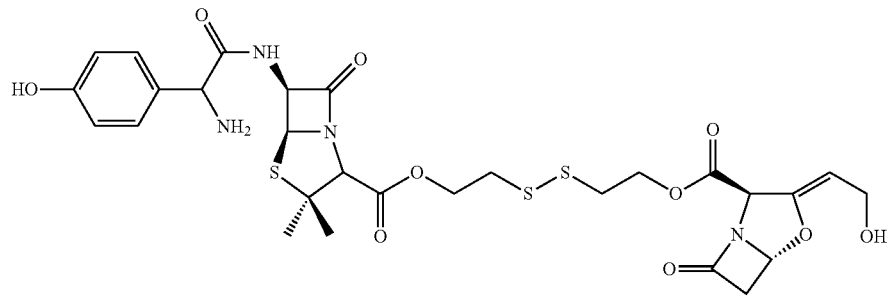
I-CC-MPD6
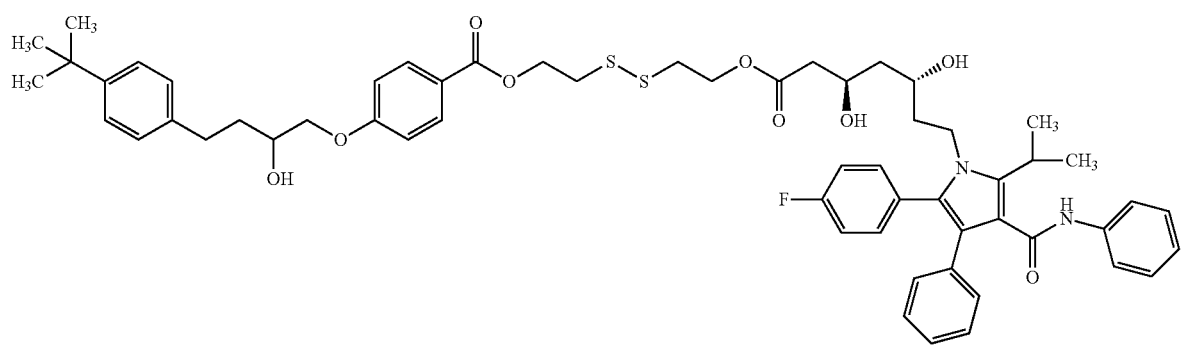
(c) From Two Hydroxyl-Containing Drugs
I-HH-MPD1
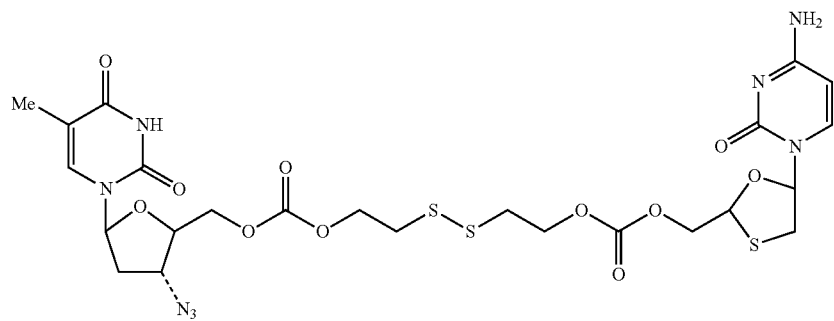
I-HH-MPD2
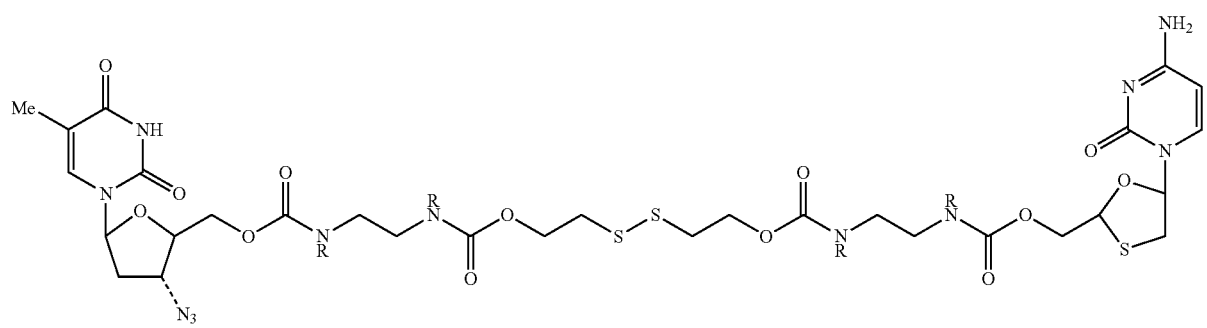
R = H or Me or alkyl I-HH-MPD3
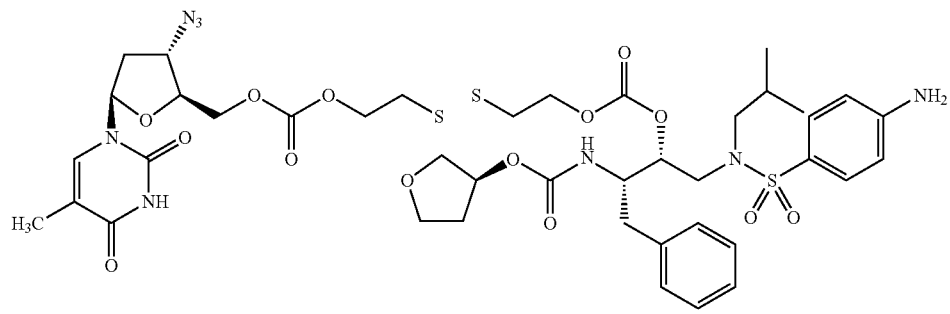
I-HH-MPD4
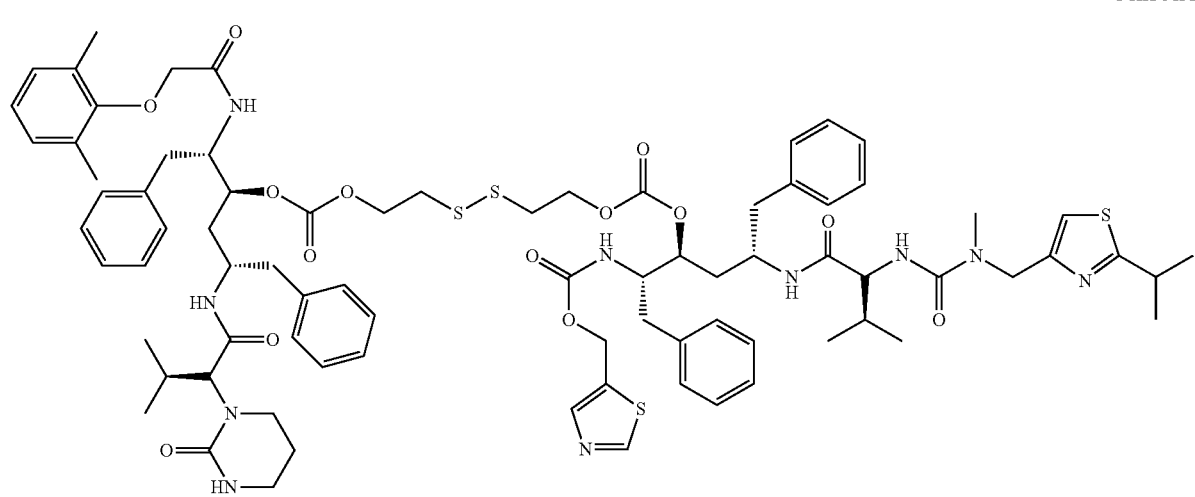
I-HH-MPD5
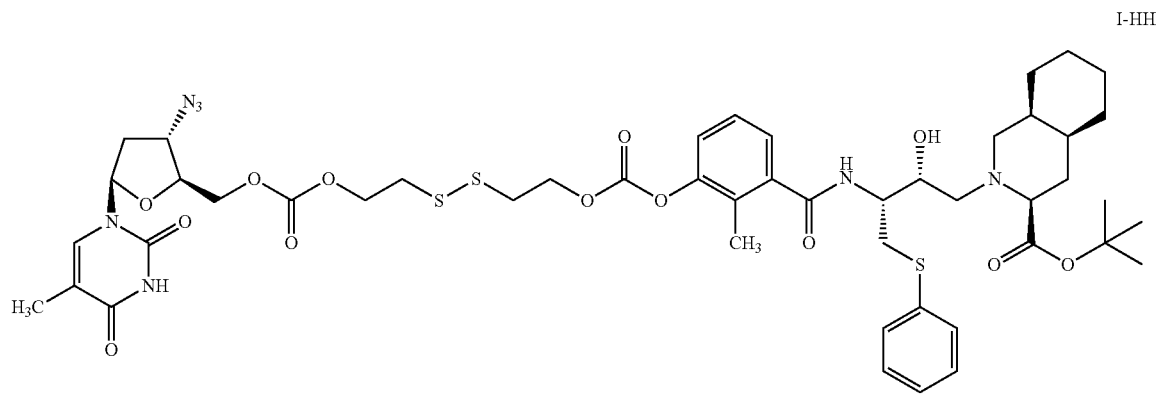
I-HH-MPD6
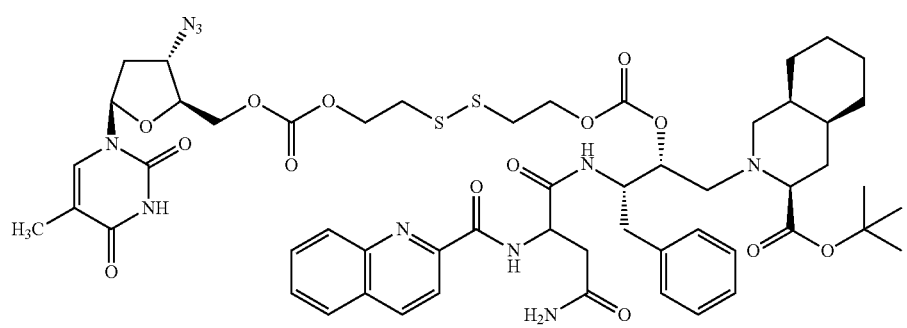

-continued
I-HH-MPD7
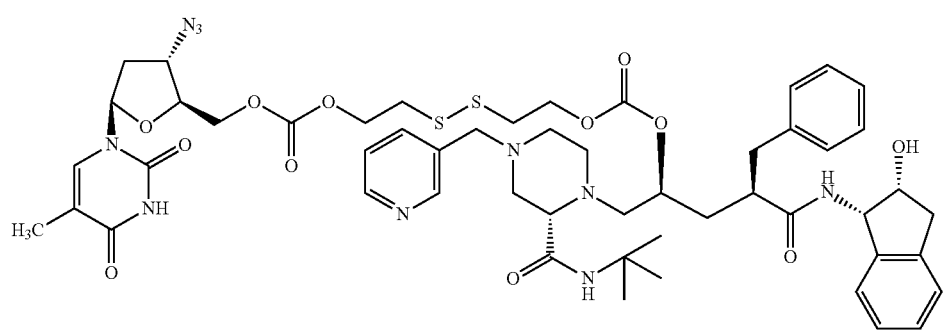
I-HH-MPD8
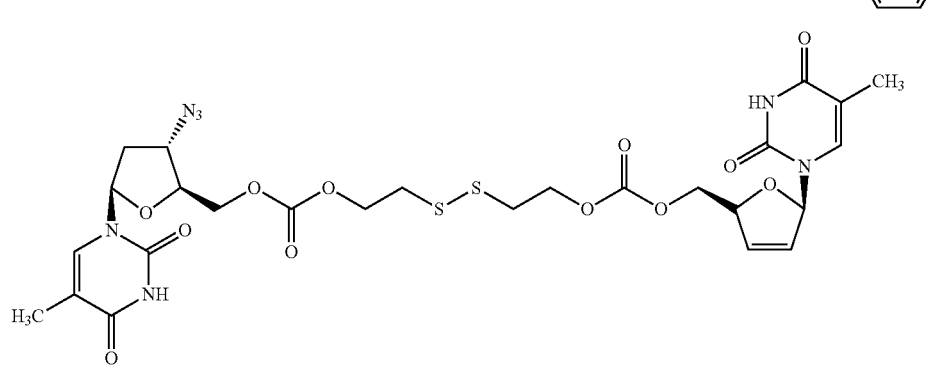
I-HH-MPD9
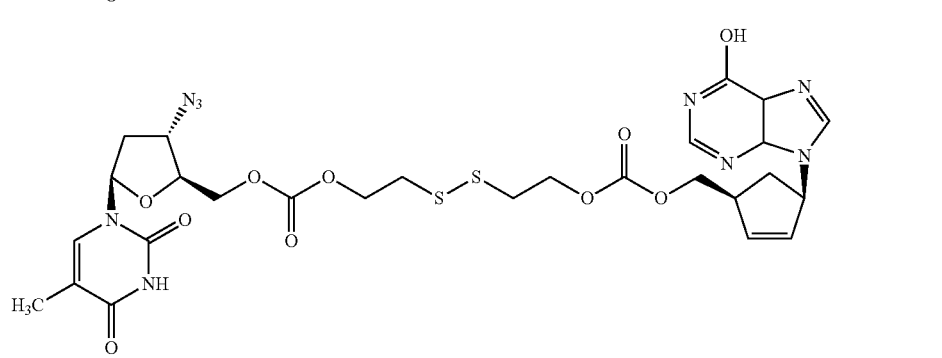
I-HH-MPD10
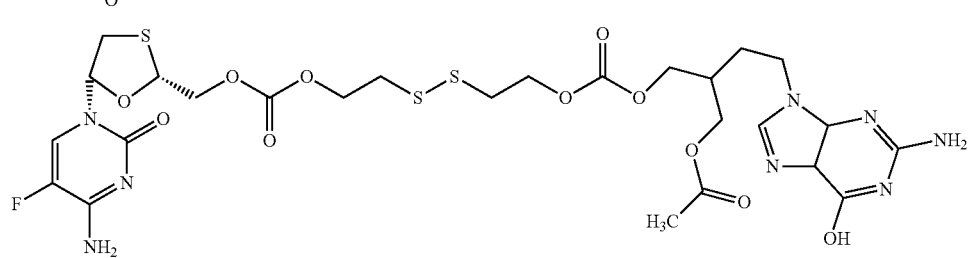
I-HH-MPD11          I-HH-MPD12
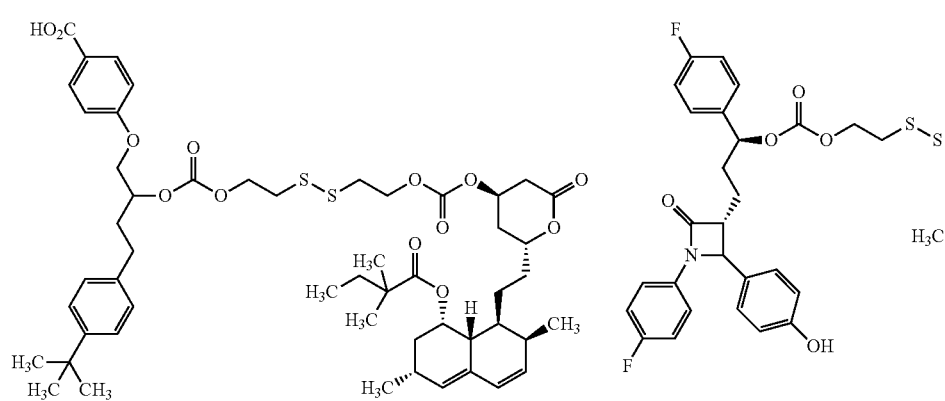

-continued
I-HH-MPD13
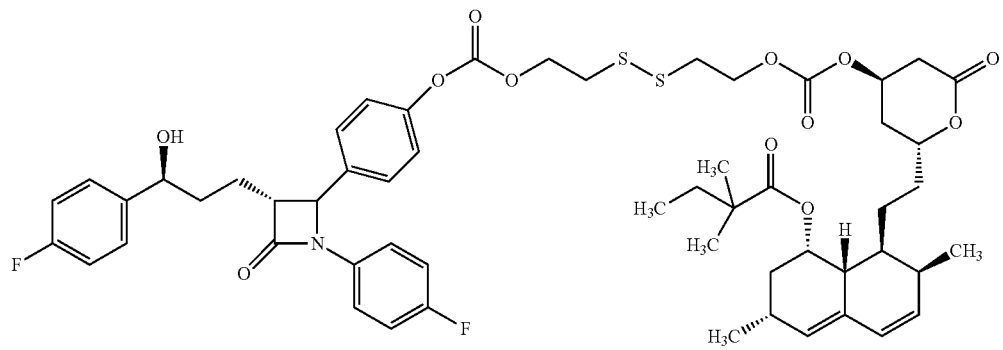
I-HH-MPD14
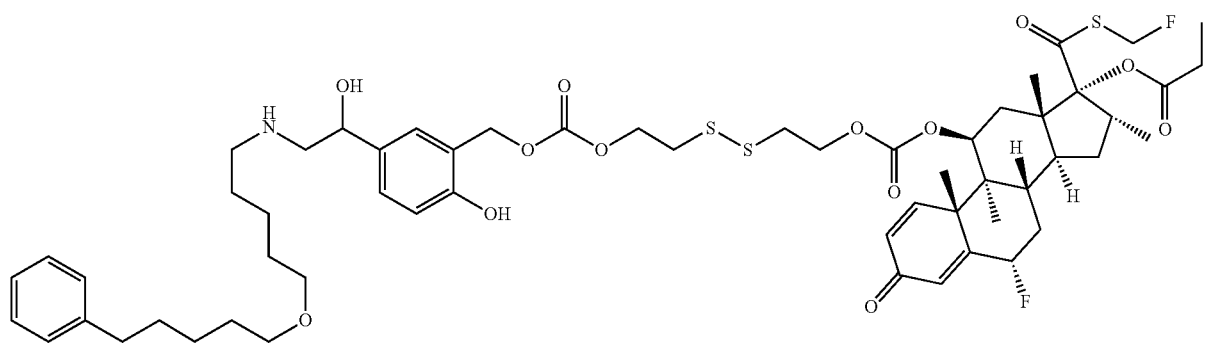
I-HH-MPD15
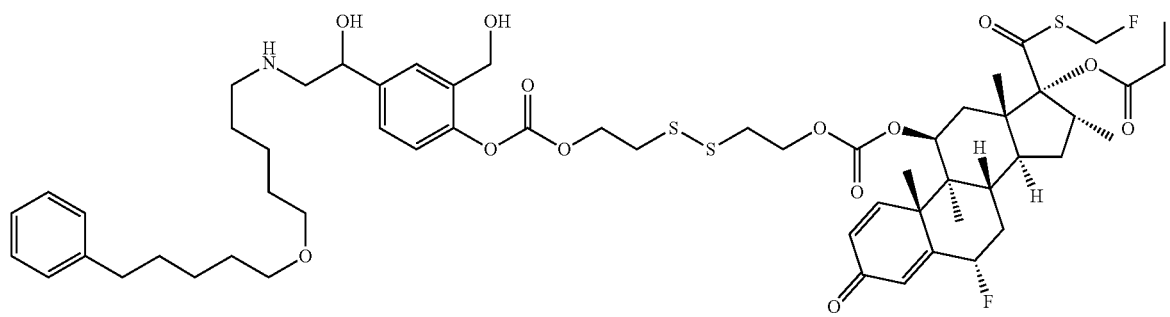
I-HH-MPD16
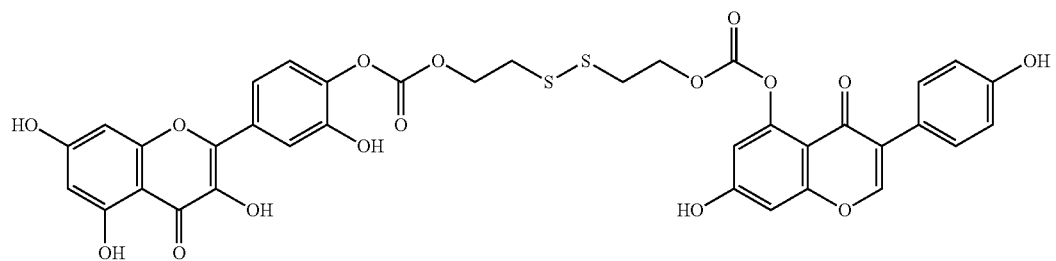
I-HH-MPD17
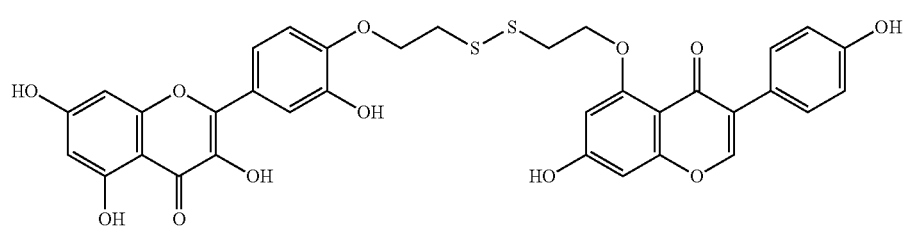

I-HH-MPD18
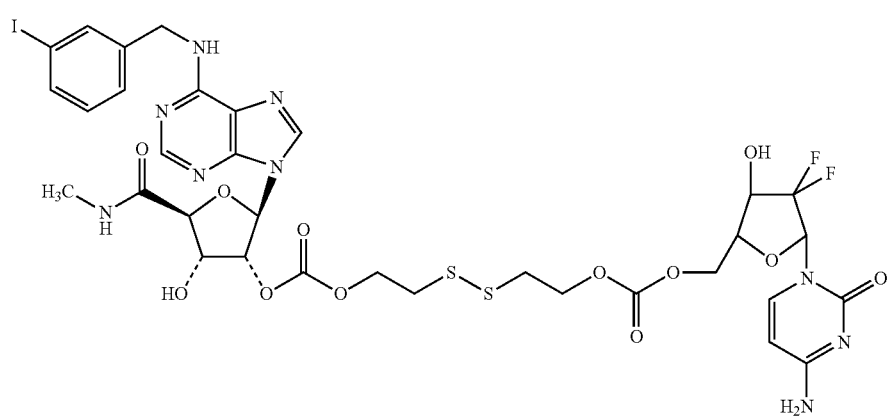
I-HHAH-TMPD1
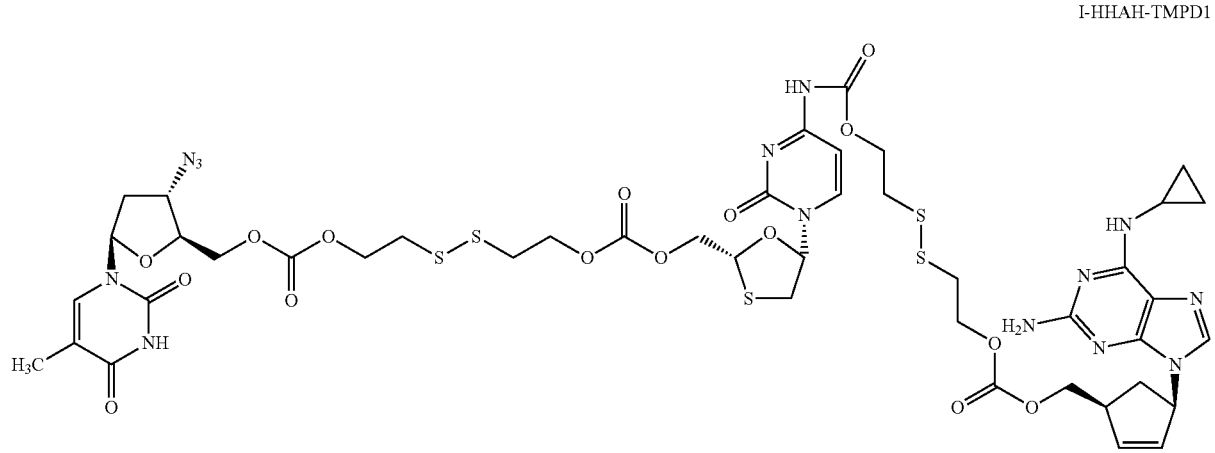
(d) From an Amino-Containing Drug and a Carboxyl-Containing Drug:
I-CA-MPD1
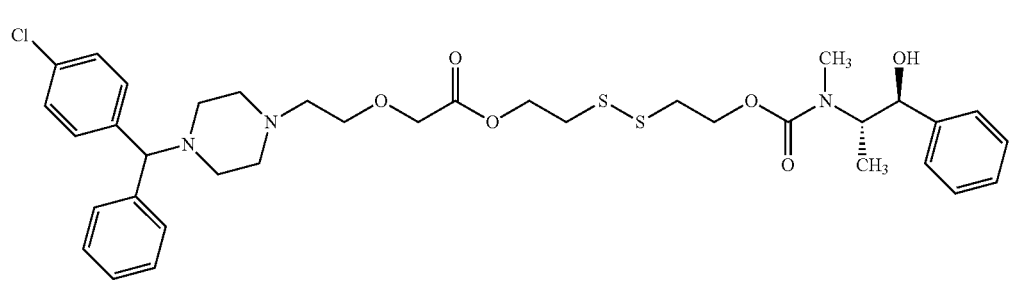
I-CA-MPD2
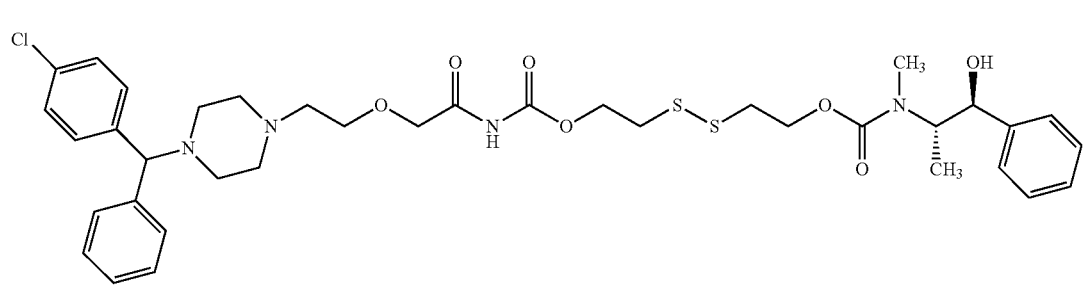

-continued
I-CA-MPD3
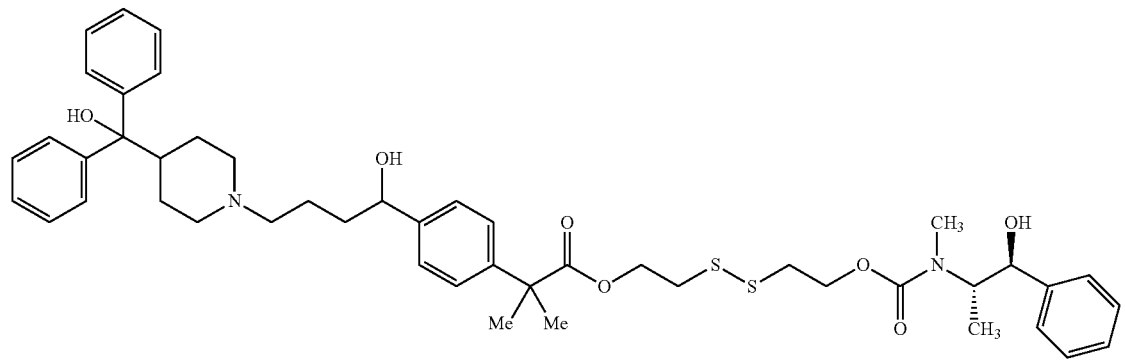
I-CA-MPD4
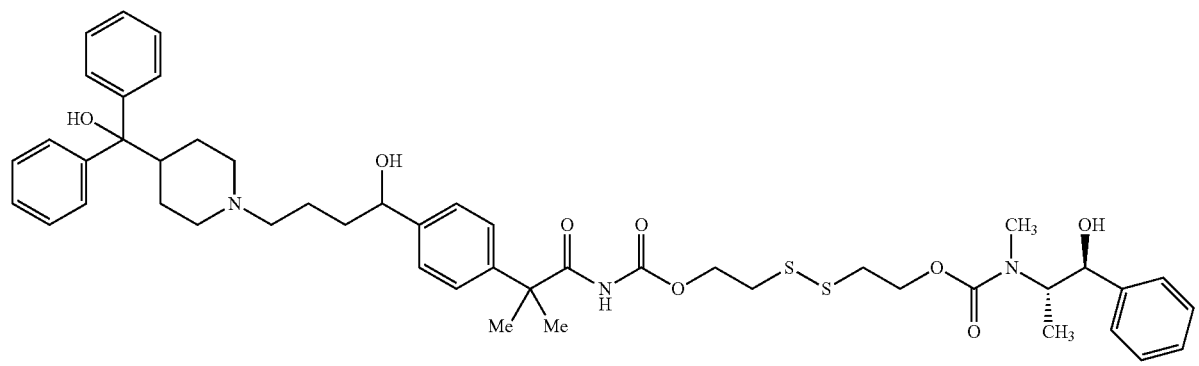
I-CA-MPD5
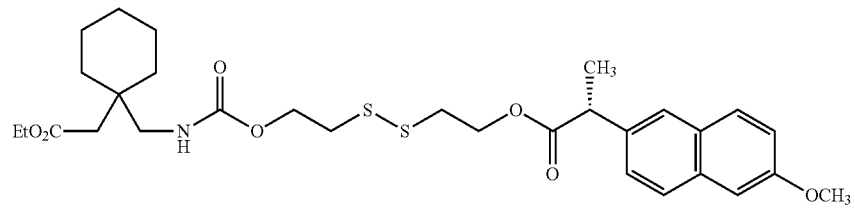
I-CA-MPD6
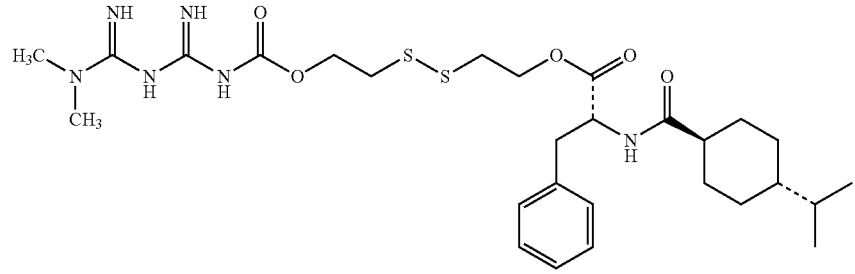
I-CA-MPD7
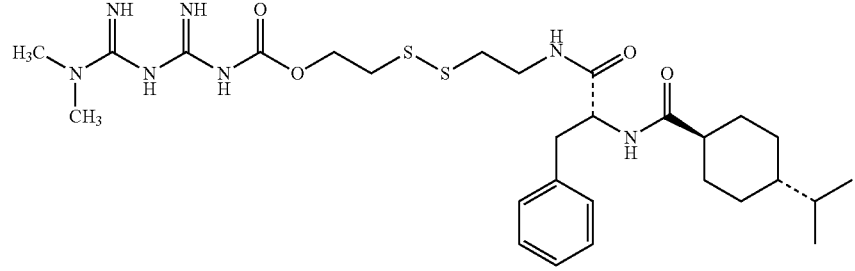

I-CA-MPD8
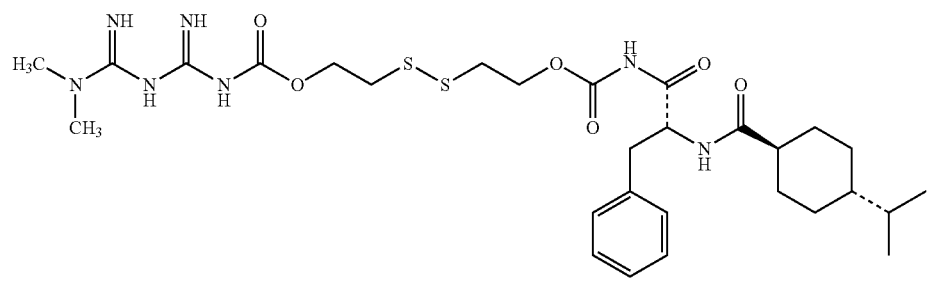
I-CA-MPD9
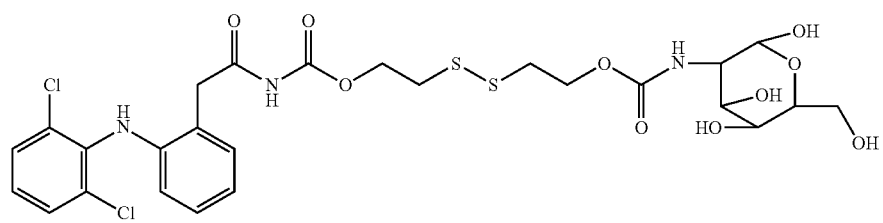
I-CA-MPD10
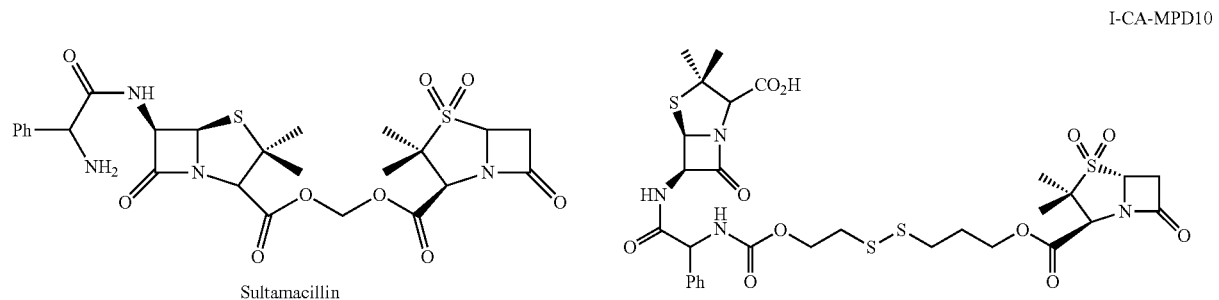
I-CA-MPD11
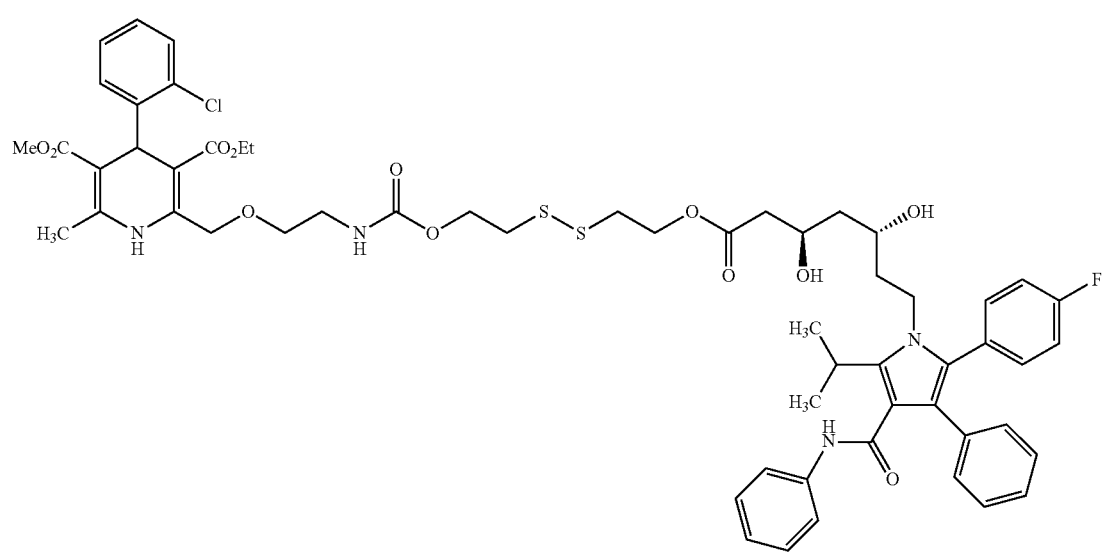

I-CA-MPD12
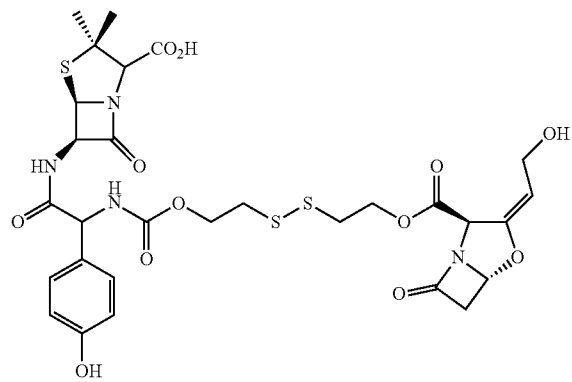
I-CA-MPD13
I-CA-MPD14
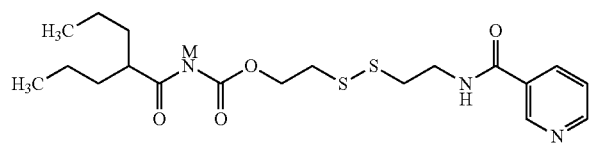
M = H or a metal ion
I-CA-MPD15
I-CA-MPD16
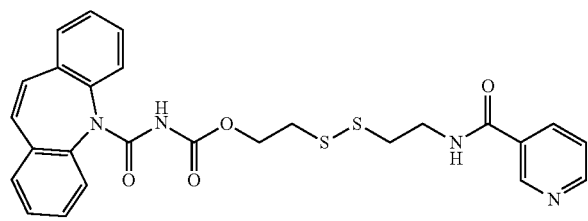
I-CA-MPD17
I-CA-MPD18
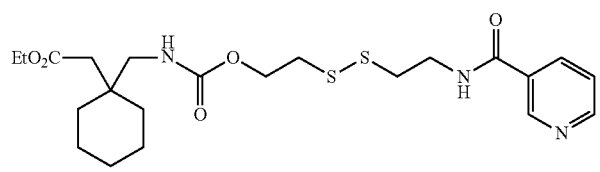
I-CA-MPD19
I-CA-MPD20
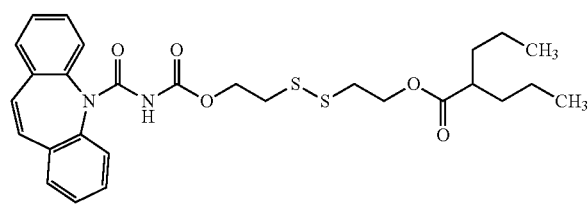
I-CA-MPD21
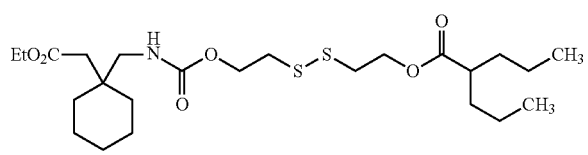
I-CA-MPD22
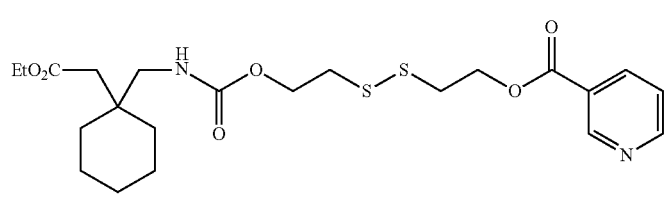

I-CA-MPD23
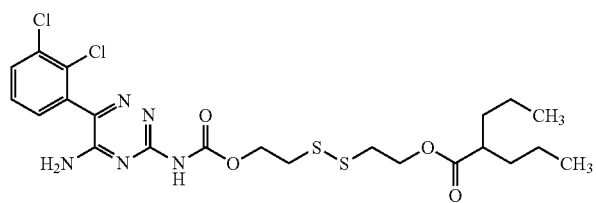 or 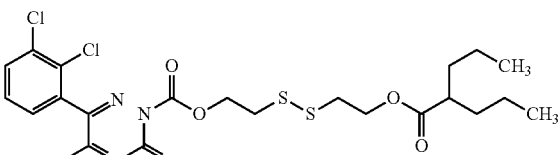
I-CA-MPD24
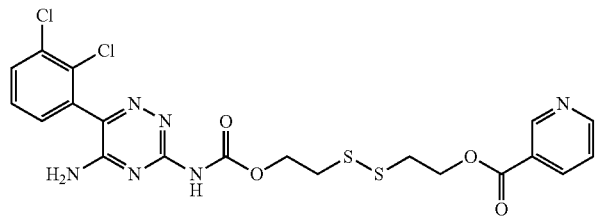 or 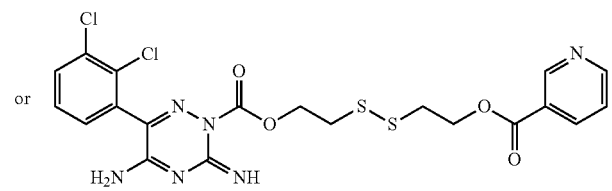
I-CA-MPD25
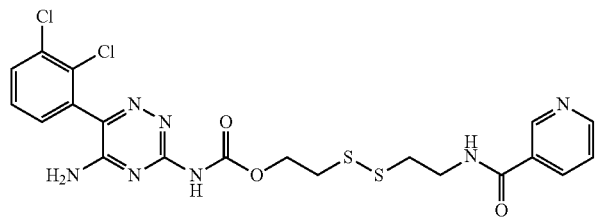 or 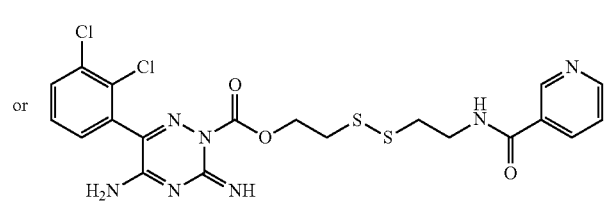
I-CA-MPD26
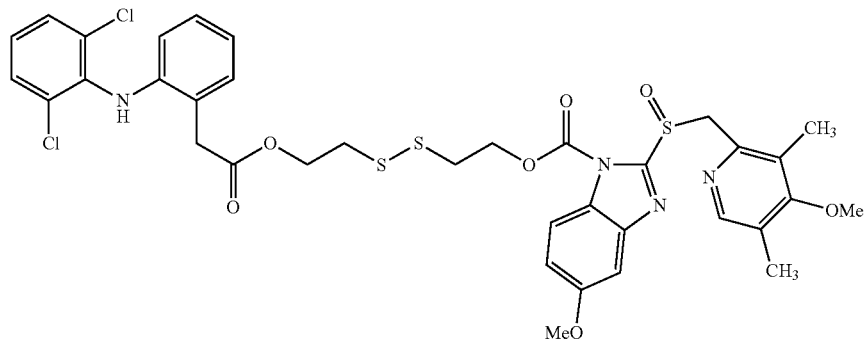
I-CA-MPD27
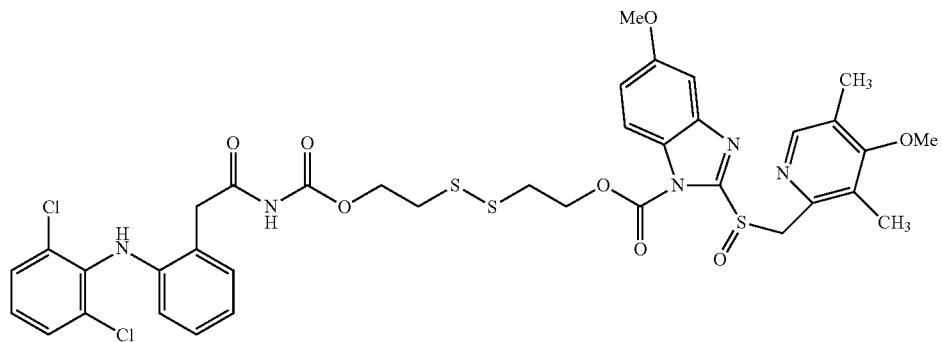

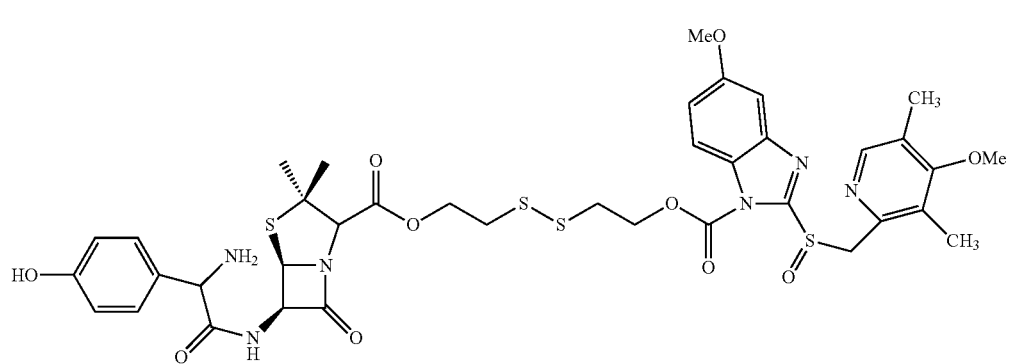
I-CA-MPD28
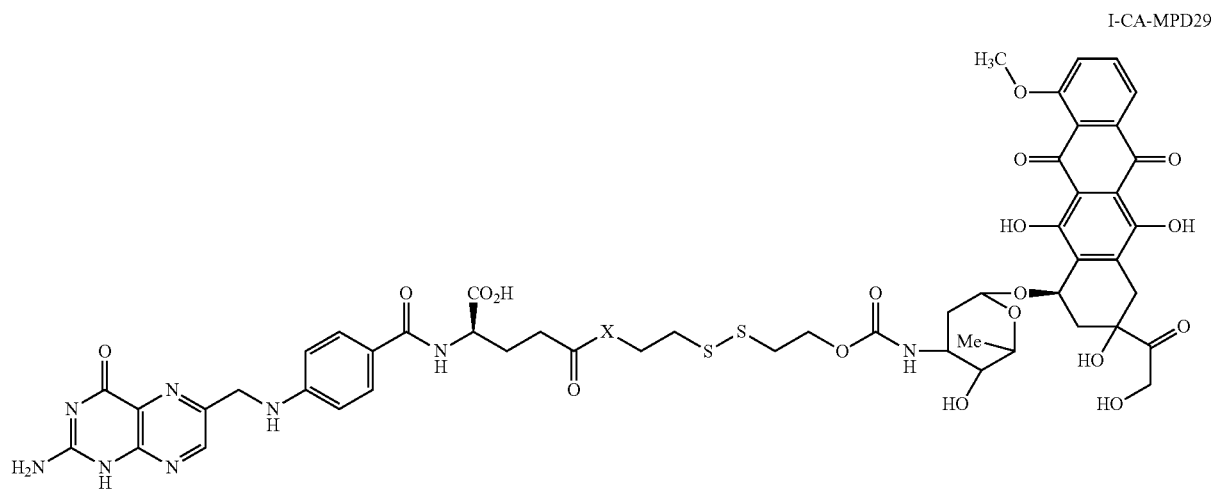
I-CA-MPD29
I-CA-MPD30
(e) Mutual Prodrugs of One Carboxyl-Containing and One Hydroxyl-Containing Drugs
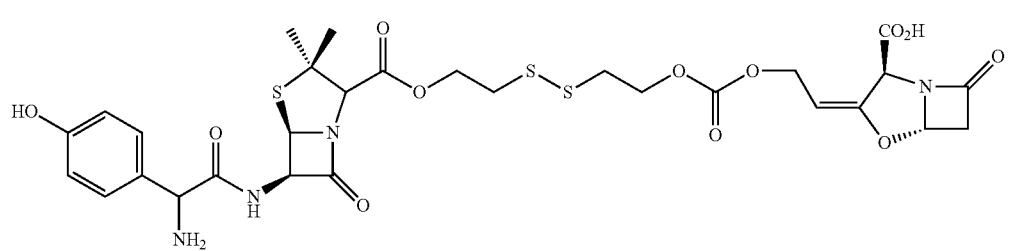
I-CH-MPD1

-continued
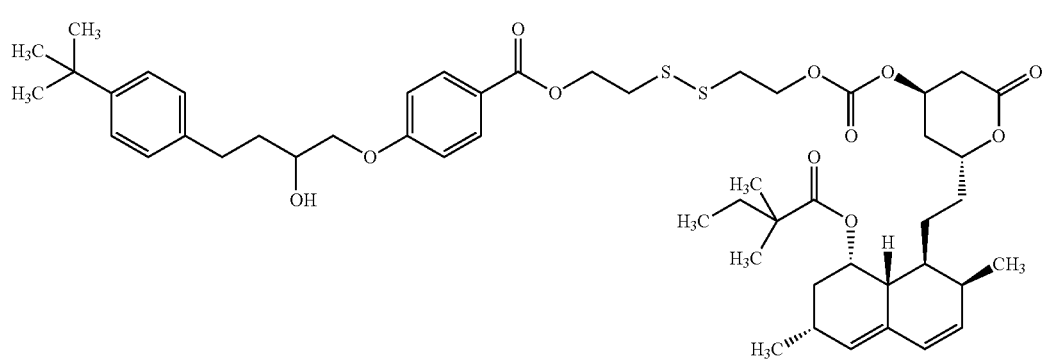
I-CH-MPD2
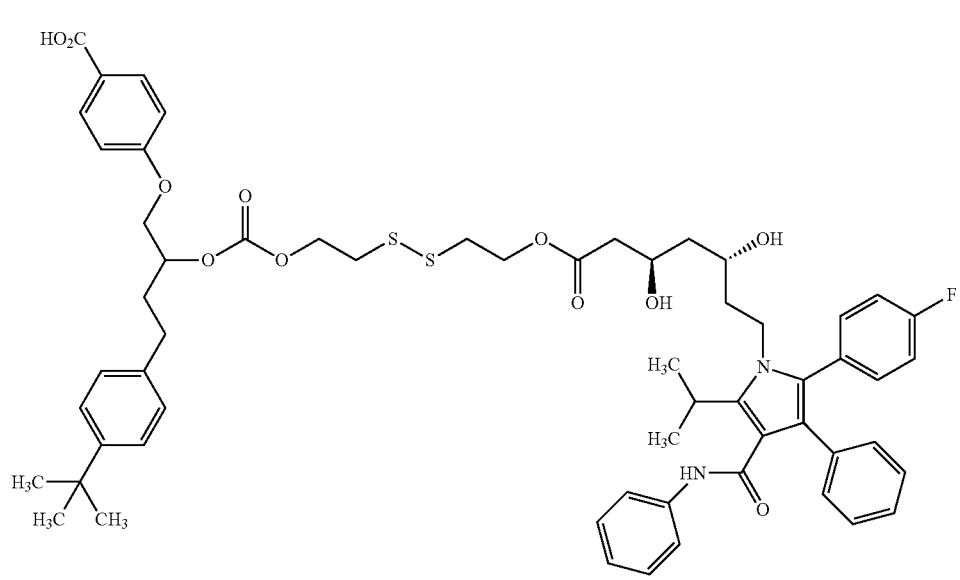
I-CH-MPD3
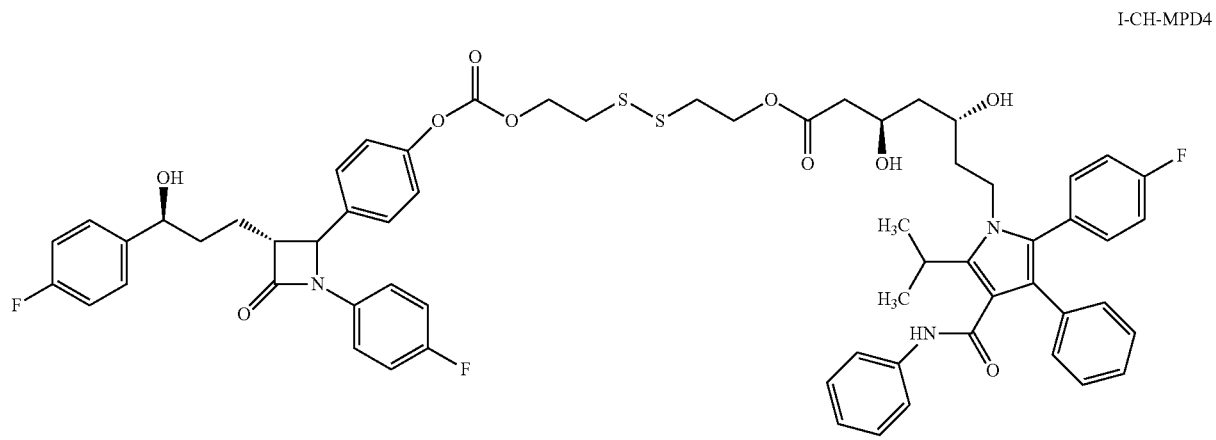
I-CH-MPD4

I-CH-MPD5
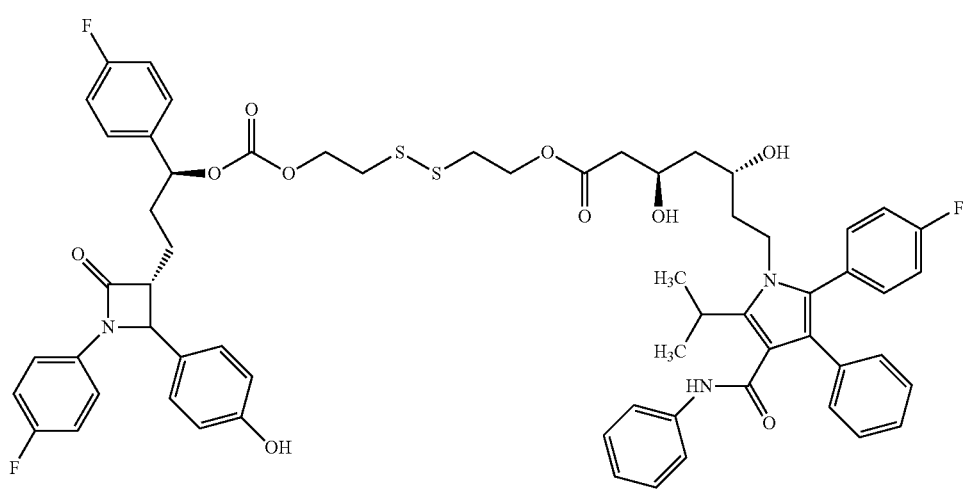
I-CH-MPD6
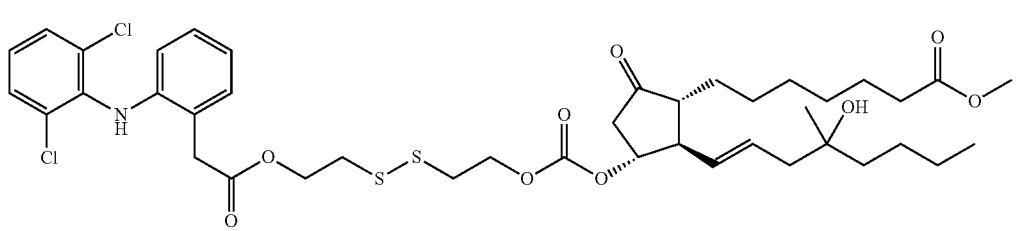
I-CH-MPD6
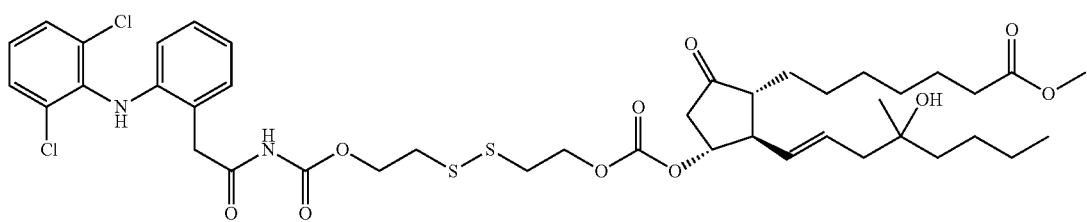
(f) Mutual Prodrugs of One Amino-Containing and One Hydroxyl-Containing Drugs
I-AH-MPD1
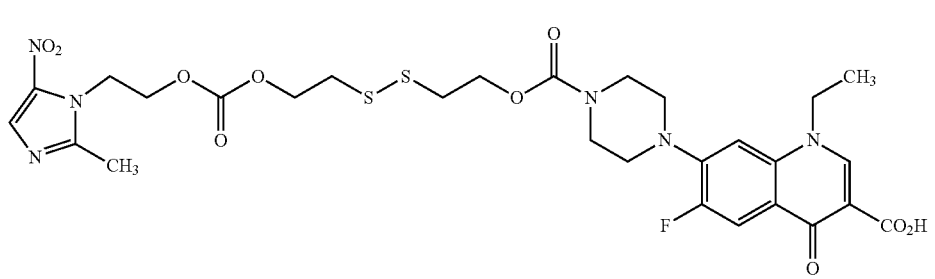
I-AH-MPD2
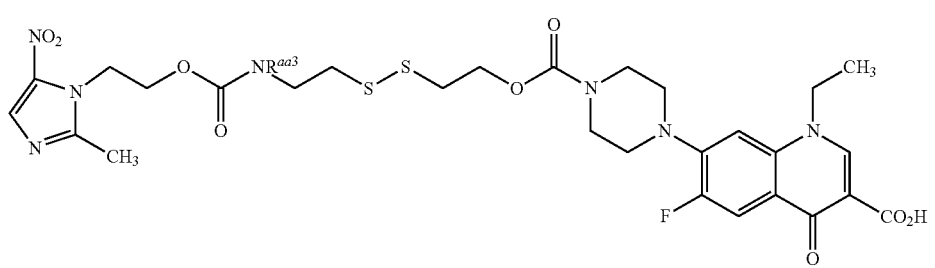
$R^{aa3}$ = H, lower alkyl, cycloalkyl, etc.

-continued
I-AH-MPD3
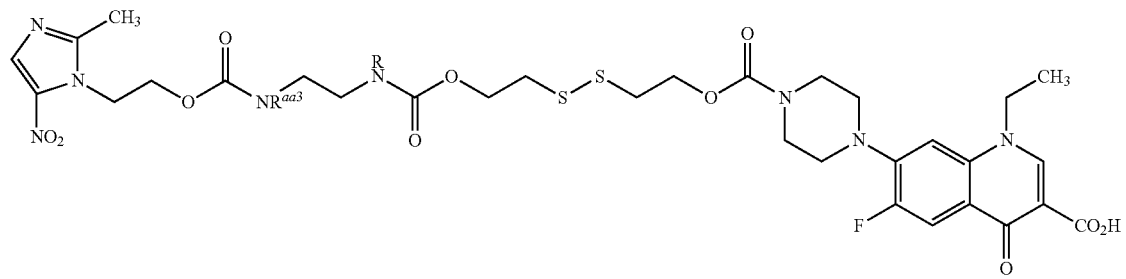
R$^{aa3}$ = H, Me, Lower alkyl, cycloalkyl, aralkyl, etc.
I-AH-MPD4
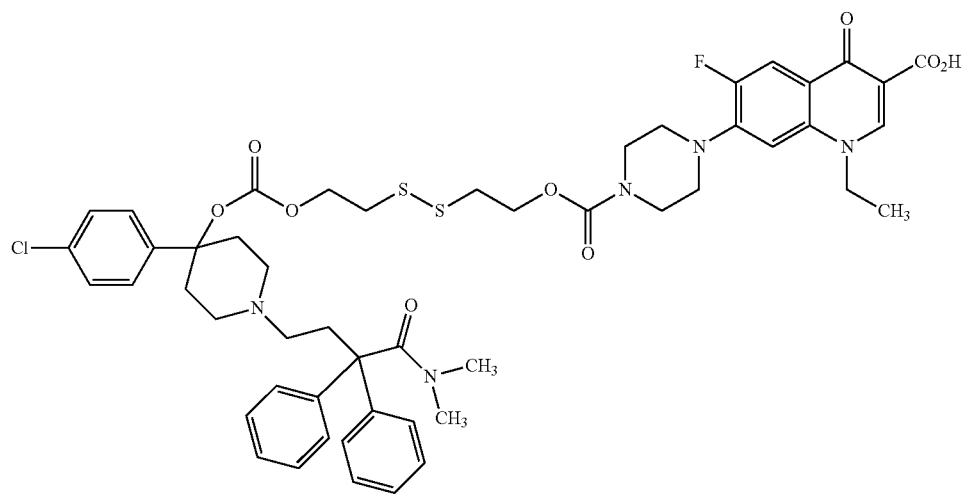
I-AH-MPD5
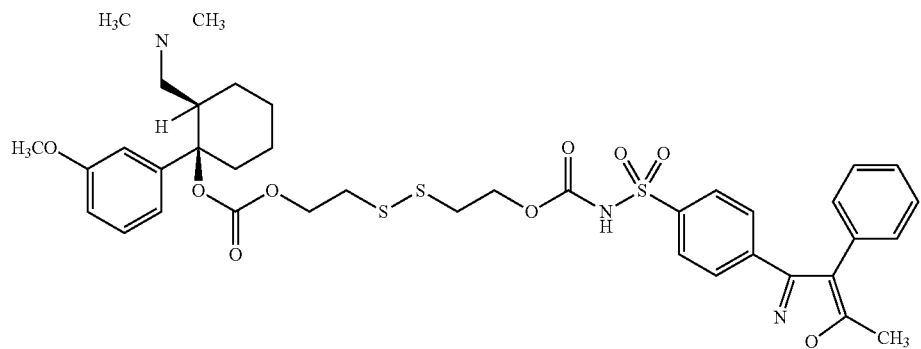
I-AH-MPD6
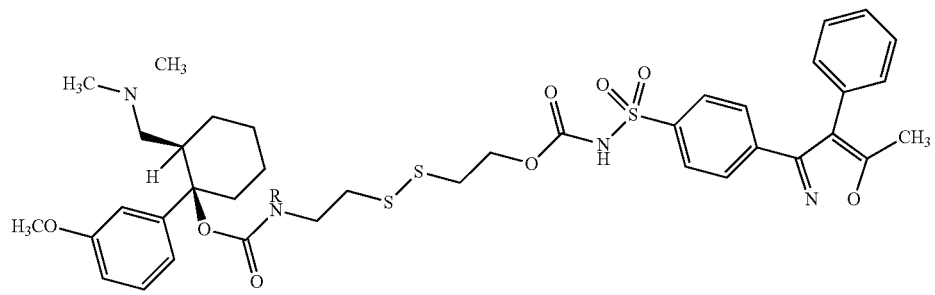

I-AH-MPD7
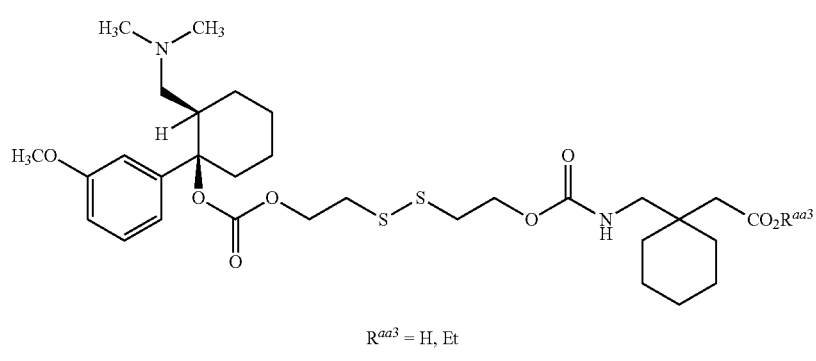
$R^{aa3}$ = H, Et
I-AH-MPD8
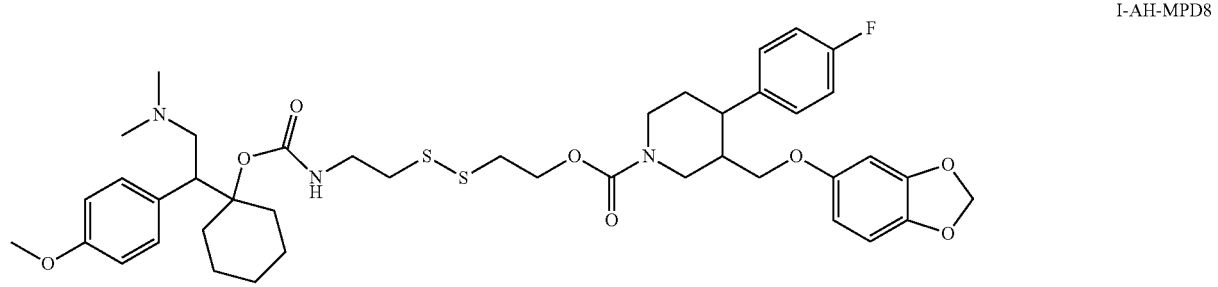
I-AH-MPD9
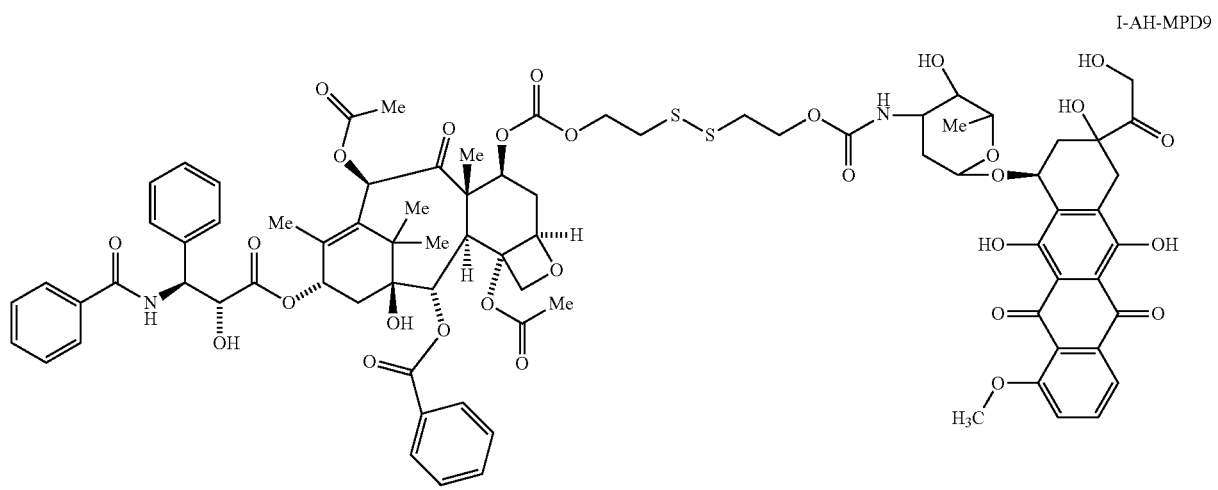
I-AH-MPD10
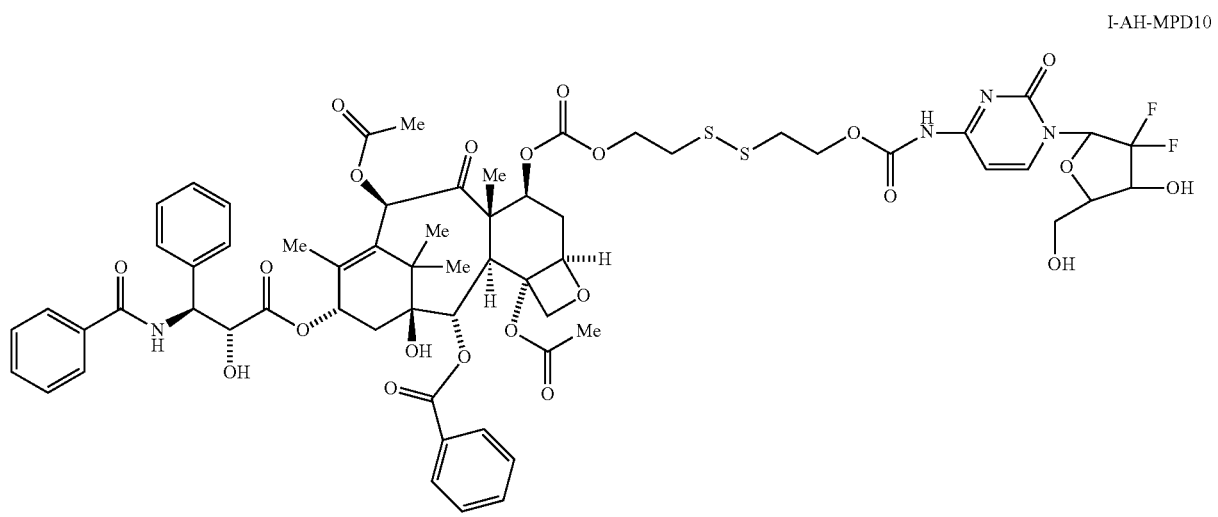

I-AH-MPD11
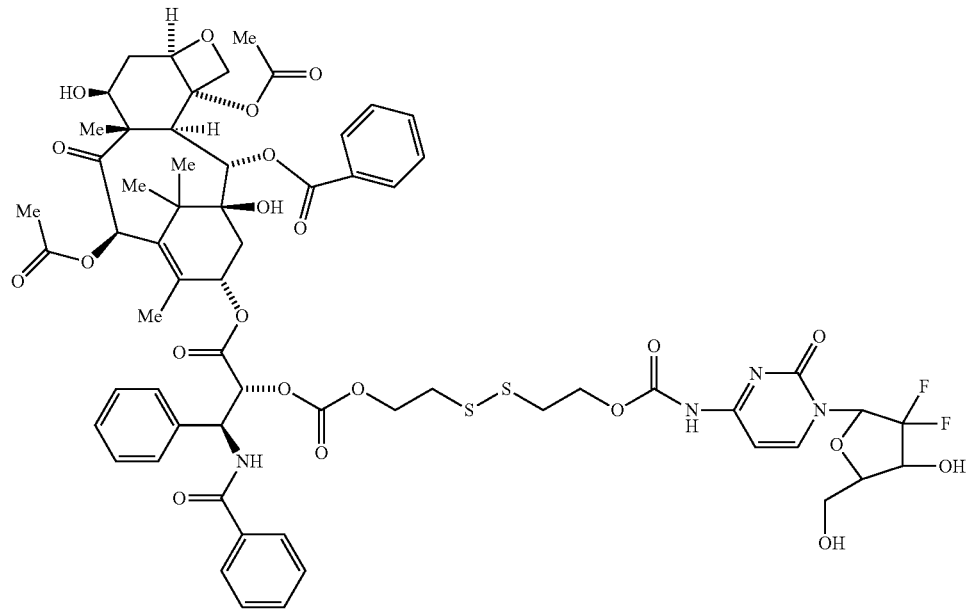
I-AH-MPD12
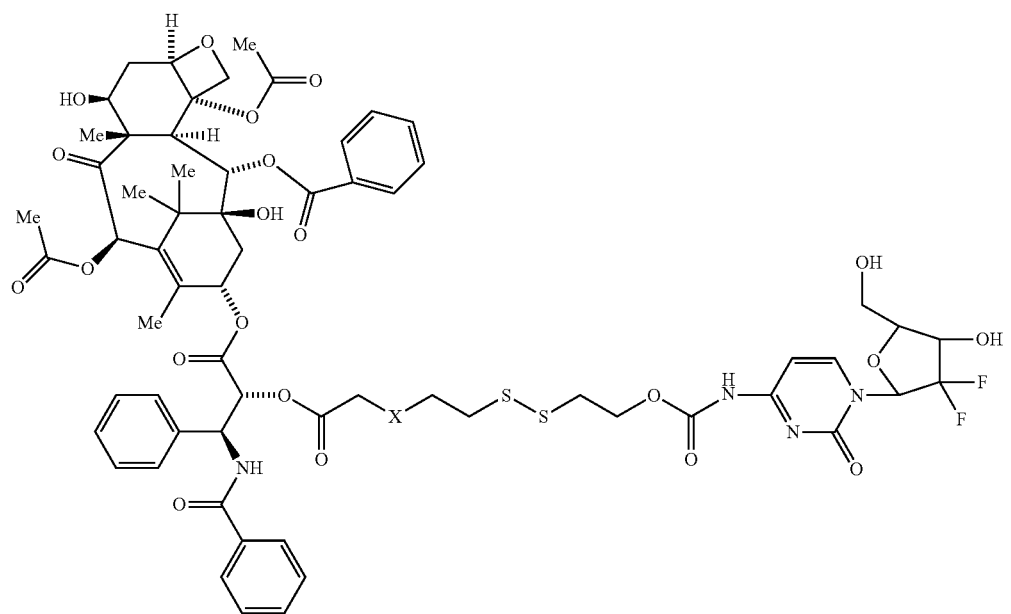
X = O, NRx1 (Rx1 = H, Alkyl, Aralkyl, etc)
I-AH-MPD13
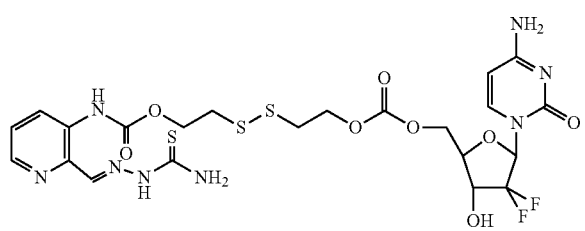
I-AH-MPD14
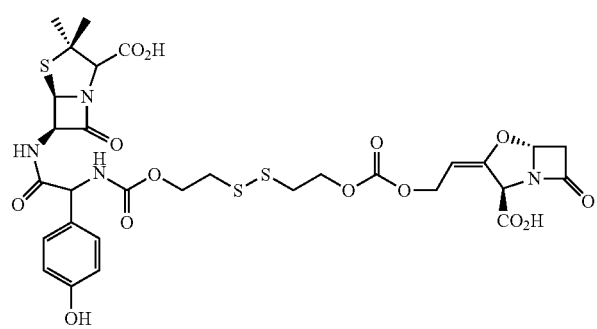

I-AH-MPD15
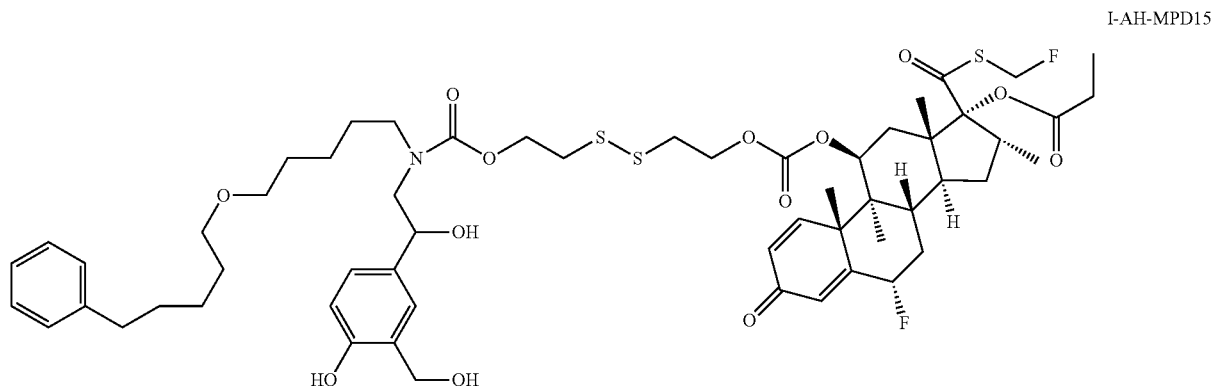
I-AH-MPD16
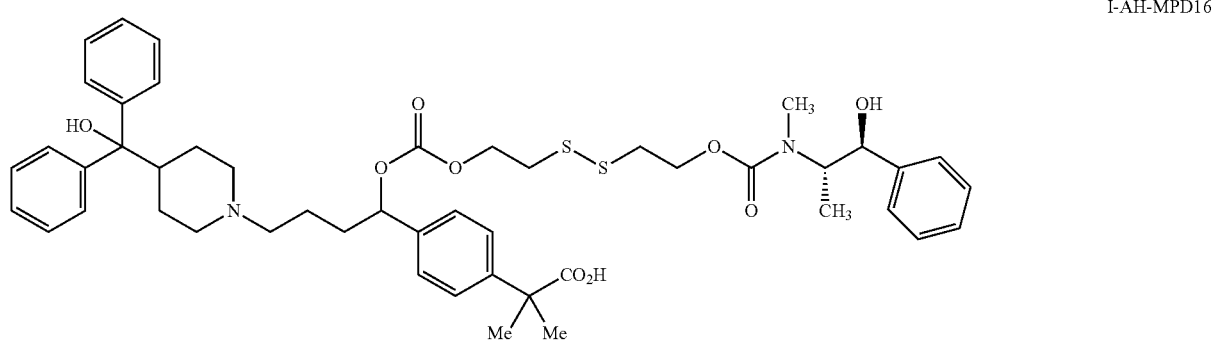
I-AH-MPD17
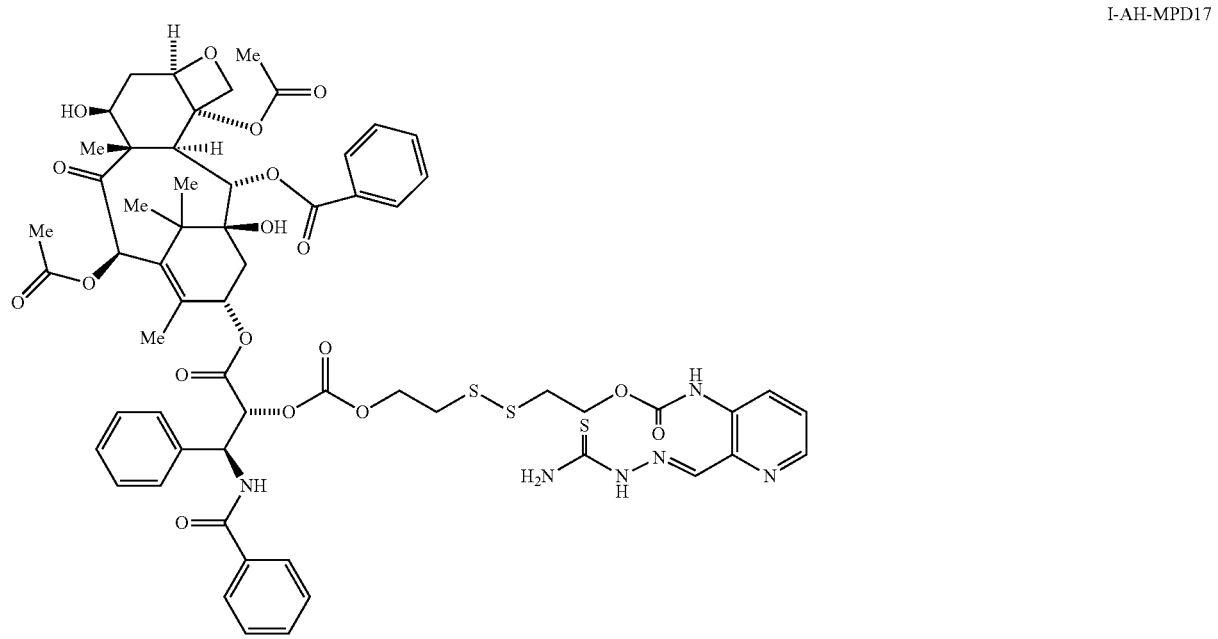

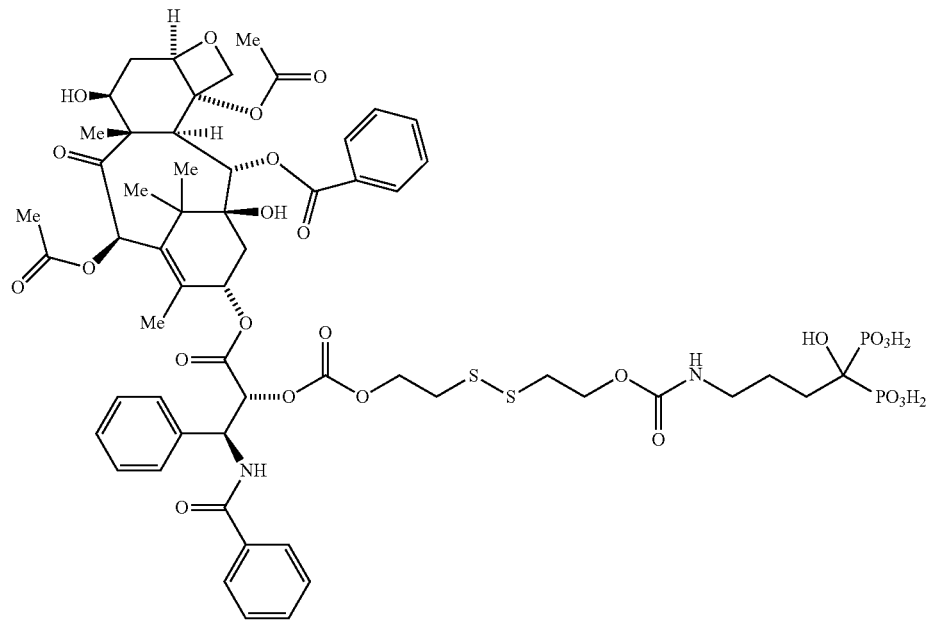
I-AH-MPD18
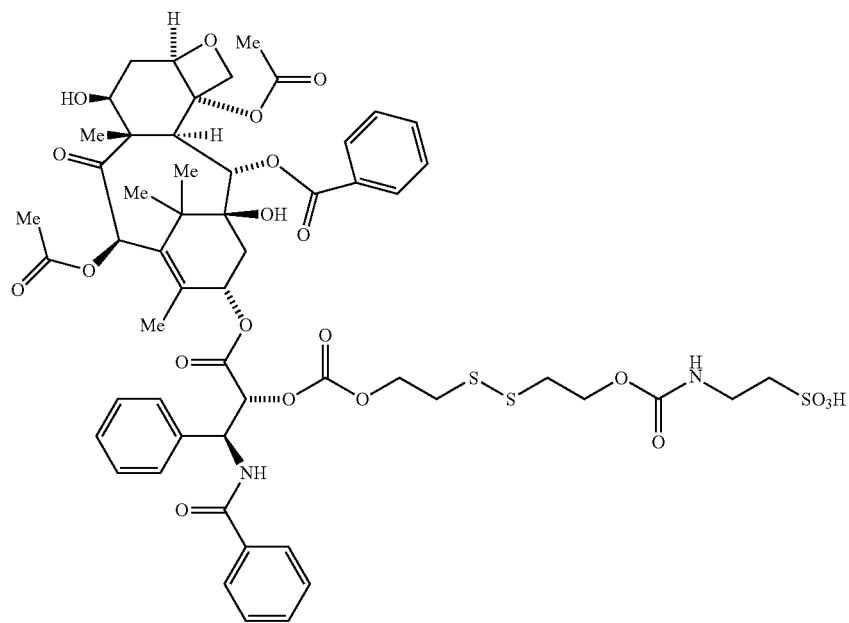
I-AH-MPD19

-continued
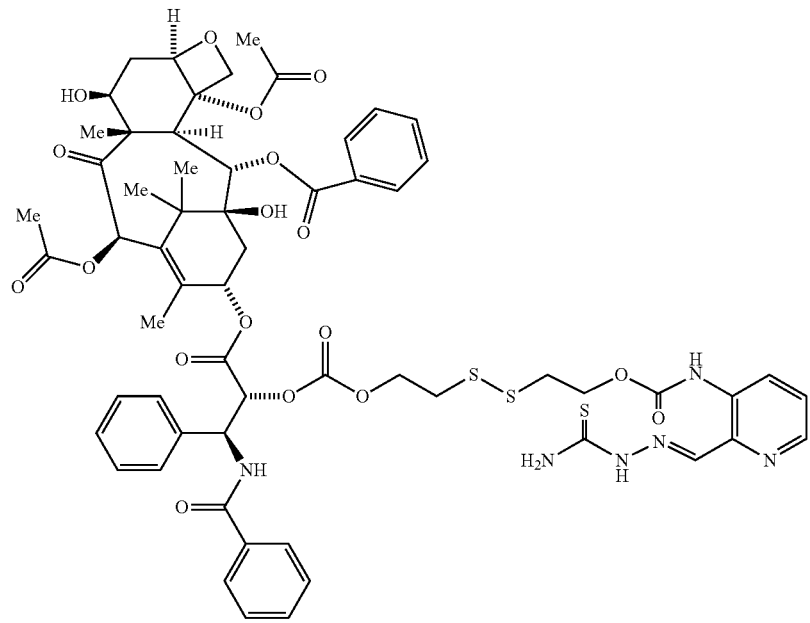
I-AH-MPD20
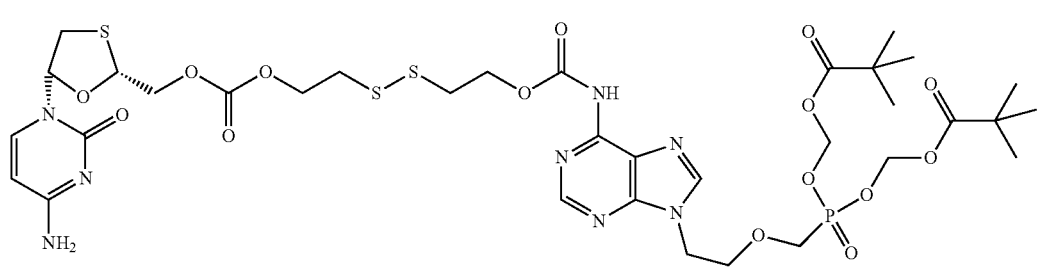
I-AH-MPD21
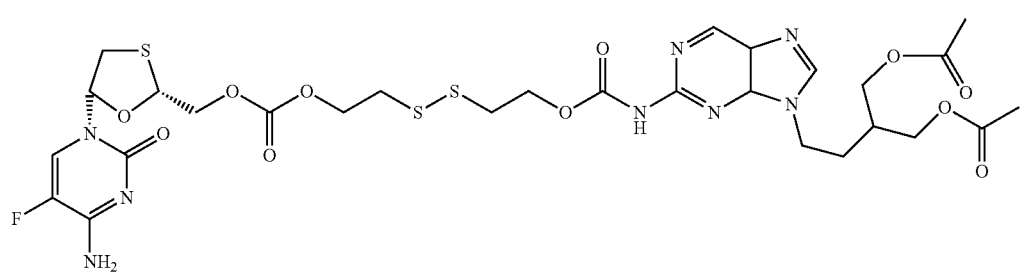
I-AH-MPD22
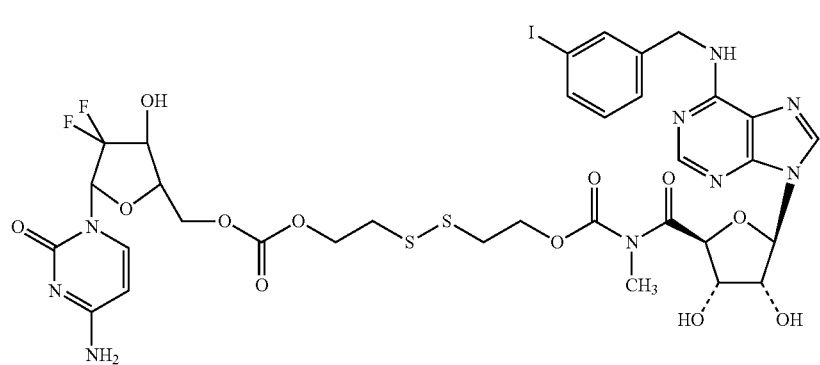
I-AH-MPD23

I-AH-MPD24
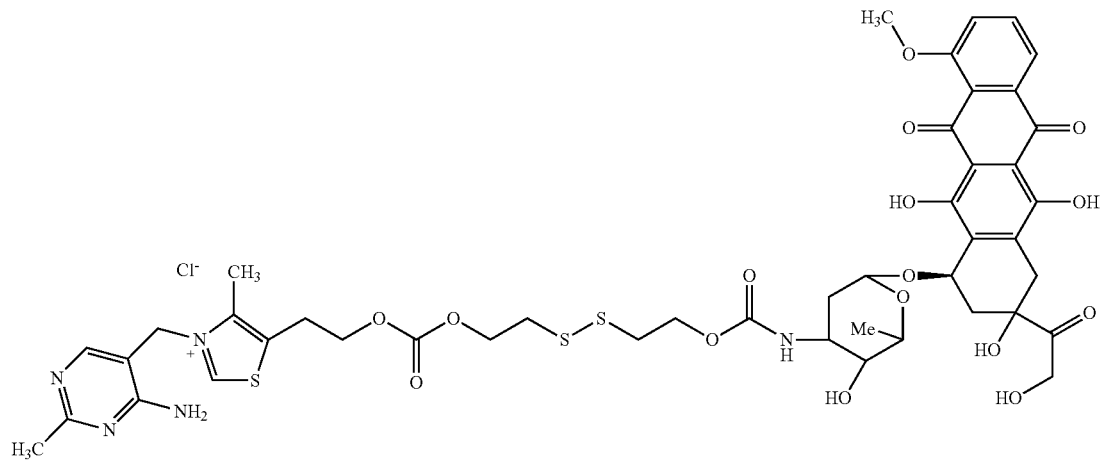
I-AH-MPD25
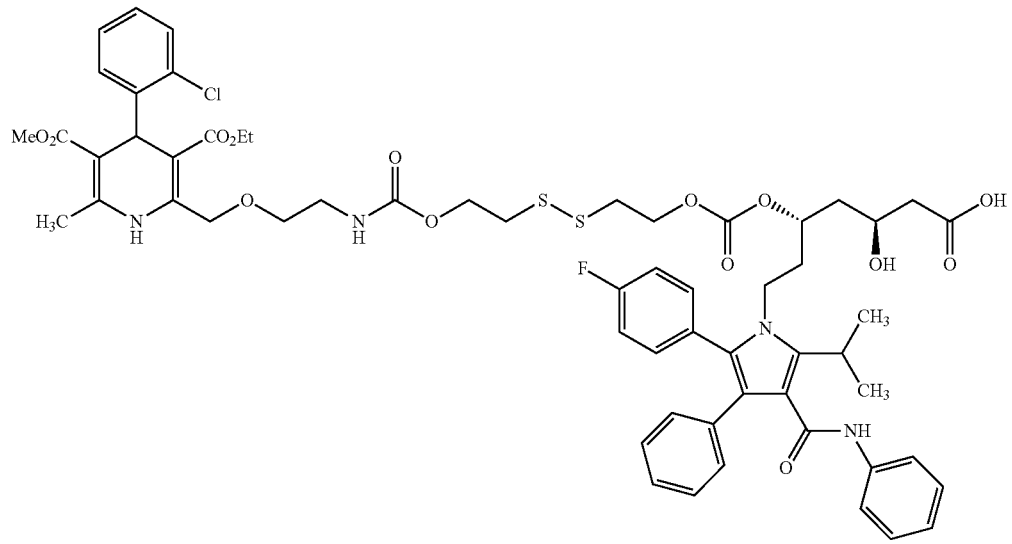
I-AH-MPD26
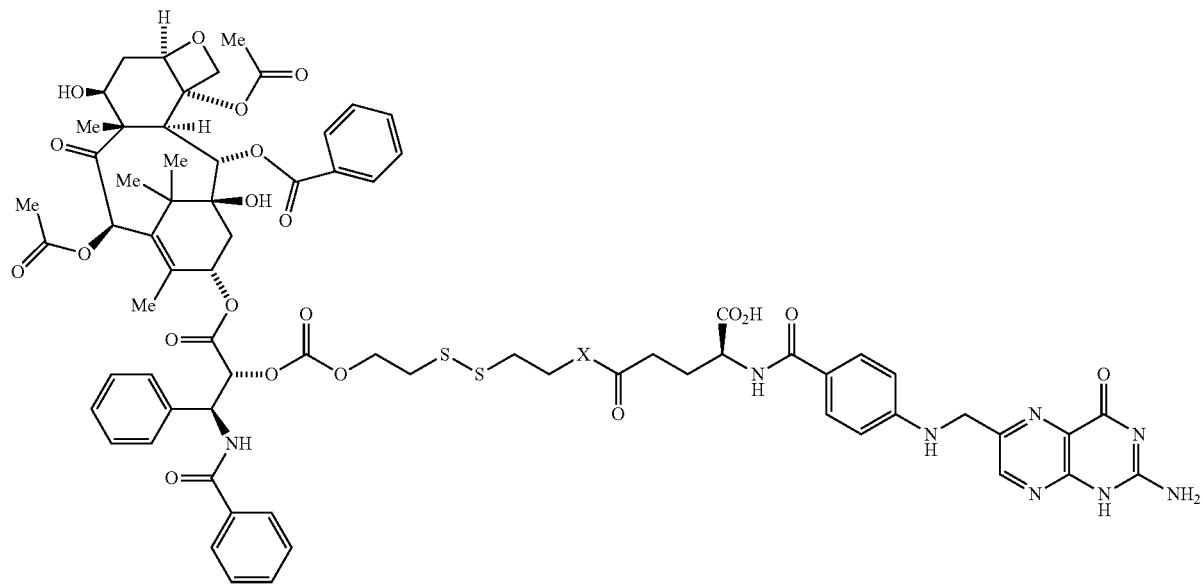

An embodiment of the invention is a pharmaceutical composition comprising a therapeutically effective amount of the compound of formula I, or a pharmaceutical salt thereof and one or more pharmaceutically acceptable carriers, vehicles or diluents.

Another embodiment of the invention is a pharmaceutical composition comprising a therapeutically effective amount of the compound of formula I selected from the group consisting of I-C1-PD1, I-C1-PD2, I-C1-PD3, I-C1-PD4, I-C1-PD4a, I-C1-PD4b, I-C1-PD5, I-C1-PD6, I-C1-PD7, I-C1-PD8, I-C1-PD9, I-C1-PD10, I-C1-PD11, I-C1-PD12, I-C1-PD13, I-C1-PD14, I-C1-PD15a, I-C1-PD15b, 1-A1-PD1, I-A1-PD2, I-A1-PD3, I-A1-PD4, I-A1-PD5, I-A1-PD6, I-A1-PD7, I-A1-PD8, I-A1-PD9, I-A1-PD10, I-A1-PD11, I-A1-PD12, I-A1-PD13, I-A1-PD14, I-A1-PD15A, I-A1-PD15Aa, I-A1-PD15B, I-A1-PD15Bb, I-A1-PD16, I-A1-PD17, I-A2-PD1, I-A2-PD2, I-A2-PD2b, I-A2-PD3a, I-A2-PD3b, 1-A2-PD4, I-A2-PD5, I-A3-PD1, I-A3-PD2a, I-A3-PD2b, I-A3-PD3a, I-A3-PD3b, 1-A3-PD4, I-A3-PD5, I-A3-PD6, I-A3-PD7b, I-H1-PD1, I-H1-PD2, I-H1-PD3, I-H1-PD4, I-H1-PD5, I-H1-PD6, I-H1-PD7, I-H1-PD8, I-H1-PD9, I-H1-PD10, I-H1-PD11, I-H1-PD12, I-H1-PD13, I-Taxol-PD1, I-Taxol-PD2, I-Taxol-PD3, I-Taxol-PD4, I-Taxol-PD5, I-Taxol-PD6, I-S23-PD1, I-C1-NOPD1, I-C1-NOPD2, I-C1-NOPD3a, I-C1-NOPD3b, I-C1-NOPD4, I-C1-NOPD5a, I-C1-NOPD5b, I-C1-NOPD6, I-C1-NOPD7, I-C1-NOPD8a, I-C1-NOPD8b, I-C1-NOPD9, I-C1-NOPD10, I-C1-NOPD11a, I-C1-NOPD13, I-C1-NOPD14a, I-C1-NOPD14b, I-C1-NOPD15b, I-C1-NOPD16, I-C1-NOPD17a, I-C1-NOPD17b, I-C1-NOPD18, I-C1-NOPD19, I-C1-NOPD20a, I-C1-NOPD20b, I-C1-NOPD21, I-C1-NOPD22, I-C1-NOPD23b, I-C1-NOPD24, I-C1-NOPD25, I-C1-NOPD26, I-A1-NOPD1, I-A1-NOPD2, I-A1-NOPD3A, I-A1-NOPD3B, I-A1-NOPD4, I-A1-NOPD5, I-A1-NOPD6, I-A1-NOPD7, I-A1-NOPD8, I-A1-NOPD9, I-A1-NOPD10a, I-A1-NOPD10b, I-A2-NOPD1a, I-A2-NOPD1b, I-A2-NOPD2a, I-A2-NOPD2b, I-A3-NOPD1a, I-A3-NOPD1b, I-A3-NOPD2a, I-A3-NOPD2b, I-H1-NOPD1, I-H1-NOPD2a, I-H1-NOPD2b, I-H1-NOPD3, I-H1-NOPD4, I-H1-NOPD5b, I-H1-NOPD6, I-H1-NOPD7, I-H1-NOPD8, I-H1-NOPD9, I-H1-NOPD10, I-AA-MPD1, I-AA-MPD2, I-AA-MPD3a, I-AA-MPD4, I-AA-MPD5, I-AA-MPD6, I-AA-MPD7, I-AA-MPD8, I-AA-MPD9, I-AA-MPD10, I-AA-MPD11, I-AA-MPD12, I-AA-MPD13, I-AA-MPD14, I-AA-MPD15, I-AA-MPD16, I-AA-MPD17, I-AA-MPD18, I-AA-MPD19, I-AA-MPD20, I-AA-MPD21, I-AA-MPD22, I-AA-MPD23, I-AA-MPD24, I-AA-MPD25, I-AA-MPD26, I-AA-MPD27, I-CC-MPD1, I-CC-MPD2, I-CC-MPD3, I-CC-MPD4, I-CC-MPD5, I-CC-MPD6, I-HH-MPD1, I-HH-MPD2, I-HH-MPD3, I-HH-MPD4, I-HH-MPD5, I-HH-MPD6, I-HH-MPD7, I-HH-MPD8, I-HH-MPD9, I-HH-MPD10, I-HH-MPD11, I-HH-MPD12, I-HH-MPD13, I-HH-MPD14, I-HH-MPD15, I-HH-MPD16, I-HH-MPD17, I-HH-MPD18, I-HHAH-TMPD1, I-CA-MPD1, I-CA-MPD2, I-CA-MPD3, I-CA-MPD4, I-CA-MPD5, I-CA-MPD6, I-CA-MPD7, I-CA-MPD8, I-CA-MPD9, I-CA-MPD10, I-CA-MPD11, I-CA-MPD12, I-CA-MPD13, I-CA-MPD14, I-CA-MPD15, I-CA-MPD16, I-CA-MPD17, I-CA-MPD18, I-CA-MPD19, I-CA-MPD20, I-CA-MPD21, I-CA-MPD22, I-CA-MPD23, I-CA-MPD24, I-CA-MPD25, I-CA-MPD26, I-CA-MPD27, I-CA-MPD28, I-CA-MPD29, I-CA-MPD30, I-AH-MPD1, I-AH-MPD2, I-AH-MPD3, I-AH-MPD4, I-AH-MPD5, I-AH-MPD6, I-AH-MPD7, I-AH-MPD8, I-AH-MPD9, I-AH-MPD10, I-AH-MPD11, I-AH-MPD12, I-AH-MPD13, I-AH-MPD14, I-AH-MPD15, I-AH-MPD16, I-AH-MPD17, I-AH-MPD18, I-AH-MPD19, I-AH-MPD20, I-AH-MPD21, I-AH-MPD22, I-AH-MPD23, I-AH-MPD24, I-AH-MPD25, I-AH-MPD26, I-CH-MPD1, I-CH-MPD2, I-CH-MPD3, I-CH-MPD4, I-CH-MPD5, and I-CH-MPD6 or a pharmaceutical salt thereof and one or more pharmaceutically acceptable carriers, vehicles or diluents.

An embodiment of the invention is a method of treating a mammal or human in need thereof comprising administering a therapeutically effective amount of the pharmaceutical composition comprising the compound of formula I.

Another embodiment of the invention is the below listed novel intermediates:

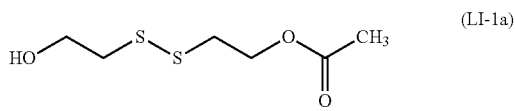

2-((2-Hydroxyethyl)disulfanyl)ethyl acetate (LI-1a)

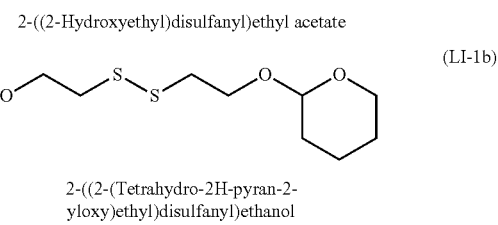

2-((2-(Tetrahydro-2H-pyran-2-yloxy)ethyl)disulfanyl)ethanol (LI-1b)

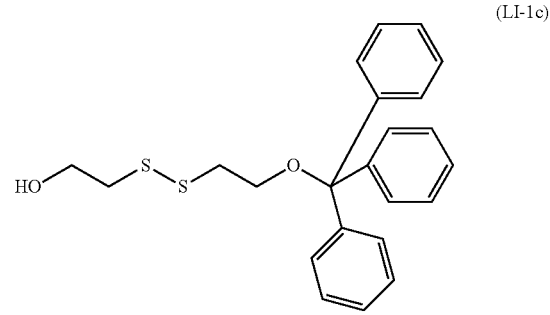

2-((2-(Trityloxy)ethyl)disulfanyl)ethanol (LI-1c)

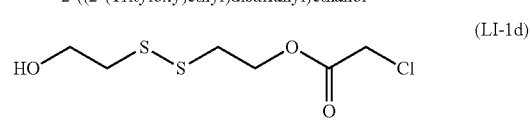

2-((2-Hydroxyethyl)disulfanyl)ethyl 2-chloroacetate (LI-1d)

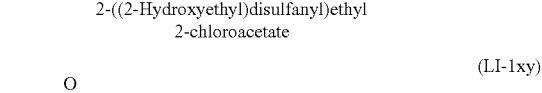

(LI-1xy)

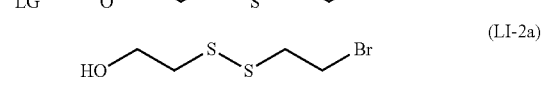

2-((2-Bromoethyl)disulfanyl)ethanol (LI-2a)

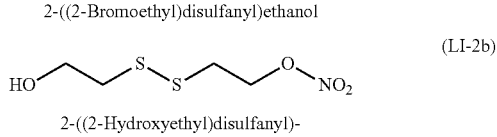

2-((2-Hydroxyethyl)disulfanyl)-ethyl nitrate (LI-2b)

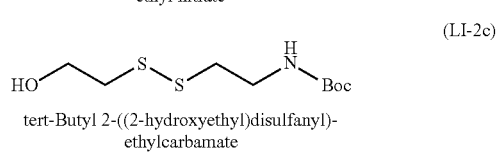

tert-Butyl 2-((2-hydroxyethyl)disulfanyl)-ethylcarbamate (LI-2c)

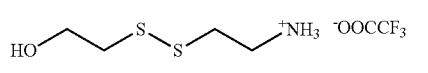
2-((2-Hydroxyethyl)disulfanyl)-
ethyl nitrate
(LI-2c.TFA)

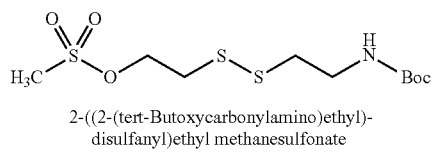
2-((2-(tert-Butoxycarbonylamino)ethyl)-
disulfanyl)ethyl methanesulfonate
(LI-2d)

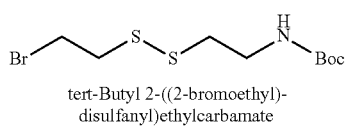
tert-Butyl 2-((2-bromoethyl)-
disulfanyl)ethylcarbamate
(LI-2e)

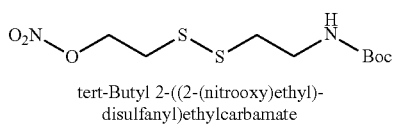
tert-Butyl 2-((2-(nitrooxy)ethyl)-
disulfanyl)ethylcarbamate
(LI-2f)

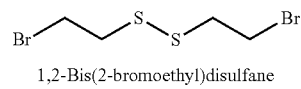
1,2-Bis(2-bromoethyl)disulfane
(LI-3a)

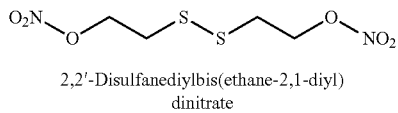
2,2'-Disulfanediylbis(ethane-2,1-diyl)
dinitrate
(LI-3b)

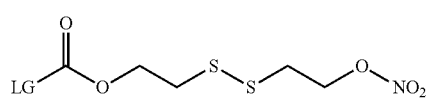
(LI-4x)

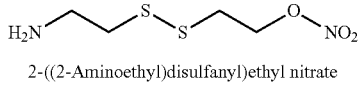
2-((2-Aminoethyl)disulfanyl)ethyl nitrate
(LI-5)

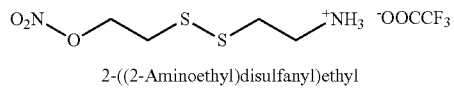
2-((2-Aminoethyl)disulfanyl)ethyl
nitrate.acid salt
(LI-5.TFA)

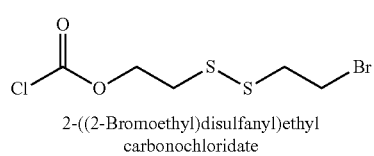
2-((2-Bromoethyl)disulfanyl)ethyl
carbonochloridate
(LI-6)

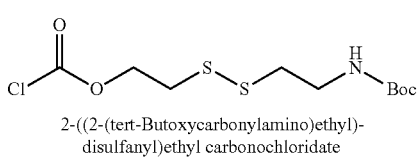
2-((2-(tert-Butoxycarbonylamino)ethyl)-
disulfanyl)ethyl carbonochloridate
(LI-7)

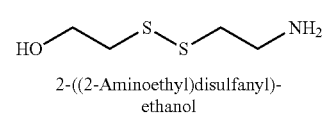
2-((2-Aminoethyl)disulfanyl)-
ethanol
(SL-2)

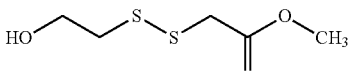
Methyl 2-((2-hydroxyethyl)-
disulfanyl)acetate
(L312a)

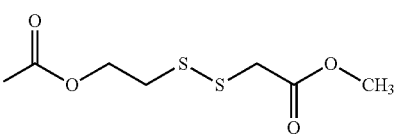
Methyl 2-((2-(chlorocarbonyloxy)-
ethyl)disulfanyl)acetate
(L313a)

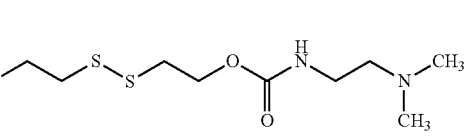
2-Methyl-6-oxo-7-oxa-10,11-dithia-2,5-
diazatridecan-13-yl acetate
(LI-8)

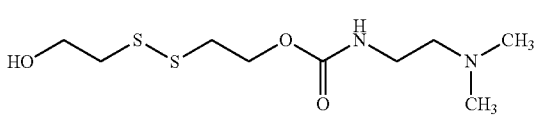
2-((2-Hydroxyethyl)disulfanyl)ethyl 2-
(dimethylamino)ethylcarbamate
(LI-9)

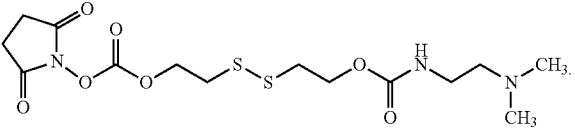
2-((2-((2,5-Dioxopyrrolidin-1-yloxy)carbonyloxy)ethyl)-
disulfanyl)ethyl 2-(dimethylamino)ethylcarbamate
(LI-10)

Another embodiment of the invention is use of the above listed novel intermediates in the processes for the preparation of compounds of formula I.

Further embodiments include methods of preparation and methods of use of compounds of formula (I) or pharmaceutically acceptable salts thereof.

Another embodiment of the invention is process for the preparation of compounds of formula I, or pharmaceutically acceptable salts thereof, wherein the process comprises of:

monoprotection of Bis-(2-hydroxyethyl)disulphide (SL-1) with an appropriate hydroxyl protecting group to give a corresponding monoprotected intermediate, conversion of the corresponding monoprotected intermediate to an activated formyl intermediate by treating with phosgene or its equivalent, and reaction of the activated formyl intermediate with an appropriate amino- or hydroxy containing $D^1$ to give the corresponding compound of formula I.

Another embodiment of the invention is a process for the preparation of compounds of formula I, or pharmaceutically acceptable salts thereof, wherein the process comprises of:

converting carboxy containing D1 into an activated intermediate comprising acyl halide, imidazolide or isocyanate, and reacting the activated intermediate with a linker intermediate to obtain the compound of formula I.

In another embodiment, the invention is a process in which the monoprotected intermediate is LI1x, and the activated formyl intermediate is LI1xy.

Another embodiment of the invention is a process for preparation of compounds of formula (I), wherein $D_2$ is $NO_2$ or pharmaceutically acceptable salts thereof, wherein the process comprises, mixing a selectively protected and activated. D1 with a solution of 2-((2-hydroxyethyl)dithio)ethyl nitrate (LI-2b) in a suitable solvent in presence of a suitable coupling agent.

Another embodiment of the invention is a process for preparation of compounds of formula (I), wherein $D^2$ is $NO_2$ or pharmaceutically acceptable salts thereof, wherein a process comprises, converting 2-((2-hydroxyethyl)dithio)ethyl nitrate (LI-2b) into its formyl halide or imidazolide (LI-4x) by using a phosgene or its equivalent reagent and mixing/reacting the resulting reactive intermediate with a suitable amino- or hydroxy-containing drug in suitable solvent in presence of a suitable base.

Another embodiment of the invention is a process for preparation of compounds of formula (I), wherein $D^2$ is $NO_2$ or pharmaceutically acceptable salt thereof, wherein the process comprises, mixing/reacting a selectively protected and activated drug with a solution of 2-((2-aminoethyl)dithio) ethyl nitrate (LI-5) in a suitable solvent in presence of a suitable coupling agent and/or base.

Another embodiment of the invention is a process for preparation of mutual prodrugs of compounds of formula (I), or pharmaceutically acceptable salts thereof, wherein a process comprises,
A) monoprotection of Bis-(2-hydroxyethyl)disulphide (SL-1) with an appropriate hydroxyl protecting group to give the corresponding monoprotected intermediate LI-1x,
B) reaction of formyl linker intermediate LI-1xy with amino or hydroxyl containing drug ($D^1$) to obtain the prodrug of formula I with free hydroxyl group on the linker,
C) conversion of the intermediate obtained in the step B into activated formyl halide or imidazolide derivative, and
D) reaction of the intermediate obtained in the step C with the drug $D^2$ to obtain the mutual prodrug of formula I.

Further embodiments of the invention are processes for the preparation of compounds of formula I, or pharmaceutically acceptable salts thereof, wherein the processes comprise of the steps that are generally depicted in the schemes 1-23.

Further embodiments include the pharmaceutical composition comprising a therapeutically effective amount of novel intermediates or a pharmaceutically acceptable salt thereof and one or more pharmaceutically acceptable carriers, vehicles or diluents.

Another embodiment of the invention is use of compounds of formula (I) or pharmaceutically acceptable salt thereof, in the treatment of disease conditions originally treatable by the corresponding free drug(s).

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow. The contents of the articles, patents, and patent applications, and all other documents mentioned or cited herein, are hereby incorporated by reference in their entirety to the same extent as if each individual publication was specifically and individually indicated to be incorporated by reference.

Yet another embodiment of the invention is a compound of formula I containing an amino-containing therapeutic agent selected from the group consisting of: I-AA-MPD1, I-AA-MPD2, I-AA-MPD3, and I-AA-MPD4.

Another embodiment of the invention is double prodrug of formula (I) selected from the group consisting of: I-AA-MPD5, I-AA-MPD6, I-AA-MPD7, and I-AA-MPD8.

The present invention also provides mutual prodrugs of formula (I) selected from the group consisting of: I-CA-MPD1, I-CA-MPD2, I-CA-MPD3, I-CA-MPD4, I-CA-MPD5, I-CA-MPD6, I-CA-MPD7, I-CA-MPD8, I-CA-MPD9, I-CA-MPD10, I-CA-MPD11, I-CA-MPD12, I-CA-MPD13, I-CA-MPD14, I-CA-MPD15, I-CA-MPD16, I-CA-MPD17, I-CA-MPD18, I-CA-MPD19, I-CA-MPD20, I-CA-MPD21, I-CA-MPD22, I-CA-MPD23, I-CA-MPD24, I-CA-MPD25, I-CA-MPD26, I-CA-MPD27, I-CA-MPD28, I-CA-MPD29, and I-CA-MPD30.

In another embodiment, the invention provides compounds of formula (I) selected from the group of mutual prodrugs made from amino-containing therapeutic agent and a hydroxyl-containing therapeutic agent such as: I-AH-MPD1, I-AH-MPD2, I-AH-MPD3, I-AH-MPD4, I-AH-MPD5, I-AH-MPD6, I-AH-MPD7, I-AH-MPD8, I-AH-MPD9, I-AH-MPD10, I-AH-MPD11, I-AH-MPD12, I-AH-MPD13, I-AH-MPD14, I-AH-MPD15, I-AH-MPD16, I-AH-MPD17, I-AH-MPD18, I-AH-MPD19, I-AH-MPD20, I-AH-MPD21, I-AH-MPD22, I-AH-MPD23, I-AH-MPD24, I-AH-MPD25, and I-AH-MPD26.

Yet another embodiment of the invention relates to compounds of formula (I) of mutual prodrugs made from a hydroxyl-containing therapeutic agent and a hydroxyl-containing therapeutic agent such as: I-HH-MPD1, I-HH-MPD2, I-HH-MPD3, I-HH-MPD4, I-HH-MPD5, I-HH-MPD6, I-HH-MPD7, I-HH-MPD8, I-HH-MPD9, I-HH-MPD10, I-HH-MPD11, I-HH-MPD12, I-HH-MPD13, I-HH-MPD14, I-HH-MPD15, I-HH-MPD16, I-HH-MPD17, and I-HH-MPD18.

The present invention also provides compounds of formula (I) containing water-soluble prodrugs of insoluble or sparingly-soluble therapeutic agents such as: I-H1-PD1, I-H1-PD2, I-H1-PD3, I-H1-PD4, I-H1-PD5, I-H1-PD6, I-H1-PD7, I-H1-PD8, I-H1-PD9, I-H1-PD10, I-H1-PD11, I-H1-PD12, I-H1-PD13, I-A1-PD1, I-A1-PD2, I-A1-PD3, I-A1-PD4, I-A1-PD5, I-A1-PD6, I-A1-PD7, I-A1-PD8, I-A1-PD9, I-A1-PD10, I-A1-PD11, I-A1-PD12, I-A1-PD13, I-A1-PD14, I-A1-PD15A, I-A1-PD1Aa, I-A1-PD15B, I-A1-PD15Bb, I-A1-PD16, I-A1-PD17, I-A2-PD1, I-A2-PD2, I-A2-PD2b, I-A2-PD3a, I-A2-PD3b, I-A2-PD4, I-A2-PD5, I-A3-PD1, I-A3-PD2a, I-A3-PD2b, I-A3-PD3a, I-A3-PD3b, I-A3-PD4, I-A3-PD5, I-A3-PD6, I-A3-PD7b, I-H1-PD1, I-H1-PD2, I-H1-PD3, I-H1-PD4, I-H1-PD5, I-H1-PD6, I-H1-PD7, I-H1-PD8, I-H1-PD9, I-H1-PD10, I-H1-PD11, I-H1-PD12, I-H1-PD13, I-Taxol-PD1, I-Taxol-PD2, I-Taxol-PD3, I-Taxol-PD4, I-Taxol-PD5, I-Taxol-PD6, and I-S23-PD1.

Another embodiment of the invention relates to the compounds of formula (I), selected from the group of NO-releasing prodrugs consisting of: I-C1-NOPD1, I-C1-NOPD2, I-C1-NOPD3a, I-C1-NOPD3b, I-C1-NOPD4, I-C1-NOPD5a, I-C1-NOPD5b, I-C1-NOPD6, I-C1-NOPD7, I-C1-NOPD8a, I-C1-NOPD8b, I-C1-NOPD9, I-C1-NOPD10, I-C1-NOPD11a, I-C1-NOPD13, I-C1-NOPD14a, I-C1-NOPD14b, I-C1-NOPD15b, I-C1-NOPD16, I-C1-NOPD17a, I-C1-NOPD17b, I-C1-NOPD18, I-C1-NOPD19, I-C1-NOPD20a, I-C1-NOPD20b, 1-C1-NOPD21, I-C1-NOPD22, I-C1-NOPD23b, I-C1-NOPD24, I-C1-NOPD25, I-C1-NOPD26, I-A1-NOPD1, I-A1-NOPD2, I-A1-NOPD3A, I-A1-NOPD3B, I-A1-NOPD4, I-A1-NOPD5, I-A1-NOPD6, I-A1-NOPD7, I-A1-NOPD8, I-A1-NOPD9, I-A1-NOPD10a, I-A1-NOPD10b, I-A2-NOPD1a, I-A2-NOPD1b, I-A2-NOPD2a, I-A2-NOPD2b, I-A3-NOPD1a, I-A3-NOPD1b, I-A3-NOPD2a, I-A3-NOPD2b, I-H1-NOPD1, I-H1-NOPD2a, I-H1-NOPD2b, I-H1-NOPD3, I-H1-NOPD4, I-H1-NOPD5b, I-H1-NOPD6, I-H1-NOPD7, I-H1-NOPD8, I-H1-NOPD9, I-H1-NOPD10.

Another aspect of the invention provides the use of the compounds of formula (I) in combination with a compound used to treat cardiovascular diseases selected from the group consisting of: beta adrenergic blockers, calcium channel blockers, angiotensin II receptor antagonists, antithrombotics, HMGCoA reductase inhibitors, aspirin or nitrooxy derivatives of aspirin, nitrosated beta blockers, nitrosated or nitrosilated calcium channel blockers. Suitable drugs are described in the literature such as the Merck Index, IDdb, Prous Science's Integrity®, Prous Science Drugs of the Future™, The Ensemble® and the like.

Another aspect of the invention provides the use of the pharmaceutical compositions containing compounds of formula (I) in combination with a compound, used to treat other diseases such as cardiovascular diseases, selected from beta adrenergic blockers, calcium channel blockers, angiotensin II receptor antagonists, antithrombotics, HMGCoA reductase inhibitors, aspirin or nitrooxy derivatives of aspirin, nitrosated beta blockers, nitrosated or nitrosilated calcium channel blockers. Pharmaceutical compositions containing two or more of compounds of the invention can be used for the purpose of combination therapy. These pairs of compounds of invention can be from the same therapeutic area or from different therapeutic areas for treating one or more diseases or conditions.

The compounds of the invention, which have one or more asymmetric carbon atoms, can exist as the optically pure enantiomers, pure diastereomers, enantiomer racemic mixtures, diastereomer racemic mixtures, racemates or racemate mixtures. Within the scope of the invention are also all the possible isomers, stereoisomers and their mixtures of the compounds of formula (I).

Another embodiment of the invention relates to the pharmaceutical composition comprising one or more compounds of formula (I) or pharmaceutically acceptable salts thereof and one or more pharmaceutically acceptable carriers, vehicles or diluents.

Another embodiment of the invention relates to the pharmaceutical composition comprising one or more compounds of formula (I) or pharmaceutically acceptable salts thereof and at least another pharmaceutically active compound. The pharmaceutically active compound can be from the same or different therapeutic areas for treating one or more disease condition(s) together with one or more pharmaceutically acceptable carriers, vehicles or diluents.

Further embodiments include methods of use of compounds of formula (I) or pharmaceutically acceptable salts thereof.

Another embodiment of the invention is a process for preparation of compounds of formula (I) or pharmaceutically acceptable salts thereof, wherein the process comprises, mixing a selectively protected and activated drug with a solution of 2-((2-hydroxyethyl)dithio)ethyl nitrate in a suitable solvent in presence of a suitable coupling agent. Another embodiment of the invention is a compound or intermediate generated in the above methods and processes.

Another embodiment of the invention is a process for preparation of compounds of formula (I) or pharmaceutically acceptable salts thereof, wherein a process comprises, converting 2-((2-hydroxyethyl)dithio)ethyl nitrate into its formyl halide or imidazolide by using a phosgene or its equivalent reagent and mixing/reacting the resulting reactive intermediate with a suitable drug in suitable solvent in presence of a suitable base.

Another embodiment of the invention is a process for preparation of compounds of formula (I) or pharmaceutically acceptable salt thereof, wherein the process comprises, mixing/reacting a selectively protected and activated drug with a solution of 2-((2-aminoethyl)dithio)ethyl nitrate (or its acid salt) in a suitable solvent in presence of a suitable coupling agent and/or base.

Another embodiment of the invention comprises the novel intermediates formed in the preparation of present invention. Further embodiments include a pharmaceutical composition comprising a therapeutically effective amount of novel intermediates or a pharmaceutically acceptable salt thereof and one or more pharmaceutically acceptable carriers, vehicles or diluents.

Another embodiment of the invention is processes for the preparation of compounds of formula (I) or pharmaceutically acceptable salt thereof, as well as the starting materials and intermediates involved as depicted in schemes 1-23.

Another embodiment of the invention the novel intermediates obtained in the preparation of compounds of formula I, wherein the intermediates are selected from:

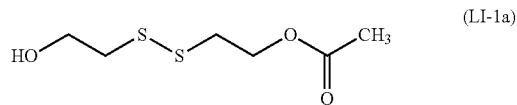

2-((2-Hydroxyethyl)disulfanyl)ethyl acetate (LI-1a)

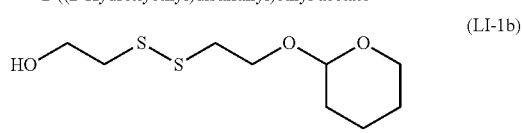

2-((2-(Tetrahydro-2H-pyran-2-yloxy)ethyl)disulfanyl)ethanol (LI-1b)

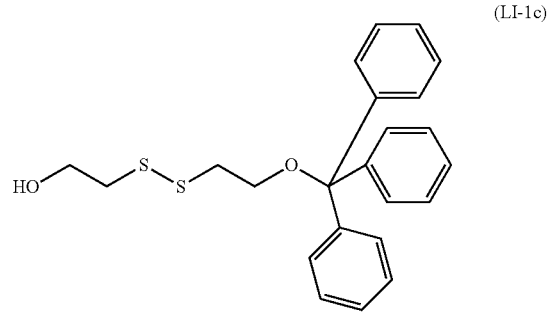

2-((2-(Trityloxy)ethyl)disulfanyl)ethanol (LI-1c)

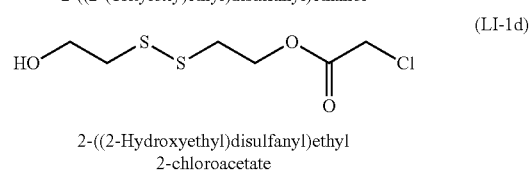

2-((2-Hydroxyethyl)disulfanyl)ethyl 2-chloroacetate (LI-1d)

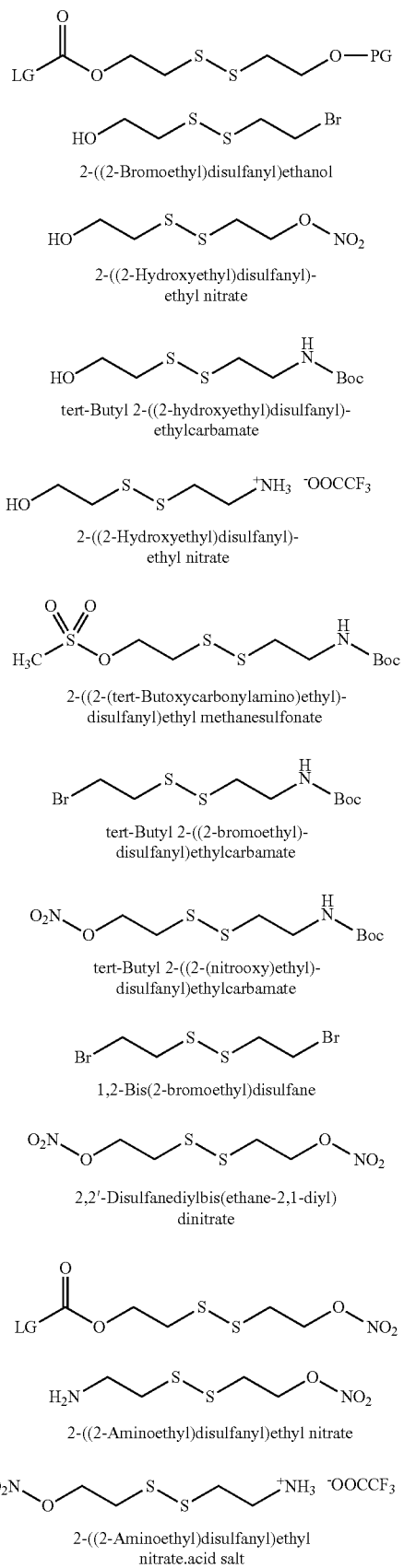
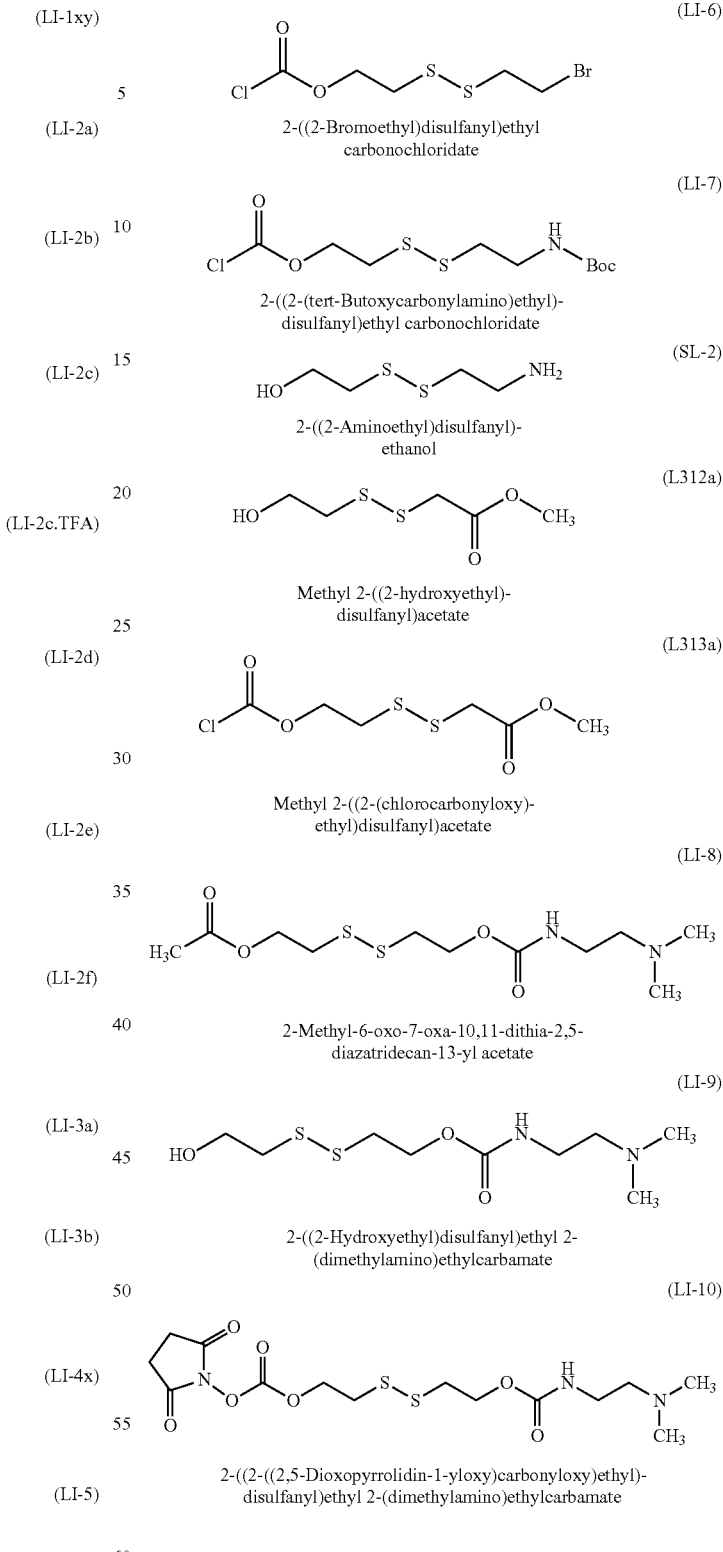

Another embodiment of the invention is use of compounds of formula (I) or pharmaceutically acceptable salts thereof, in the treatment of disease conditions originally treatable by the corresponding free drugs.

Another embodiment of the invention includes but not limited to a pharmaceutical composition comprising the compounds of formula (I), or pharmaceutically acceptable salts thereof, selected from the group of NO-releasing prodrugs described herein, and one or more pharmaceutically acceptable carriers, vehicles or diluents.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow. The contents of the articles, patents, and patent applications, and all other documents mentioned or cited herein, are hereby incorporated by reference in their entirety to the same extent as if each individual publication was specifically and individually indicated to be incorporated by reference.

Potential Examples of Mutual Prodrugs/Codrugs

Mutual prodrugs made from an amino-containing therapeutic agent and another amino-containing therapeutic agent:

A Mutual Prodrug of desloratadine and pseudoephedrine (I-AA-MPD1) is proposed as a potential treatment option for seasonal allergic rhinitis (SAR). Desloratadine (an active metabolite of loratadine) is a new, non-sedating, long-acting histamine antagonist and has been shown effective in the treatment of nasal and non-nasal symptoms associated with SAR. Pseudoephedrine is an oral decongestant.

A Mutual Prodrug of amlodipine (Pfizer's Norvasc®) and lisinopril (Zeneca's Zestril®) (I-AA-MPD2) is proposed as a potential treatment option for hypertension and congestive heart failure. Amlodipine is a calcium channel blocker and is used as an antihypertensive and antianginal agent. Lisinopril is an angiotensin-converting enzyme (ACE) inhibitor and is used for the treatment of hypertension and congestive heart failure. A combination therapy using these two drugs has been proven to be more effective treatment option than monotherapy using either of these drugs.

A Mutual Prodrug of amlodipine (Pfizer's Norvasc®) and losartan (Merck's Cozaar®) (I-AA-MPD3a) is proposed as a potential treatment option for mild to moderate hypertension. Amlodipine is a calcium channel blocker and is used as an antihypertensive and antianginal agent. Losartan potassium is an angiotensin II blocker and is used for the treatment of hypertension. A combination therapy using these two drugs has been proven to be more effective treatment option than monotherapy using either of these drugs.

Examples of mutual prodrugs and double prodrugs of valdecoxib and celecoxib containing a disulfide linker are: I-AA-MPD4 and I-AA-MPD5.

Examples of double prodrugs of valdecoxib or celecoxib containing non-disulfide linkers: I-AA-MPD6, I-AA-MPD7, I-AA-MPD8.

A Mutual Prodrug of fluoxetine (Lilly's Prozac®) and olanzapine (Lilly's Zyprexa®) (I-AA-MPD9) is proposed for potential treatment of patients with Bipolar disorder. Fluoxetine and Olanzapine are used in combination to treat patients with bipolar disorder while being spared the treatment-emergent mania that such patients often get on antidepressant monotherapy.

Example of double prodrug of gabapentin is proposed as potential antiepileptic agent: I-AA-MPD10.

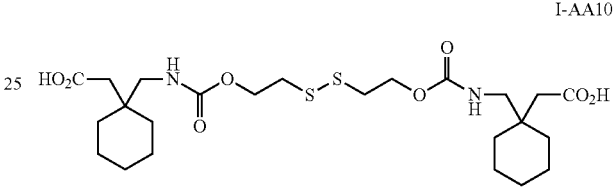

I-AA10

Mutual Prodrugs Made from an Amino-Containing Therapeutic Agent and a Carboxyl-Containing Therapeutic Agent:

A mutual prodrug of cetirizine and pseudoephedrine (I-CA-MPD1) is proposed for treatment of rhinitis. Cetirizine is an antihistamine and pseudoephedrine is a nasal decongestant.

Mutual prodrugs of gabapentin and valproic acid are potential antiepileptic agents. This same kind of prodrug may be a potential treatment option for patients with bipolar disorder and other mental illnesses. The following are some of the examples:

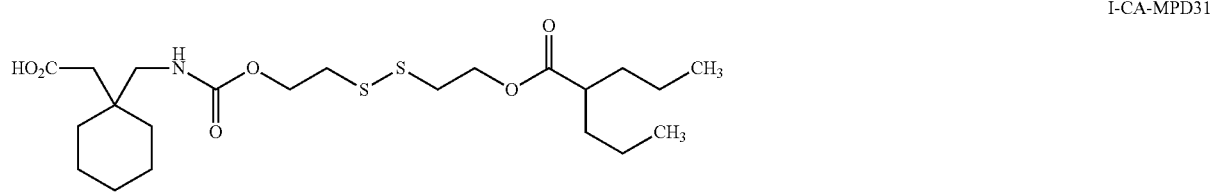

I-CA-MPD31

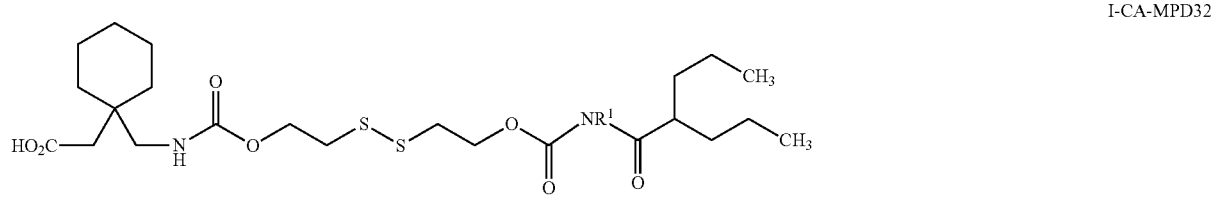

I-CA-MPD32

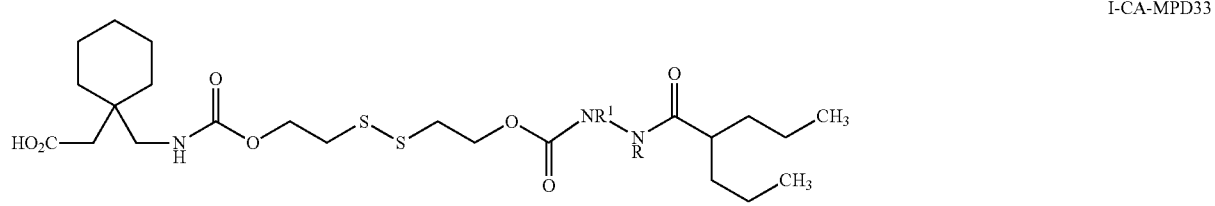

I-CA-MPD33

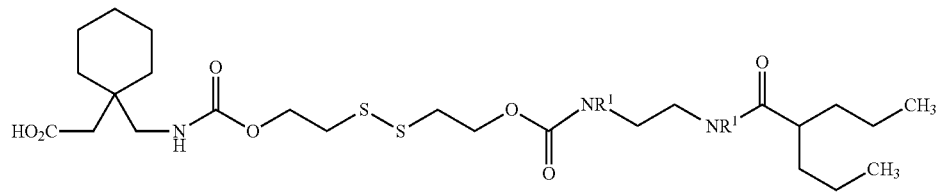
I-CA-MPD34
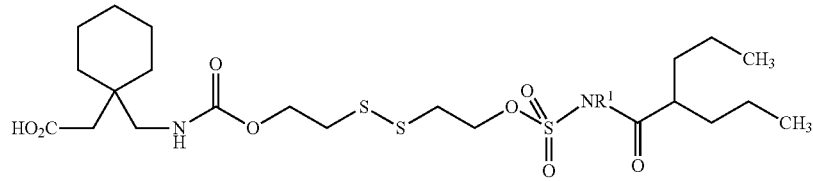
I-CA-MPD34
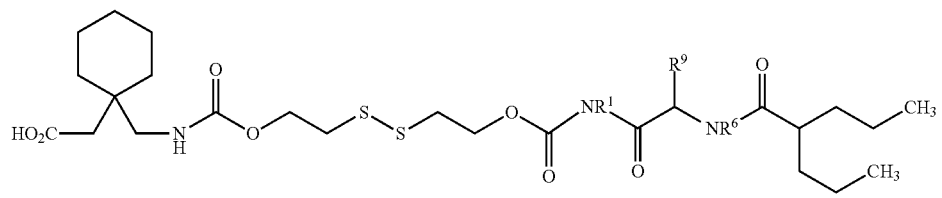
I-CA-MPD35
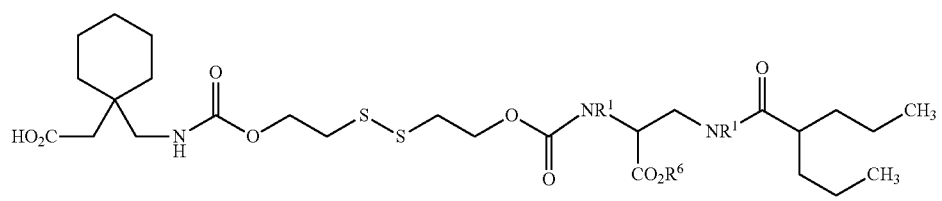
I-CA-MPD36
I-CA-MPD37      I-CA-MPD38
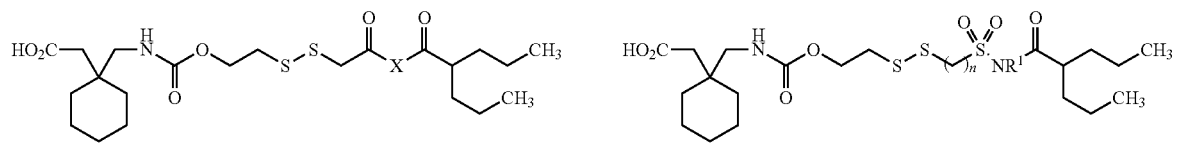
n = 1-4
I-CA-MPD39
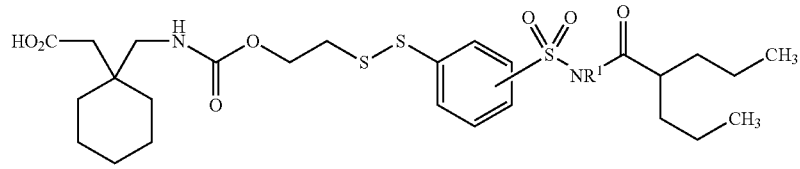
I-CA-MPD40
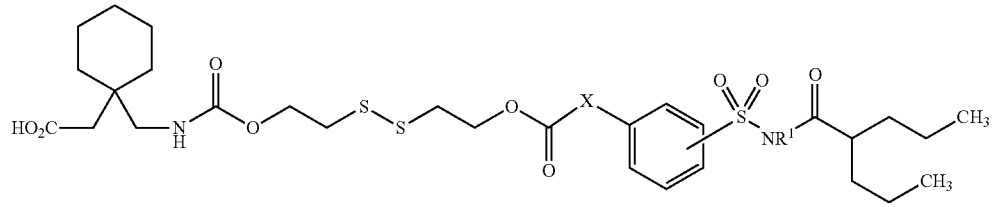
I-CA-MPD41
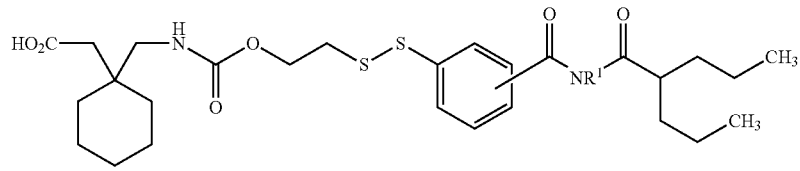

I-CA-MPD42

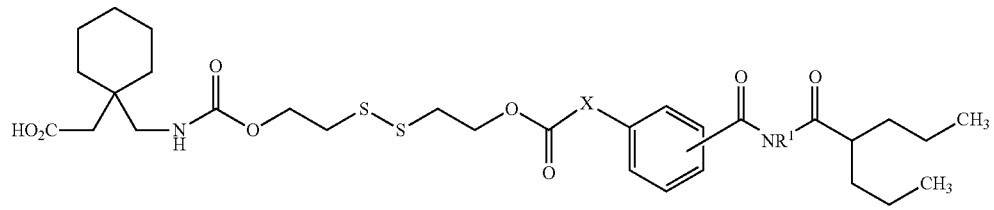

I-CA-MPD43

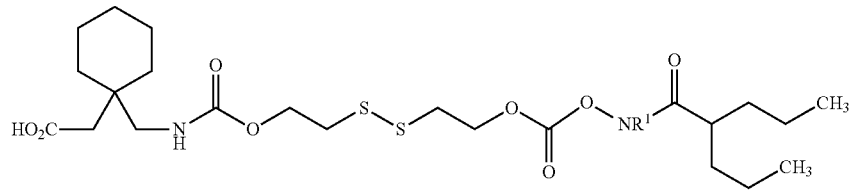

I-CA-MPD44

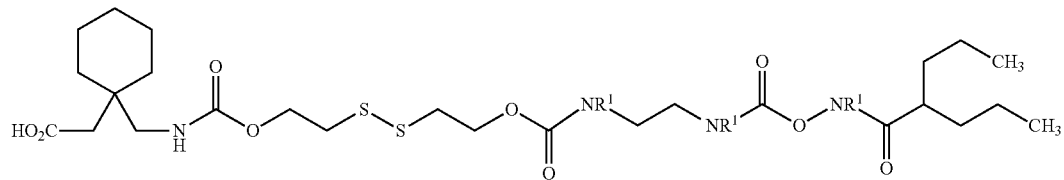

Other illustrative examples of mutual prodrugs under this category include the following: Mutual prodrugs of valproic acid and other carboxyl-, hydroxyl-, and amino-containing (including amide-, and sulfonamide-containing) anticonvulsant agents such as levetiracetam, lamotrigine, pregabalin, carbamazepine, oxcarbamazepine, licarbazepine, felbamate, topiramate and the like. (Structures are given below). The list also includes investigational antiepileptic agents such as antipamezole, licarbazepine, Eslicarbazepine Acetate (BIA 2-093), fluorofelbamate, isovaleramide (NPS 1776), retigabine (D-23129), safinamide (NW-1015), stiripentol (STP), talampanel (TLP), (2S)-2-[(4R)-2-oxo-4-propylpyrrolidin-1-yl]butanamide 83alpha (ucb 34714), valrocemide (TV 1901), and the like.

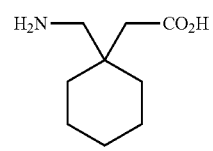

GABAPENTIN

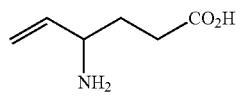

VIGABATRIN

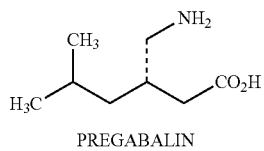

PREGABALIN

-continued

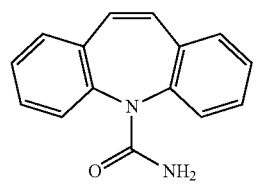

CARBAMAZEPINE

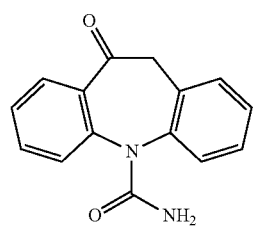

OXCARBAMAZEPINE

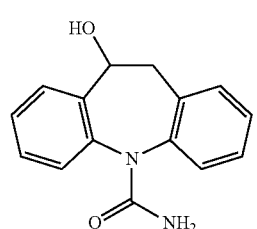

LICARBAZEPINE

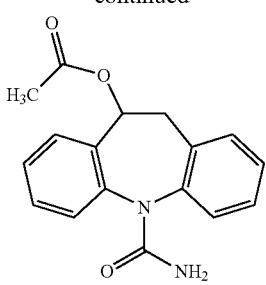

BIA 2-093

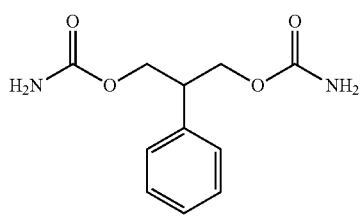

FELBAMATE

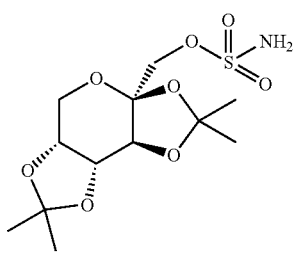

TOPIRAMATE

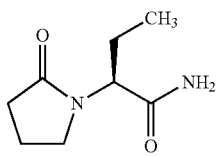

LEVETIRACETAM

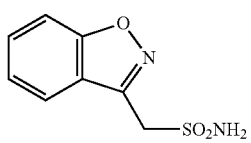

ZONISAMIDE

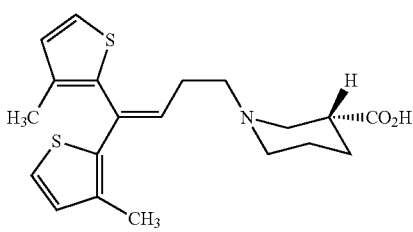

TIAGABINE

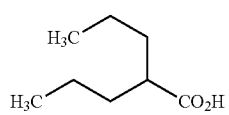

VALPROIC ACID

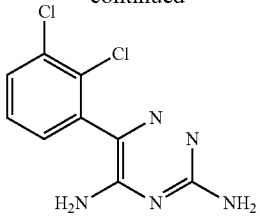

LAMOTRIGINE

Mutual Prodrugs can be made from combination of any two anti-convulsant agents listed above or any other suitable anticonvulsant agents.

Mutual prodrug of gabapentin and naproxen (I-CA-MPD22) is proposed for potential treatment option for neurological pain and inflammation.

Mutual Prodrugs Made from an Amino-Containing Therapeutic Agent and a Hydroxyl-Containing Therapeutic Agent:

Mutual prodrugs of norfloxacin and metronidazole (I-AH-MPD1, I-AH-MPD2, I-AH-MPD3) are proposed for potential treatment of diarrhea and dysentery of bacterial, amoebic and mixed origin. Metronidazole is an antianaerobic agent and used in combination with antibiotics such as norfloxacin, ciprofloxacin, etc. for the treatment of patients with diarrhea and dysentery of bacterial, amoebic and mixed origin.

A mutual prodrug of loperamide and norflaxacin (I-AH-MPD4) is proposed for potential treatment of diarrhea and dysentery.

A mutual prodrug of valdecoxib and tramadol (I-AH-MPD5 and I-AH-MPD6) as a potential therapy in postoperative pain management.

A mutual prodrug of gabapentin and tramadol (I-AH-MPD7) is proposed for potential treatment of neuropathic pain after spinal cord injury.

A mutual prodrug of venlafaxine and paroxetine (I-AH-MPD8) is proposed for potential treatment of neurological and depression related disorders.

Mutual Prodrugs Made from a Hydroxyl-Containing Therapeutic Agent and Another Hydroxyl-Containing Therapeutic Agent:

Mutual prodrugs of zidovudine (AZT/Retrovir) and lamivudine (3TC/Epivir) (I-HH-MPD1, I-HH-MPD2) are proposed as a potential treatment option for HIV and other viral infections.

Potential Examples of Water-Soluble Prodrugs

Water-soluble prodrugs of insoluble/sparingly-soluble therapeutic agents can be prepared using the same linker technology.

Water-soluble prodrugs of metronidazole include: I-H1-PD-2, I-H1-PD-3, I-H1-PD-4.

Water-soluble prodrugs of valdecoxib include: I-A3-PD1, I-A3-PD2a, I-A3-PD2b, I-A3-PD3a, I-A3-PD3b, I-A3-PD4, I-A3-PD5, I-A3-PD6, and I-A3-PD7b.

Water-soluble prodrugs of paclitaxel include: I-Taxol-PD1, I-Taxol-PD2,1-Taxol-PD3, I-Taxol-PD4, I-Taxol-PD5, I-Taxol-PD6, and I-S23-PD1.

Potential Examples of NO-Releasing Prodrugs

In the following potential examples, X is O, $NR^1$ ($R^1$=H, alkyl) or a bond; Y is CO, $SO_2$, $P(=O)XR^1$ or bond; $R^1$ is H, alkyl, aralkyl, or a metal ion; A is a bond, 1,4-/1,3-/1,2-phenylene or $(CH_2)_o$ (o=0-6) and m is 1-2 unless otherwise stated;

Prodrugs of Valproic Acid (Anticonvulsant):
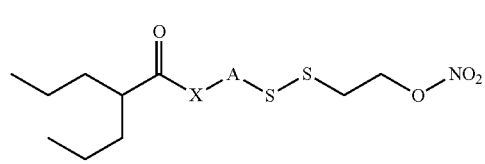 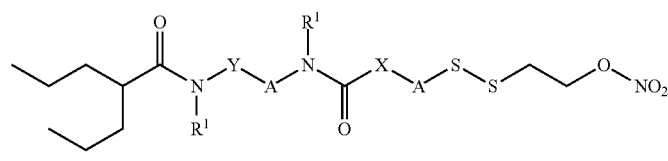
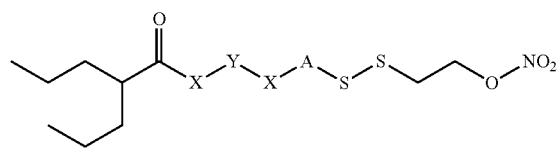 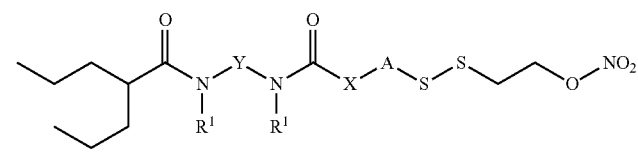
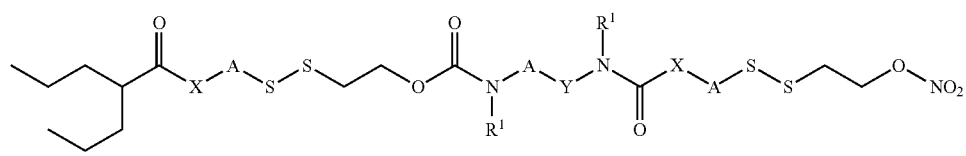
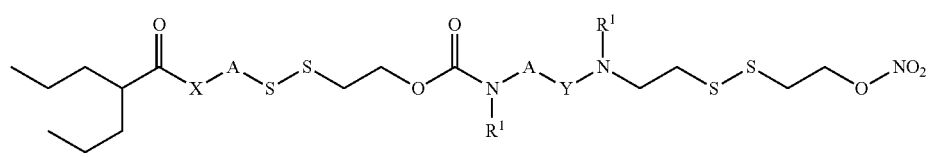
Drugs Containing Reactive Primary and Secondary Amines, Amide-NH, Urea-NH, Sulfonamide-NH, Sulfamate-NH, and Carbamate-NH:
Prodrugs of Gabapentin (Anticonvulsant):
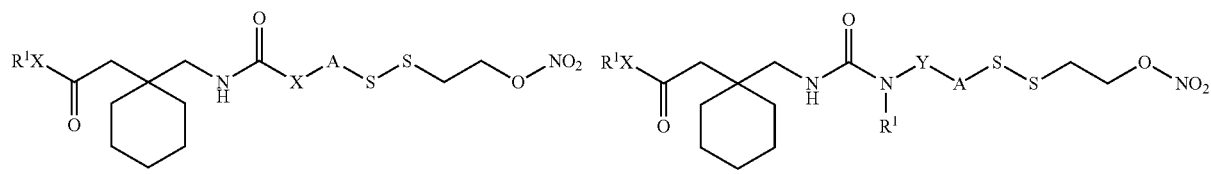 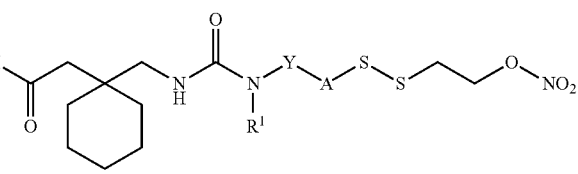
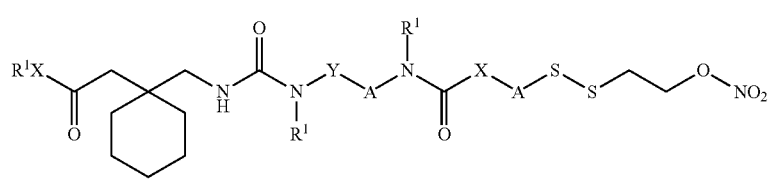
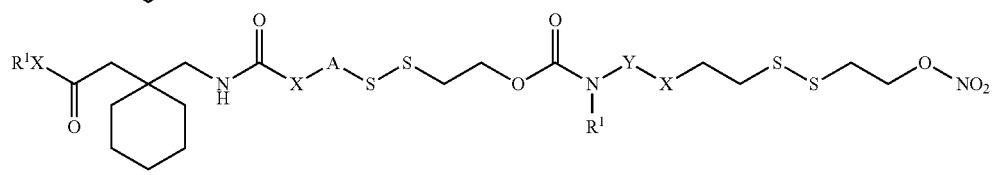
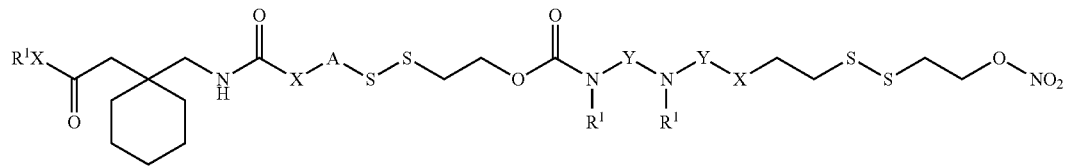

Prodrugs of Lamotrigine (Anticonvulsant):
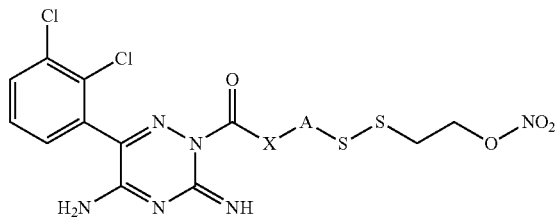
Prodrugs of Carbamazepine (Anticonvulsant):
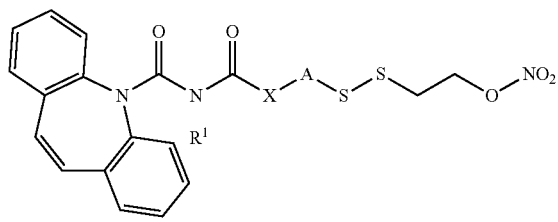
Prodrugs of Levetiracetam (Anticonvulsant):
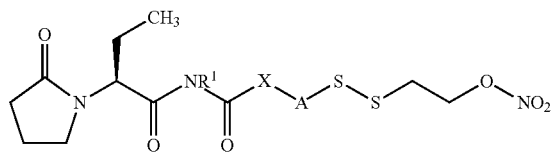
Prodrugs of Felbamate (Anticonvulsant):
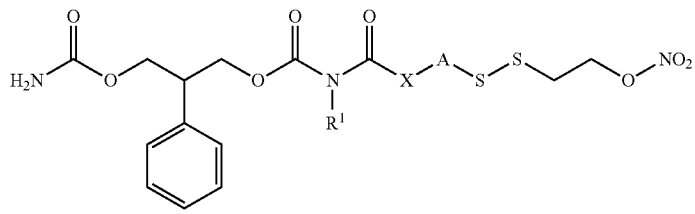
Prodrugs of Topiramate (Anticonvulsant):
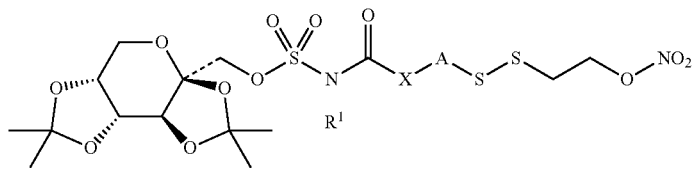
Prodrugs of Celecoxib (Cox-2 Inhibitor):
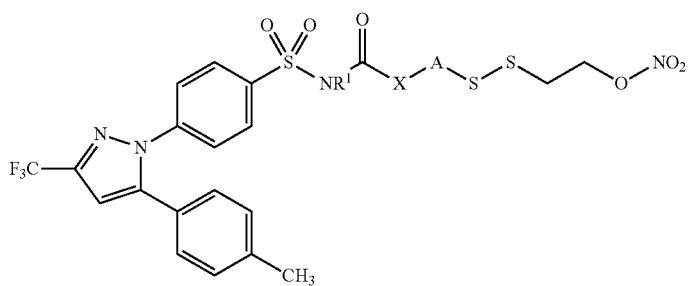

Prodrugs of Celecoxib (Cox-2 Inhibitor:
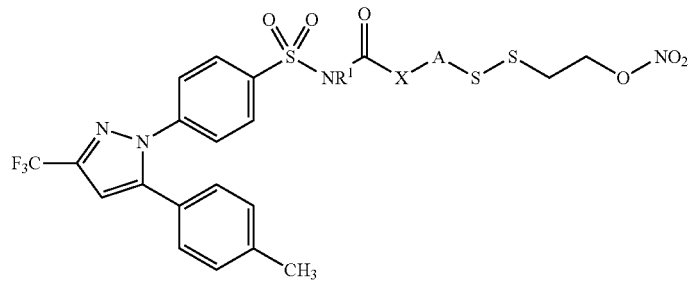
NO-Releasing Prodrugs of Paracetamol/Acetaminophen (Analgesic and Antipyretic):
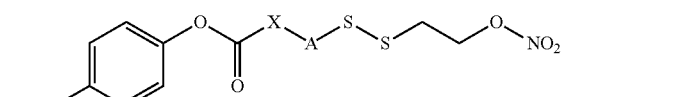
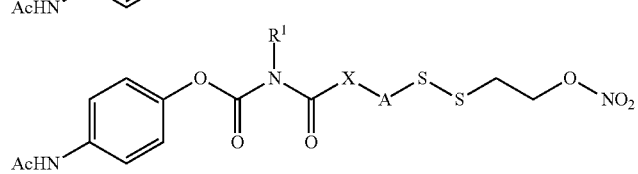
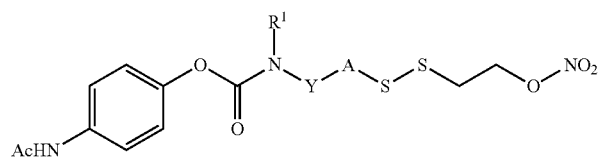
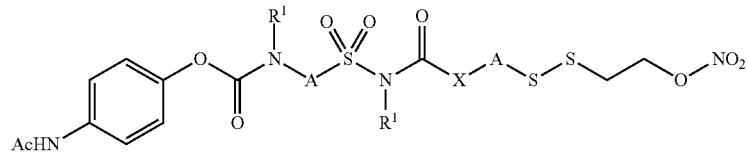
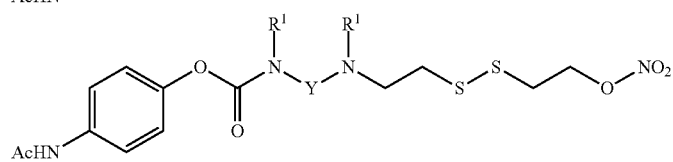
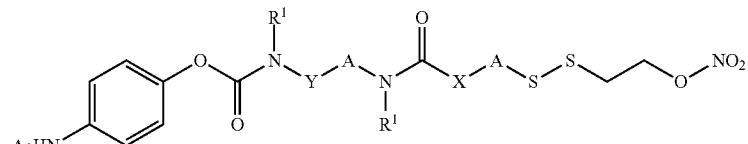
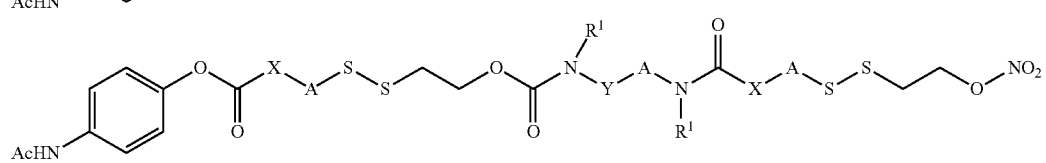
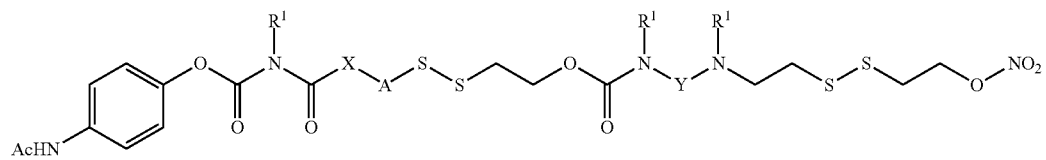

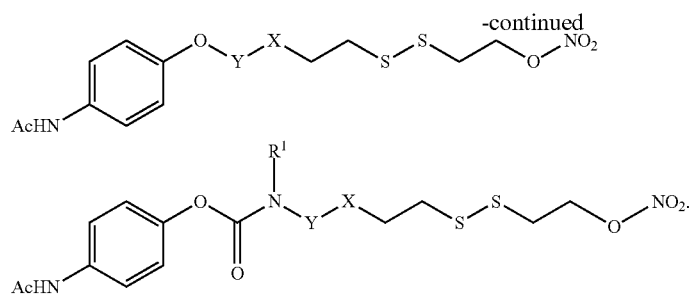
Additional Potential Examples
In the following additional potential examples, X is O, NR$^1$ (R$^1$=H, alkyl) or a bond; Y is CO, SO$_2$, P(=O)XR$^1$ or bond; R$^1$ is H, alkyl, aralkyl, or a metal ion; A is a bond, 1,4-/1,3-/1,2-phenylene or (CH$_2$)$_o$ (o=0-6) and m is 1-2 unless otherwise stated;
NO-Releasing Prodrugs of Nicotinamide:
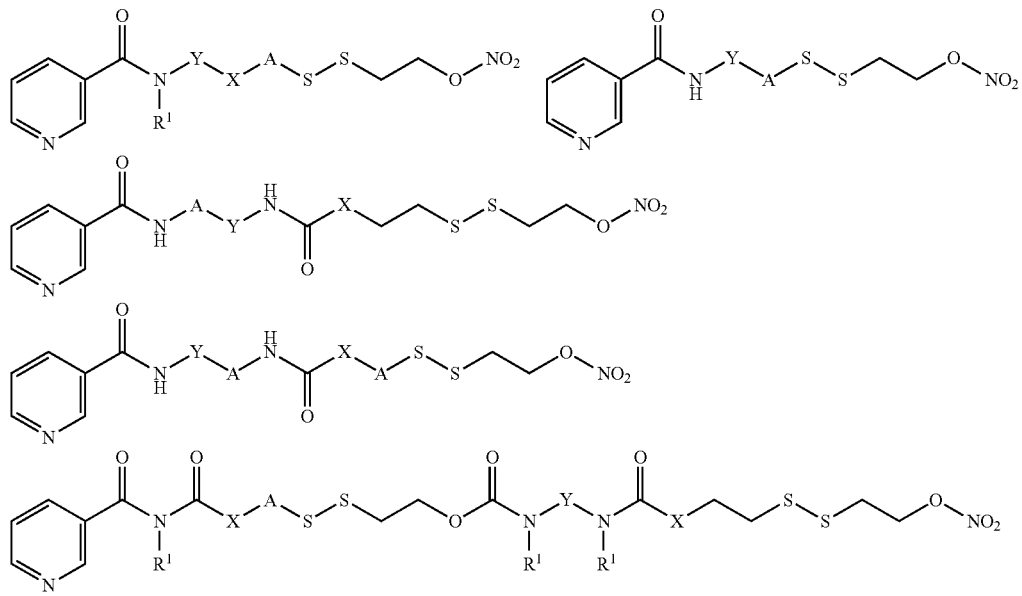
NO-Releasing Prodrugs of NSAIDs:
NO-Releasing Prodrugs of Aspirin
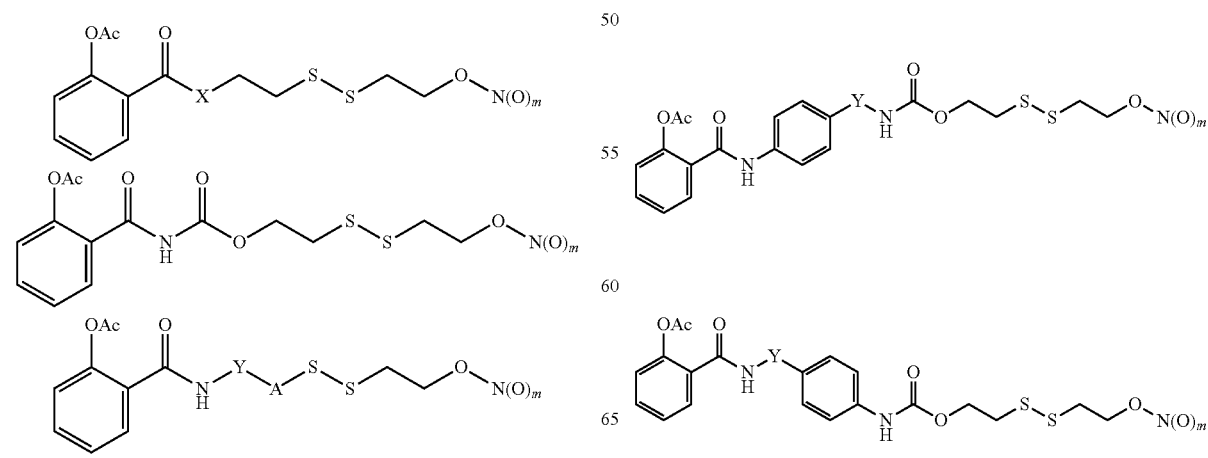

NO-Releasing Prodrugs of Paracetamol
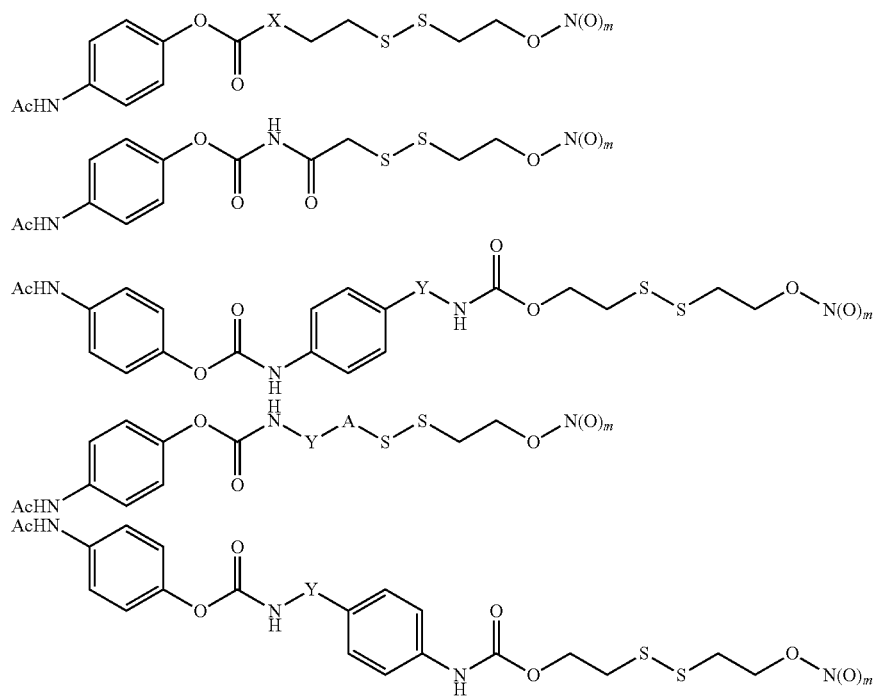
NO-Releasing Prodrugs of Mesalamine
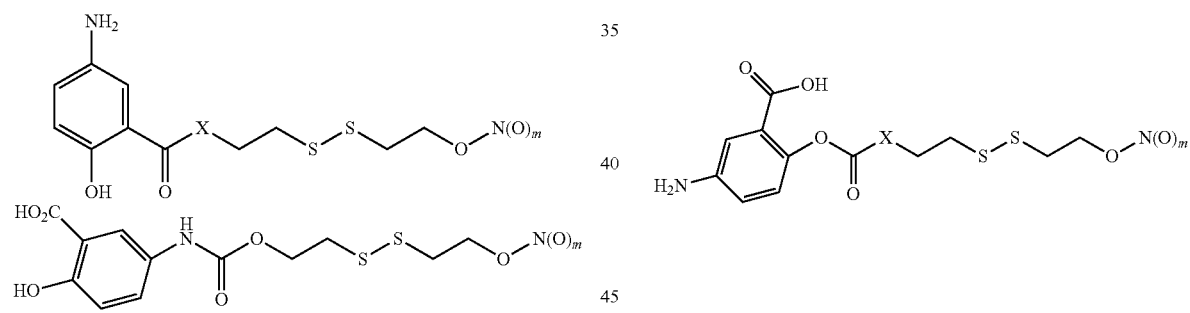
NO-Releasing Prodrugs of Naproxen
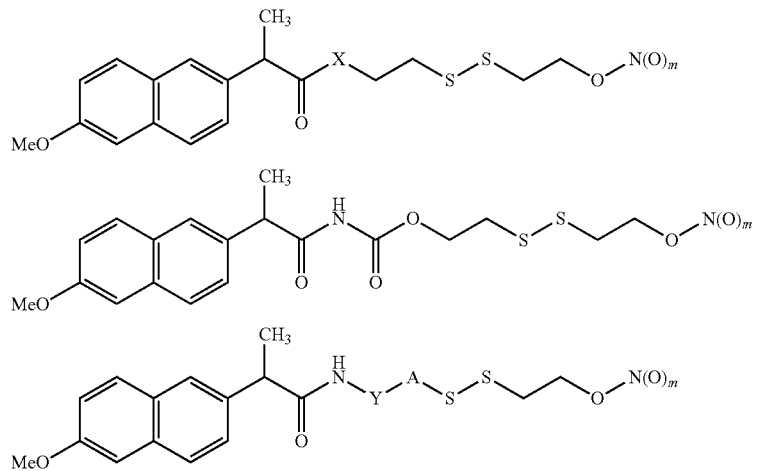

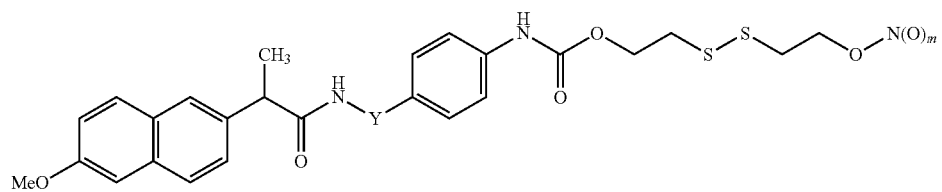
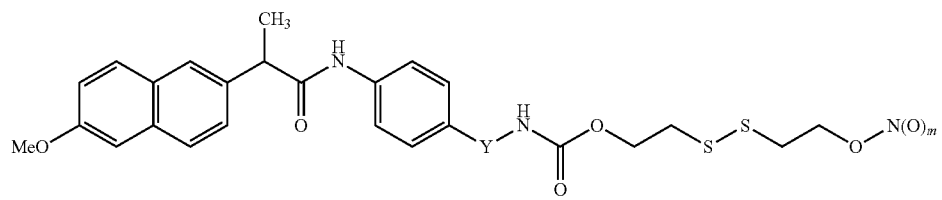
NO-Releasing Prodrugs of Flurbiprofen
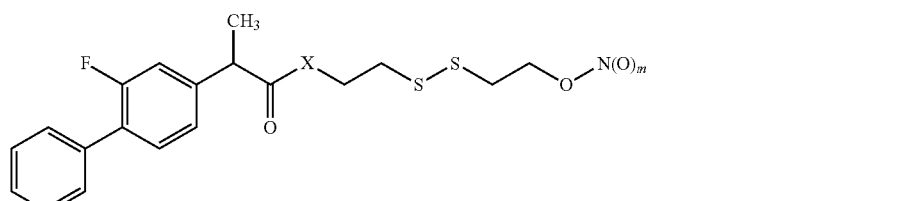
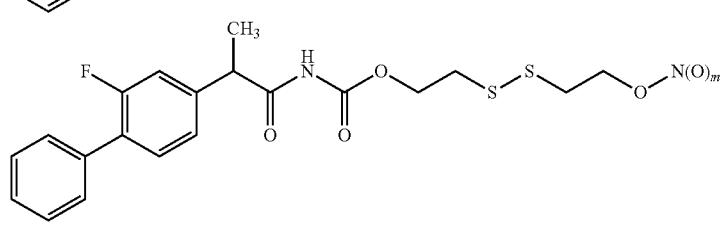
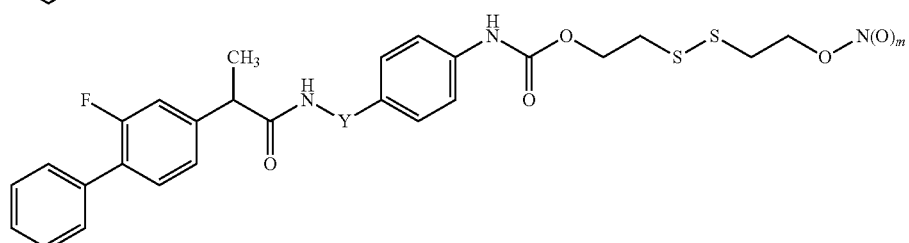
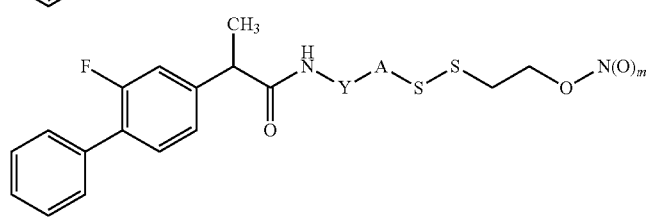
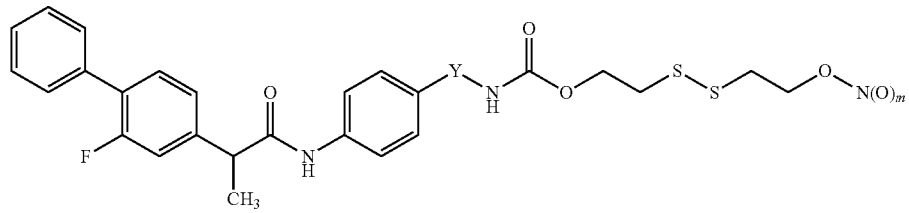

NO-Releasing Prodrugs of Sulindac
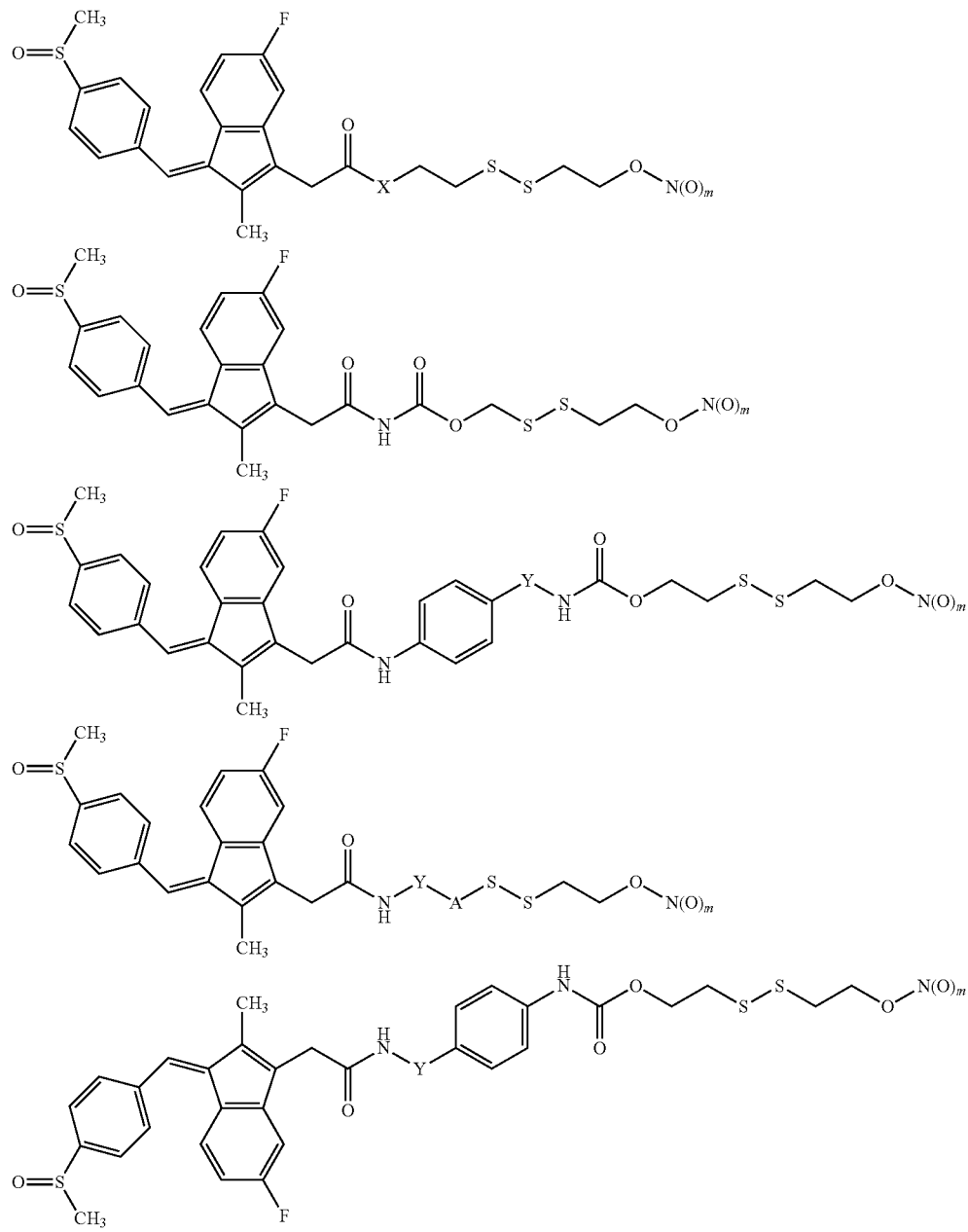
NO-Releasing Prodrugs of Ketoprofen
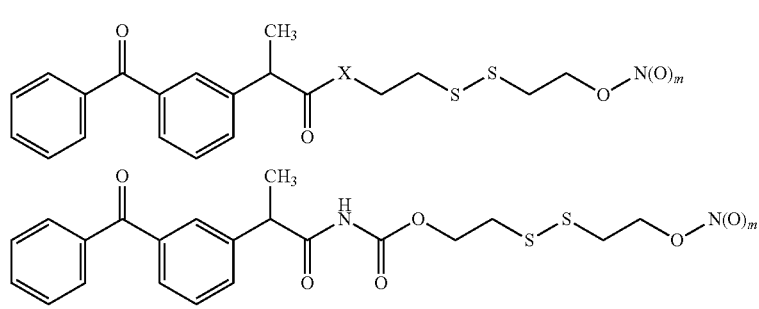

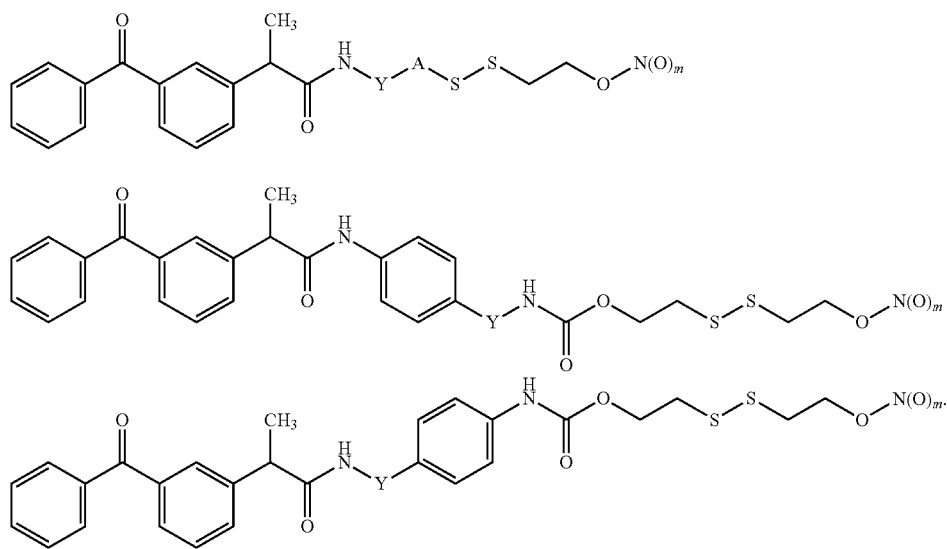
NO-Releasing Prodrugs of Indomethacin
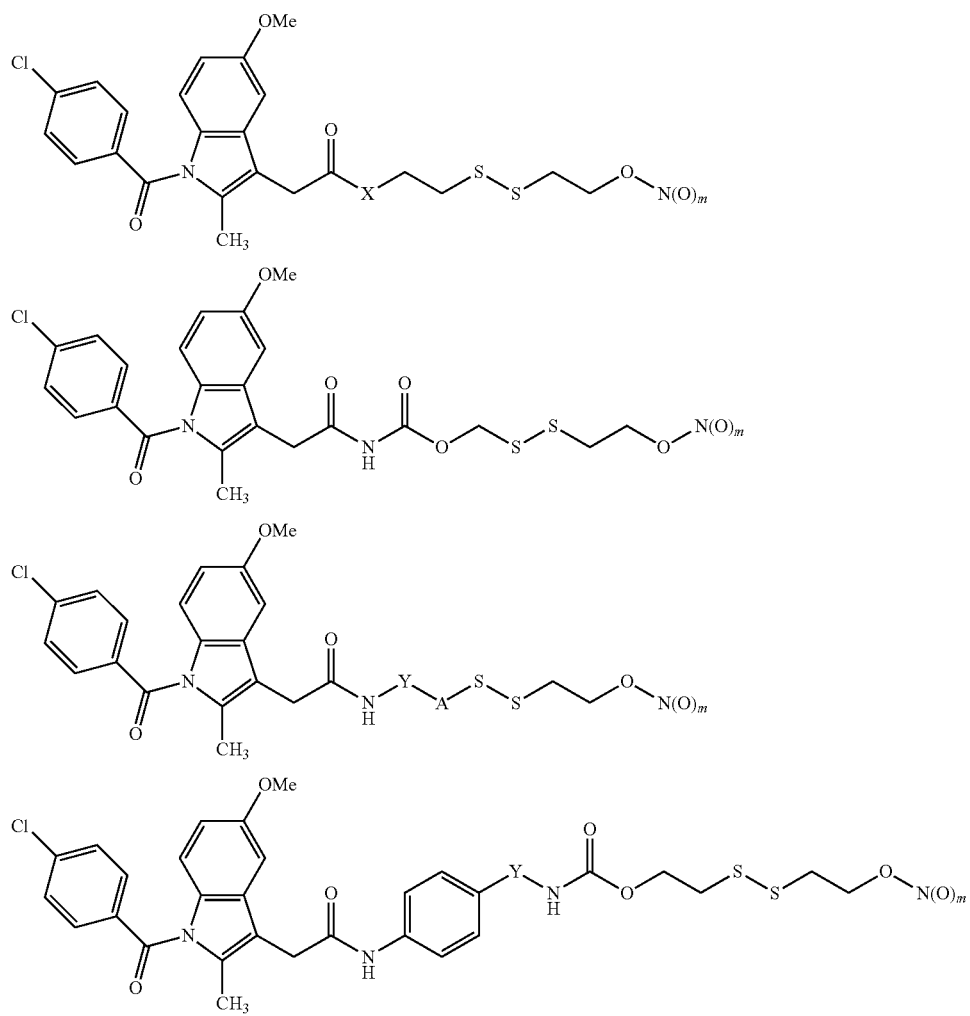

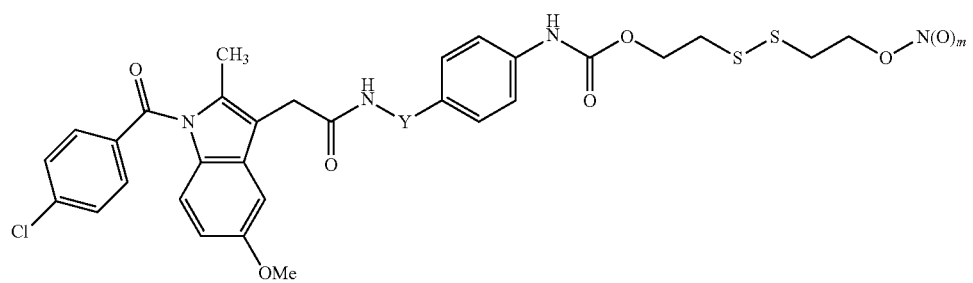
NO-Releasing Prodrugs of Ibuprofene
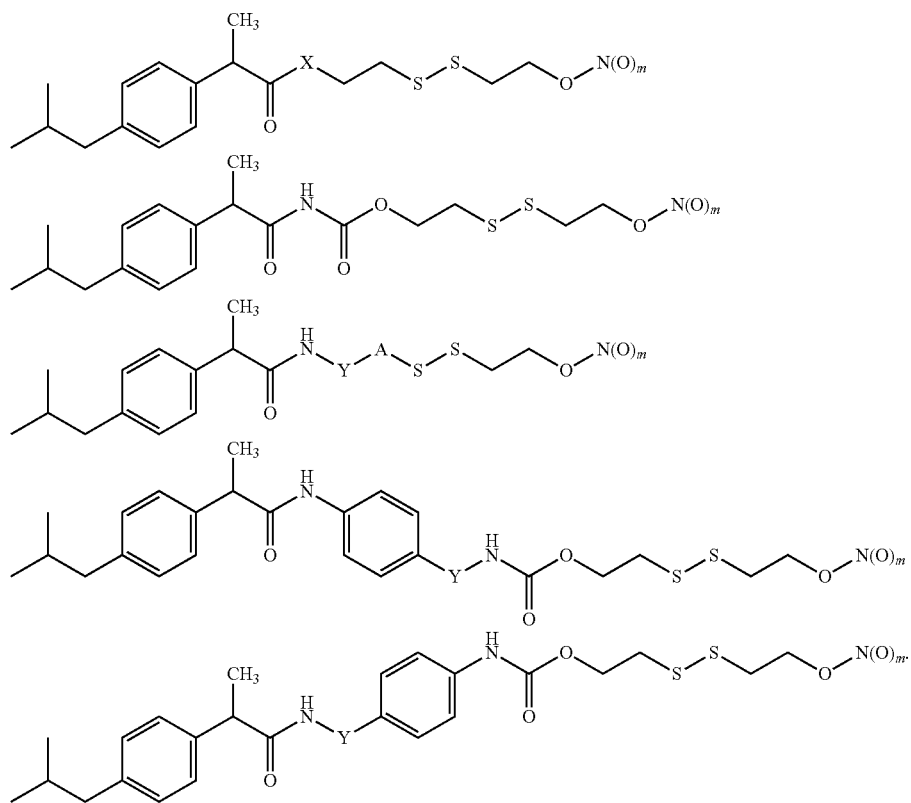
NO-Releasing Prodrugs of Ketorolac
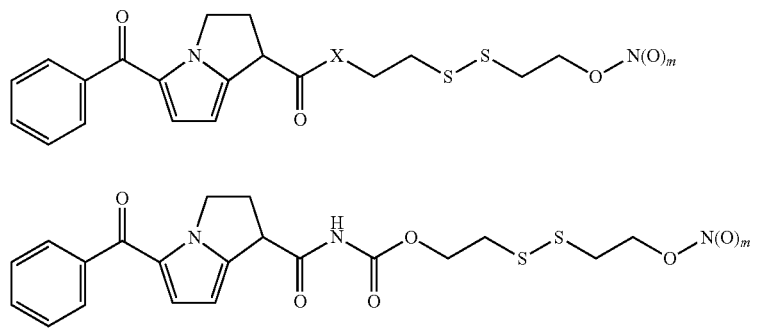

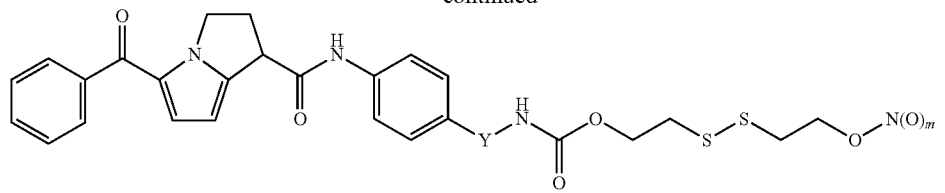
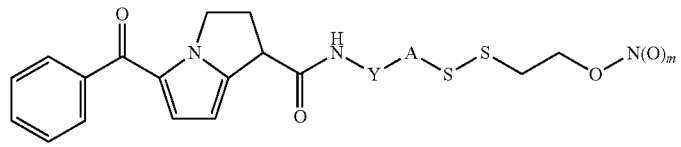
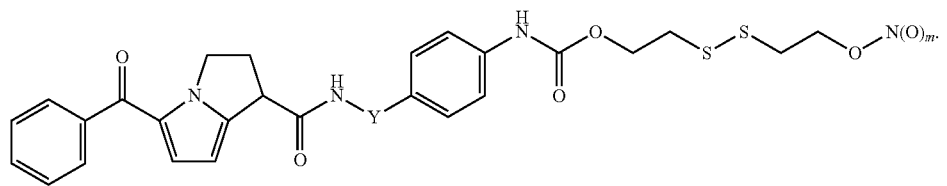
NO-Releasing Prodrugs of Diclofenac
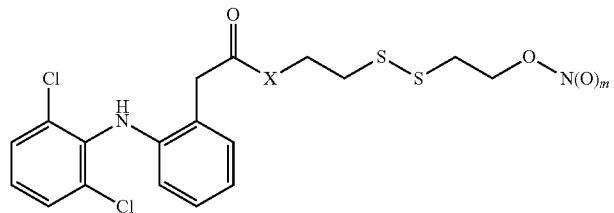
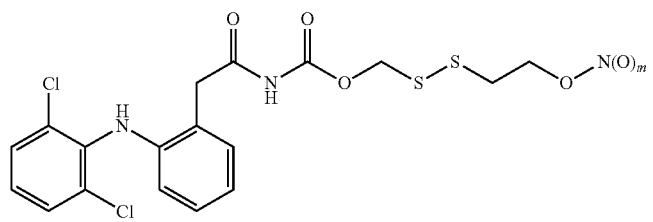
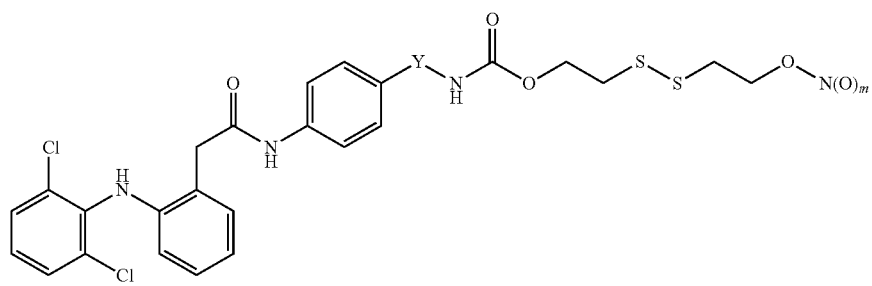
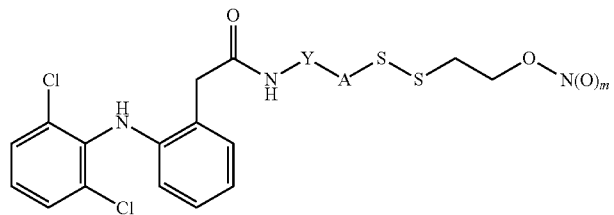

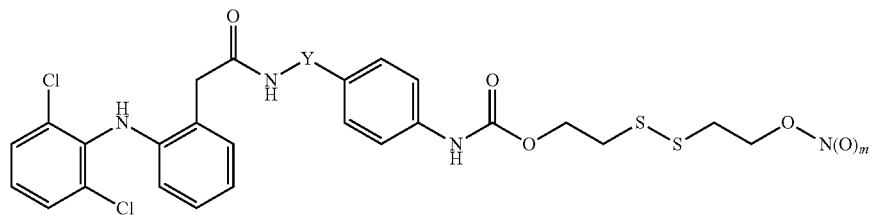
NO-Releasing Prodrugs of Glucocorticoids:
NO-Releasing Prodrug of Prednisolone
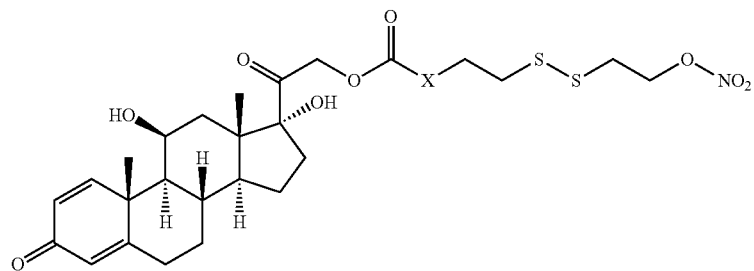
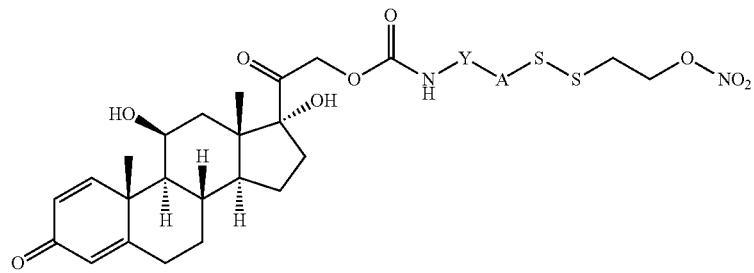
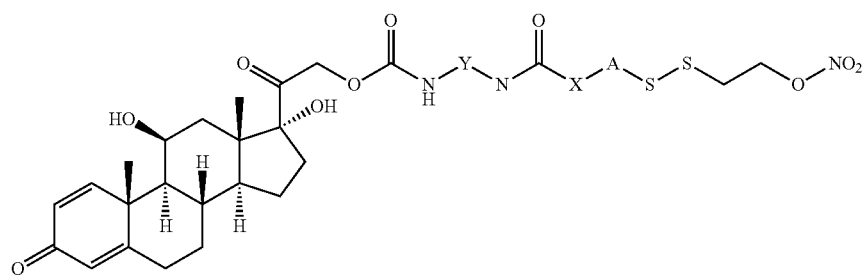
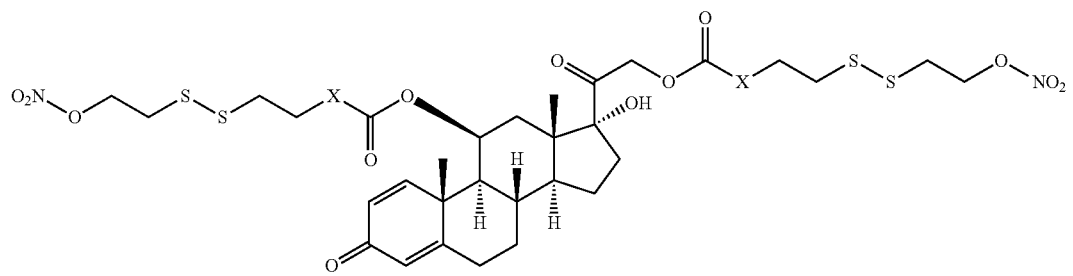

NO-Releasing Prodrug of Ursodeoxycholic Acid
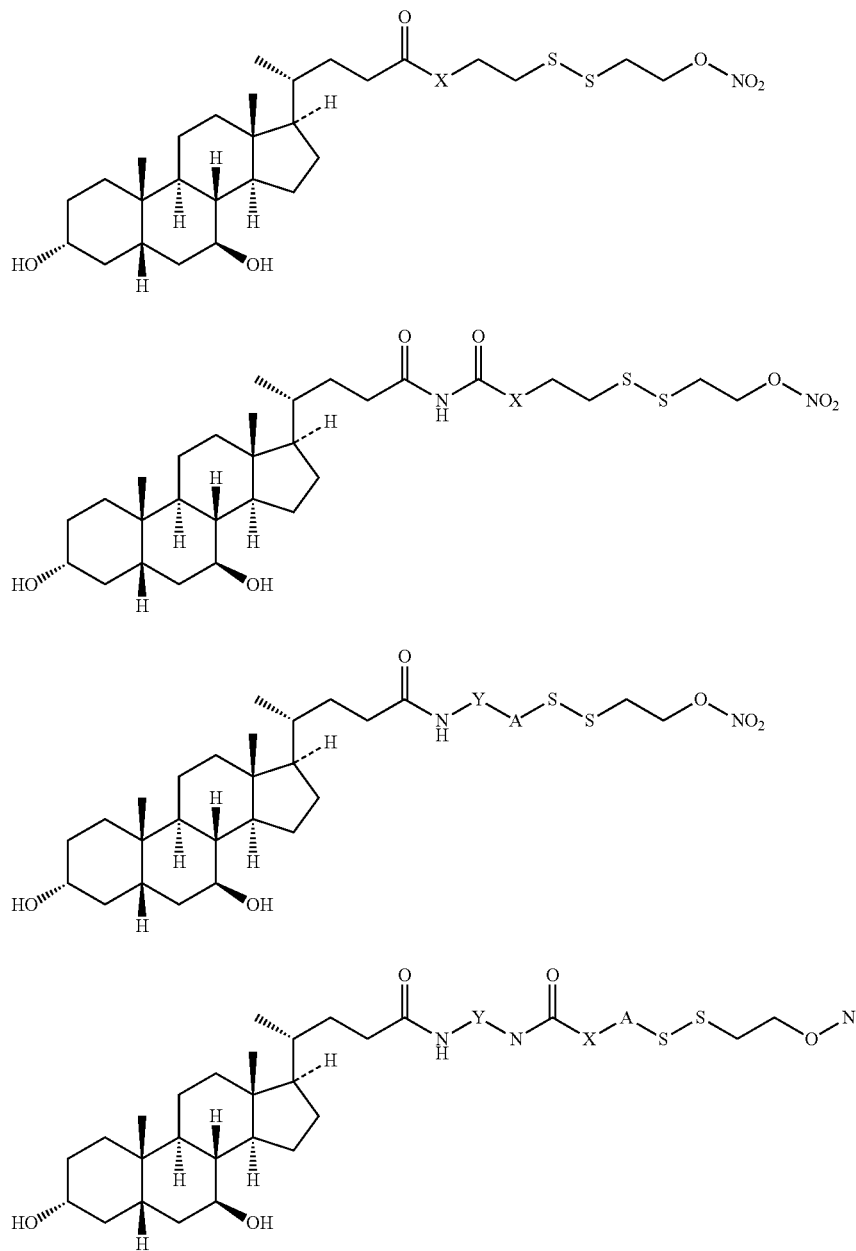
NO-Releasing Prodrug of Hydrocortisone
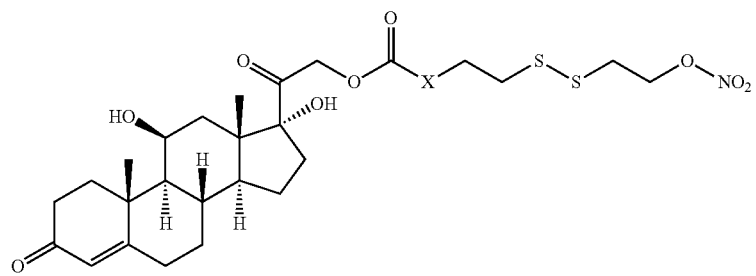

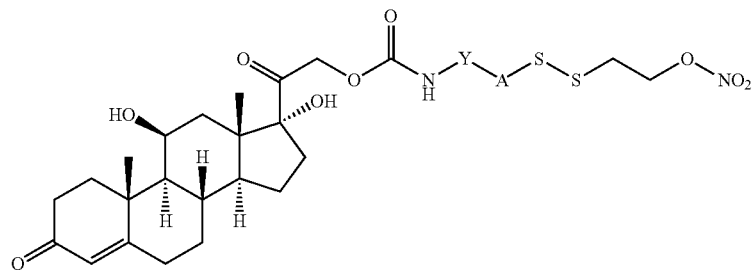
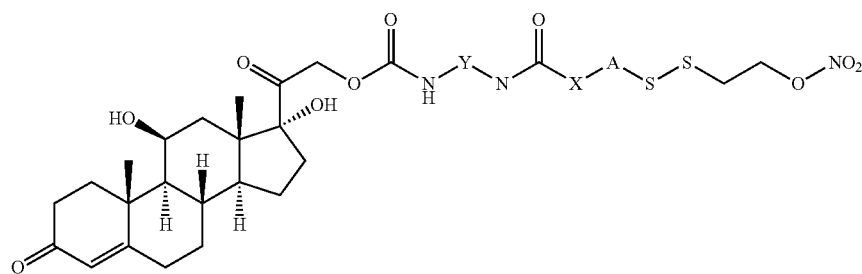
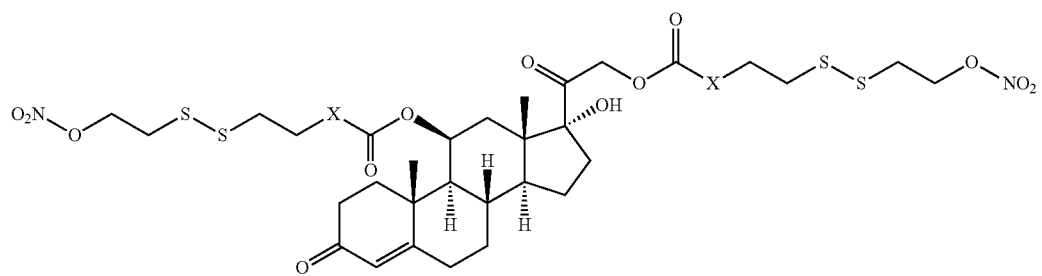
NO-Releasing Prodrug of Budesonide
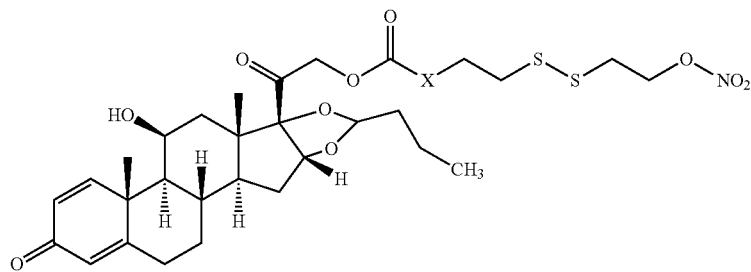
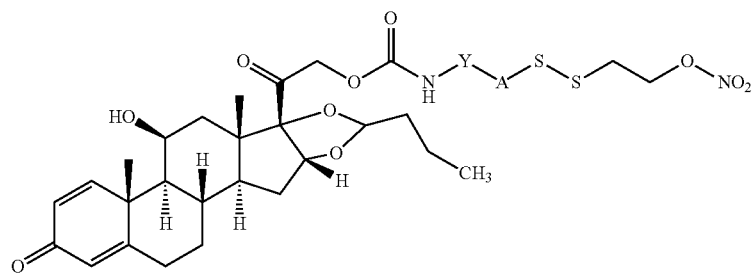

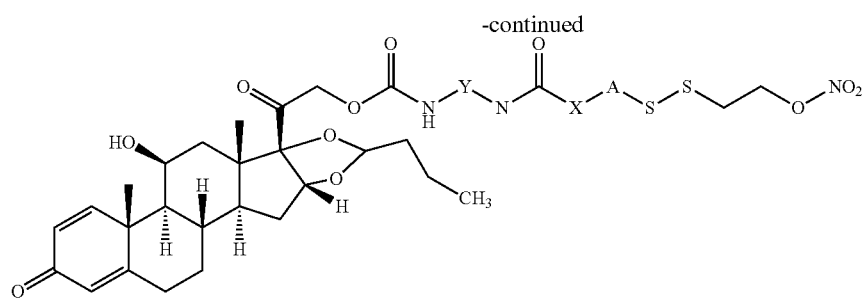
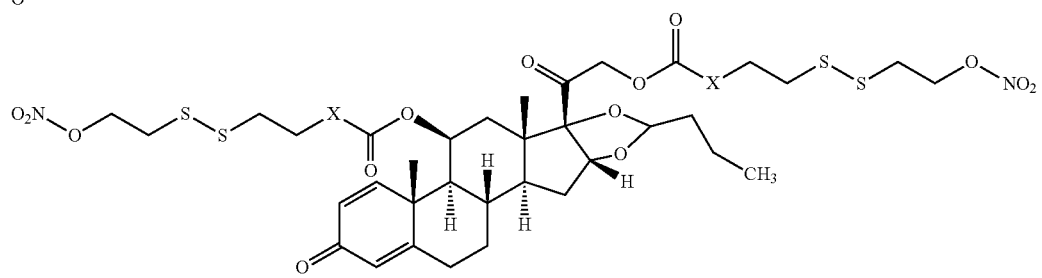
NO-Releasing Prodrugs of Antioxidants and for Free Radical Scavengers:
NO-Releasing Prodrug of TEMPOL (4-Hydroxy-TEMPO):
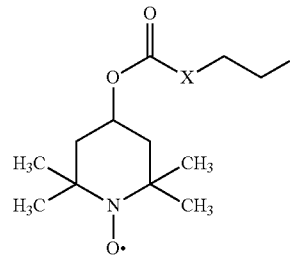
-continued
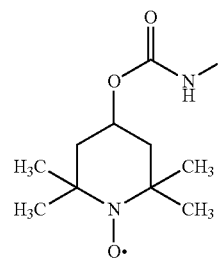
NO-Releasing Prodrugs of Probucol and AGI-1067:
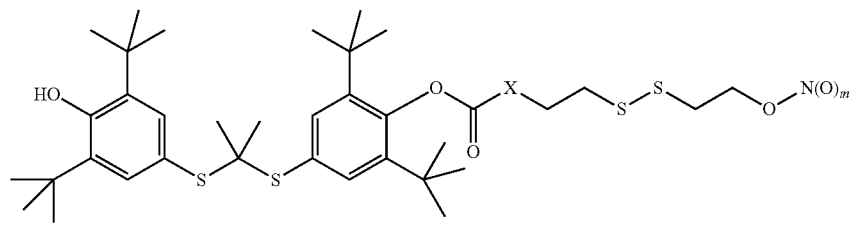
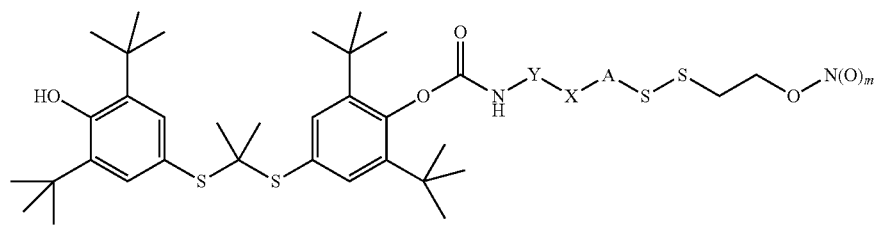
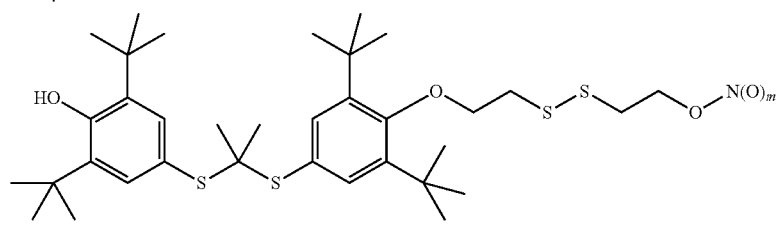

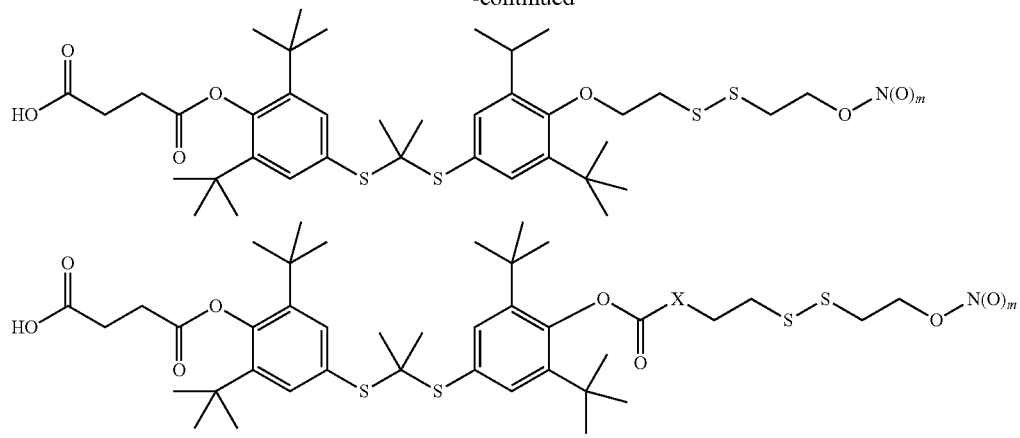
NO-Releasing Prodrugs of Lipoic Acid:
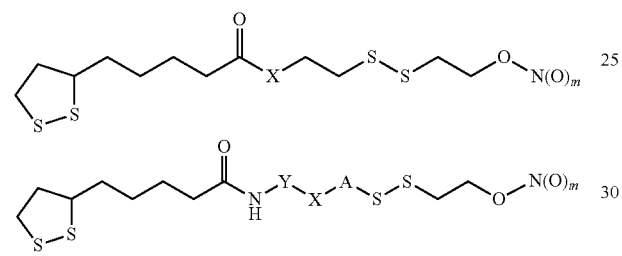
NO-Releasing Prodrugs of Vitamin E (Alfa-Tocopherol):
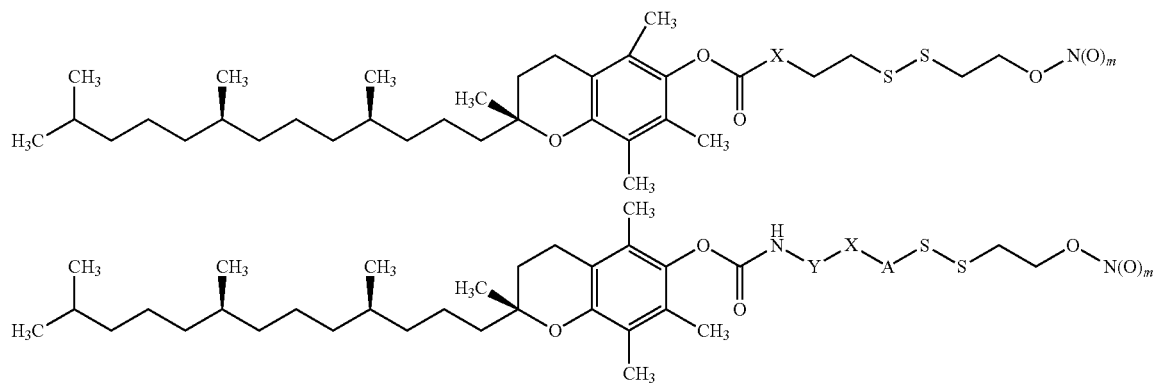
NO-Releasing Prodrugs of Edaravone (3-Methyl-1-Phenyl-2-Pyrazolin-5One):
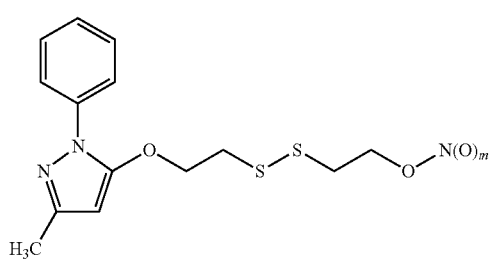
-continued NO-Releasing Prodrugs of Antibiotics:
NO-Releasing Prodrugs of Metronidazole
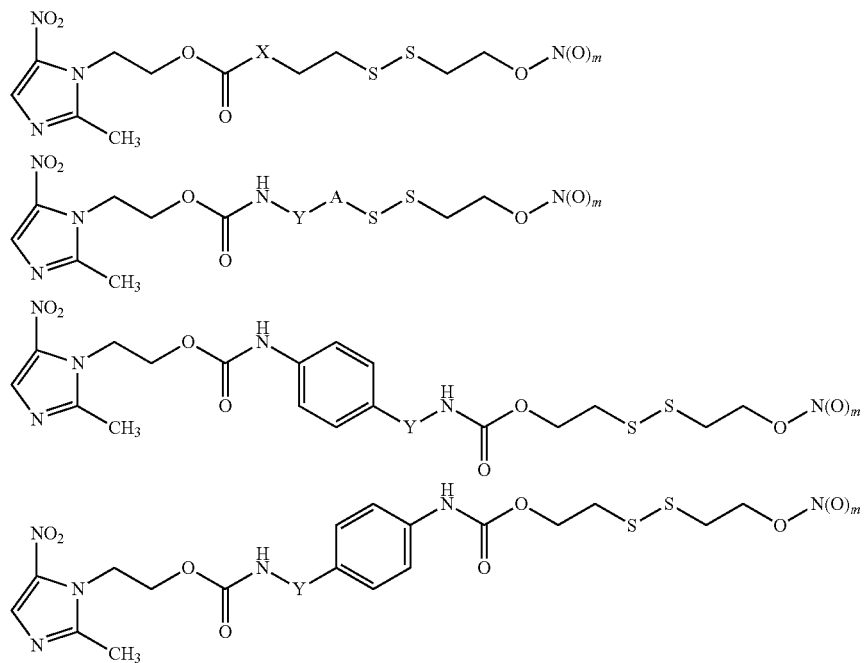
NO-Releasing Prodrugs of Norfloxacin:
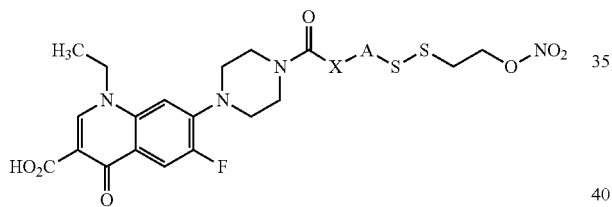
NO-Releasing Prodrugs of Antiepileptic Agents:
NO-Releasing Prodrugs of Valproic Acid
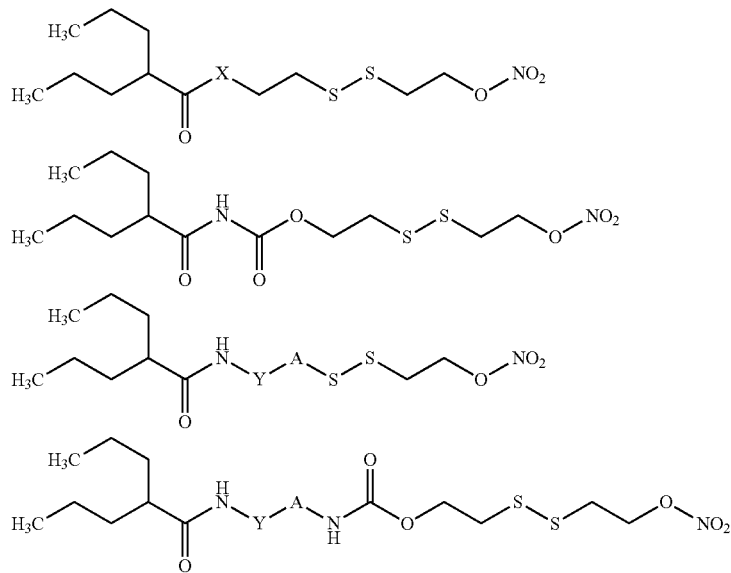

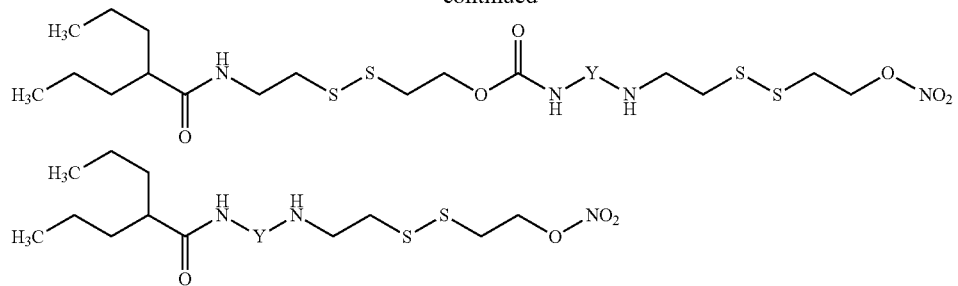
NO-Releasing Prodrug of Gabapentin
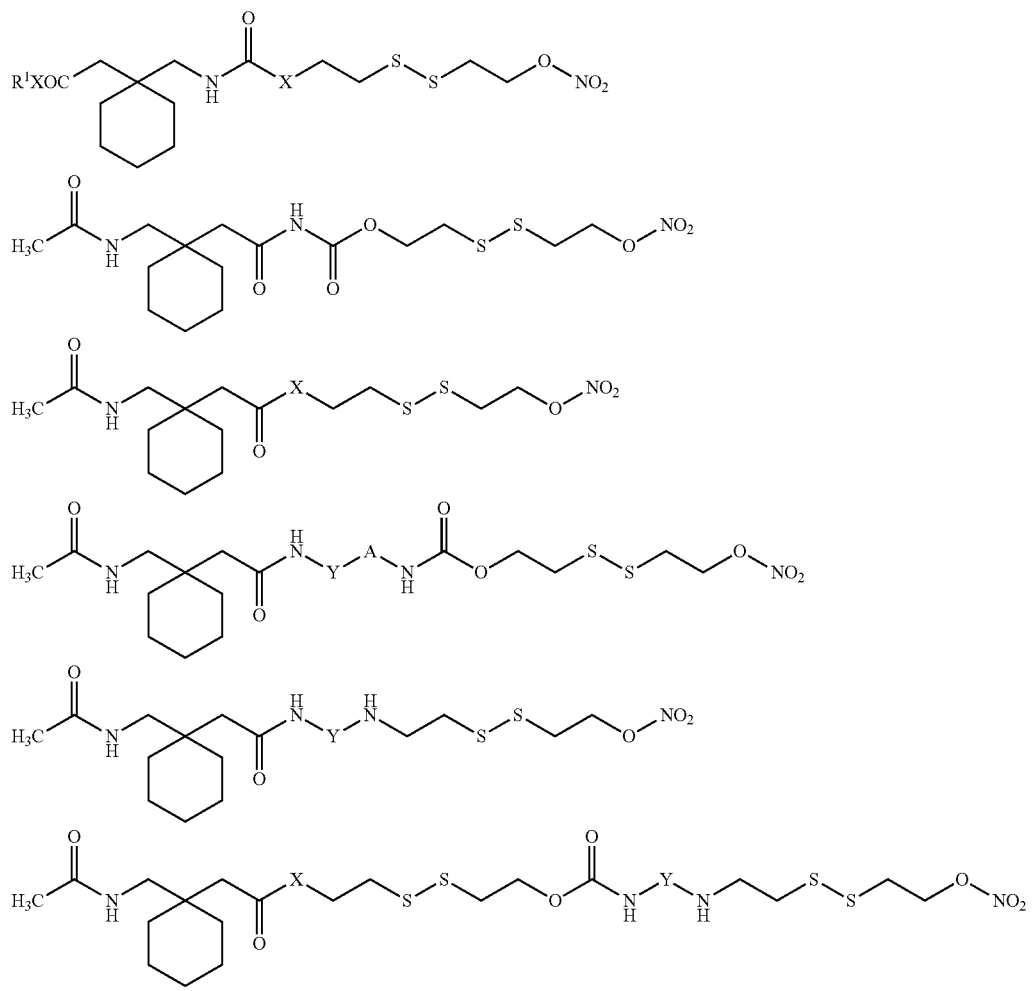
NO-Releasing Prodrug of Levetiracetam
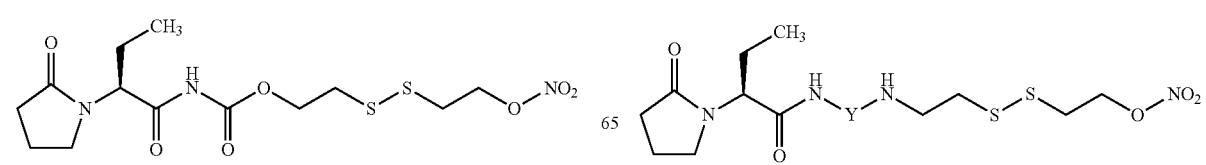

-continued

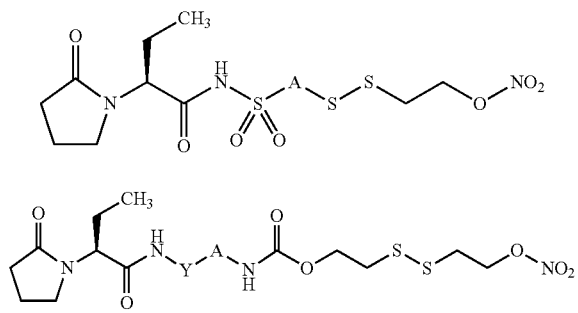

NO-Releasing Prodrug of Lamotrigine

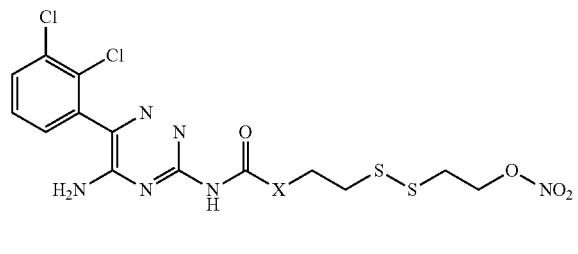

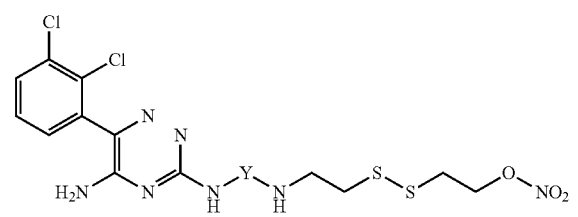

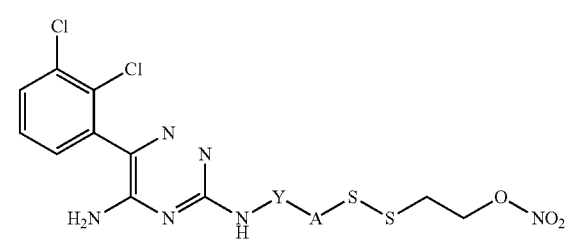

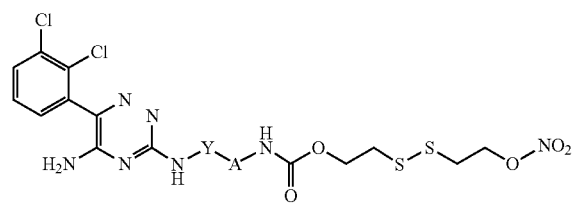

NO-Releasing Prodrug of Carbamazepine

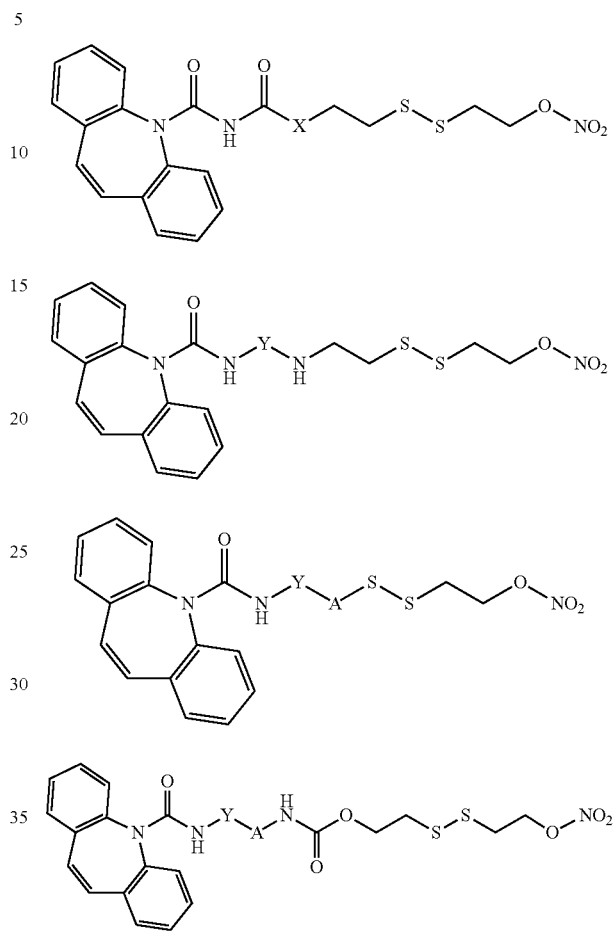

Plausible Mechanisms of Drug Release from Prodrugs

Drugs can be released from the prodrugs and mutual prodrugs via cleavage of bio-labile linker(s) in vivo (cleavage can be either chemical or enzymatic or both) by illustrative mechanisms as shown in Schemes M1 through M5.

Plausible mechanisms for concomitant release of nitric oxide (NO) and free drug from NO-releasing prodrug(s) of amino-, hydroxyl-, or carboxyl-containing drug(s) are illustratively shown in Scheme M1. Thus, the attack of thiolate ion (from GSH or any other sulfahydryl-containing species) on nitrooxy-containing prodrug would release carboxylic acid-containing free drug, episulfide (d) and the intermediate conjugate (a) according to path 1. If the prodrugs are made from amino-, or hydroxyl-containing drugs, then the prodrug would be cleaved via path 2 to release the corresponding free drug, the cyclic thiocarbonate intermediate (c) and the intermediate conjugate (a). The cyclic thiocarbonate intermediate may further breakdown into episulfide (d) and carbon dioxide. The reactive episulfide (d) would be further neutralized by glutathione. The nitrate ester-containing intermediate conjugate can further break down in the presence of GSH to glutathione dimer (GS-SG) and transient intermediate (b), which can break down via path 3 to release NO. It is also possible the same transient intermediate can break down via path 4 to yield episulfide (d) and a relatively innocuous nitrate anion ($NO_3^-$).

Scheme M1
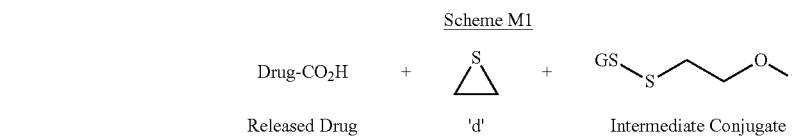
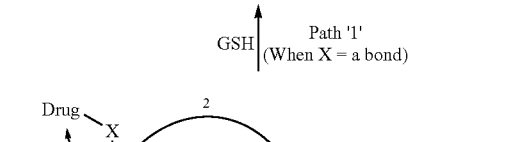
$X = O, NR^1 (R^1 = H$ or alkyl or a group linked to the drug) or a bond
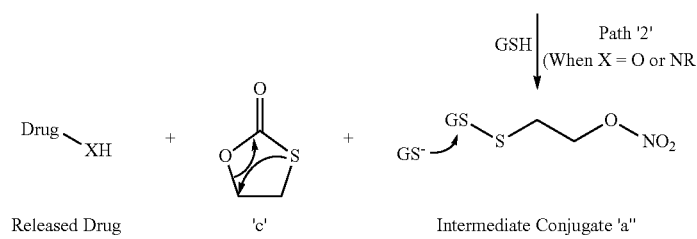
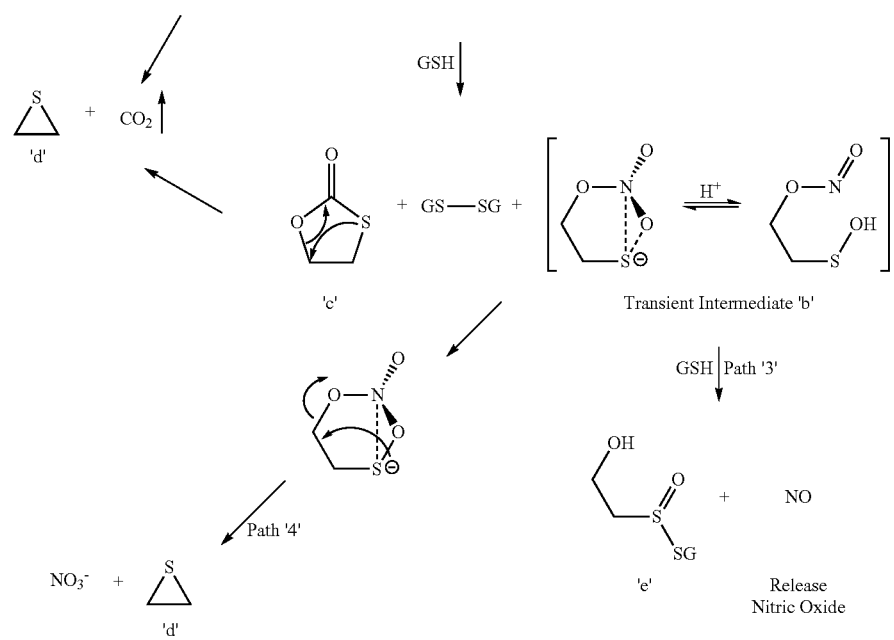
Plausible mechanisms of drug release from mutual prodrugs of one carboxyl-containing and one amino-/hydroxyl-containing drug is shown in Scheme M2.
Scheme M2
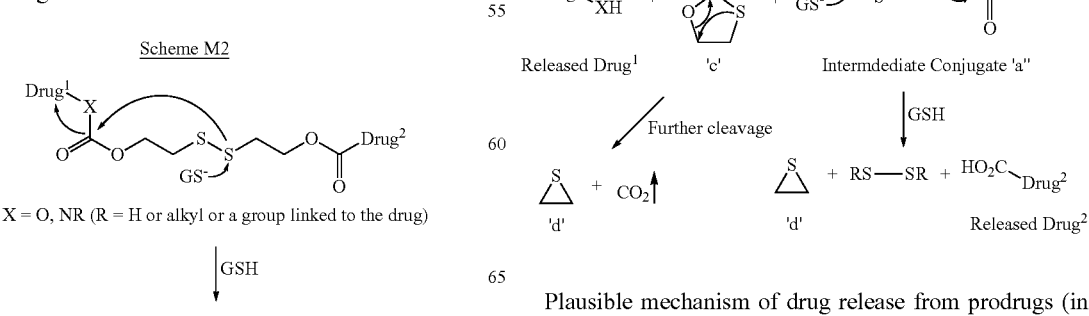
Plausible mechanism of drug release from prodrugs (including mutual and NO-releasing prodrugs of amino-, hydroxyl- and carboxyl-containing drugs) containing modified bio-labile linkers is shown in Scheme M3. Thus, the thiolate anion derived from the attack of glutathione on disulfide of the prodrug may trigger cyclization to release the free drug (D1-$X^{m1}$H) and a stable six-membered (or five-membered, if $X^{m2}$ is a bond) thio-lactone intermediate.

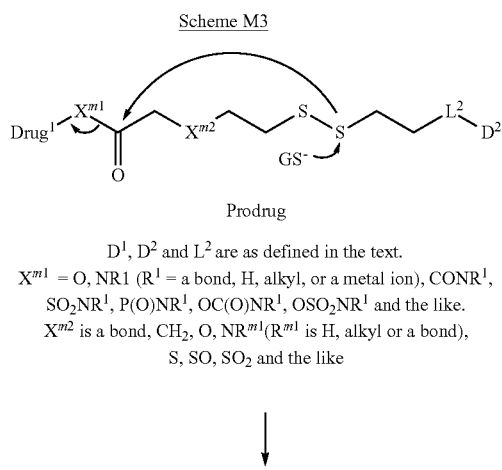

Scheme M3

Prodrug $D^1$, $D^2$ and $L^2$ are as defined in the text.
$X^{m1}$ = O, NR1 ($R^1$ = a bond, H, alkyl, or a metal ion), $CONR^1$, $SO_2NR^1$, $P(O)NR^1$, $OC(O)NR^1$, $OSO_2NR^1$ and the like.
$X^{m2}$ is a bond, $CH_2$, O, $NR^{m1}$($R^{m1}$ is H, alkyl or a bond), S, SO, $SO_2$ and the like

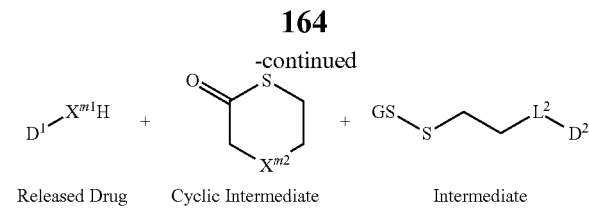

Released Drug   Cyclic Intermediate   Intermediate

↓ RSH

Releases the second drug or NO or promoiety via plausible mechanisms as shown in Schemes M1 and M2

Plausible mechanisms of drug release from double/mutual prodrugs containing additional linkages to couple two hydroxyl-containing drugs are shown in Scheme M4. Thus, the thiolate anion generated by the attack of glutathione on disulfide bond of the prodrug triggers further cleavage as shown to release the free drug ($D^1$-OH) and a five-membered 2-imidazolidone. Through in vitro decomposition studies, we have found that the drug release from this type of prodrug is more facile when R group is an alkyl group.

Scheme M4

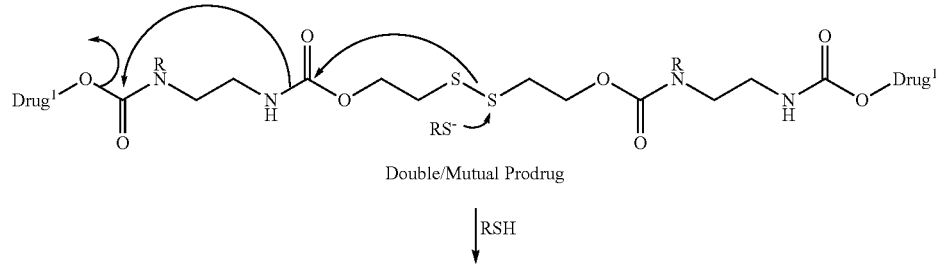

Double/Mutual Prodrug

↓ RSH

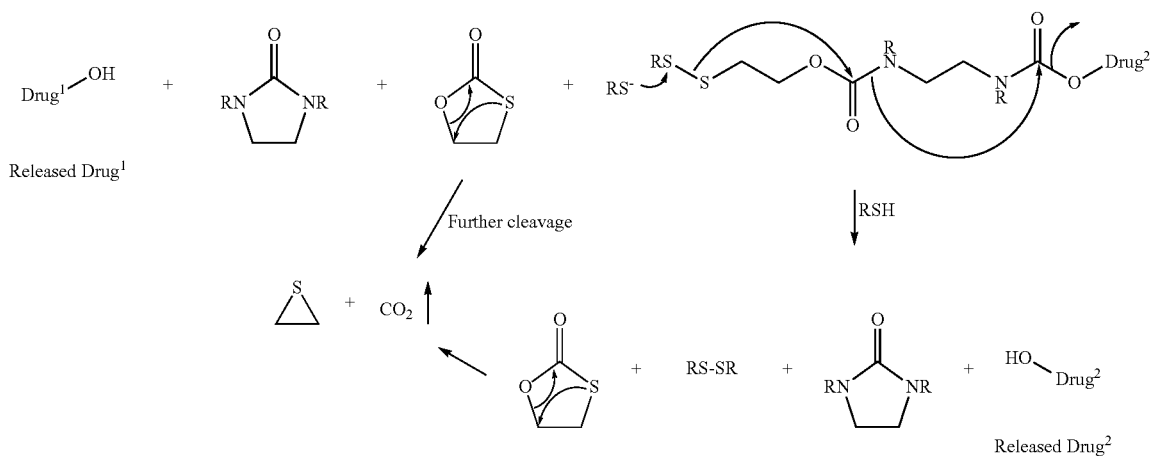

This invention also covers novel bio-labile linkers containing 1,4-phenylene group and 1,2-phenylene group as shown in Schemes 5 and 6, respectively. As depicted in Scheme M5, the linker is expected to release the free Drug[1] upon glutathione-assisted cleavage and may generate 1,4-quinonemethid (ea) as a byproduct via 1,6-elimination process. Similarly, the free Drug[2] is expected to be released from the intermediate conjugate (a) as shown in the scheme.

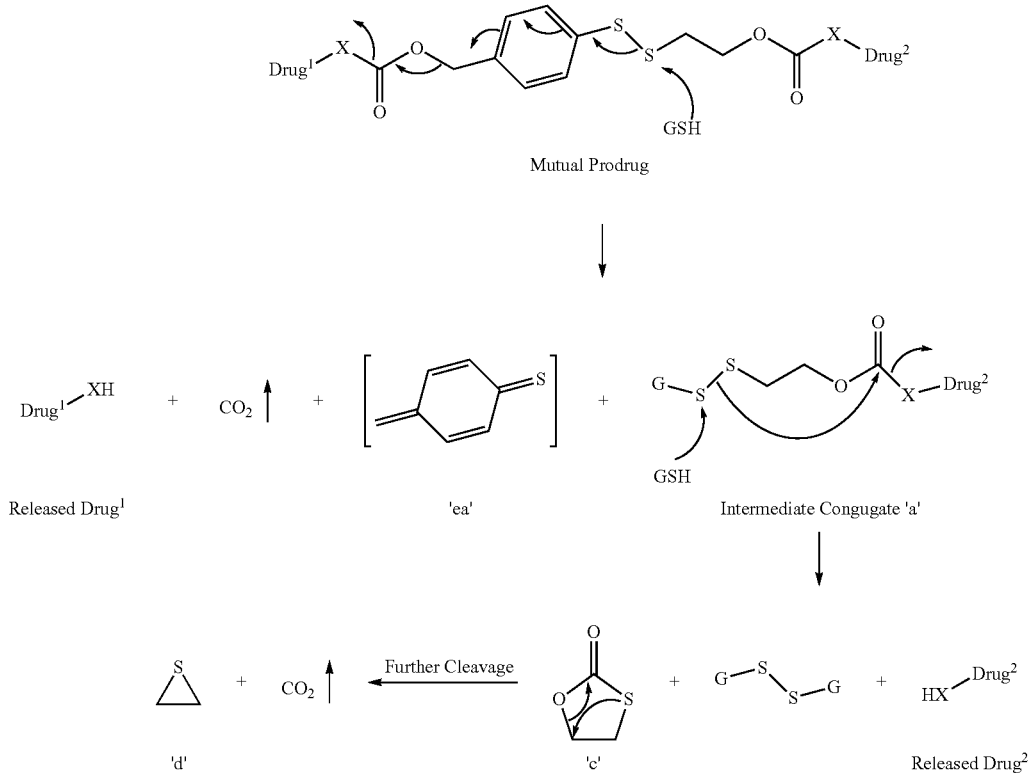

As depicted in Scheme M6, the 1,2-phenylene-containing linker is also expected to release free drugs upon glutathione assisted cleavage and generate 1,2-quinonemethid (eb) as a byproduct via 1,4-elimination process (via pathway 'b'). However, this linker can also cleave via pathway 'a' to generate benzo-monothiocarbonate as a byproduct. Although the generated byproducts seem to be toxic, they are likely to be quickly neutralized by detoxification enzymes in the body.

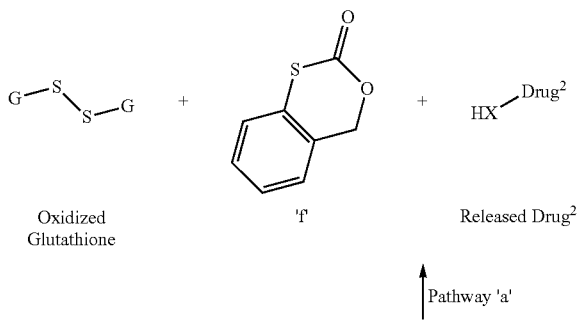

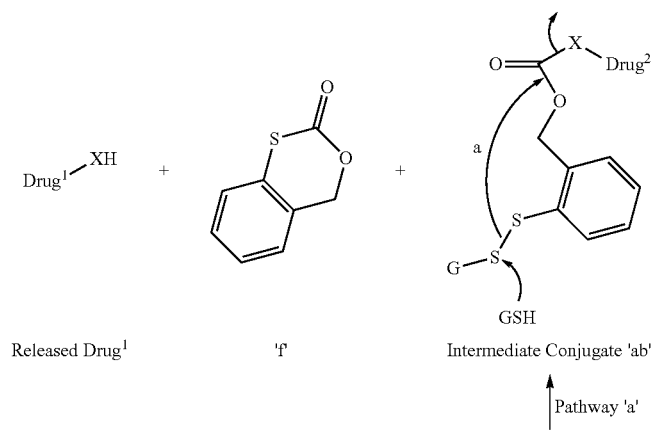
Released Drug¹      'f'      Intermediate Conjugate 'ab'
Pathway 'a'
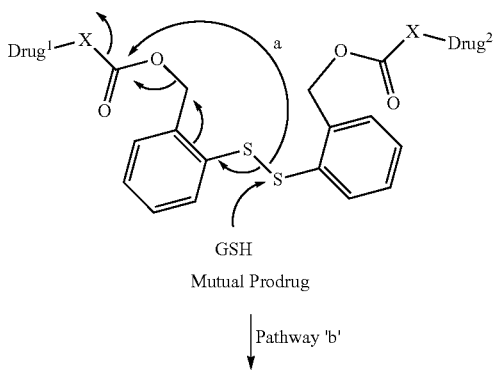
Mutual Prodrug
Pathway 'b'
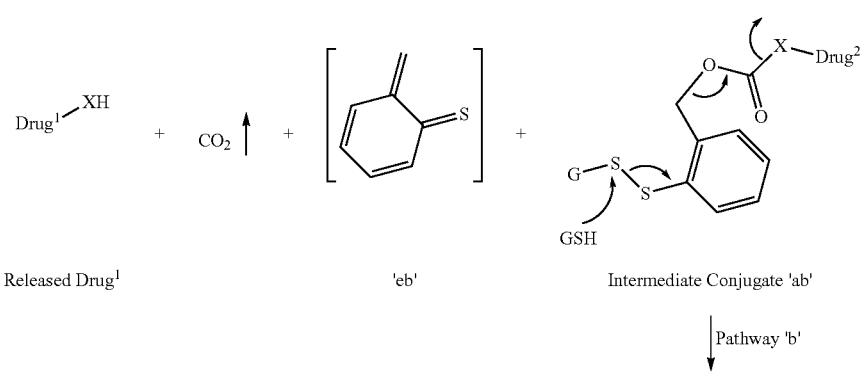
Released Drug¹     'eb'     Intermediate Conjugate 'ab'
Pathway 'b'
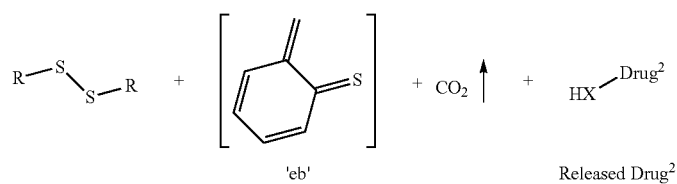
'eb'     Released Drug²

Scheme M7: Plausible mechanism of diazepam formation from an acyclic prodrug of diazepam

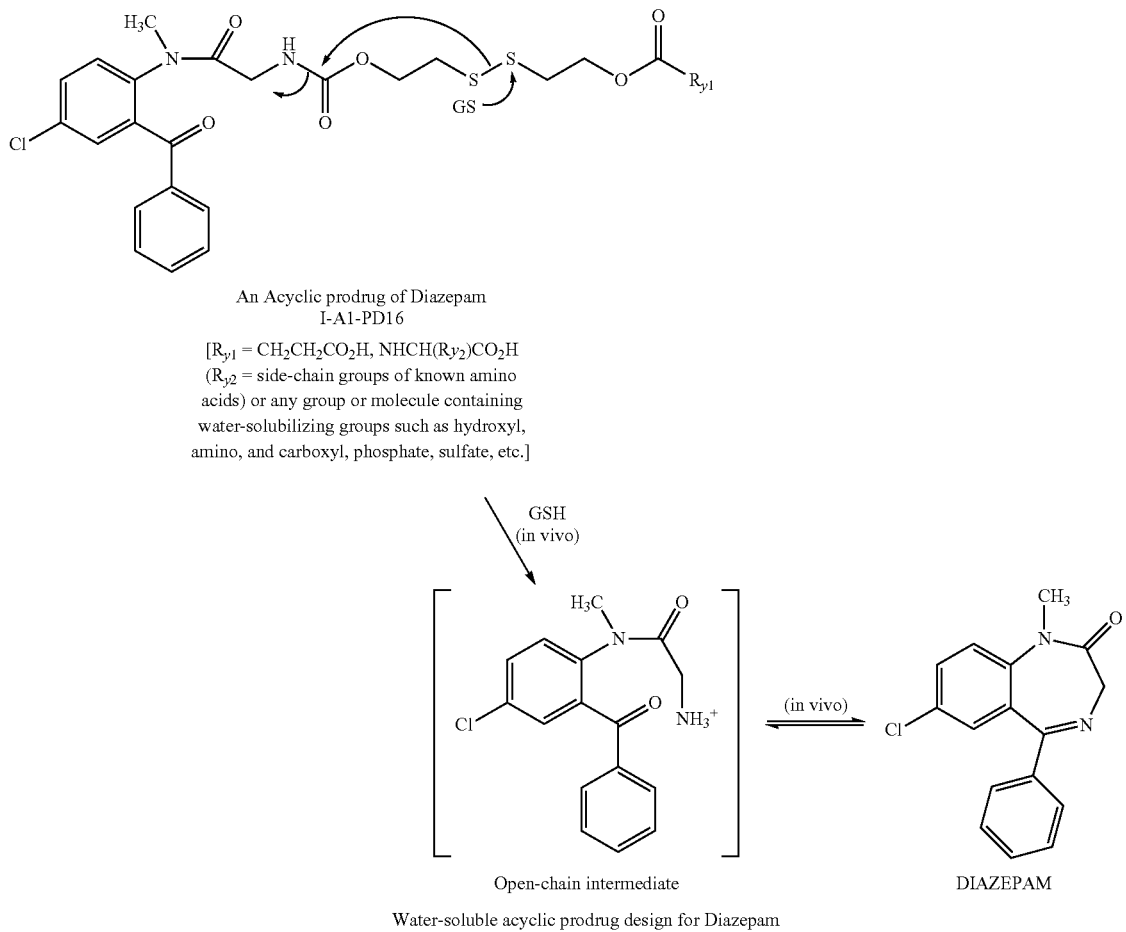

An Acyclic prodrug of Diazepam
I-A1-PD16

[$R_{y1}$ = $CH_2CH_2CO_2H$, $NHCH(Ry_2)CO_2H$
($R_{y2}$ = side-chain groups of known amino
acids) or any group or molecule containing
water-solubilizing groups such as hydroxyl,
amino, and carboxyl, phosphate, sulfate, etc.]

Open-chain intermediate     DIAZEPAM

Water-soluble acyclic prodrug design for Diazepam

Diazepam, a benzodiazepine tranquilizer, is very sparingly water-soluble drug and a water-soluble acyclic prodrug of diazepam can be made by using our linker technology. As shown in the Scheme M7, reduction of disulfide bond in the prodrug triggers release of open-chain intermediate of diazepam which spontaneously cyclizes to diazepam in vivo.

Where GSH is glutathione (reduced) or any other in vivo bioreductive agent that can reduce the disulfide bond. As illustrated, cleavage of disulfide bond triggers further breakage of the remaining portion of the linker to release the free drugs. In the process, some byproducts are generated and these are either eliminated or further degraded by some biological process. For clarity, the mechanism of cleavage of the linker is shown as occurring in stepwise manner. However, both the steps can possibly occur in a concomitant fashion to release both the drugs simultaneously.

As illustrated in Scheme M3 and M4, Linkers may have additional spacer groups between one side (or both sides) of the linkers and the drug molecule and some of these spacer groups may be cleaved independently by a chemical or enzymatic process to release the drugs prematurely before the cleavage of disulfide linkage. The prodrugs and mutual prodrugs containing such spacer groups may be useful when faster release of drug(s) is desired.

Lists of Candidate Drugs Useful for Prodrug Synthesis:

Drugs listed in the following list can be converted to prodrugs of formula I. This list is in no way limiting the scope of drugs covered in this invention, but given as representative examples. All the amino- (including amide-NH and sulfonamide-NH, carbamate-NH, sulfamate-NH, hydrazone-NH, semicarbazone-NH, thiosemicarbazone-NH, urea-NH, phosphoramide-NH and the like. See above, for the description of "amino-containing drugs"), carboxyl-, hydroxyl-(including oxime-OH), and carbonyl (both aldehyde and keto groups)-containing drugs under various therapeutic categories as listed in Merck Index (13th editions) and other data bases such as prous science's ensemble, integrity, and the like and also all the qualified (i.e., amino-, and/or hydroxyl-, and/or carboxyl-, and/or carbonyl-containing) investigational drugs as listed in databases such Merck Index (13th editions), iddb, ensemble, integrity, and the like, are covered under this invention without any limitation.

Anti-Inflammatory Drugs:

Amino-containing (including Amide NH and Sulphonamide NH and Phosphomide NH, etc.): Ampiroxicam, Bucolome, Celecoxib, Difenpiramide, Mofebutazone, Nimesulide, Paranyline, Parecoxib, Parsalmide, Piketoprofen, Talniflumate, Tenidap, Terofenamate, and Valdecoxib.

Hydroxyl-containing: 21-Acetoxypregnenolone, Alclometasone, alfa-Bisabolol, Budesonide, Deflazacort, Diflorasone, Desonide, Desoximetasone, Diflorasone, Diflucortolone, Difluprednate, Ditazol, Fluazacort, Fluocinonide, Fluocortin Butyl, Fluprednidene Acetate, Glucametacin, Halcinonide, Halobetasol Propionate, Halometasone, Halopredone Acetate, Ibuproxam, Loteprednol Etabonate, Mazipredone, Mometasone Furoate, Oxyphenbutazone, Perisoxal, Rimexolone.

Hydroxyl-, and Amino-containing (including Amide NH and Sulphonamide NH and Phosphomide NH, etc.): Bufexamac, Etofenamate, Fepradinol, Ibuproxam, Isoxicam, Lornoxicam, Meloxicam, Oxametacine, Piroxicam, and Tenoxicam.

Hydroxyl- and sulphahydryl-containing: Tixocortol.

Carboxyl- and Amino-containing (including amide NH and sulphonamide NH and phosphomide NH, etc.): Aceclofenac, Alminoprofen, Amfenac, 3-Amino-4-hydroxybutyric Acid, Carprofen, Diclofenac, Enfenamic Acid, Etodolac, Flufenamic Acid, Meclofenamic Acid, Mefenamic Acid, Niflumic Acid, and Tolfenamic Acid.

Carboxyl-containing: Acemetacin, Acetamidocaproic Acid, Bendazac, Benoxaprofen, Bermoprofen, Bucloxic Acid, Butibufen, Cinmetacin, Clidanac, Clopirac, Felbinac, Fenbufen, Fenclozic Acid, Fenoprofen, Fentiazac, Flunoxaprofen, Flurbiprofen, Ibuprofen, Indomethacin, Isofezolac, Isoxepac, Ketoprofen, Lonazolac, Loxoprofen, Metiazinic Acid, Mofezolac, Naproxen, Oxaprozin, Pirazolac, Pirprofen, Pranoprofen, Protizinic Acid, Sulindac, Suprofen, Suxibuzone, Tiaprofenic Acid, Tolmetin, and Tropesin.

Carboxyl- and Hydroxyl-containing: Balsalazide, Enoxolone, Fendosal, Olsalazine, Oxaceprol, and Ximoprofen.

Amino-, Carboxyl- and Hydroxyl-containing: 3-Amino-4-hydroxybutyric Acid, Mesalamine, and Sulfasalazine.

Keto-containing: Nabumetone, and Piketoprofen.

Carboxyl- and keto-containing: Bermoprofen, Bucloxic Acid, Isoxepac, Ketoprofen, Loxoprofen, and Zaltoprofen.

Analgesic and/or Antipyretic Drugs:

Amino-containing: Aminochlorthenoxazin, Aminopropylon, Anileridine, Antrafenine, Benorylate, Benzpiperylon, p-Bromoacetanilide, Butacetin, Carsalam, Difenamizole, Etersalate, Ethenzamide, Ethoxazene, Flipirtine, Isonixin, Nifenazone, Phenacetin, Phenazopyridine, Phenocoll, Phenopyrazone, Piminodine, Piritramide, Propacetamol, Ramifenazone, Piperylone, Salverine, and Tinoridine.

Hydroxyl-containing: Aluminum bis(acetylsalicylate), Benzylmorphine, Buprenorphine, Butorphanol, Chlorobutanol, Ciramadol, Codeine, Desomorphine, Dihydrocodeine, Dihydromorphine, Dihydroxyaluminum acetylsalicylate, Dimepheptanol, Eptazocine, Ethylmorphine, Eugenol, Hydroxypethidine, Levorphanol, Meptazinol, Metazocine, Morphine, Nalbuphine, Pentazocine, Phenazocine, Phenoperidine, Phenylsalicylate, Salicin, Tramadol, and Viminol.

Carboxyl-containing: Acetylsalicylsalicylic acid, Alclofenac, Aspirin, Benoxaprofen, 5-Bromosalicylic acid acetate, Cinchophen, Diacerein, Dipyrocetyl, Fosfosal, Ibufenac, Indoprofen, and Salicysulfuric acid.

Amino- and Hydroxyl-containing: Acetaminophen, Acetaminosalol, Bucetin, Capsaicine, Dezocine, Floctafenine, Glafenine, Isoladol, p-Lactophenetide, Norlevorphanol, Normorphine, Phenylramidol, Salacetamide, and Salicylamide.

Amino- and Carboxyl-containing: Actarit, Bumadizone, Clonixin, and Salicylamide O-acetic acid.

Carboxyl- and Hydroxyl-containing: Diflunisal, Gentisic acid, and Salsalate.

Keto-containing: Amtolmetin, Dipipanone, Hydrocodone, Isomethadone, Methadone, Norpipanone, and Phenadoxone.

Hydroxy- and Keto-containing: Hydromorphone, Ketobemidone, Metopon, Oxycodone, and Oxymorphone.

Carboxyl- and Keto-containing: Clometacin, Ketorolac, and Zomepirac.

Amino- Carboxyl- and Keto-containing: Bromfenac.

Antihypertensive Drugs:

Amino-containing: Alfuzosin, Benzylhydrochlorothiazide, Bethanidine, Bopindolol, Budralazine, Bunazosin, Ciclosidomine, Clonidine, Clopamide, Cyclopenthiazide, Debrisoquin, Edeserpidine, Diazoxide, Dihydralazine, Doxazosin, Endralazine, Guanabenz, Guanacline, Guanazodine, Guanethidine, Guanochlor, Guanadrel, Guanfacine, Guanoxan, Hydracarbazine, Hydralazine, Hydroflumethiazide, Indapamide, Indoramin, Irbesartan, Ketanserin, Lofexidine, Mebutamate, Mecamylamine, Methyl 4-pyridyl ketone thiosemicarbazone, Mibefradil, Minoxidil, Monatepil, Moxonidine, Pheniprazine, Pinacidil, Prazosin, Raubasine, Rescinnamine, Reserpiline, Reserpine, Rilmenidine, Syrosingopine, Tasosartan, Terazosin, Tiamenidine, Todralazine, Tolonidine, Tripamide, and Urapidil.

Hydroxy-containing: Ajmaline, Cicletanine, Levcromakalim, Naftopidil, Phenactropinium chloride, and Protoveratrines.

Carboxyl-containing: Eprosartan, Fosinopril, and Telmisartan,

Amino- and Carboxyl-containing: Alacepril, gama-Aminobutyric acid, Benazepril, Candesartan, Carmoxirole, Caronapril, Cilazapril, Detapril, Enalapril, Enalaprilat, Imidapril, Lisinopril, Moexipril, Moveltipril, Perindopril, Quinapril, Ramipril, Saralasin, Spirapril, Temocapril, Trandolapril, and Valsartan.

Amino- and Hydroxyl-containing: Acebutolol, Alprenolol, Amosulalol, Arotinolol, Atenolol, Betaxolol, Bisoprolol, Bosentan, Bucindolol, Bufeniode, Bunitrolol, Bupranolol, Butofilolol, Cadralazine, Celiprolol, Carazolol, Carteolol, Cetamolol, Carvedilol, Epanolol, Indenolol, Nadolol, Dilevalol, Fenoldopam, Guanoxabenz, Labetalol, Losartan, Mepindolol, Metipranolol, Metoprolol, Moprolol, Nebivolol, Olmesartan, Oxprenolol, Penbutolol, Phentolamine, Pildralazine, Pindolol, Propranolol, Rescimetol, Sulfinalol, Talinolol, Tertatolol, Timolol, and Trimazosin.

Amino-, Hydroxyl- and Carboxyl-containing: Methyldopa, and Sampatrilat, Sulfahydryl- and Carboxyl-containing: Captopril, and Omapatrilat, Carbonyl-containing: Aranidipine, and Eplerenone, Antibiotics:

All the known amino-, hydroxyl-, and carboxyl-containing antibiotics such as Amoxicillin, Ampicillin, Olivanic acid, Metronidazole, and the like as listed in Merck Index. 13$^{th}$ edition and other drug databases integrity, ensemble, iddb, and the like. These antibiotics can be used in combination with beta-lactamase inhibitor such as clavulanic acid, penicillinic acid sulfone and the like. The following lists of antibacterial and antifungal agents are given for clarity.

Antibacterial Agents:

Amino-containing: Acedapsone, Acetosulfone sodium, Ambazone, Bacampicillin, Benzylsulfamide, Brodimoprim, Cefcapene pivoxil, Cefpodoxime proxetil, Chloramine-B, Chloramine-T, Capreomycin, Clofazimine, Cyacetacide, Cycloserine, Dapsone, Ethionamide, Furazolium chloride, N2-Formylsulfisomidine, Furonazide, Isoniazid, Lenampicillin, Linezolide, Mafenide, 4'-(Methylsulfamoyl)sulfanilanilide, Morphazinamide, Nifuradene, Nitrofurantoin, Penamecillin, Penethamate hydriodide, Pexiganan, Pivampicillin, Pivcefalexin, Picloxydine, Protionamide, Pyrazinamide, Solasulfone, Subathizone, 4,4'-Sulfinyldianiline, Sulfoxone sodium, 4'-Sulfanilylsulfanilamide, Sulfoniazide, Sulfabenzamide, Sulfacetamide, Sulfachlorpyridazine, Sulfacytine, Sulfadiazine, Sulfadicramide, Sulfadimethoxine, Sulfadoxine, Sulfaethidole, Sulfaguanidine, Sulfaguanole, Sulfalene, Sulfamerazine, Sulfameter, Sulfamethazine, Sulfamethizole, Sulfamethomidine, Sulfamethoxazole, Sulfamethoxypyridazine, Sulfamethylthiazole, Sulfametrole, Sulfamidochrysoidine, Sulfamoxole, Sulfanilamide, p-Sulfanilylbenzylamine, Sulfanilylurea, N-Sulfanilyl-3,4-xylamide, Sulfaperine, Sulfaphenazole, Sulfaproxyline, Sulfapyrazine, Sulfasomizole, Sulfasymazine, Sulfathiazole, Sulfathiourea, Sulfisomidine, Sulfisoxazole, Sultamicillin, Sulfatolamide, Talampicillin, Taurolidine, Tetroxoprim, Thiazosulfone, Thiacetazone, Tiocarlide, and Trimethoprim.

Hydroxyl-containing: Azithromycin, Chloroxylenol, Chlorquinadol, Clofoctol, Cloxyquin, Diathymosulfone, Glucosulfone sodium, Nifurpirinol, Nifurtoinol, Nitroxoline, Roxarsone, Roxithromycin, Xanthocillin, and Xibornol.

Carboxyl-containing (including sulfate, phosphate and phosphonate-containing): Amdinocillin, Cinoxacin, Difloxacin, Fosfomycin, and Hydnocarpic acid.

Amino- and Carboxyl-containing (including sulfate-, sulfonic acid-, phosphate and phosphonate-containing): Acediasulfone, Amphomycin, Ampicillin, Azidocillin, Azlocillin, Aztreonam, Bacitracin, Balofloxacin, Betamipron, Carbenicillin, Carindacillin, Carumonam, Cefaclor, Cefazedone, Cefazolin, Cefclidin, Cefditoren, Cefepime, Cefetamet, Cefixime, Cefmenoxime, Cefmetazole, Cefodizime, Ceforanide, Cefotaxime, Cefotetan, Cefotiam, Cefoxitin, Cefozopran, Cefpimizole, Cefpirome, Cefroxadine, Cefsulodin, Ceftazidime, Cefteram, Ceftezole, Ceftibuten, Ceftizoxime, Ceftriaxone, Cefuroxime, Cefuzonam, Cephacetrile sodium, Cephalexin, Cephaloglycin, Cephaloridine, Cephalosporin C, Cephalothin, Cephapirin sodium, Cephradine, Cilastatin, Ciproflaxacin, Clinafloxacin, Clometocillin, Cyclacillin, Dicloxacillin, Enoxacin, Epicillin, Fenbenicillin, Floxacillin, Hetacillin, Loracarbef, Metampicillin, Methicillin, Mezlocillin, Nafcillin, Noprysulfamide, Opiniazide, Oxacillin, Penicillin(s), Penimepicycline, Phenethicillin, Phthalylsulfacetamide, Phthalylsulfathiazole, Piperacillin, Propicillin, Quinacillin, Succinylsulfathiazole, Succisulfone, Sulbenicillin, Sulfachrysoidine, Sulfanilic acid, Temocillin, Ticarcillin, and Tigemonam.

Amino- and Hydroxyl-containing: Amikacin, p-Aminosalicylic acid hydrazide, Arbekacin, Azidamfenicol, Bambermycins, 5-Bromosalicylhydroxamic acid, Butirosin, Clindamycin, Clomocycline, Chloramphenicol, Cloxacillin, Colistin, Demeclocycline, Deoxydihydrostreptomycin, Dibekacin, Dihydrostreptomycin, Dirithromycin, Doxycycline, Enviomycin, Ethambutol, Forimicins, Gentamycin, Glyconiazide, N4-beta-D-Glucosylsulfanilamide, Gramicidin(s), Isepamicin, Kanamycin(s), Lincomycin, Meclocycline, Methacycline, Micronomicin, Neomycin, Netilmicin, Novobiocin, Paromomycin, Phenyl aminosalicylate, Pipacycline, Polymyxin, Primycin, Ramoplanin, Ribostamycin, Rifabutin, Rifalazil, Rifamide, Rifamycin SV, Rifampin, Rifapentine, Rifaximin, Ristocetin, Salinazid, Sancycline, Sisomicin, Streptolydigin, Streptomycin, Streptonicozid, 2-p-Sulfanilylanilinoethanol, Thiamphenicol, Thiostrepton, Tobramycin, Tuberactinomycin, Viomycin, and Virginiamycin.

Hydroxyl- and Carboxyl-containing (including sulfate, phosphate and phosphonate-containing): Fropenem, Nadifloxacin, Biapenem, Fusidic acid, and Merbromin.

Hydroxyl- and Aldehyde-containing: Josamycin, Leucomycins, Midecamycins, Miokamycin, Rokitamycin, and Spiramycin.

Amino-, Hydroxyl-, and Carboxyl-containing (including sulfate, phosphate and phosphonate-containing): p-Aminosalicylic acid, Apicycline, Amoxicillin, Apalcillin, Aspoxicillin, Benzoylpas, Cefadroxil, Cefamandole, Cefatrizine, Cefbuperazone, Cefdinir, Cefminox, Cefonicid, Cefoperazone, Cefoselis, Cefpiramide, Cefprozil, Ertapenem, Flomoxef, Imipenem, Lymecycline, Meropenem, Moxalactam, Negamycin, Panipenem, Ritipenem, Salazosulfadimidine, Sulfaloxic acid, 4-Sulfanilamidosalicylic acid, Teicoplanin, Tyrocidine, and Vancomycin.

Keto-containing: Troleandomycin.

Hydroxy- and Keto-containing: Carbomycin, Clarithromycin, Erythromycin, all erythromycin ester derivatives, Oleandomycin, and Telithromycin.

Hydroxy-, Aldehyde-, and Keto-containing: Rosaramicin.

Amino- and Keto-containing: Porfiromycin.

Carboxyl- and Keto-containing: Fleroxacin, Flumequine, Miloxacin, Nalidixic acid, Ofloxacin, Oxolinic acid, Pefloxacin, Piromidic acid, Prulifloxacin, Rosoxacin, and Rufloxacin.

Amino-, hydroxyl-, and Keto-containing: Chlortetracycline, Dalfopristin, Guamecycline, Mikamycin, Minocycline, Oxytetracycline, Pristinamycin, Quinupristin, Rolitetracycline, Spectinomycin, and Trospectomycin.

Amino-, carboxyl-, and keto-containing: Garenoxacin, Gatifloxacin, Gemifloxacin, Grepafloxacin, Lomefloxacin, Moxifloxacin, Norfloxacin, Pazufloxacin, Pipemidic acid, Sitafloxacin, Sparfloxacin, Tosufloxacin, and Trovafloxacin.

Sulfahydryl-containing: Pyrithione.

Antifungal Agents:

Amino-containing: Chlordantoin, Exalamide, Flucytosine, Loflucarban, Magenta I, and Pyrrolnitrin.

Hydroxy-containing: Chlorphenesin, Ciclopirox, Dermostatin, Filipin, Fluconazole, Fungichromin, Pecilocin, Posaconazole, Ravuconazole, Rubijervine, Siccanin, 2,4,6-Tribromo-m-cresol and Voriconazole.

Carboxyl-containing: Undecylenic acid (10-undecenoic acid), and Propionic acid,

Amino- and Carboxyl-containing: Azaserine.

Amino- and Hydroxyl-containing: Salicylanilide, Acrisorcin (9-Aminoacrindine compound with 4-Hexylresorcinol (1:1)), Anidulafungin, Bromosalicylchloranilide, Buclosamide, Caspofungin, Micafungin, and Tubercidin.

Amino-, Carboxyl- and Hydroxyl-containing: Natamycin, Amphotericin B, Lucensomycin, and Nystatin.

Carbonyl-containing: sodium propionate and griseofulvin.

Hydroxy- and carbonyl-containing: Viridin.

Amino-, hydroxyl-, and carbonyl-containing: Perimycin and Mepartricin.

Amino-, carboxyl-, hydroxyl-, and carbonyl-containing: Candicidin.

Antiviral Drugs:

Hydroxy-containing: Edoxudine, Floxuridine, Idoxuridine, Kethoxal, Podophyllotoxin, Sorivudine, Stavudine, Trifluridine, and Zidovudine.

Amino-containing: Amantadine, Amidinomycin, Atevirdine, Capravirine, Delavirdine, Efavirenz, Famciclovir, Imiquimod, Lamivudine, Methisazone, Moroxydine, Nevirapine, Oseltamivir, Rimantadine, Stallimycin, mantadine, and Valacyclovir.

Amino- and Hydroxyl-containing: Abacavir, Acyclovir, Adefovir, Amprenavir, Atazanavir, Cidofovir, Didanosine, Dideoxyadenosine, Emtricitabine, Entecavir, Indinavir, Lamivudine, Lopinavir, 5-(methylamino)-2-deoxyuridine (MADU), Nelfinavir, Penciclovir, Resiquimod, Ribavirin, Ritonavir, Saquinavir, Tenofovir, Tipranavir, Valganciclovir, Vidarabine, and Zalcitabine.

Carboxyl- and Hydroxyl-containing: Foscarnet sodium, and Ganciclovir.

Amino-, Carboxyl- and Hydroxyl-containing: Zanamivir.
Antimalarial:
Amino-containing: Chlorguanide, Chloroquine, Chlorproguanil, Cycloguanil, Pamaquine, Plasmocid, Primaquine, Quinocide, and Tafenoquine.
Hydroxyl-containing: Artemisinin alcohol, Bebeerines, Cinchonidine, Cinchonine, Dihydroartemisinin, Halofantrine, Lumefantrine, Quinine and Yingzhaosu A.
Carboxyl-containing: Arteflene and Artesunate.
Amino-, and Hydroxyl-containing: Amodiaquin, Hydroxychloroquine, Mefloquine, and Pyronaridine.
Hydroxyl, and carbonyl-containing: Fosmidomycin.
Carbonyl-containing: Arteflene.
Antineoplastic Drugs:
Hydroxy-containing: Aclacinomycins, Arzoxifene, Batimastat, Broxuridine, Calusterone, Capecitabine, CC-1065, Chromomycins, Diethylstilbestrol, Docetaxel, Doxifluridine; Droloxifene, Dromostanolone, Enocitabine, Epitiostanol, Estramustine, Etanidazole, Etoposide, Fenretinide, Flavopiridol, Formestane, Fosfestrol, Fulvestrant, Gemcitabine, Irinotecan, Melengestrol, Menogaril, Miltefosine, Mitobronitol, Mitolactol, Mopidamol, Nitracrine, Nogalamycin, Nordihydroguaiaretic Acid, Olivomycins, Paclitaxel and other known paclitaxel analogs, Plicamycin, Podophyllotoxin, Retinoic acid (including all trans-retinioc acid), Roquinimex, Rubitecan, Seocalcitol, Temoporfin, Teniposide, Tenuazonic Acid, Topotecan, Valrubicin, Vinblastine, Vincristine, and Zosuquidar.
Amino-containing (including Amide-NH and Sulphonamide-NH, Carbamate-NH, Sulfamate-NH, and Phosphomide-NH): 9-Aminocamptothecin, Aminolevulinic Acid, Amsacrine, Bisantrene, Cactinomycin, Carboquone, Carmofur, Carmustine, Cyclophosphamide, Dacarbazine, Dactinomycin, Demecolcine, Diaziquone, 6-Diazo-5-oxo-L-norleucine (DON), Edatrexate, Efaproxiral, Eflornithine, Eniluracil, Erlotinib, Fluorouracil, Gefitinib, Gemcitabine, Goserelin, Histamine, Ifosfamide, Imatinib, Improsulfan, Lanreotide, Leuprolide, Liarozole, Lobaplatin, Cisplatin, Carboplatin, Lomustine, Lonafarnib, Mannomustine, Melphalan, Methotrexate, Methyl Aminolevulinate, Miboplatin, Mitoguazone, Mitoxantrone, Nilutamide, Nimustine, Nolatrexed, Oxaliplatin, Pemetrexed, Phenamet, Piritrexim, Procarbazine, Raltitrexed, Tariquidar, Temozolomide, Thiamiprine, Thioguanine, Tipifarnib, Tirapazamine, 3-Aminopyridine-2-carboxaldehyde thiosemicarbazone (3-AP)/3-Aminopyridine-4-methyl-2-carboxaldehyde thiosemicarbazone (3-AMP/Triapine/OCX-191/OCX-0191), Trimetrexate, Uracil Mustard, Uredepa ([Bis(1-aziridinyl)phosphinyl]carbamic acid ethyl ester, ethyl carbamate and Meturedepa.
Both Hydroxy- & Amino-containing (including Amide-NH and Sulphonamide-NH, Carbamate-NH, Sulfamate-NH, and Phosphomide-NH): Ancitabine, Anthramycin, Azacitidine, Bleomycins, Bropirimine, Buserelin, Carubicin, Chlorozotocin, Cladribine, Cytarabine, Daunorubicin, Decitabine, Defosfamide, Docetaxel, Doxorubicin, Ecteinascidins, Epirubicin, Gemcitabine, Hydroxyurea, Idarubicin, Marimastat, 6-Mercaptopurine, Pentostatin, Peplomycin, Perfosfamide, Pirarubicin, Prinomastat, Puromycin, Ranimustine, Streptonigrin, Streptozocin, Tiazofurin, Troxacitabine, Vindesine and Zorubicin.
Carboxyl-containing: Butyric acid.
Antioxidants/Free Radical Scavengers:
Amino-containing (including some investigational drugs): BTX-51072 (4,4-dimethyl-3,4-dihydro-2H-1,2-benzoselenazine), Carnosine, Melatonin, (+)-R-Pramipexole, and Stobadine.
Hydroxyl-containing (including some investigational drugs): Ascorbic acid, Curcumin, Dexanabinol, Edaravon, (−) Epigallocatechin Gal late, Emoxipin, Hydroxytyrosol, Idebenone, Luteolin, Nicanartine, NZ-419, Oxyresveratrol, Probucol (including probucol prodrugs such as AGI-1067 and AGI-1096), Quercetin, Reductic acid, Silybin, Tempol (4-Hydroxy-TEMPO), and alfa-Tocopherol (Vitamin E).
Carboxyl-containing (including some investigational drugs): N-Acetyl L-cysteine, Alfa-Lipoic acid, Raxofelast, and Tetomilast.
Amino-/Hydroxyl-, and Carboxyl-containing (including some investigational drugs): N-Acetyl carnosine, L-Carnitine, and SCMC-Lys (S-carboxymethyl-L-cysteine Lysine salt $H_2O$).
Amino- and Hydroxyl-containing (including some investigational drugs): BN-82451, and Zeatin.
Benzodiazepine Tranquilizers and Hypnotics:
Diazepam, Triazolam, Alprazolam, and the like.
Antiulcer Agents:
Amino-containing (including Amide NH and Sulphonamide NH and Phosphomide NH, etc.): Aldioxa, Benexate HCl, Cimetidine, Ebrotidine, Ecabapide, Esaprazole, Esomeprazole, Famotidine, Irsogladine, Lafutidine, Lansoprazole, Omeprazole, Pantoprazole, Pirenzepine, Polaprezinc, Rabeprazole, Ranitidine, Roxatidine, and Troxipide.
Hydroxyl (and Keto and Keto and/or Carboxyl)-containing: Enprostil, Misoprostol, Ornoprostil, Plaunotol, Rioprostil, Trimoprostil, and Oryzanol A.
Carboxyl-containing: Acetoxolone, Carbenoxolone, Rebamipide, and Sofalcone.
Amino (or Hydroxyl)- and Carboxyl-containing: Cetraxate, Ecabet, S-Methylmethionine, Rosaprostol, and Rotraxate.
Carbonyl-containing: Spizofurone, and Teprenone.
Anticonvulsants:
Amino-containing (including Amide NH and Sulphonamide NH and Phosphomide NH, etc.): Acetylpheneturide, Albutoin, N-benzyl-3-chloropropionamide, Carbamazepine, Cinromide, Clonazepam, Decimemide, Dimethadione, Doxenitoin, Ethosuximide, Ethotoin, Felbamate, Fosphenyloin, Lamotrigine, Levetiracetam, Mephenyloin, Mephobarbital, Metharbital, Methetoin, Nitrazepam, Oxcarbazepine, Oxicarbamazepine, Phenacemide, Phenetharbital, Pheneturide, Phenobarbital, Phenylmethylbarbituric Acid, Phenyloin, Phethenylate Sodium, Primidone, Progabide, Remacemide, Rufinamide, Suclofenide, Sulthiame, Talampanel, Tetrantoin, Topiramate, Valpromide, Zonisamide, 5-Methyl-5-(3-phenanthryl)hydantoin, and 3-Methyl-5-phenylhydantoin.
Hydroxyl-containing: Ganaxolone.
Hydroxyl-, and Amino-containing (including Amide NH and Sulphonamide NH and Phosphomide NH): 4-Amino-3-hydroxybutyric Acid, Atrolactamide, and Buramate.
Carboxyl- and Amino-Containing (including Amide NH and Sulphonamide NH and Phosphomide NH): Gabapentin, Pregabalin, and Vigabatrin.
Carboxyl-containing: Tiagabine, and Valproic Acid.
Antiparkinson'S: Levodopa & Carbidopa.
Antidepressant:
Amino-containing (including Amide NH and Sulphonamide NH and Phosphomide NH, etc.): Amoxapine, Caroxazone, Demexiptiline, Desipramine, Duloxetine, Fluoxetine, Fluvoxamine, Indalpine, Indeloxazine Hydrochloride, Iproclozide, Iproniazid, Isocarboxazid, Levophacetoperane, Maprotiline, Metapramine, Milnacipran, Minaprine, Moclobemide, Nialamide, Nomifensine, Nortriptyline, Octamoxin, Oxypertine, Paroxetine, Protriptyline, Reboxetine, Rolipram, Sertraline, Tofenacin, Tranylcypromine, Viloxazine, Benmoxine, and Rolicyprine.

Hydroxyl-containing: Befloxatone, Bupropion, Fenpentadiol, Hypericin, Opipramol, Pyrisuccideanol, Toloxatone, and Venlafaxine.

Hydroxyl-, and Amino-containing (including Amide NH and Sulphonamide NH and Phosphomide NH): S-Adenosylmethionine, 5-Hydroxytryptophan, and Roxindole.

Carboxyl- and Amino-Containing (including Amide NH and Sulphonamide NH and Phosphomide NH): Amineptine, and Tianeptine.

Antihistaminic

Amino-containing (including Amide NH and Sulphonamide NH and Phosphomide NH, etc.): Antazoline, Astemizole, Clobenzepam, Desloratadine, Epinastine, Metron S, Mizolastine, and Tritoqualine.

Hydroxyl-containing: Terfenadine, and N-Hydroxyethylpromethazine Chloride.

Hydroxyl-, and Amino-containing (including Amide NH and Sulphonamide NH and Phosphomide NH, etc.): Cetoxime.

Carboxyl-containing: Acrivastine, Bepotastine, Cetirizine, and Levocabastine,

Carboxyl- and Hydroxyl-containing: Fexofenadine.

Anticancer, Antioxidative, Antiinflammatory, and Cardioprotective Agent: Trans-Resveratrol [(E)-3,4',5-Trihydroxystilbene).

Antidiabetic: Metformin, and Nateglinide/Glipizide/Glibenclamide (Glyburide).

It should be understood that while the lists of names of various categories of drugs have been included above, such lists are presented in a way of illustration of the structural features of the qualifying drugs in this invention and therefore, the number and types of listed drugs are not necessarily limited thereto. In principal, any amino-, and/or carboxyl, and/or carbonyl-, and/or hydroxyl-containing drug (from both known and investigational drugs), irrespective of its therapeutic category and their mechanism of action, as listed in drug databases such as Merck Index, prous science's ensemble, integrity, iddb, and the like, are generally covered within the true spirit and scope of the present invention. For clarity, in addition to the above lists of drugs, any amino-, and/or carboxyl-, and/or carbonyl-, and/or hydroxyl-containing drug(s) (both known and investigational drugs) from the following therapeutic areas are covered without any limitation:

CENTRAL NERVOUS SYSTEM: Sedatives, Hypnotics, Antidepressants, Antipsychotics and Antimanics, Analgesics & Antipyretics, Antimigraine agents, Anticonvulsants, Drugs used in parkinsonism and movement disorders, Drug for dementia, Antiemtics, drugs for Vertigo, CNS Stimulants & activators.

EYE: Antiinfective eye preparations, Antiinflammatory and antiallergic preparations, antiglucoma drugs and other preparations to cure eye diseases.

EAR, NOSE and OROPHARYNX: Drugs used aural, nasal and oropharyngeal preparation.

CARDIOVASCULAR SYSTEM: Antiarrhythemic drugs, Antihypertensives (including alfa/beta-blockers, channel blockers, ACE inhibitors, Angiotensin II receptor antagonists, diuretics, etc.), Antianginals (including nitrates, calcium channel blockers, etc.), Drugs for cardiac failure and shock, Vasodilators, Coagulants, Anticoagulants, Thrombolytics and antiplatelet drugs.

RESPIRATORY SYSTEM: Respiratory stimulants, Antitussives, Expectorants, Mucolytics and Decongestants, Antihistamine agents, and antiasthmatics.

GASTRO INTESTINAL TRACT: Antiulcer and Antisecretory drugs (including $H_2$ receptor antagonists, Proton Pump Inhibitors, Prostaglandin analogues, etc.), Antacids, Antispasmodics and drugs modifying intestinal motility, Antidiarrhoeals (including antimotility and antimicrobial drugs) and drugs acting on gall bladder.

GENITO URINARY SYSTEM: Urinary antiinfectives, Diuretics, Urinary analgesics & antispasmodics, Antiinfective drugs acting on urethra and vagina, drugs acting on uterus, Drugs for prostatic hypertrophy (including alfa blockers and antiandrogens), Drugs for erectile dysfunction, and Spermicidal & nonhormonal contraceptives.

SKIN: Emollients and keratolytics, topical antiinfectives, topical antifungals, topical parasiticidals, topical steroids, topical drugs for acne vulgaris, drugs for psoriasis, pigmentation disorders, and Anti seborrhoeics.

MUSCULO-SKELETAL DISORDERS: Non Steroidal Anti Inflammatory Drugs (NSAIDs) including COX-2 inhibitors, Antiarthritic agents, Immunosuppressants, Topical analgesics, Muscle relaxants and Neuromuscular Drugs.

INFECTIONS AND INFESTATIONS: Penicillin antibiotics, Cephalosporin antibiotics, Quinolone & Fluoroquinolone antibiotics, Macrolide antibiotics, Chloramphenicol, Tetracycline antibiotics, Sulfonamides, Antianaerobics such as Metronidazole, Antitubercular drugs, Antileprosy drugs, Antifungals, Antiprotozoals, Anthelminthics & Antiinfective Drugs, Antimalarials and Antivirals.

ENDOCRINE SYSTEM: Anabolic and androgenic steroids, Corticosteroids, Oestrogens, Progestogens and Hormonal contraceptives, Fertility Agents, Trophic hormones and related drugs, Thyroid and antithyroid drugs, Antidiabetics and hyperglycaemics.

NUTRITION: Vitamins, Amino acids, Anti-obesity drugs

METABOLISM: Hypolipidaemic drugs (including fibric acid derivatives, statins [(i.e., HMG CoA reductase inhibitors), nicotinic acid group, etc.], Drugs used for Gout and Drugs affecting bone metabolism (including bisphosphonates).

NEOPLASTIC DISORDERS: Anticancer drugs such as alkylating agents, cytotoxic antibiotics, antimetabolites such as cytarbine, Fludarbine, 5-Fluorouracil, Mercaptopurine, Thioguanine, etc., Vinca alkaloids and Etoposide, Taxanes, Topoisomerase 1 inhibitors, Cytotoxic immunosuppressants, Immunostmulants, Cytoprotectives such as Amifostine, Oestrogens, Progestogens, hormon antagonists and other antineoplastic drugs.

ALLERGY AND IMMUNOLOGY: Antiallurgics such as non-sedative antihistamins (e.g., Cetirizine, Desloratadine, Terfenadine, Fexofenadine, etc.), sedative histamines and histamine receptor blockers.

ANAESTHETICS & SURGICALS: Local anaesthetics, intravenous anaesthetics, inhalation anaesthetics and muscle relaxants.

Drug Combinations:

It is appreciated that prodrugs of any two or more drugs from the above lists of potential drugs can be used in combination depending on the medical application/need. While a combination formulation may occasionally consist of more than two drugs (depending on the medical need), the following pairs of drugs are covered in this invention as illustrative pairs of candidate drugs for combination therapy.

ANTICANCER: Paclitaxel and Doxorubicin, Paclitaxel and Mitomycin C; Paclitaxel and 9-aminocamptothecin, 3-Aminopyridine-2-carboxaldehyde thiosemicarbazone (3-AP)/3-Aminopyridine-4-methyl-2-carboxaldehyde thiosemicarbazone (3-AMP) and another known anticancer drug such as Paclitaxel, Doxorubicin, Mitomycin C and the like; CC-1065 and another known anticancer drug such as Paclitaxel, Doxorubicin, Mitomycin C and the like; Trans-Resveratrol [(E)-3,4',5-trihydroxystilbene) and another known anticancer drug such as Paclitaxel, Doxorubicin, Mitomycin C and the like; Retinoic acid (including all trans-retinoic acid) and Butyric acid. Paclitaxel and Captopril, Doxorubicin and Biotin. 5-Fluorouracil and Cytarabine. Edatrexate and Paclitaxel; Cephalosporanic acid and Paclitaxel; Cephalosporin and Paclitaxel; and Paclitaxel and Gemcitabine.

ANTIPARKINSON'S: Levodopa and Carbidopa.

ANTIBIOTICS: Amoxicillin and Clavulanic acid; Ampicillin and Clavulanic acid, Amoxicillin and Pencillinic acid sulfone; Ampicillin and Pencillinic acid sulfone; Olivanic acid (or any carbapenem antbiotic) and a renal dipeptidase (dehydropeptidase I) inhibitor such as 3-substituted Z-2-acylaminopropionic acid and the like.

ANTILIPIDEMIC AND HYPERTENSION: Lifibrol and Lovastatin/Pravastatin/Fluvastatin/Atorvastatin/Simvastatin; Ezetimibe and Lovastatin/Pravastatin/Fluvastatin/Atorvastatin/Simvastatin;

Amlodipine and Lovastatin/Pravastatin/Fluvastatin/Atorvastatin/Simvastatin.

ANTIDIABETIC: Metformin and Nateglinide/Glipizide/Glibenclamide (Glyburide)

ANTIDIABETIC AND HYPERTENSION: Metformin and Lovastatin/Pravastatin/Fluvastatin/Atorvastatin/Simvastatin.

ANTIASTHMATIC, ALLERGIC RHINITIS AND CHRONIC OBSTRUCTIVE PULMONARY DISEASE (COPD): Pseudoephedrine and Fexofenadine/Cetirizine/Desloratadine/Epinastine; Salbutamol and Ipratropium bromide; Mometasone and Formoterol/Salmeterol; Fluticasone and Formoterol/Salmeterol; Budesonide and Formoterol/Salmeterol.

ANTIARTHRITIS, INFLAMMATION AND ULCERS: Diclofenac (any known NSAID) and Misoprostol; Diclofenac (any known NSAID) and a proton pump inhibitor such as Omeprazole, Lansoprazol, Rabeprazole, Leminoprazole, Pantoprazole, and the like; A known antibacterial agent and a proton pump inhibitor such as Omeprazole, Lansoprazol, Rabeprazole, Leminoprazole, Pantoprazole, and the like; Naproxen (or any known NSAID) and Prophenazone; Acetaminophen and chlorzoxazone/metaxalone/mephenoxalone.

ANTIVIRAL (HIV/AIDS, HEPATITIS B AND OTHER VIRAL INFECTIONS): Zidovudine and Lamivudine; Triple prodrug of Zidovudine; Lamivudine and Abacavir (Ziagen); Lopinavir and Ritonavir; Lamivudine and Adefovir or its prodrug adefovir dipivoxil; Amprenavir and Zidovudine; Nelfinavir and a nucleoside reverse transcriptase inhibitor such as Zidovudine, Lamivudine, and the like; Stavudine and an antiretroviral agent such as Zidovudine, Lamivudine, and the like; Dideoxyinosine and an antiretroviral agent such as Zidovudine, Lamivudine, and the like; Emtricitabine and Penciclovir/Famciclovir; Acyclovir (or any other known antiviral compound) and a bile acid such as cholate, deoxycholate, chenodeoxycholate, and ursodeoxycholate (for targeting bile acid transporters for enhanced oral bioavailability of the drug; Triple and prodrug of Zidovudine, Lamivudine and Efavirenz.

In addition to the above list of drugs, the present invention also covers newer drugs with the above mentioned active functional groups as listed in the Merck index (13$^{th}$ edition) and other drug databases such as Prous Science's ensemble, integrity and the investigational drugs as listed in databases such as iddb, ensemble, integrity, and the like without any limitation.

It should be understood that either or both of any selected pair of drugs (in any proportion) can be in the form of nitrate ester (NO-releasing) prodrug(s) of formula (I) or pharmaceutically acceptable salts thereof and the other drug can be in its native form. For clarity, let us assume that Ibuprofen and Paracetamol are present as active principles in a pharmaceutical composition. Then, either or both of these drugs can be in their prodrug form (i.e., NO-Paracetamol and Ibuprofen/Paracetamol and NO-Ibuprofen/NO-Paracetamol and NO-Ibuprofen, etc.) and they can be present in any proportion.

It should also be understood that a pharmaceutical composition consisting of two or more of the above listed/qualified drugs, one of the drugs can be in the form of NO-releasing (nitrooxy derivative) prodrug and the other drug(s) in the combination can be in the form another type of prodrug(s).

It should also be understood that a pharmaceutical composition containing a combination of one of the above listed/qualified drug(s) and its own prodrug is also covered (i.e., a pharmaceutical composition consisting of NO-Paracetamol and Paracetamol in any proportion). In such pharmaceutical combinations, the free drug will be useful for faster onset of action and the prodrug will be useful for extension of the duration of action as it releases the drug in a controlled fashion over a longer period of time. Such combination drug therapy may also minimize the toxicity and other side effects due to excessive plasma concentration of free drug. It should also be understood that a pharmaceutical combination may contain a prodrug of one of the above listed/qualified drugs and an another type of prodrug of the same drug (i.e., NO prodrug of paracetamol and mutual prodrug of paracetamol with another drug) and these can be present in any therapeutic proportion depending on the medical need.

EXPERIMENTAL

Abbreviations Used

BOP: Benzotriazol-1-yl-oxy-tris(dimethylamino)phosphonium hexafluorophosphate
DMF: N,N-Dimethylformamide
DSC: N,N'-Disuccinimidyl carbonate
CDI: N,N'-Carbonyldiimidazole
DTE: Dithioerythritol
DTT: Dithiothreitol
DCC: N,N'-Dicyclohexylcarbodiimide
EDAC. HCl: 1-Ethyl-(3-dimethylaminopropyl)carbodiimide hydrochloride
HBTU: O-(Benzotriazol-1-yl)-N,N,N',N'-tetramethyluronium hexafluorophosphate
TBTU: O-(Benzotriazol-1-yl)-N,N,N',N'-tetramethyluronium tetrafluoroborate
EtOH: Ethanol
Et$_2$O: Diethyl ether
THF: Tetrahydrofuran
DMSO: Dimethyl sulfoxide
TEA: Triethylamine
DIPEA: N,N-Diisopropylethylamine
DCM: Dichloromethane
EtOAc: Ethyl acetate
DME: Dimethoxyethane
MeOH: Methanol
PE: Petroleum ether
RT: Room temperature
TFA: Trifluoroacetic acid
HOBT: N-Hydroxybenzotriazole Synthetic Methods:

The prodrugs described herein can be prepared by any number of methods known/obvious to those skilled in the art. The synthetic approaches and the linkages are chosen depending upon the functional groups such as carboxyl, hydroxyl, amino or carbonyl groups present in the drug molecules to be used. The following illustrative methods, as shown in Schemes 1 through 9, can be utilized to make carbonate, urethane, amide, ester, N-acyl carbamate, N-acyl amide, N-acyl sulfamate, and N-acyl sulfonamide, N-acyl phosphoramide, N-oxycarbonylsulfonamide, N-oxycarbonylcarbamate linkages, etc., between drug(s) and linker(s).

Method(s) of Making Carbonate Linkage(s):

As depicted in the scheme 1, the carbonate linkage between the drug and the linker can be made by reacting the hydroxyl-containing drug (alternatively, hydroxyl group of the linker) with phosgene or its equivalents such as diphosgene, triphosgene, N,N'-carbonyldiimidazole (CDI), N,N'-disuccinimidyl carbonate (DSC), 4-nitrophenyl chloroformate and the like, to give a reactive alkoxycarbonyl derivative, where LG is suitable leaving group such as a halide, imidazole, O-succinimide, 4-nitrophenoxide and the like, which can be reacted with hydroxyl group of the linker (alternatively, hydroxyl group of drug if the linker is converted to active alkoxycarbonyl derivative) in the presence of a suitable base and solvent.

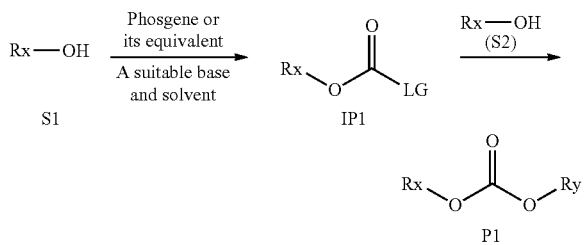

Rx and Ry are any monovalent organic radicals;

Bases such as triethylamine, diisopropylethylamine, 4-(dimethylamino)pyridine (DMAP), and the like, can be used. Suitable solvents include $CH_2Cl_2$, $CHCl_3$, DMF, THF, ACN, ethyl acetate, ethyl ether and the like.

Method(s) of Making Urethane Linkage(s):

As shown in scheme 2, the urethane linkage between the drug and the linker can be made by reacting the hydroxyl-containing linker with phosgene or its equivalents (defined above) to give a reactive alkoxycarbonyl derivative, which can be reacted with amino-containing drug in the presence of a suitable base and solvent. Alternatively, a urethane linkage can be made by adding an alcohol to an isocyanate.

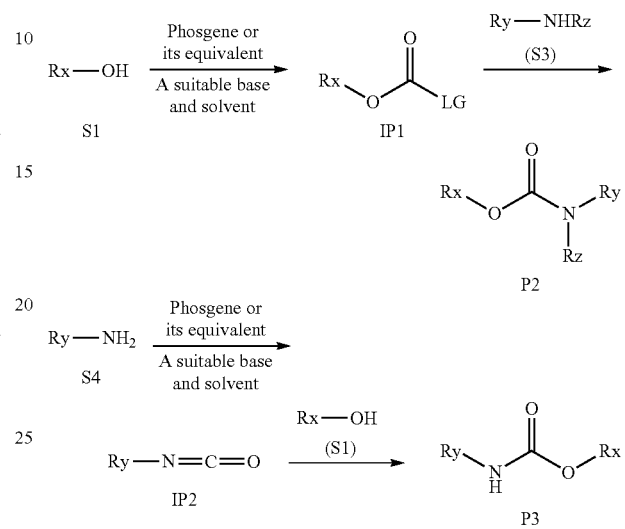

Rx, Ry and Rz are any monovalent organic radicals;

Suitable bases and solvents are same as defined above.

Method(s) of Making Amide or Ester Linkage(s):

As shown in the Scheme 3, an amide or ester linkage between the drug and the linker can be made by reacting a carboxyl-containing drug with an amino- or hydroxyl-containing linker in the presence of a suitable coupling agent, base and solvent. Alternatively, the carboxyl-containing compound can be first converted to reactive carbonyl derivative such as an acid halide, a succinimide ester, a pentafluorophenyl ester, an imidazolide and the like, which can be treated with amino-containing or hydroxyl-containing linker in the presence of a suitable base and solvent to afford the corresponding amide or ester linkage(s), respectively (see, Bodanszky, M. and Bodanszky, A., The Practice of Peptide Synthesis, Springer-Verlag, New York, 1984)

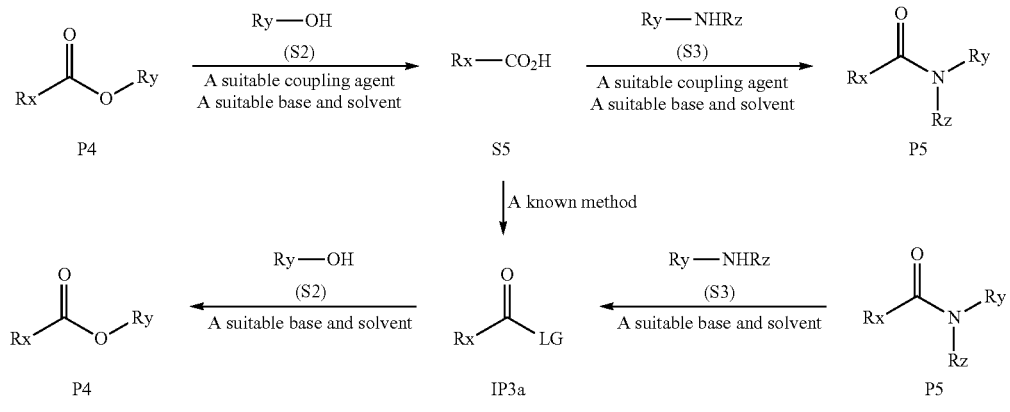

Rx, Ry and Rz are any monovalent organic radicals;

Suitable coupling agents include DCC, EDCl.HCl, BOP, HBTU, TBTU, DCC/HOBT, EDC/HOBT, and the like. Suitable bases and solvents are same as defined above.

Method(s) of Making N-Acyl Carbamate and N-Acyl Urea Linkage:

The linkage such as N-acyl carbamate linkage between the linker and drug can be made as shown in Scheme 4. Thus, treatment of an alcohol with phosgene or its equivalent can yield the corresponding carbonochloridate, which upon treatment with ammonia gas can give the corresponding carbamate intermediate. The carbamate nitrogen can be acylated by a suitable carboxylic acid derivatives such as anhydride or acid halide, a succinimide ester, a pentafluorophenyl ester, an imidazolide, and the like, in the presence of a suitable base to yield the corresponding N-acyl carbamate. Alternatively, N-acyl carbamate can be made by the reaction of an alcohol with N-acyl isocyanate, which can be prepared either by the reaction of the corresponding amide with oxalyl chloride (See, Speziale, A. J. et al., J. Org. Chem. 1962, 27, 3742; Speziale, A. J. et al., J. Org. Chem. 1963, 28, 1805-1811) or by the reaction of the corresponding acid chloride with silver cyanate. (See, Hill, A. J. et. al., J. Am. Chem. Soc., 1940, 62, 1595; Kim, D. K. J. Heterocyclic Chem. 1995, 32, 1625).

rophenyl ester, an imidazolide, and the like, in the presence of a suitable base to yield the corresponding N-acyl amide.

Scheme 5

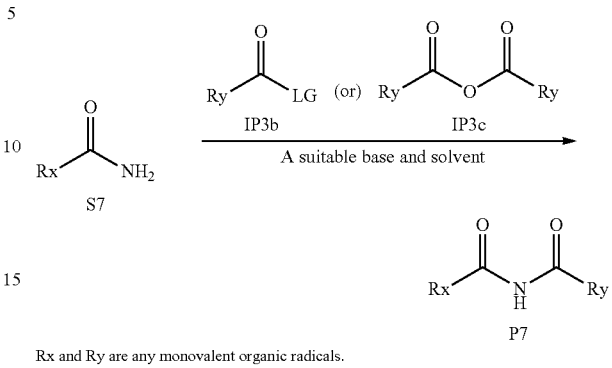

$R_x$ and $R_y$ are any monovalent organic radicals.

Suitable bases and solvents are same as defined above.

Method(s) of Making N-Acyl Sulfamate Linkage:

The linkage such as N-acyl sulfamate between the linker and drug can be made as shown in Scheme 6. Thus, treatment

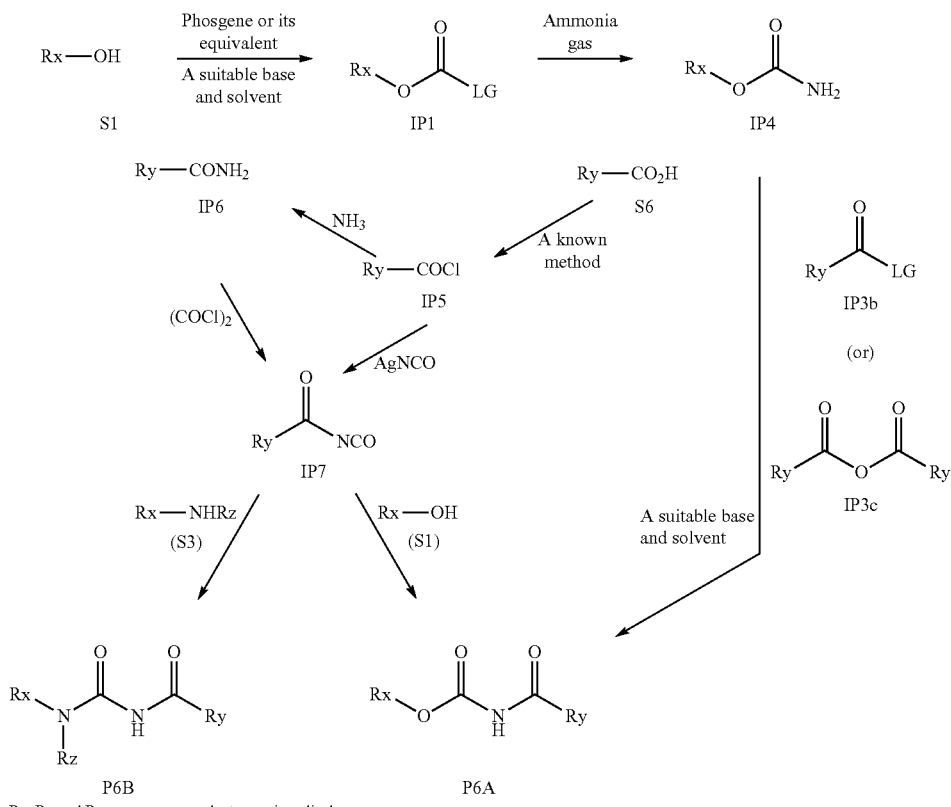

Scheme 4

$R_x$, $R_y$ and $R_z$ are any monovalent organic radicals.

Suitable bases and solvents are same as defined above.

Method(s) of Making N-Acyl Amide Linkage:

The N-acyl amide linkage between the linker and drug can be made as shown in Scheme 5. Thus, the amide nitrogen can be acylated by a suitable carboxylic acid derivatives such as anhydride or acid halide, a succinimide ester, a pentafluoof an alcohol with sulfuryl chloride in the presence of suitable base gives the intermediate sulfochloridate, which can be converted to the corresponding sulfamate. Acylation of sulfamate nitrogen with a suitable carboxylic acid derivatives such as anhydride or acid halide, a succinimide ester, a pentafluorophenyl ester, an imidazolide, and the like, can yield the corresponding N-acyl sulfamate.

Scheme 6

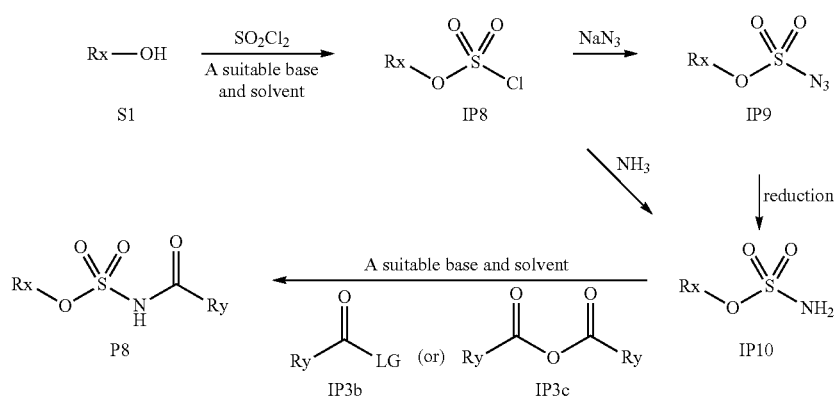

Rx and Ry are any monobalent organic radicals.

Suitable bases and solvents are same as defined above.

Method(s) of Making N-Acyl/Oxycarbonyl Sulfonamide Linkages:

The N-acyl/oxycarbonyl sulfonamide linkage between the linker and drug can be made as shown in Scheme 7. Thus, a sulfonamide nitrogen can be acylated by a suitable carboxylic acid derivatives such as anhydride or acid halide, a succinimide ester, a pentafluorophenyl ester, an imidazolide, and the like, to yield the corresponding N-acylsulfonamide, which can be metallated using an inorganic base. Similarly, the sulfonamide nitrogen can be acylated by a suitable formyl chloride derivative such as alkyloxycarbonyl chloride, imidazolide and the like, to yield the corresponding N-alkyloxycarbonyl sulfonamide as shown in the scheme. Alternatively, the same linkage can be made by the reaction of an alcohol with sulfonyl isocyanate which can be prepared by known methods such by treatment of sulfonamide with oxalyl chloride (see, Hans Krzikalla et al., U.S. Pat. No. 2,666,787 or Smith, J. et al., J. Org. Chem. 1965, 30, 1260-1262) or by treatment of sulfonyl chloride with silver cyanate (See, Smith, J. et al., J. Org. Chem. 1965, 30, 1260-1262).

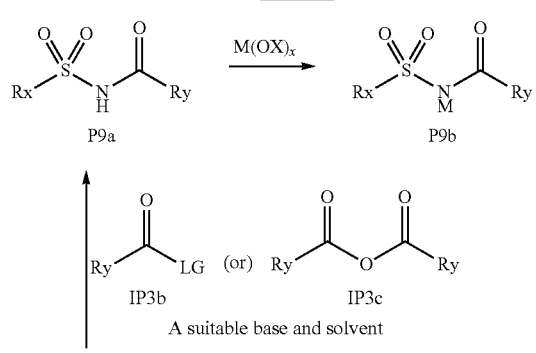

Scheme 7

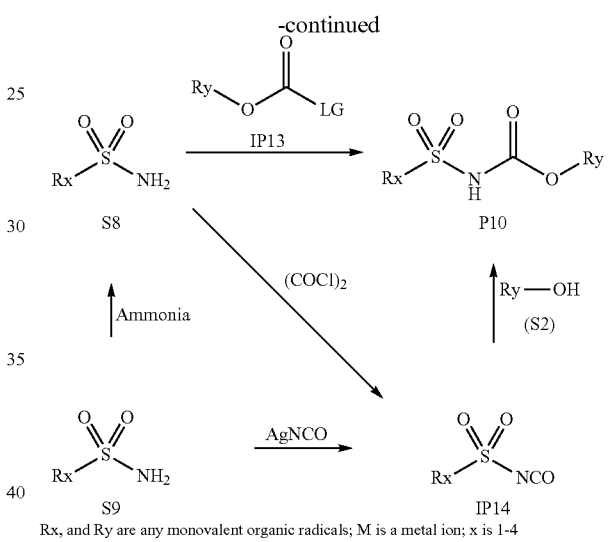

Rx, and Ry are any monovalent organic radicals; M is a metal ion; x is 1-4

Suitable bases and solvents are same as defined above.
Method(s) of Making N-Oxycarbonylcarbamate and N-Oxycarbonylurea Linkages:

The N-oxycarbonylcarbamate (or N-oxycarbonylurea) linkage between the linker and drug can be made as shown in Scheme 8. Thus, carbamate nitrogen can be acylated by suitable formyl chloride derivatives such as alkyloxycarbonyl chloride, imidazolide and the like, to yield the corresponding N-alkyloxycarbonylcarbamate as shown in the scheme. Alternatively, the N-oxycarbonylcarbamate (or N-oxycarbonylurea) linkage between the linker and drug can be made by the reaction of an alcohol (or an amine) with carbamoyl isocyanate (IP15A), which can be prepared by known methods such by treatment of carbamate with oxalyl chloride (See, Grehn L, et al., Synthesis, 1988, 922-994) or by treatment of a formyl chloride with silver cyanate (See, Kim, D. K. et al., J. Heterocyclic Chem. 1995, 32, 1625). Alternatively, N-oxycarbonylcarbamate (or N-oxycarbonylurea) can be prepared in two steps. Step 1: reaction of an alcohol or phenol with chlorocarbonyl isocyanate to give N-oxycarbonyl carbamoyl chloride intermediate (IP15B). Step 2: reaction of the intermediate IP15B with the same or another alcohol or phenol or an amine. (For a review on chemistry of chlorocarbonyl isocyanate, see, Gorbatenko, V. I. Tetrahedron, 1993, 49, 3227).

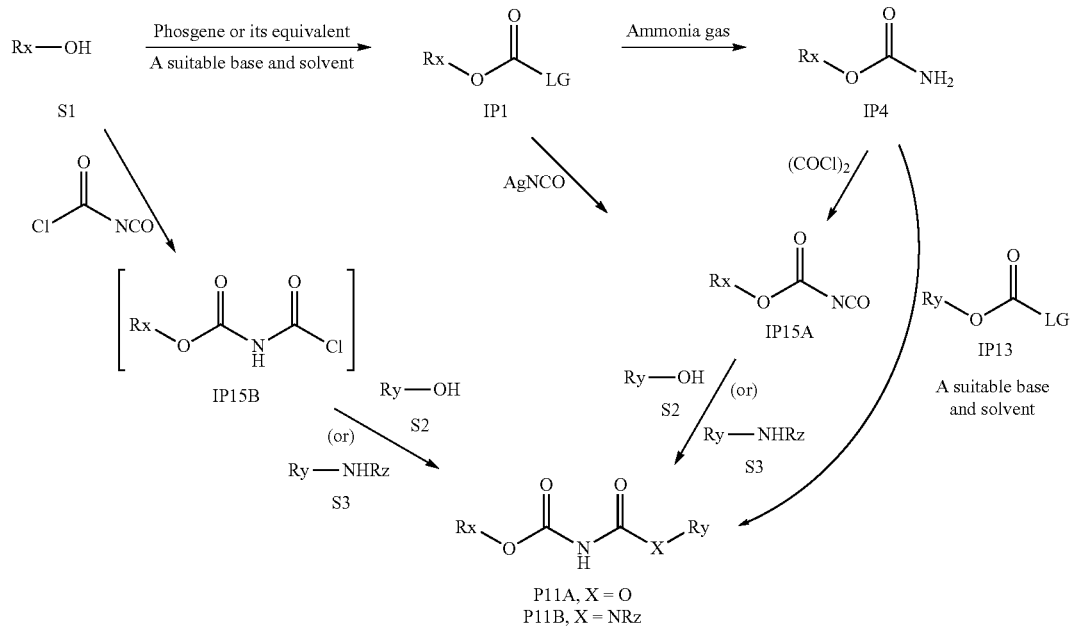

Scheme 8

Rx, Ry and Rz are any monovalent organic radicals.

Suitable bases and solvents are same as defined above.

Method(s) of Making Nitrate (Nitrooxy) or Nitrite (Nitrosyloxy) Esters:

The nitrate or nitrite esters can be made as shown in Scheme 9. Thus, a nitrate or nitrite ester can be made by treating an alcohol with $HNO_3/H_2SO_4$ (or $HNO_3/Ac_2O$) or nitrosyl chloride, respectively. Alternatively, a nitrate ester can be made by treating a halide (bromide or iodide is preferred) with silver nitrate in a polar aprotic solvent such as acetonitrile.

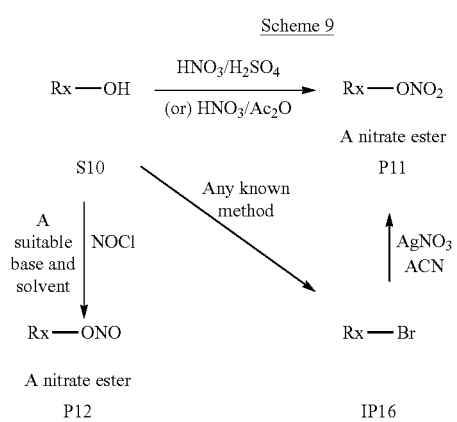

Scheme 9

Rx is any monovalent organic redical.

Compounds (Prodrugs) of the formula (I) containing biocleavable linkers and linkages can be synthesized by various methods obvious to those skilled in the art. As a matter of illustration, any of the approaches shown in the following schemes can be used to make such prodrugs of the formula (I) described herein.

Monoprotection of diol or aminoalcohol or diamino compounds [i.e., linker(s)] with suitable protecting groups and their selective removal at appropriate stage of the synthesis are carried out as described in Theodora W. Greene and Peter G. M. Wuts, "Protective Groups in Organic Synthesis", $3^{rd}$ edition, John Wiley and Sons, Inc. New York (1999), the disclosures of which are incorporated herein by reference. Suitable protecting groups (PGs) include, but not limited to, acetyl, Boc, Fmoc, benzoyl, pivaloyl, trityl, tetrahydropyranyl (THP), and silyl (TBDMS, TMS, etc.). Obviously, selection of a suitable protecting group is very crucial for the success of a chosen method for the synthesis of prodrugs described in this invention.

Synthesis of appropriately derivatized/modified bio-labile linker is shown in Scheme 10.

Scheme 10: Synthesis of appropriately derivatized/modified linker intermediates
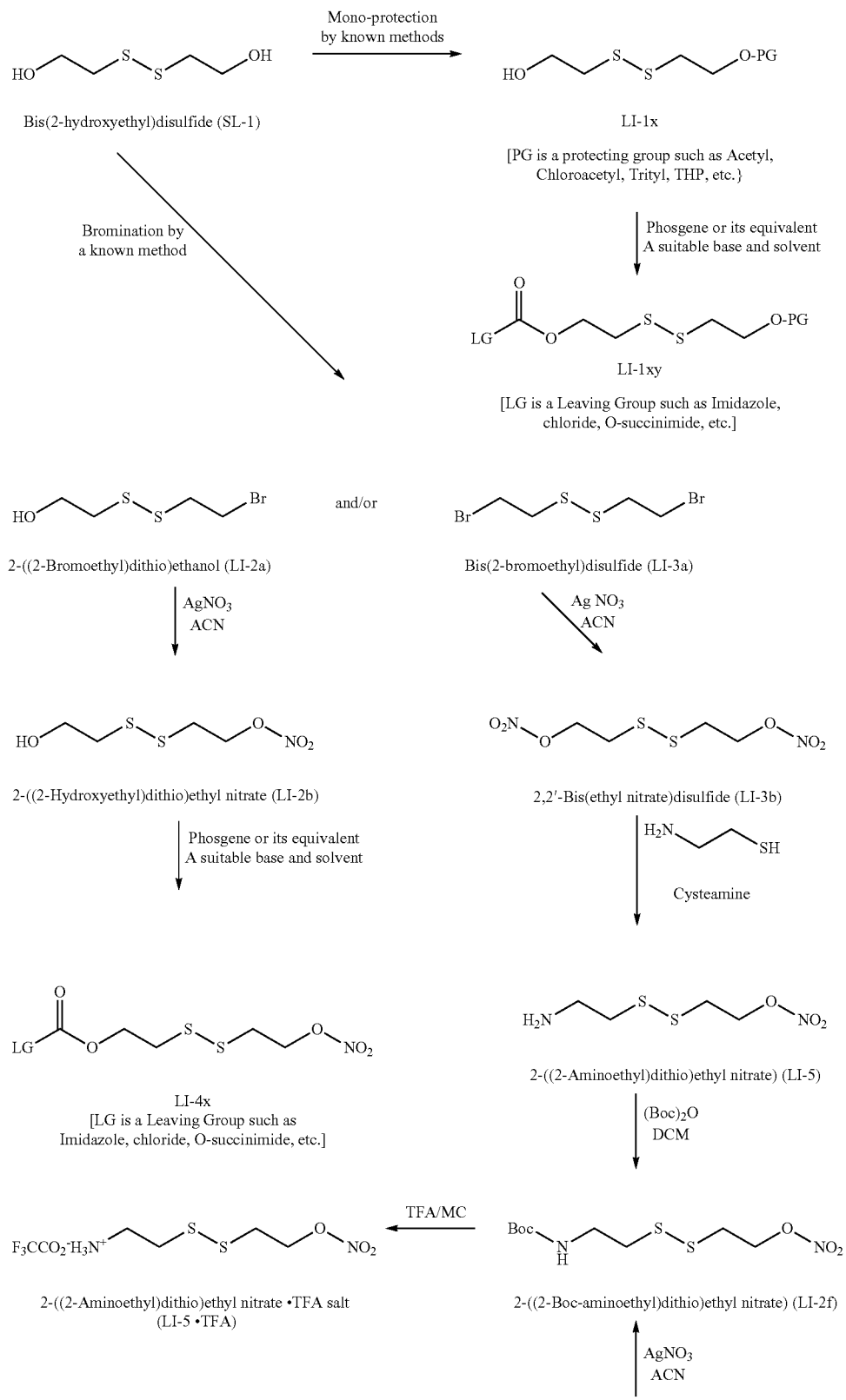

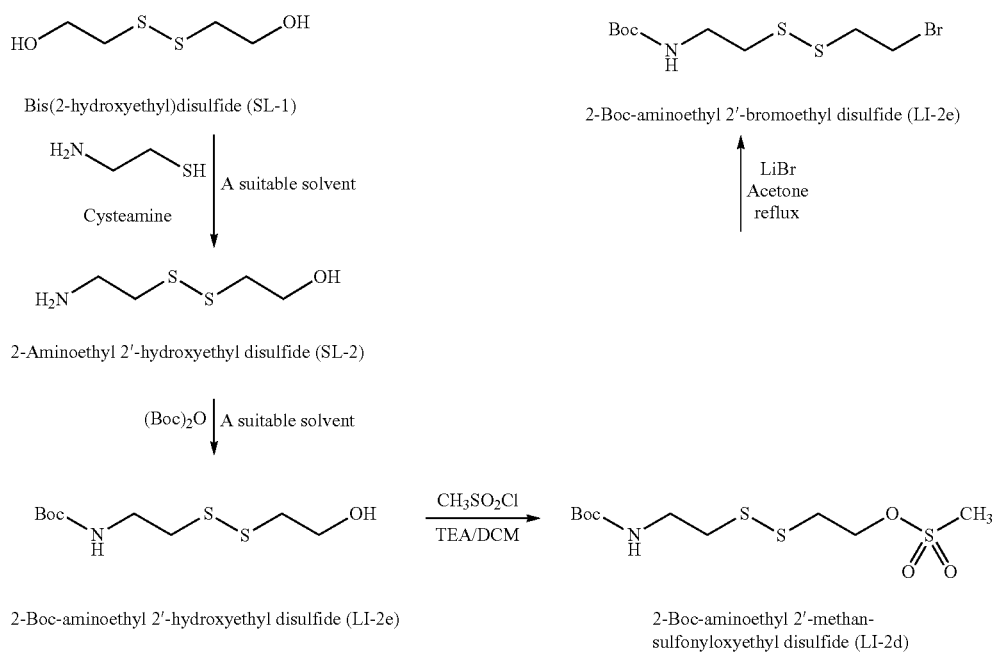
Some of the methods for the synthesis of prodrugs (including NO-releasing prodrugs) of carboxyl-, amino-, and hydroxyl-containing drugs are shown in Schemes 11 through 14.
Scheme 11: Synthesis of Prodrugs of Carboxyl-containing Drugs
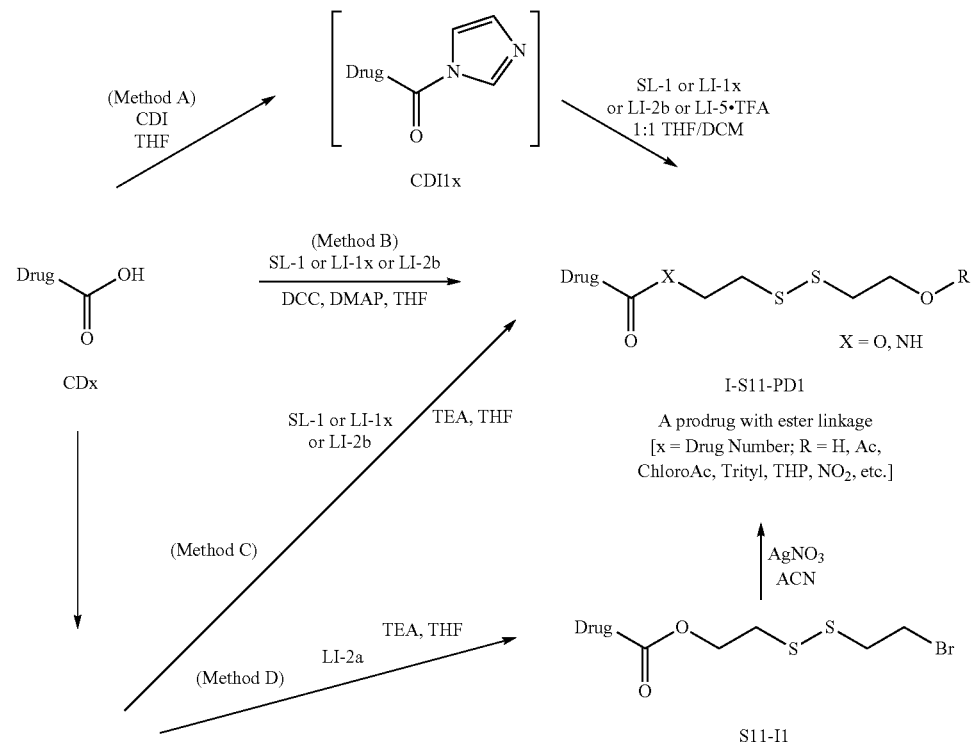

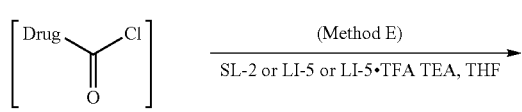
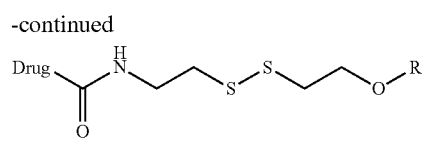
-continued
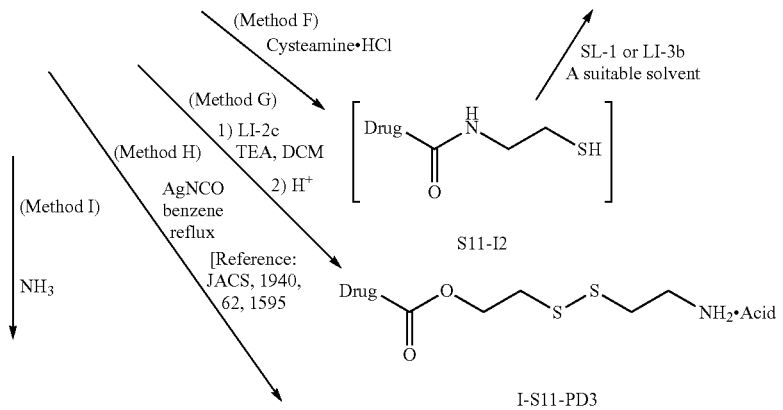
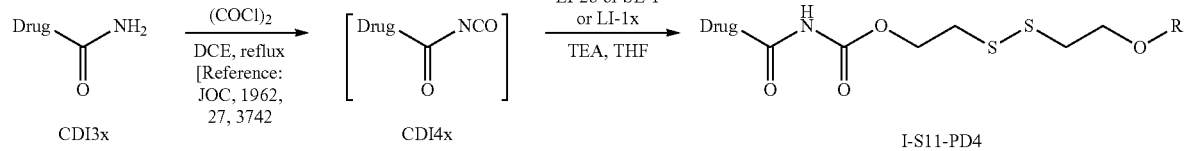
Scheme 12: Synthesis of Prodrugs of Amino-containing Drugs
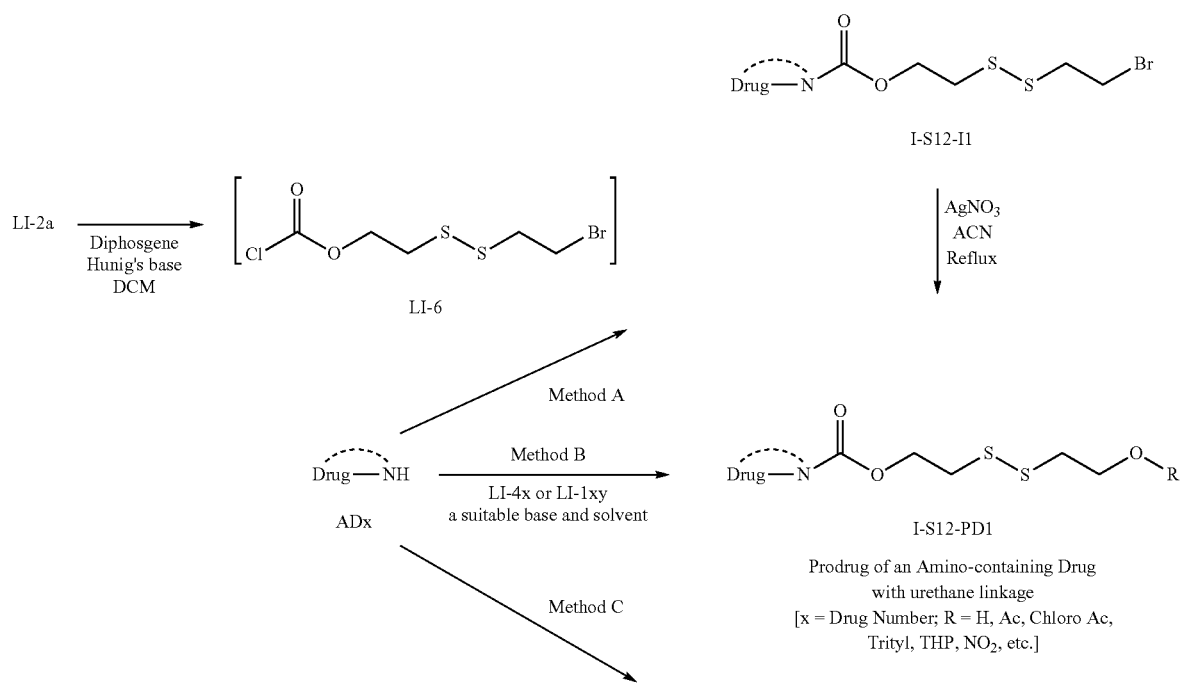

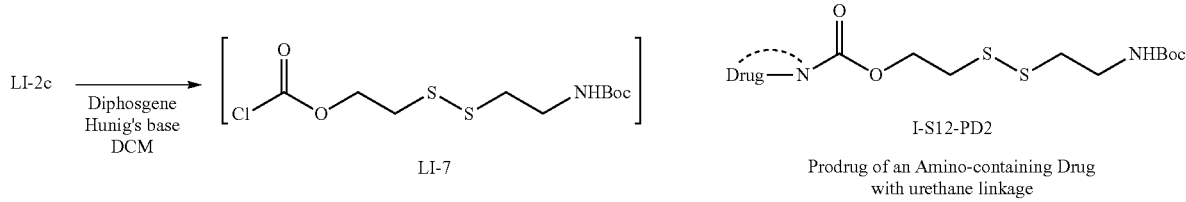
Scheme 13: Synthesis of Prodrugs of Amide/Sulfonamide-containing Drugs:
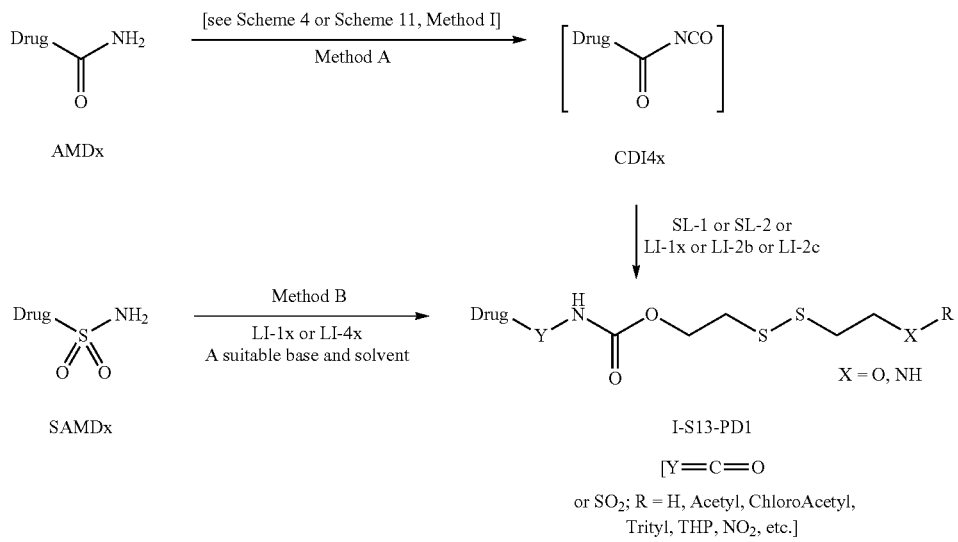
AMDx is a CONH$_2$-containing drugs such as vapromide, levotiracetam, carbamazepine, and the like.
SAMDx is a SO$_2$NH$_2$-containing drugs such as valdecoxib, celecoxib, and the like.
Scheme 14: Synthesis of Prodrugs of Hydroxyl-containing Drugs
A) Prodrugs with carbonate and carbamate linkages:
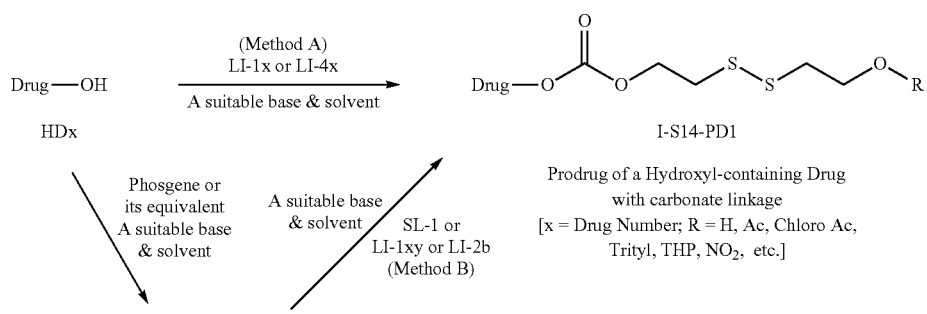

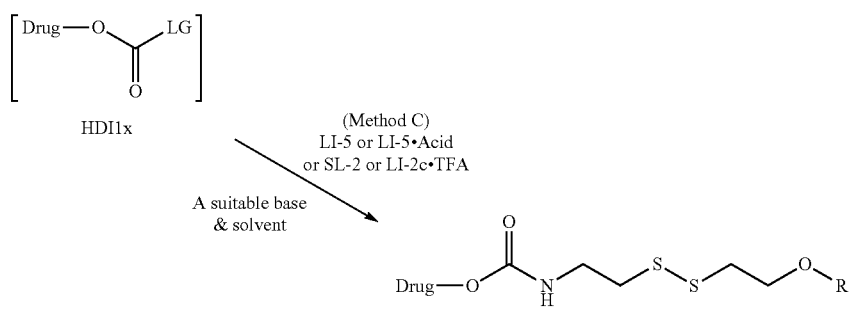
B) Prodrugs with N-oxycarbonylcarbamate linkage:
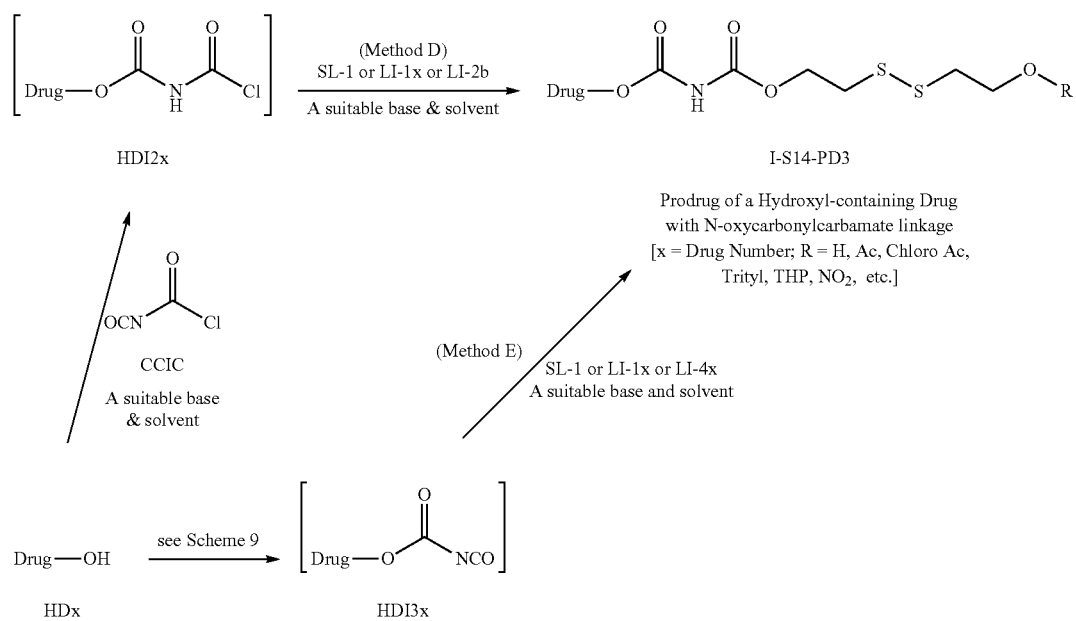
Some of the methods for the synthesis of prodrugs (including NO-releasing prodrugs and water-soluble prodrugs) are shown in Schemes 15 and 16.
Scheme 15: Synthesis of Water-soluble Prodrug(s) using a bio-cleavable linker(s) and spacer linker (s)
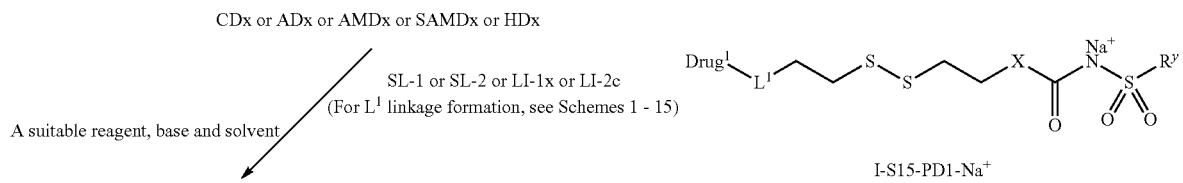

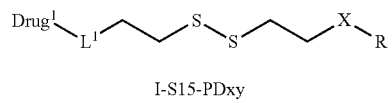

I-S15-PDxy

L¹ linkages are same as defined in the description
[x is a number corresponding to drug;
y is a number correponding to R group]

↓ Removal of protecting group

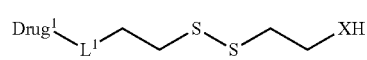

I-S15-PDx

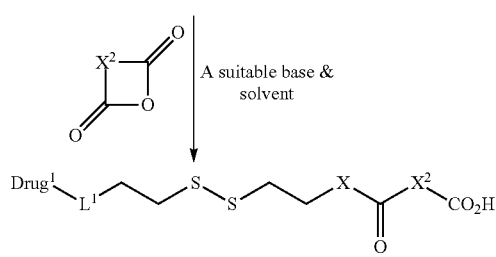

I-S15-PD3

X is a bond, O or N; $X^2 = $ —CH$_2$X$^3$CH$_2$—

[$X^3 = (CH_2)_n$ (n = 0-4), O, S, SO, SO$_2$, NR$^x$
($R^x$ = H, alkyl, CO$_2$H, CH$_2$CO$_2$H, etc.) and the like.

-continued

I-S15PDx-Cy  ↑ A suitable base such as sodium hydride, hydroxide, alkoxide and the like

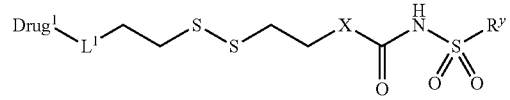

I-S15-PD1

[Ry = alkyl, aryl, or a drug residue or R—X$^4$]

↑ A suitable base & solvent   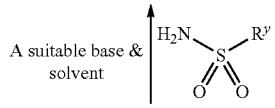

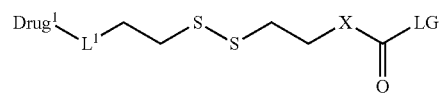

I-S15-PDI1

[LG is a Leaving Group such as chloride, imdazole, O-Succinimide, etc.]

↓ A suitable base & solvent   R—X$^4$H

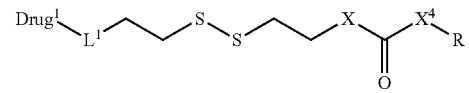

I-S15-PD2

X is a bond, O or N; R—X$^4$H is an amino/hydroxyl-containing molecule with one or more solubilizing groups such as amino, carboxyl, hydroxyl, sulfate, phosphate (including bis-phosphonate), and the like.

Scheme 16: Synthesis of Prodrugs containing a biocleavable linker and various types linkages

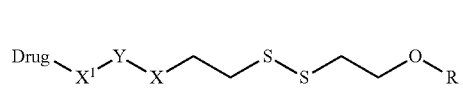

I-S16-PD1      $X^1$ = a bond, O or S or NR$^2$ ($R^2$ = a bond, H, alkyl, etc.)

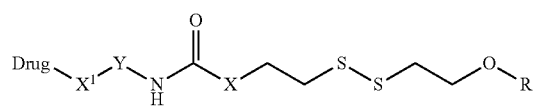

I-S16-PD2

Drug—X$^1$—Y—LG

DI2x

↑ AgNCO

Drug—X$^1$—Y—LG

DI1x $X^1$ = a bond, O or S

Drug—X$^1$—Y—LG

DI1x

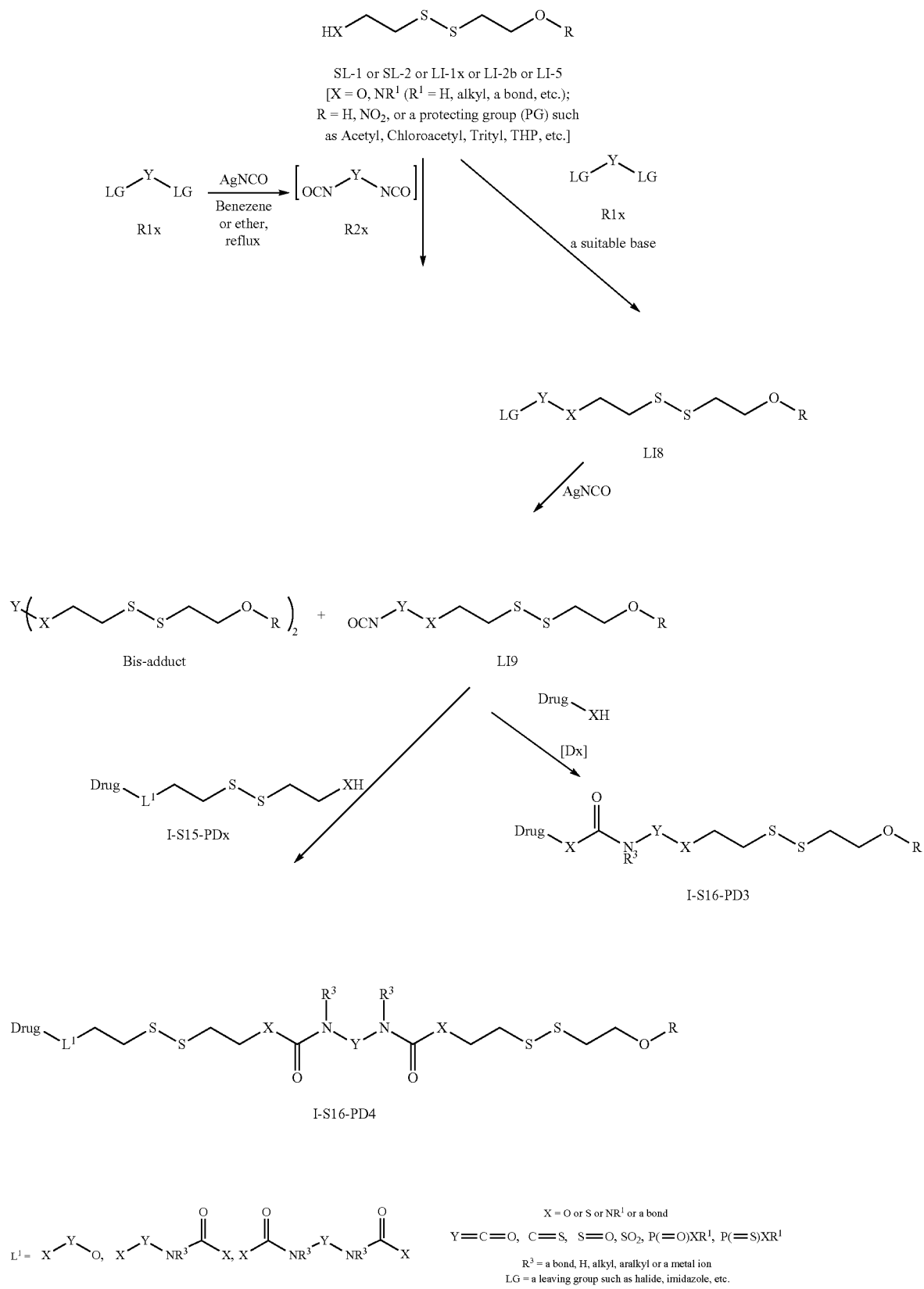

Double/Mutual prodrugs described in this invention can be synthesized by any of the approaches depicted in Schemes 17 through 19.
Scheme 17: Synthesis of Mutual Prodrug(s) using a bio-cleavable linker(s) and spacer linker (s)
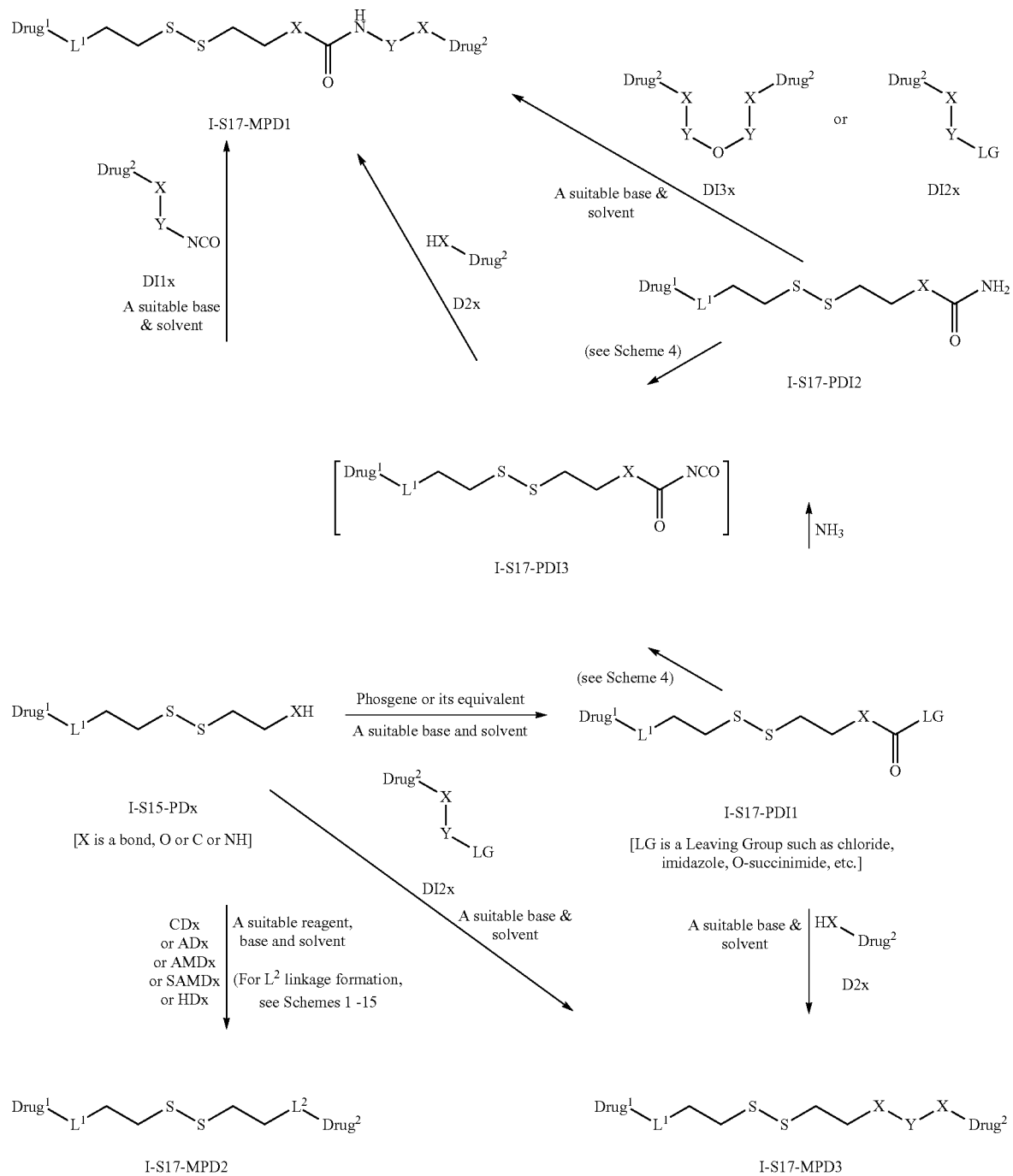

Scheme 18: Synthesis of Double/Mutual Prodrug(s) with additional linkers
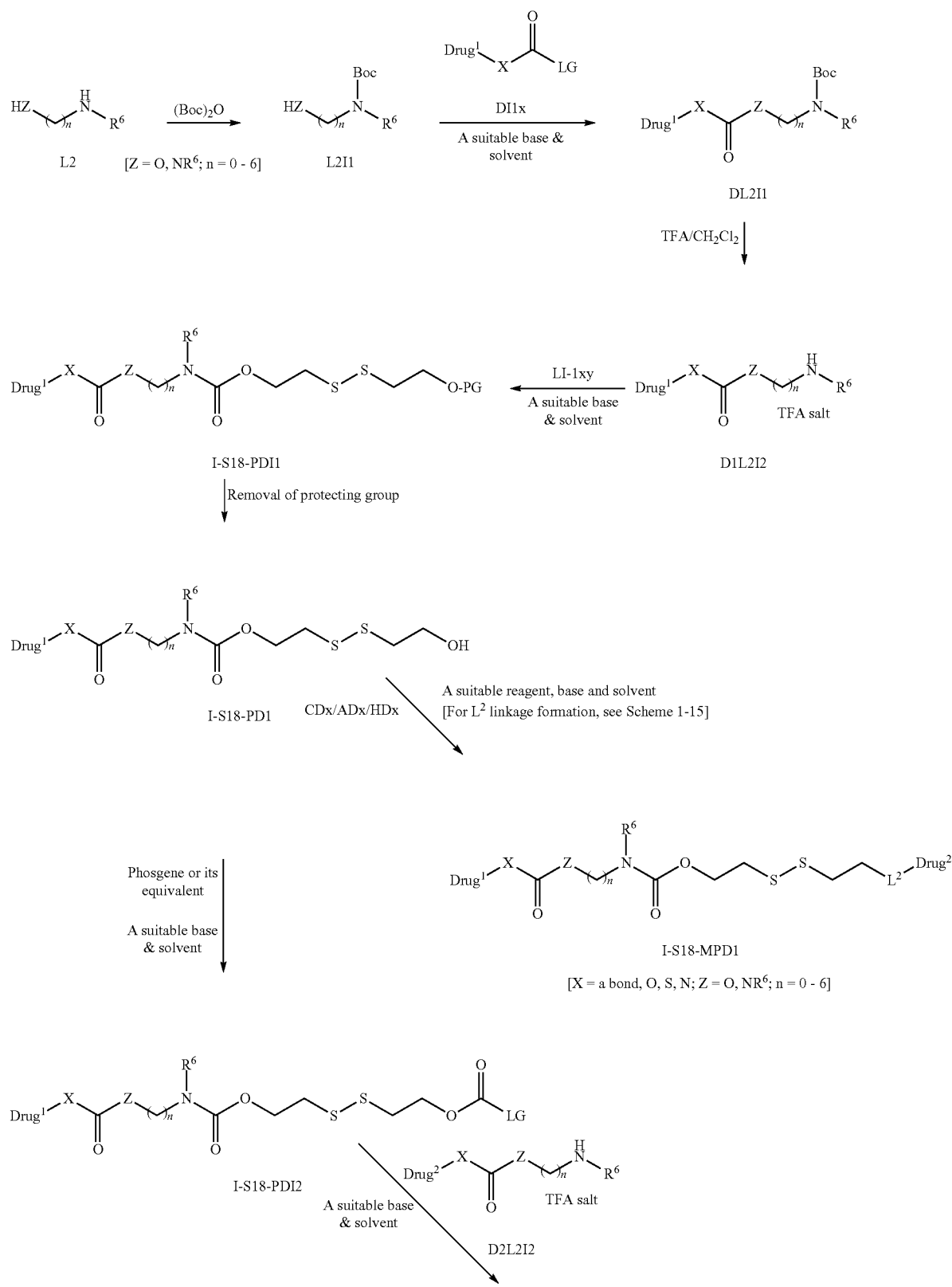

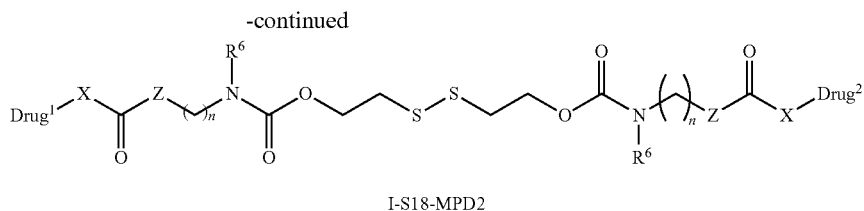
I-S18-MPD2
Scheme 19: Synthesis of Mutual Prodrug(s) using modified bio-cleavable linker(s)
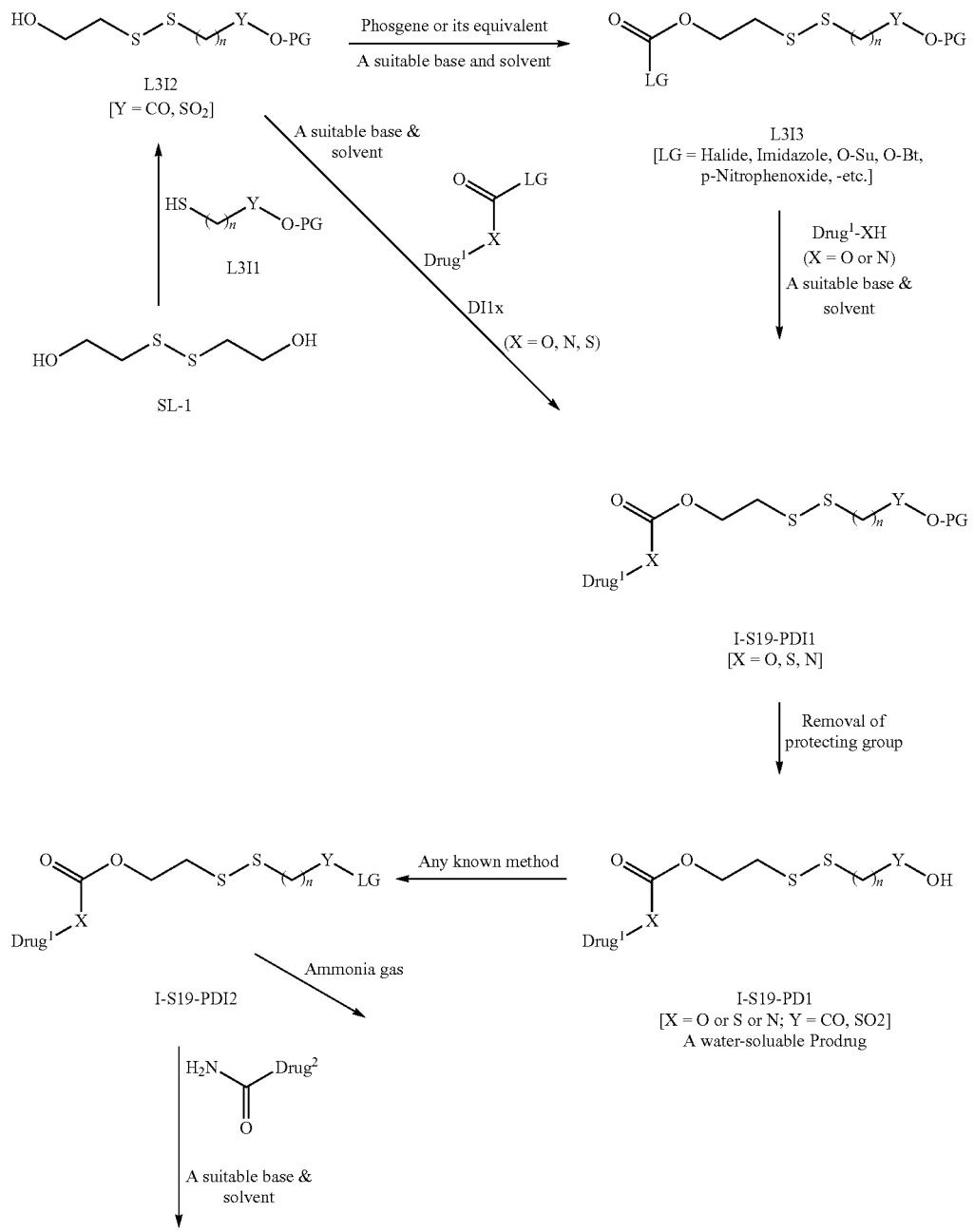

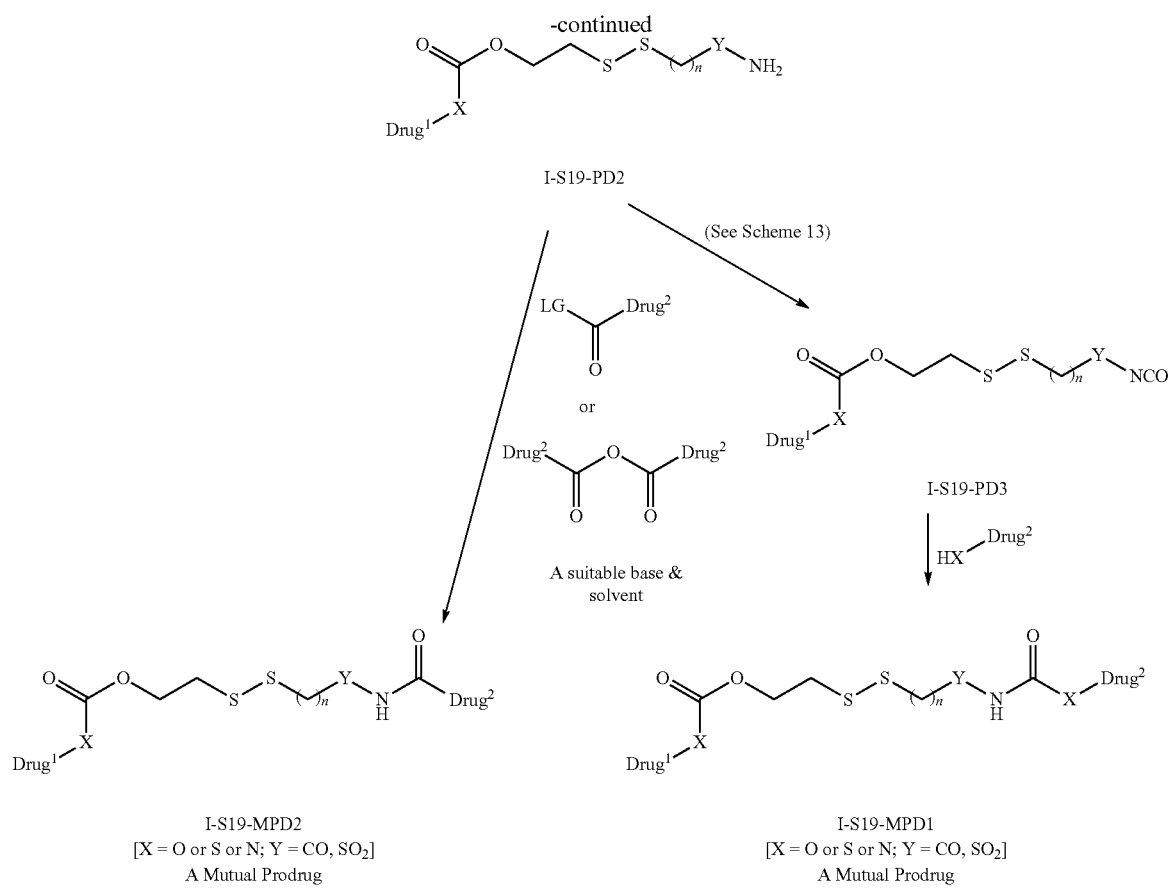
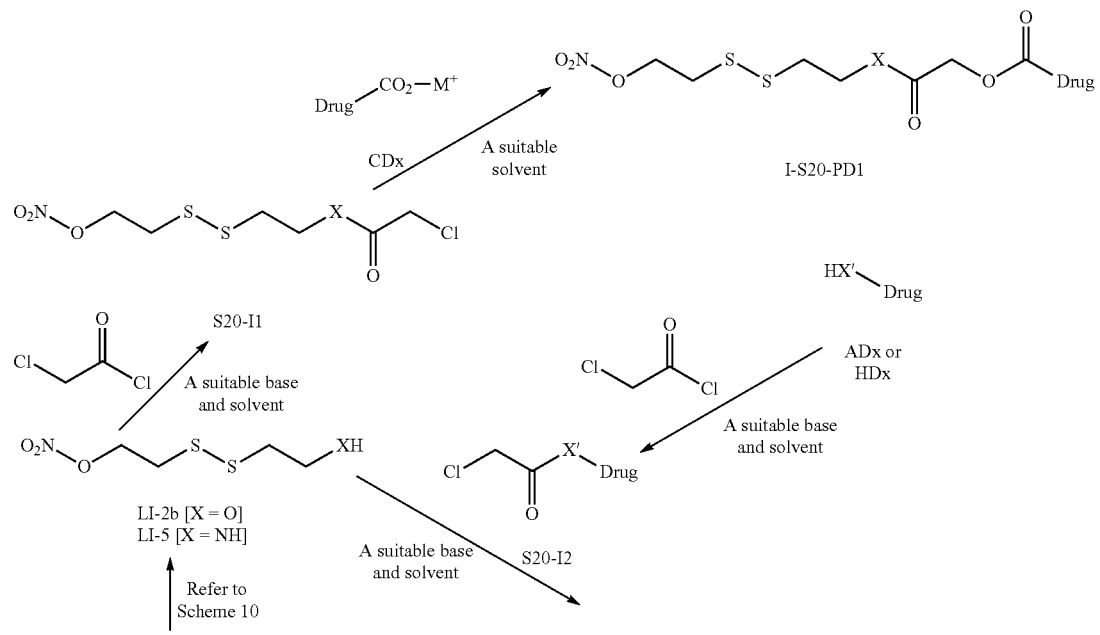
Scheme 20: Synthesis of Mutual Prodrug(s) using modified bio-cleavable linker(s)

211
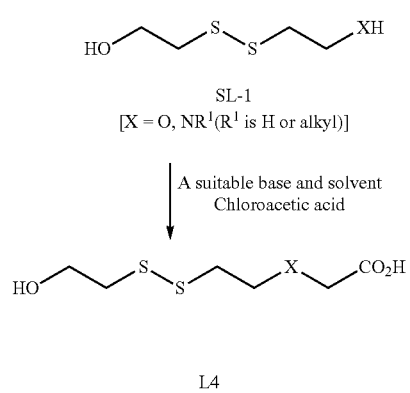
212
-continued
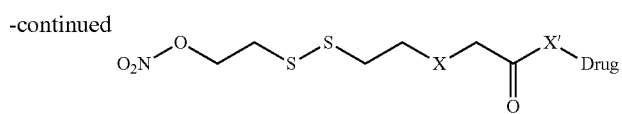
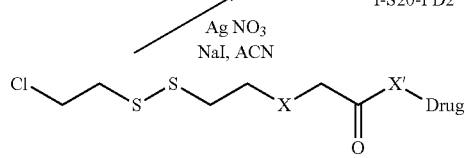
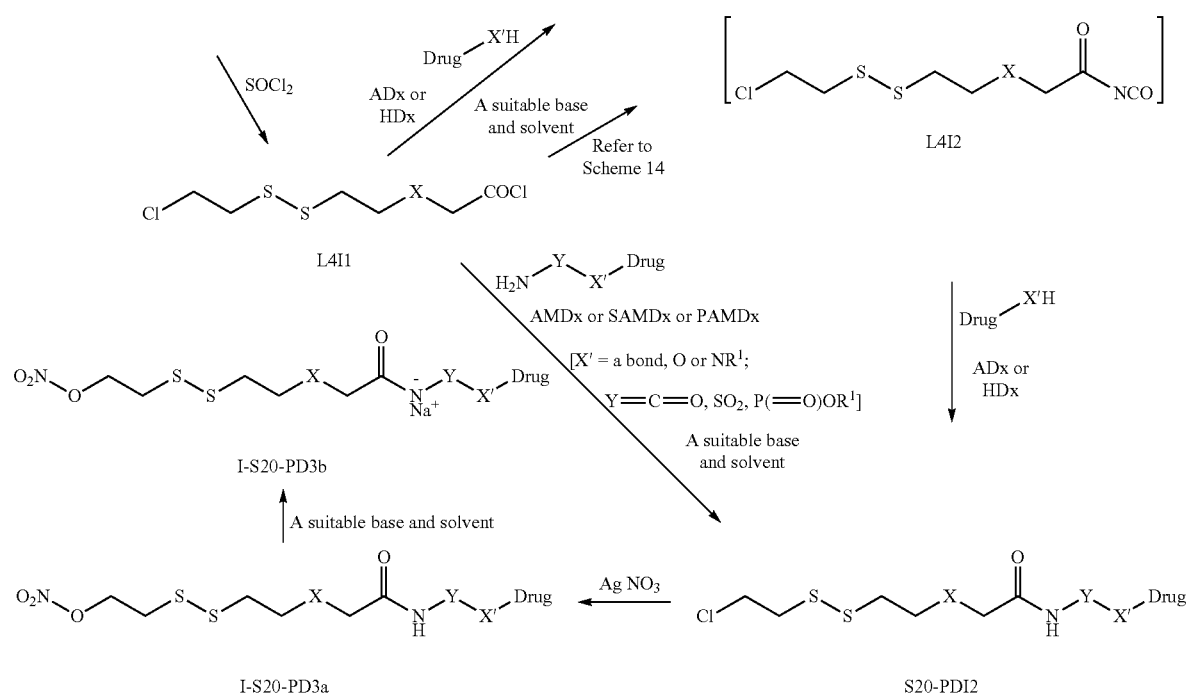
As a matter of illustration, mutual prodrug of desloratadine and pseudoephidrine was synthesized as depicted in Scheme 21.
Scheme 21: A Mutual Prodrug of Desloratadine and Pseudoephedrine
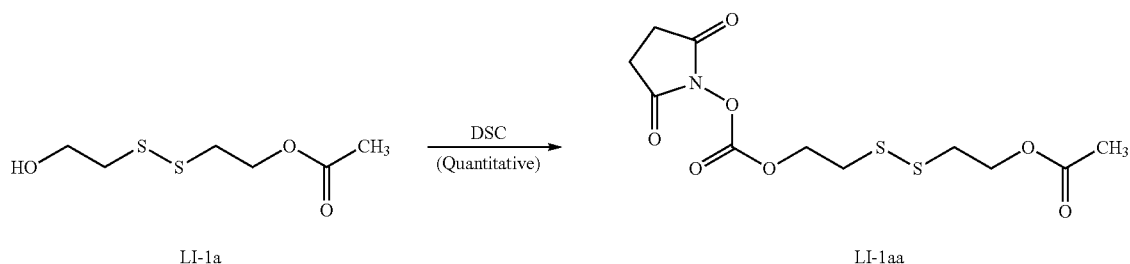

-continued
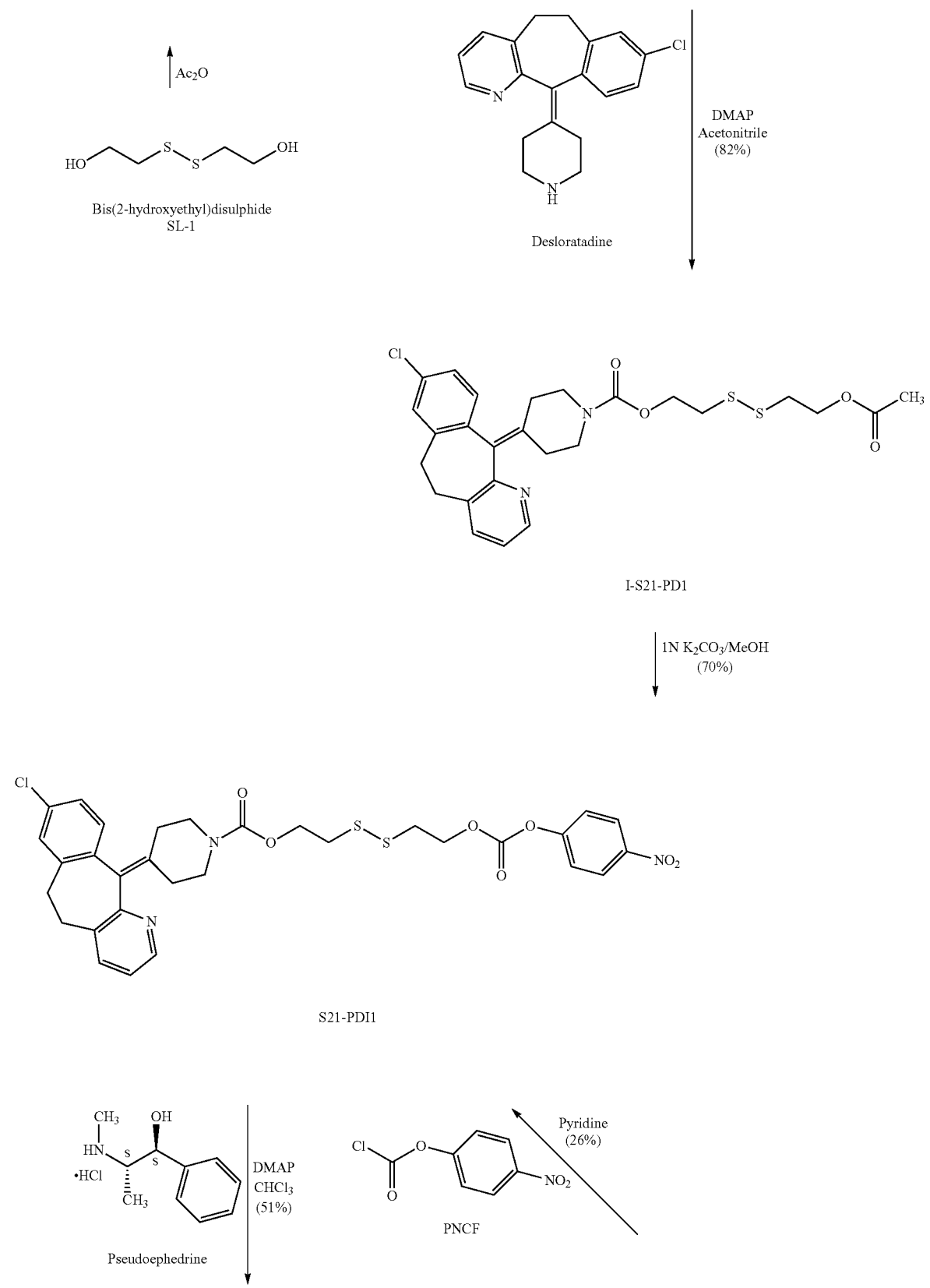

-continued
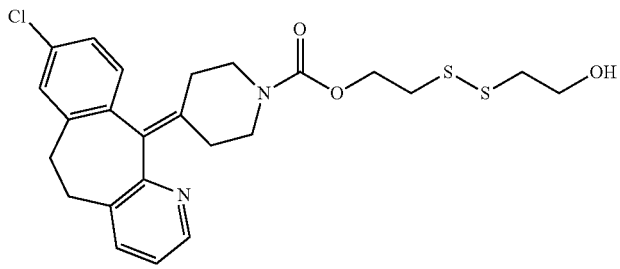
I-S21-PD2
↓ Diphosgene
Pyridine
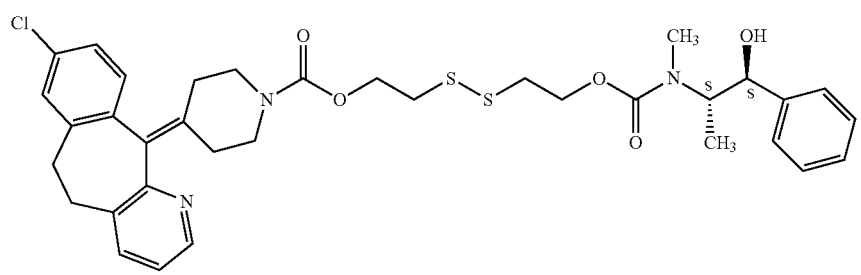
I-S21-MPD1
Mutual Prodrug of Desloratadine and Pseudoephedrine
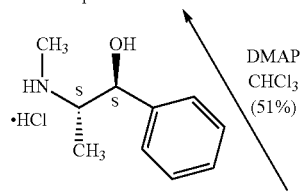
Pseudoephedrine
↗ DMAP
CHCl₃
(51%)
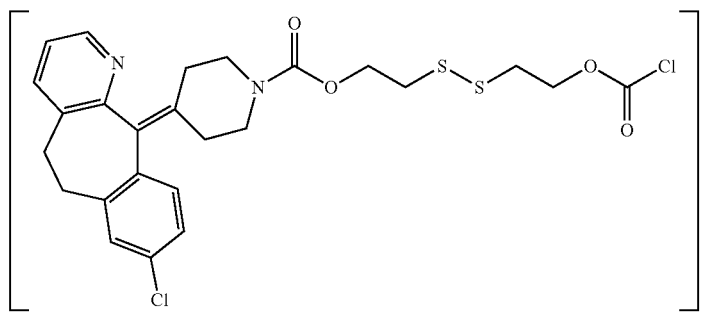
I-S21-PDI2

Scheme 22: Synthesis of a water-soluble prodrug of paclitaxel
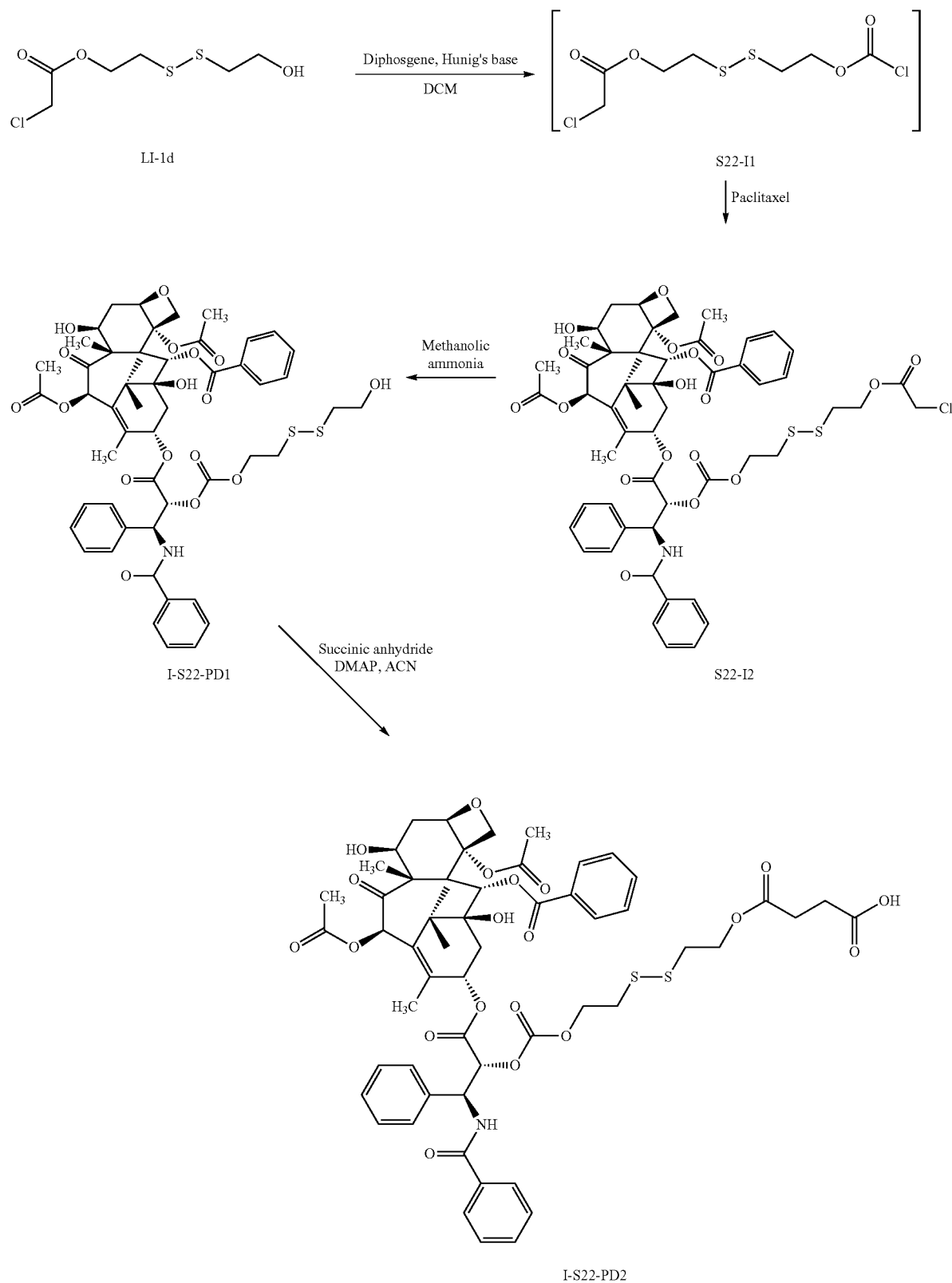

Scheme 23: Generation of Paclitaxel from a Prodrug of Isotaxel
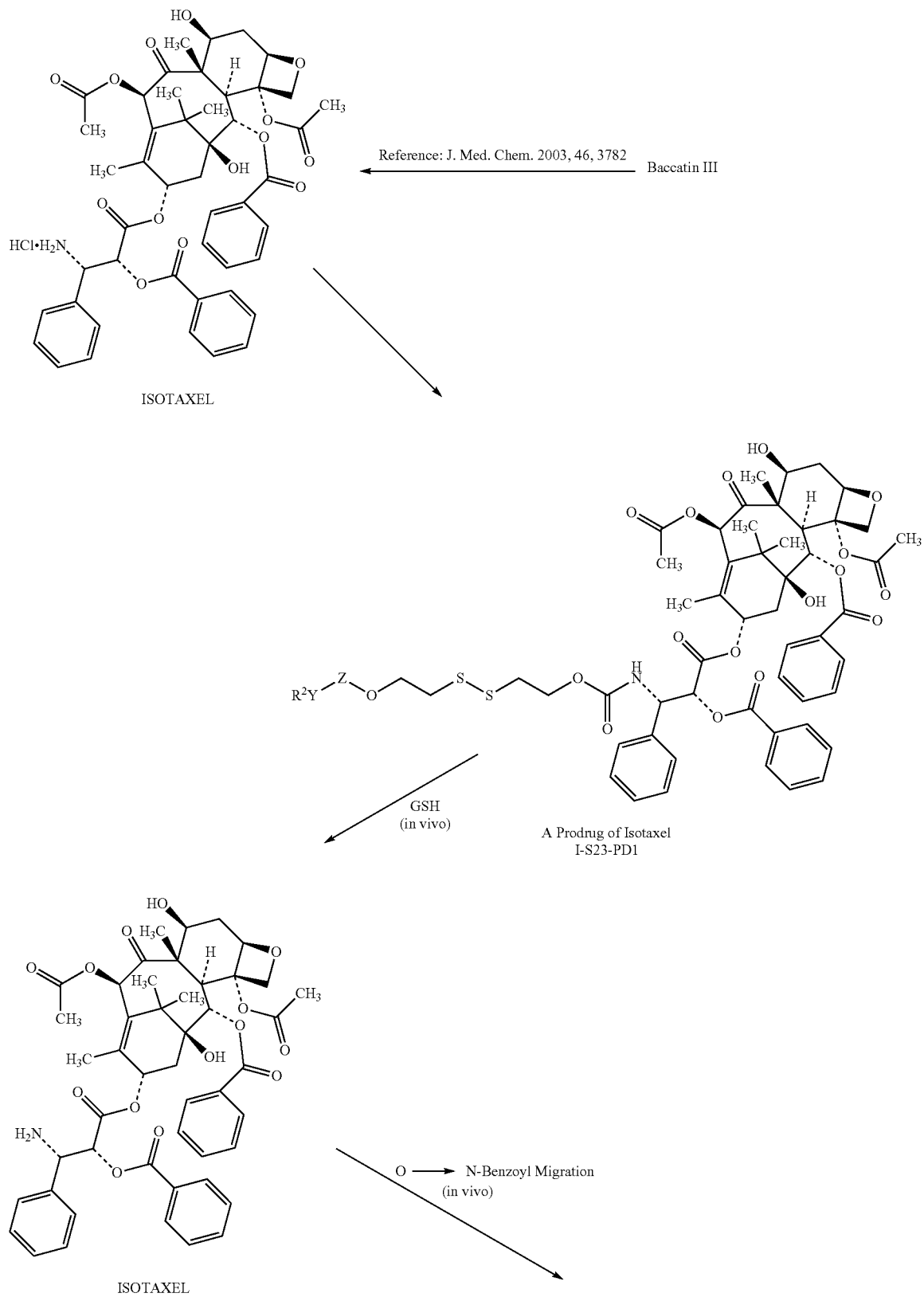

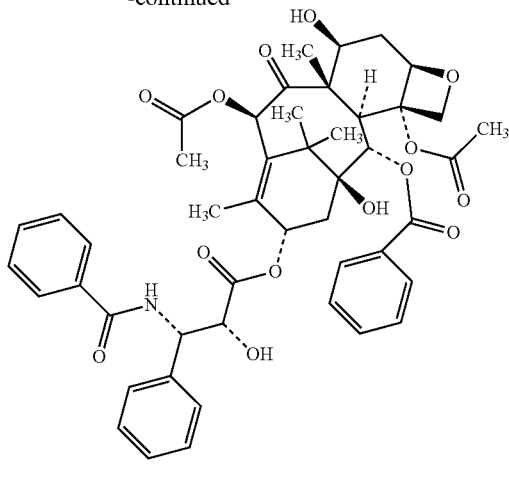

PACLITAXEL

Y=O, NR¹ (R¹=H, Alkyl, Aralkyl, Cycloalkyl), $(CH_2)_nC$ (=O) (n=1-6), $(CH_2)_nCO_2^-$
Z=C=O, $SO_2$, P(=O)YR³ (R³=H or a metal ion)
R²=H, a bond, $CH_2CH_2N(CH_3)_2 \cdot HCl$, an Amino acid, or any molecule containing solubilizing groups such as carboxylic acid, sulphonic acid, hydroxyl, amino groups, polyethyleneglycol (PEG), a metal ion such a $Na^+$, $Ca^{2+}$, etc.

disulfide (SL-1, 15.39 g, 99.78 mmol) in DCM (350 mL) at RT and the mixture was stirred at RT for 16 h. The mixture was concentrated and the residue, after usual aqueous work-up and chromatographic purification, afforded 8.16 g (42%) of LI-1a as a pale yellow oil. ¹H-NMR (300 MHz, $CDCl_3$): δ 2.00 (bs, 1H), 2.08 (s, 3H), 2.80-2.95 (m, 4H), 3.89 (t, 2H, J=6 Hz), 4.35 (t, 2H, J=6 Hz), MS: (m/z) 219 [M]⁺.

Scheme 24: An alternative method for the synthesis of Linker Intermediates LI-2b and LI-5

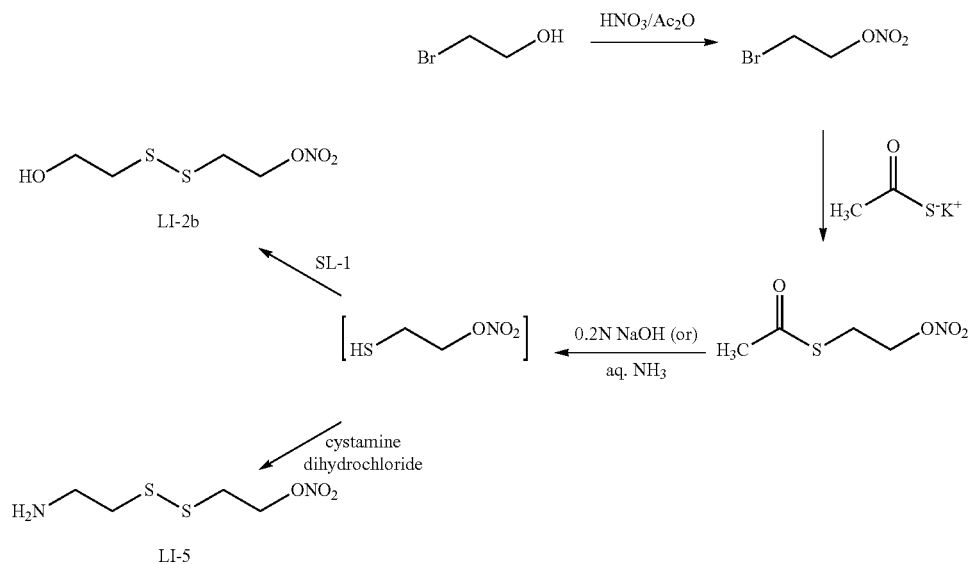

Example 1

Synthesis of 2-[(2-hydroxyethyl)dithio]ethyl acetate (LI-1a)

Acetic anhydride (5.67 ml, 56.87 mmol) and pyridine (40.4 ml, 499 mmol) were added to a solution of 2-(hydroxyethyl)

Example 2

Synthesis of 2-{[2-(tetrahydro-2H-pyran-2-yloxy) ethyl]dithio}ethanol (LI-1b)

This compound was synthesized by a method described by K. F. Bernady et al., *J. Org. Chem.*, 1979, 44, 1438. Dihydropyran (8.41 g, 100 mmol) was added to a solution of SL-1 (15.4 g, 100 mmol) in DCM (200 mL) at 0-5° C., followed by PTSA (~5%) and stirred at RT for 5 h. The mixture, after usual aqueous work-up and chromatographic purification, afforded 14.5 g (50%) of LI-1b. $^1$H-NMR (300 MHz, CDCl$_3$): δ 1.5-1.9 (m, 6H), 2.88 (t, 2H, J=6 Hz), 2.94 (t, 2H, J=6 Hz), 3.45-3.57 (m, 1H), 3.67-3.78 (m, 1H), 3.85-4.05 (m, 2H), 3.90 (t, 2H, J=6 Hz), 4.65 (s, 1H).

Example 3

Synthesis of 2-{[2-(Trityloxy)ethyl]dithio}ethanol (LI-1c)

This compound was synthesized by a method described by O. Hernandez et al., *Tetrahedron Letters*, 1981, 22, 1491-1494. Thus, 8.58 g (21.4 mmol) of 4-dimethylamino-N-triphenylmethylpyridinium chloride (A. V. Bhatia et al., *Organic Synthesis*, 1997, 75, 184-185) was added to a solution of SL-1 (3.0 g, 19.45 mmol) in DCM (90 mL) and stirred at RT for 24 h. The mixture, after usual aqueous work-up and chromatographic purification, afforded 2.86 g (37%) of LI-1c. $^1$H-NMR (300 MHz, CDCl$_3$): δ 2.70 (t, 2H, J=6.0 Hz), 2.88 (t, 2H, J=6.0 Hz), 3.39 (t, 2H, J=6.0 Hz), 3.80 (q, 2H, J=6.0 Hz), 7.24-7.33 (m, 10H), 7.44-7.46 (m, 5H). MS (m/z): 396 [M]$^+$ Example 4

Synthesis of chloroacetic acid 2-(2-hydroxyethyldisulfanyl)ethyl ester (LI-1d)

To a solution of SL-1 (23 g, 150 mmol) in DCM (250 mL) at 0° C. were added TEA (10.12 g, 100 mmol) and chloroacetyl chloride (11.3 g, 100 mmol) and stirred overnight at RT. The reaction mixture was concentrated and purified by column chromatography to afford 8.3 g (37%) of LI-1d. $^1$H-NMR (300 MHz, CDCl$_3$): δ 2.88 (t, 2H, J=5.7 Hz), 2.95 (t, 2H, J=6.6 Hz), 3.89 (t, 2H, J=5.7 Hz), 4.09 (s, 2H), 4.47 (t, 2H, J=6.6 Hz).

Example 5

Synthesis of 2-((2-hydroxyethyl)dithio)ethyl nitrate (LI-2b) and 2,2'-bis(ethyl nitrate)disulfide (LI-3b)

These intermediates were synthesized in two steps as shown in Scheme 10.

Step 1: Synthesis of 2-((2-bromoethyl)dithio)ethanol (LI-2a) and bis(2-bromoethyl)disulfide (LI-3a): These compounds can be synthesized via bromination of SL-1 by a known bromination method. (For a suitable bromination method, see Fruniss, B. S. et al., Vogel's Text Book of Practical Organic Chemistry, 5$^{th}$ edition, Pearson Education, Singapore, 1989; pp 559-579). The following methods were explored:

Method 1: To a solution of SL-1 (15 g, 97.4 mmol) in DMF (50 mL) was added PPh$_3$ (25.5 g, 97.4 mmol) and cooled to 0° C. Bromine (3.33 mL, 64.9 mmol) was added drop-wise and stirred at RT for 18 h. TLC of the mixture showed the monobromo derivative LI-2a as the major product with only trace amounts of dibromide LI-3a. The mixture was diluted with water and extracted with EtOAc. After usual aqueous work-up and chromatographic purification, 3.65 g (26%) of LI-2a were obtained. $^1$H-NMR (300 MHz, CDCl$_3$): δ 1.82 (s, 1H), 2.88 (t, 2H, J=5.8 Hz), 3.08 (t, 2H, J=7.90H), 3.63 (t, 2H, J=7.90 Hz), 3.90 (t, 2H, J=5.8 Hz).

Method 2: To a solution of SL-1 (40 g, 0.26 mol) in DCM (400 mL) at 0° C. was added a solution of PBr$_3$ (24.62 mL, 0.26 mol) in DCM (50 mL) and the mixture was stirred at RT for 15 h. TLC indicated formation of LI-3a as the major product with trace amounts of LI-2a. The reaction was quenched by the addition of water and extracted with DCM. After usual aqueous work-up and chromatographic purification, 33 g (45.3%) of LI-3a were obtained. $^1$H-NMR (500 MHz, CDCl$_3$): δ 3.1-3.15 (m, 4H), 3.60-3.66 (m, 4H). MS (Cl)$^+$ m/z: 277.69 [M+H]$^+$, 279.66. An alternative synthesis of LI-3a has been reported. (Sharma, M. et al, *Bioorg. Med. Chem. Lett.*, 2004, 14, 5347-5350).

Method 3: To a cold suspension of SL-1 (20 g, 129 mmol) in DCM (400 mL) was added CBr$_4$ (42 g, 129 mmol) and stirred for 10 min. PPh$_3$ (34 g, 129 mmol) was then added and stirred at RT for 14 h. The reaction mixture was concentrated and the residue purified by column chromatography to give 13.5 g (52.3%) of LI-2a and 13.0 g (36%) of LI-3a. These compounds were identical (by TLC, NMR and MS) to those obtained in Methods 1 and 2 described above.

Synthesis of 2-((2-hydroxyethyl)dithio)ethyl nitrate (LI-2b): To a solution of LI-2a (2 g, 9.21 mmol) in acetonitrile (15 mL) was added AgNO$_3$ (1.88 g, 11.05 mmol) portion-wise and the mixture was stirred at RT in the dark for 45 min. The reaction mixture was filtered through celite and the filtrate was concentrated. The residue, after usual aqueous work-up and chromatographic purification gave 1.46 g (74%) crude LI-2b which was used for the next reaction without further purification. An analytical sample was obtained by chromatographic purification. $^1$H-NMR (300 MHz, CDCl$_3$): δ 2.89 (t, 2H, J=6.0 Hz), 2.98 (t, 2H, J=7.5 Hz), 3.90 (t, 2H, J=6.0 Hz), 4.74 (t, 2H, J=7.5 Hz); MS (EI)$^+$ (m/z): 199 [M]$^+$.

Synthesis of 2,2'-bis(ethyl nitrate)disulfide (LI-3b): AgNO$_3$ (8.01 g, 47.12 mmol) was added portion-wise to a solution of LI-3a (6.0 g, 21.42 mmol) in acetonitrile (40 mL) at RT in the dark and stirred for 30 min. The mixture was filtered through celite and the filtrate was concentrated in vacuo at 35° C. to afford 4.6 g (88%) of LI-3b, which was used without further purification. An analytical sample was obtained by chromatographic purification (3-15% EtOAc in petroleum ether). $^1$H-NMR (300 MHz, CDCl$_3$): δ 3.10 (t, 4H, J=6.7 Hz), 4.71 (t, 4H, J=6.7 Hz). MS (EI)$^+$ m/z: 244 [M]$^+$.

Example 6

Synthesis of tert-butyl 2-[(2-hydroxyethyl)dithio]ethylcarbamate (LI-2c): To a solution of cysteamine hydrochloride (15 g, 132 mmol) in MeOH (130 mL) at 0-5° C. was added TEA (37 mL, 264 mmol), followed by a solution of SL-1 (20.4 g, 132 mmol) in DCM (50 mL) and stirred at RT for 6 h. The mixture, which contained the intermediate SL-2, was cooled and (Boc)$_2$O (63.4 g, 290.4 mmol) was added and stirred overnight. MeOH was removed under vacuum. After usual aqueous work-up and chromatographic purification, LI-2c was obtained as a colorless oil (14.6 g, 44%).

The above linker intermediate can also be prepared by the following method:

Step 1: TEA (37 ml, 264 mmol) and a solution of (Boc)$_2$O (48 g, 220 mmol) in DCM (100 mL) were added to a suspension of cystamine dihydrochloride (20 g, 88.8 mmol) in of DCM (300 mL) and stirred at RT for 15 h. The mixture was concentrated and the residue, after usual aqueous work-up and chromatographic purification, gave 30 g (96%) of tert-butyl 2-({2-[(tert-butoxycarbonyl)amino]ethyl}dithio)ethylcarbamate as a white solid. $^1$H-NMR (300 MHz, CDCl$_3$): δ 1.43 (s, 18H), 2.78 (t, 4H, J=6.3 Hz), 3.44 (q, 4H, J=6.0 Hz), 5.00 (bs, 1H). MS (m/z): 353.18 [M+H]$^+$, 375:24 [M+Na]$^+$.

Step 2: A solution of 2-mercaptoethanol (1.44 g, 18.5 mmol) in DCM (10 mL) was added to a mixture of tert-butyl 2-({2-[(tert-butoxycarbonyl)amino]ethyl}dithio)ethyl carbamate (5.0 g, 14.2 mmol) and TEA (3.87 ml, 27.7 mmol) in DCM (30 mL) and stirred overnight at RT. After usual aqueous work-up and chromatographic purification, 2.0 g (56%) of LI-2c was obtained. $^1$H-NMR (300 MHz, CDCl$_3$): δ 1.43 (s, 9H), 2.79 (t, 2H, J=6.5 Hz), 2.87 (t, 2H, J=5.7 Hz), 3.48 (q, 2H, J=6 Hz), 3.88 (t, 2H, J=5.5 Hz), 4.8 (bs, 1H). MS (m/z): 254 [M+H]$^+$, 276.13 [M+Na]$^+$.

Removal of the Boc group of LI-2c was accomplished as described in Example 10 to afford the TFA salt, LI-2c.TFA.

Obviously, the linker intermediates LI-2b and LI-2c can also be synthesized by following the method outlined in Scheme 24.

Example 7

Synthesis of 2-Boc-aminoethyl-2'-methansulfonyloxyethyl disulfide (LI-2d): To an ice-cold solution of LI-2c (9 g, 35.52 mmol) in DCM (80 mL) and TEA (9.9 mL, 71.04 mmol) was added methanesulfonyl chloride (4.2 mL, 53.28 mmol). The reaction mixture was stirred at 0-5° C. for 45 min, then diluted with DCM. After usual aqueous work-up and chromatographic purification, 13.38 g of LI-2d were obtained, which was pure enough for further use. $^1$H-NMR (300 MHz, CDCl$_3$): δ 1.43 (s, 9H), 2.80 (t, 2H, J=6.4 Hz), 2.98 (t, 2H, 5.7 Hz), 3.05 (s, 3H), 3.35-3.45 (m, 2H), 4.45 (t, 2H, J=6.7 Hz), 4.78 (br s, 1H).

Example 8

Synthesis of 2-Boc-aminoethyl-2'-bromoethyl disulfide (LI-2e): To a solution of LI-2d (13 g, 39.27 mmol) in acetone (100 mL) at RT was added LiBr (6.82 g, 78.54 mmol) and stirred under reflux for 1 h. The reaction mixture was concentrated and the residue, after usual aqueous work-up and chromatographic purification, afforded 8.8 g (78%) of LI-2e. $^1$H-NMR (300 MHz, CDCl$_3$): δ 1.44 (s, 9H), 2.80 (t, 2H, J=6.32 Hz), 3.06 (t, 2H, J=6.73 Hz), 3.44 (q, 2H), 3.61 (t, 2H, J=7.62 Hz), 4.87 (br s, 1H). MS (EI)$^+$ m/z: 317 [M+H]$^+$.

Example 9

Synthesis of 2-((2-Boc-aminoethyl)dithio)ethyl nitrate (LI-2f): To a solution of LI-2e (8 g, 25.3 mmol) in acetonitrile (80 mL) was added AgNO$_3$ (5.16 g, 30.36 mmol) portion-wise and stirred at RT for 1 h in the dark. The mixture was filtered through celite and the filtrate was concentrated. The residue obtained was purified by column chromatography to afford 6.34 g (84%) of LI-2f. $^1$H-NMR (300 MHz, CDCl$_3$): δ 1.44 (s, 9H), 2.80 (t, 2H, J=6.32 Hz), 3.06 (t, 2H, J=6.73 Hz), 3.44 (q, 2H), 4.70 (t, 2H, J=7.62 Hz), 4.87 (br s, 1H). MS (EI)$^+$ m/z: 299 [M+H]$^+$.

The above linker intermediate was also prepared by the following method: TEA (3.56 g, 35.2 mmol) was added to a solution of cysteamine hydrochloride (2 g, 17.60 mmol) and LI-3b (4.29 g, 17.6 mmol) in methanol (25 mL) at 0° C. and stirred at RT for 4 h. To the mixture, which contained the intermediate free amine (LI-5), a solution of (Boc)$_2$O (7.68 g, 35.2 mmol) and TEA (3.56 g, 35.2 mmol) in MeOH (10 mL) was added and the mixture was stirred overnight. The reaction mixture was filtered through celite and evaporated to dryness. The residue was purified by column chromatography to afford 0.380 g (7%) of LI-2f.

Example 10

Synthesis of 2-((2-Aminoethyl)dithio)ethyl nitrate. TFA salt (LI-5.TFA): To an ice-cold solution of LI-2f (2 g, 6.7 mmol) in DCM (20 mL) was added TFA (5 mL) and stirred at room temperature for 1 h. The mixture was concentrated, the residue was triturated with ether and concentrated to remove traces of TFA and finally dried to afford LI-5.TFA, which was used as such in further reactions.

The above linker intermediate LI-5.TFA was also synthesized as described below: TEA (3.56 g, 35.2 mmol) was added drop-wise to a solution of cysteamine hydrochloride (2 g, 17.60 mmol) and LI-3b (4.29 g, 17.6 mmol) in MeOH (25 mL) at 0° C. and stirred at RT for 4 h. The mixture was cooled to 0° C. and a solution of (Boc)$_2$O (7.68 g, 35.2 mmol) in MeOH (10 mL) was added, followed by TEA (3.56 g, 35.2 mmol), and stirred overnight at RT. The reaction mixture was filtered through celite and the filtrate concentrated. The residue was purified by column chromatography to afford 0.38 g (7.25%) of LI-2f, which was identical (TLC and $^1$H-NMR) to that obtained in Example 9. Removal of the Boc group from LI-2f to give LI-5.TFA was accomplished as described in Example 10.

Example 11

Synthesis of methyl [(2-hydroxyethyl)dithio]acetate (L3I2a): Methyl mercaptoacetate (10.32 g, 97.4 mmol) was added to a solution of SL-1 (10.0 g, 64.93 mmol) in DCM (150 mL) at RT, followed by TEA (18 mL, 129 mmol) and the mixture was stirred overnight at RT. After usual aqueous work-up and chromatographic purification, 2.7 g (22.9%) of L3I2a were obtained. $^1$H-NMR (300 MHz, CDCl$_3$): δ 2.95 (t, 2H, J=2.5 Hz), 3.49 (s, 2H), 3.76 (s, 3H), 3.86 (q, 2H, J=5.64). MS (m/z): 182 [M+H]$^+$.

Example 12

Synthesis of prodrug I-C1-PD10: This prodrug was synthesized as described in Scheme 11, Method B. Thus, TEA (0.73 mL, 10 mmol) was added to a suspension of cetirizine dihydrochloride (2.0 g, 4.68 mmol) in DCM (50 mL), followed by a solution of SL-1 (0.72 g, 4.67 mmol), DCC (1.13 g, 5.47 mmol) and DMAP (0.112 g, 1 mmol) and stirred at RT for 15 h. The mixture was concentrated and the residue, after usual aqueous work-up and chromatographic purification, gave 0.44 g (19%) of I-C1-PD10. $^1$H-NMR (300 MHz, CDCl$_3$): δ 2.50 (bs, 4H), 2.80 (bs, 6H), 2.87 (t, 2H, J=6.09 Hz), 2.94 (t, 2H, J=7.32 Hz), 3.75 (m, 2H), 3.86 (t, 2H, J=6.12 Hz), 4.13 (s, 2H), 4.24 (s, 1H), 4.40 (t, 2H, J=6.09 Hz) and 7.22-7.35 (m, 9H). MS (m/z): 527 [M+H]$^+$.

Example 13

Synthesis of prodrug I-C1-PD6: Step 1: To a suspension of aspirin (3 g, 16.65 mmol) in benzene (25 mL) and DMF (2 drops) at 0-5° C. was added oxalyl chloride (1.7 mL, 19.98 mmol) in benzene (5 mL). The reaction mixture was refluxed at 85° C. for 2 h, cooled to RT and concentrated to give a yellow oil.

Step 2: The yellow oil was dissolved in benzene (30 mL), silver cyanate (2.99 g, 19.98 mmol) was added and the mixture was refluxed for 1 h in the dark.

Step 3: The reaction mixture was cooled to RT, and a solution of SL-1 (2.56 g, 16.65 mmol) in benzene (5 mL). The reaction mixture was stirred for 1 h, filtered through celite, concentrated and purified by column chromatography to afford 2.24 g (54%) of I-C1-PD6. $^1$H NMR (CDCl$_3$, 300 MHz): δ 2.12 (s, 3H), 2.83-2.91 (m, 4H), 3.84 (t, J=5.9 Hz, 2H), 4.27 (t, J=5.16 Hz, 2H); 6.20 (br s, 1H), 7.06 (d, J=8.21 Hz, 1H), 7.19 (t, J=7.55 Hz, 1H), 7.59 (t, J=7.24 Hz, 1H), 7.97

(d, J=6.82 Hz, 1H). MS: m/z 360.06 [M+H]$^+$, 377.05 [M+NH$_4$]$^+$, 382.01 [M+Na]$^+$, 357.96 [M–H]$^-$.

Example 14

Synthesis of prodrug I-C1-PD11: To a solution of SL-1 (7 g, 45.45 mmol) and valproic acid (7.85 g, 54.5 mmol) in DCM (80 mL) was added DCC (11.26 g, 54.5 mmol), followed by DMAP (6.65 g, 54.5 mmol), and the resulting suspension was stirred at RT for 18 h. After usual aqueous work-up and chromatographic purification, 2.82 g (22%) of I-C1-PD11 were obtained as a colorless oil. $^1$H NMR (CDCl$_3$, 300 MHz): δ 0.86-0.93 (m, 6H), 1.22-1.29 (m, 8H), 1.32-1.59 (m, 4H), 2.37 (m, 1H), 3.89 (t, 2H, J=5.7 Hz), 4.35 (t, 2H, J=6.5 Hz).

Example 15

Synthesis of prodrug I-C1-PD13: To a solution of valpromide (5 g, 34.9 mmol) in DCE (50 mL) was added oxalyl chloride (3.7 mL, 41.88 mmol) at 0° C. and refluxed for 16 h. The mixture was added to a solution of SL-1 (10.76 g, 69.8 mmol) in DCE (80 mL) and stirred overnight at RT. After usual aqueous work-up and chromatographic purification, 5.01 g (44%) of I-C1-PD13 were obtained as a colorless oil. $^1$H NMR (CDCl$_3$, 300 MHz): δ 0.89 (t, 6H, J=7.21 Hz), 1.23-1.66 (m, 9H), 2.90 (t, 2H, 5.82 Hz), 2.97 (t, 2H, J=6.46 Hz), 3.90 (t, 2H, J=5.82 Hz), 4.44 (t, 2H, J=6.48 Hz), 7.61 (br s, 1H)

Example 16

Synthesis of prodrug I-C1-PD14: To a cold solution of diphosgene (0.9 mL, 7.14 mmol) in DCM (5 mL) was added a solution of I-C1-PD11 (1 g, 3.57 mmol) and DIPEA (1.9 mL, 10.71 mmol) in DCM (5 mL). The reaction mixture was stirred at RT for 30 min. DCM and excess phosgene were removed under vacuum and the resulting solid was dissolved in DCM (5 mL). To it was added a suspension of methanesulfonamide (0.41 g, 4.284 mmol) and DIPEA (1.9 mL, 10.71 mmol) in DCM (5 mL) at 0-5° C. and the mixture was stirred overnight at RT. After usual aqueous work-up and chromatographic purification, 1.1 g (77%) of I-C1-PD14 were obtained as a white solid. $^1$H NMR (CDCl$_3$, 300 MHz): δ 0.89 (t, 6H, J=7.22 Hz), 1.27-1.63 (m, 8H), 2.34-2.43 (m, 1H), 2.90 (t, 2H, J=7.0 Hz), 2.96 (t, 2H, J=6.13 Hz), 3.30 (s, 3H), 4.36 (t, 2H, J=6.98 Hz), 4.45 (t, 2H, J=6.14 Hz). MS: (ES$^+$) m/z 402 [M+H]$^+$, 419 [M+NH$_4$]$^+$, 424 [M+Na]$^+$, 440 [M+K]$^+$; (ES$^-$) 401 [M–H]$^-$.

Example 17

Synthesis of Prodrug I-A1-PD1

This prodrug was synthesized as shown in Scheme 14, Method B. Thus, to a solution of amlodipine (18.75 g, 45.86 mmol) in DCM (100 mL) at 0° C. was added triphosgene (4.62 g, 15.59 mmol) followed by TEA (7.71 g, 76.35 mmol) in DCM (10 mL) and stirred at RT for 3 h. To this was added a solution of LI-1a (9.0 g, 48.86 mmol) and TEA (4.63 g, 45.86 mmol) in DCM (10 mL) at 0° C. and stirred at RT for 3 d. The mixture was concentrated and the residue purified by column chromatography to yield 23 g (79.5%) of I-A1-PD1. $^1$H-NMR (300 MHz, CDCl$_3$): δ 1.16 (t, 3H, J=7.5 Hz), 2.05 (s, 3H), 2.34 (s, 3H), 2.86-2.94 (m, 4H), 3.43-3.45 (m, 2H), 3.59-3.62 (m, 5H), 4.0-4.35 (m, 4H), 4.30-4.35 (m, 4H), 4.69 (q, 2H, J=15 Hz), 5.20 (bs, 1H), 5.38 (s, 1H), 7.01-7.34 (m, 4H). MS (m/z): 631 [M+H]$^+$, 653 [M+Na]$^+$.

Example 18

Synthesis of prodrug I-A1-PD2: To a solution of I-A1-PD1 (23.0 g, 36.45 mmol) in MeOH (250 mL) at 0° C. was added a solution of K$_2$CO$_3$ (7.54 g, 54.67 mmol) in water (55 mL) and stirred for 10 min. The mixture was concentrated and purified by column chromatography to afford 18 g (83.8%) of the intermediate I-A1-PD2. $^1$H-NMR (300 MHz, CDCl$_3$): δ 1.16 (t, 3H, J=6 Hz), 2.35 (s, 3H), 2.84-2.88 (t, 2H, J=6 Hz), 2.90-2.94 (t, 2H, J=6 Hz), 3.44 (bs, 2H), 3.59-3.61 (bs, 5H), 3.84-3.91 (m, 2H), 4.0-4.03 (q, 2H, J=3.11 Hz), 4.33 (bs, 2H), 4.69 (q, 2H, J=15 Hz), 5.28 (bs, 1H), 5.37 (s, 1H), 7.12-7.36 (m, 4H). MS (ES$^+$): m/z 589 [M$^+$], 611 [M+Na]$^+$.

Example 19

Synthesis of prodrug I-A1-PD3: To a suspension of lamotrigine (13.09 g, 51.02 mmol) in toluene (100 mL) at 110° C. was added a solution of LI-1xy (synthesized from LI-1a and CDI, as described in Scheme 10) (16.27 g, 56.12 mmol) in THF (50 mL) and stirred at 110° C. overnight. The reaction mixture was purified by column chromatography to give 6.0 g (24%) of I-A1-PD3 as a white solid. $^1$H NMR (CD$_3$OD, 300 MHz) δ 2.04, (s, 3H), 2.96-3.02 (m, 4H), 4.30-4.35 (m, 2H), 4.45 (t, 2H), 7.38-7.45 (m, 2H), 7.67-7.69 (m, 1H). MS: (ES$^+$) m/z 477.9 (M+H)$^+$, 499.9 (M+Na)$^+$.

Example 20

Synthesis of prodrug I-A1-PD4: To a solution of I-A1-PD3 (2 g, 4.18 mmol) in MeOH (15 mL) and THF (5 mL) at 0° C. was added a solution of K$_2$CO$_3$ (0.886 g, 6.276 mmol) in water (5 mL) and stirred at 0° C. for 3 h. After usual aqueous work-up and chromatographic purification, 1.1 g (60%) of I-A1-PD4 were obtained as a white solid. $^1$H NMR (DMSO d$_6$, 300 MHz): δ 2.75-2.82 (m, 2H), 2.96-3.0 (m, 2H), 3.0 (s, 1H), 3.6 (t, 2H, J=6.3 Hz), 4.30 (t, 2H, J=6.6 Hz) 7.38-7.49 (m, 2H), 7.72-7.75 (m, 1H). MS: (ES+) m/z 436 (M+H)$^+$, 457 (M+Na)$^+$.

Example 21

Synthesis of prodrug I-A1-PD5: To a solution of diphosgene (0.99 mL, 8.24 mmol) in DCM (3 mL) at 0° C. was added a solution of L3I2a (0.5 g, 2.74 mmol) and Hünig's base (2.39 mL, 13.73 mmol) in DCM (3 mL). The mixture was stirred at 0° C. for 30 min and concentrated to yield the intermediate L3I3a as a light-yellow semi-solid. A solution of a mixture of gabapentin ethyl ester hydrochloride (0.77 g, 3.29 mmol) and Hünig's base (1.7 mL, 9.79 mmol) in DCM (6 mL) was added to the intermediate L3I3a at RT and stirred for 15 h. After usual aqueous work-up and chromatographic purification, 0.34 g (30%) of I-A1-PD5 were obtained as a yellow oil. $^1$H NMR (CDCl$_3$, 300 MHz): δ 1.26 (t, 3H, J=6 Hz), 1.22-1.51 (m, 10H), 2.26 (s, 2H), 2.96 (t, 2H, J=6 Hz), 3.18 (d, 2H, J=6 Hz), 3.49 (s, 2H), 3.82 (s, 3H), 4.09 (q, 2H, J=6 Hz), 4.29 (t, 2H, J=6 Hz), 5.39 (bs 1H). MS: (ES$^+$) m/z 408 (M+H)$^+$, 430 (M+Na)$^+$; (ES$^-$) m/z 406 (M–H)$^-$.

Example 22

Synthesis of prodrug I-A1-PD6: To a solution of I-A1-PD8 (1.0 g, 2.63 mmol) in DCM (3 mL) at RT was added CDI (0.46 g, 2.89 mmol) and stirred for 15 h. A suspension of serine methyl ester hydrochloride (0.61 g, 3.95 mmol) in DCM (4 mL) and TEA (1.1 mL, 7.90 mmol) was added and stirring continued for 15 h. After usual aqueous work-up and chromatographic purification, 0.706 g (51%) of I-A1-PD6 were obtained as a colorless oil. $^1$H NMR (CDCl$_3$, 300 MHz): δ 1.25 (t, 3H, J=7.1 Hz), 1.35-1.51 (m, 10H), 2.28 (s, 2H), 2.91-2.98 (m, 4H), 3.16 (d, 2H, J=9 Hz), 3.78 (s, 3H), 3.94-4.38 (m, 9H), 5.5 (bs, 1H), 6.0 (bs, 1H). MS: (ES)$^+$: m/z 525 (M+H)$^+$, 547 (M+Na)$^+$. (ES)$^-$: m/z 523 (M−H)$^+$.

Example 23

Synthesis of prodrug I-A1-PD7: To a solution of I-A1-PD8 (86 mg, 0.22 mmol) in DCM (9 mL) at RT was added CDI (40 mg, 0.24 mmol) and stirred for 15 h, after which a solution of dimethyl glutamate (80 mg, 0.45 mmol) and TEA (0.06 mL, 0.45 mmol) was added and stirred for 2 d. After usual aqueous work-up and chromatographic purification, 97 mg (74%) of I-A1-PD7 were obtained as a colorless oil. $^1$H NMR (CDCl$_3$, 300 MHz): δ 1.25 (t, 3H, J=7.13 Hz), 1.36-2.5 (m, 16H), 2.93 (t, 4H, J=6.46 Hz), 3.19 (d, 2H, J=6.67), 3.67 (s, 3H), 3.74 (s, 3H), 4.12 (q, 2H, J=7.13 Hz), 4.25-4.44 (m, 5H), 5.4 (bs, 1H), 5.65 (bs, 1H). MS: (ES$^+$) m/z 581 (M+H)$^+$, 603 (M+Na)$^+$; (ES$^-$) m/z 571 (M−H)$^-$.

Example 24

Synthesis of prodrug I-A1-PD9: To a suspension of gabapentin (10 g, 58.4 mmol) in THF (100 mL) at 0° C. was added 1N NaOH (70 mL), followed by (Boc)$_2$O. The mixture was stirred at RT for 15 h. After washing with diethyl ether (100 mL×2), the aqueous layer was acidified with solid KHSO$_4$ and extracted with EtOAc (100 mL×2). Organic extracts were washed with brine (100 mL), dried over Na$_2$SO$_4$ and concentrated to afford 10.41 g (68%) of boc-protected gabapentin as a white solid.

A mixture of boc-protected gabapentin (5.0 g, 18.45 mmol) and CDI (3.59 g, 22.14 mmol) in DCM (75 mL) was stirred for 15 h. The mixture was concentrated and dissolved in acetonitrile (50 mL), followed by the addition of 30% aqueous solution of ammonia (50 mL) and stirred for 1.5 h at RT. After usual aqueous work-up, 4.5 g (90%) of boc-protected gabapentin-amide were obtained as a white solid.

To a solution of boc-protected gabapentin-amide (2.59 g, 9.61 mmol) in DCM (12 mL) at 0° C. was added solution of TFA (4 mL) in DCM (4 mL) and stirred for 2.5 h at RT. The mixture was concentrated and dissolved in DCM (20 mL). This was treated successively with Hunig's base (6.7 mL, 38.46 mmol) and LI-1a (1.45 g, 7.39 mmol), and stirred at RT for 3 h. After usual aqueous work-up and chromatographic purification, 1.19 g (41%) of I-A1-PD9 were obtained as a yellow oil. $^1$H NMR (CDCl$_3$, 300 MHz): δ 1.28-1.48 (m, 10H), 2.06 (s, 3H), 2.15 (s, 2H), 2.91 (t, 4H, J=6.0 Hz), 3.23 (d, 2H, J=6.0 Hz), 4.28-4.38 (m, 4H), 5.7 (bs, 1H). MS: (ES)$^+$ m/z 393 (M+H)$^+$; (ES)$^-$ m/z 392 (M−H)$^-$.

Example 25

Synthesis of prodrug I-A1-PD10: A mixture of I-A1-PD8 (1.0 g, 2.63 mmol) and CDI (0.469 g, 2.89 mmol) in DMF (3 mL) was stirred for 12 h, after which N,N' dimethylethylenediamine (0.56 mL, 5.26 mmol) and DMAP (0.32 g, 2.63 mmol) was added. The mixture was stirred for 4 h. After usual aqueous work-up and chromatographic purification, 0.763 g (59%) of I-A1-PD10 were obtained as a yellow oil. $^1$H NMR (CDCl$_3$, 300 MHz): δ 1.25 (t, 3H, J=6.0 Hz), 1.28-1.53 (m, 10H), 2.24 (s, 6H), 2.29 (s, 2H), 2.42 (t, 2H, J=6.0 Hz), 2.92 (t, 4H, J=6.0 Hz), 3.20 (d, 2H, J=6.0 Hz), 3.26 (q, 4H, J=6.0 Hz), 4.13 (q, 2H, J=7.0 Hz), 4.31 (t, 4H, J=6.0 Hz), 7.26 (bs, 1H). MS: (ES)$^+$ m/z 494 (M+H)$^+$, 516 (M+Na)$^+$; (ES)$^-$ m/z 492 (M−H)$^-$.

Example 26

Synthesis of prodrug I-A1-PD11: A mixture of LI-1a (2.0 g, 10.20 mmol) and CDI (1.98 g, 12.24 mmol) in DCM (12 mL) was stirred for 2 h and concentrated. The residue was dissolved in acetonitrile, and a suspension of gabapentin (2.62 g, 15.30 mmol) in saturated NaHCO$_3$ (15 mL) was added. The mixture was stirred at RT for 15 h. Acetonitrile was removed by distillation and the basic aqueous portion was washed with diethyl ether (100 mL×2). The aqueous layer was acidified using 2N HCl and extracted in EtOAc (60 mL×3). The organic layer was concentrated and the residue was purified by chromatographic purification, 1.76 g (43%) of I-A1-PD11 were obtained as a colorless oil. $^1$H NMR (CDCl$_3$, 300 MHz): δ 1.27-1.68 (m, 10H), 2.07 (s, 3H), 2.31 (s, 2H), 2.92 (t, 4H, J=6.0 Hz), 3.22 (d, 2H, J=9.0 Hz), 4.31-4.35 (m, 4H), 5.43 (bs, 1H). MS: (ES)$^-$ m/z 392 (M−H)$^-$.

Example 27

Synthesis of prodrug I-A1-PD13: This prodrug was synthesized as shown in Scheme 12, Method B. Thus, to a solution of diphosgene (7.02 mL, 58.18 mmol) in DCM (20 mL) at 0° C. was added a solution of LI-1a (5.71 g, 29.09 mmol) and Hünig's base (25.3 mL, 145.45 mmol) in DCM (30 mL) and stirred at RT for 40 min. The mixture was concentrated and a mixture of gabapentin ethyl ester hydrochloride (7.546 g, 32 mmol) and Hünig's base (11.15 mL, 64 mmol) in DCM (50 mL) was added and stirred overnight. Reaction mixture was concentrated and, after usual aqueous work-up and column chromatography, 8.42 g (67%) of I-A1-PD13 were obtained. $^1$H NMR (CDCl$_3$, 300 MHz): δ 1.22 (t, 3H, J=7.3 Hz), 1.27-1.68 (m, 10H), 2.06 (s, 3H), 2.27 (s, 2H), 2.91 (t, 4H, J=6.6 Hz), 3.19 (d, 2H, J=6.7 Hz), 4.08-4.15 (q, 2H, J=7.1 Hz), 4.27-4.34 (q, 4H, J=6.4 Hz), 5.4 (bs, 1H). MS: m/z 422 [M+H]$^+$, 444 [M+Na]$^+$.

Example 28

Synthesis of prodrug I-A1-PD8: To an ice-cold solution of I-A1-PD13 (8.0 g, 18.98 mmol) in MeOH (30 mL) was added a solution of K$_2$CO$_3$ (5.24 g, 37.96 mmol) in water (38 mL). After 15 min, the mixture was concentrated. After usual aqueous work-up, 5.0 g (69%) of I-A1-PD8 were obtained. $^1$H NMR (CDCl$_3$, 300 MHz): δ 1.25 (t, 3H, J=7.11 Hz), 1.30-1.71 (m, 10H), 2.87-2.94 (m, 4H), 2.27 (s, 2H), 3.18 (d, 2H, J=6.6 Hz), 3.87 (t, 2H, J=5.7 Hz), 4.09-4.16 (q, 2H, J=7.12 Hz), 4.31 (t, 2H, J=6.51 Hz), 5.44 (bs, 1H). MS: m/z 380 [M+H]$^+$, 402 [M+Na]$^+$.

Example 29

Synthesis of prodrug I-A1-PD12: To a solution of diphosgene (1.91 mL, 15.81 mmol) in DCM (20 mL) at 0° C. was added a solution of I-A1-PD8 (4 g, 10.54 mmol) and Hünig's base (5.5 mL, 31.62 mmol) in DCM (30 mL). The mixture was stirred at RT for 40 min, cooled to 0-5° C., and dry ammonia gas was passed through it for 30 min. Reaction mixture was concentrated and, after usual aqueous work-up, 5.3 g (91%) of I-A1-PD12 were obtained. $^1$H NMR (CDCl$_3$, 300 MHz): δ 1.23 (t, 3H, J=7.1 Hz), 1.27-1.79 (m, 10H), 2.28

(s, 2H), 2.91-3.03 (m, 4H), 3.19 (d, 2H, J=6.7 Hz), 4.12 (q, 2H, J=7.1 Hz), 4.31 (t, 4H, J=6.4 Hz), 5.4 (t, 1H, J=6.0 Hz). MS: m/z 423 [M+H]$^+$, 446 [M+Na]$^+$.

Example 30

Synthesis of prodrug I-A1-PD14: Ethyl chloroformate (0.86 g, 7.9 mmol) was added to a solution of 3-carbamoyl-methyl-5-methylhexanoic acid (M. S. Hoekstra et al., *Org. Proc. Res. Dev.* 1997, 1, 26-38) (1.0 g, 5.3 mmol) in THF (6 mL) at −10° C., followed by TEA (2.4 mL, 17.0 mmol) and the mixture was stirred at −10° C. for 30 min. A solution of NaN$_3$ (1.73 g, 26.6 mmol) in water (10 mL) was added and stirred for 2 h at −10° C. The reaction mixture was brought to RT and extracted with EtOAc (3×25 mL), washed with water (2×25 mL), dried over Na$_2$SO$_4$ and concentrated. Toluene (20 mL) was added to the residue and refluxed for 6 h. After cooling to RT, a solution of and SL-1 (825 mg, 5.3 mmol) in DCM (10 mL) was added and stirred at RT for 14 h. After usual aqueous work-up and chromatographic purification, 318 mg (17%) of I-A1-PD14 were obtained as a colorless oil. $^1$H NMR (300 MHz, CDCl$_3$): δ 0.89-0.95 (m, 6H), 1.25-1.29 (m, 2H), 1.62-1.71 (m, 1H), 2.04-2.1 (m, 1H), 2.38 (d, J=5.2 Hz, 2H), 2.87-2.95 (m, 4H), 3.05-3.36 (m, 2H), 3.88 (t, J=5.7 Hz, 2H), 4.34 (t, J=6.2 Hz, 2H), 5.06 (br s, 1H). MS: m/z 338 [M]$^+$.

Example 31

Synthesis of prodrug I-A1-PD15Ba: To a solution of I-A1-PD4 (0.350 g, 0.802 mmol) in DMF (3 mL) at RT was added CDI (0.195 g, 1.204 mmol) and stirred at RT for 3 h. This mixture was added to a suspension of methanesulphonamide (0.304 g, 3.2 mmol) in DMF (4 mL) and NaH (0.153 g, 3.2 mmol) at 0° C. and stirred at RT for 4 h. The reaction was quenched with ice and, after usual aqueous work-up and chromatographic purification, 0.12 g (26%) of I-A1-PD15Ba were obtained as a white solid. $^1$H NMR (CDCl$_3$+CD$_3$OD, 300 MHz): δ 2.83-2.90 (m, 4H), 3.10 (s, 3H), 4.26-4.36 (m, 4H), 7.19-7.28 (m, 2H), 7.48-7.51 (m, 1H). MS: (ES$^+$) m/e 556.96 (M+H)$^+$, 578.92 (M+Na)$^+$.

Example 32

Synthesis of prodrug I-A1-PD18: CDI (4 g, 24.7 mmol) was added to a solution of LI-2c (4 g, 15.8 mmol) in THF (30 mL) and stirred at RT for 2 h. Then, a solution of gabapentin (4 g, 23.4 mmol) in 20% NaHCO$_3$ solution (10 mL) was added and stirred overnight at RT. The reaction mixture was neutralized with 0.5N HCl (pH ~4), extracted with EtOAc (4×40 mL), dried over Na$_2$SO$_4$, concentrated and purified by column chromatography to afford 4.7 g (66%) of I-S12-PD2 as a colorless oil. $^1$H NMR (300 MHz, CDCl$_3$): δ 1.45-1.49 (br s, 19H), 2.35 (s, 2H), 2.80-2.97 (m, 4H), 3.24 (d, J=5.7 Hz, 2H), 3.46 (m, 2H) 4.33 (t, J=5.7 Hz, 2H), 5.0 (br s, 1H), 5.71 (br s, 1H). MS: (m/z) [ES]$^-$ 449.1 [M−H]$^+$; [ES]$^+$ 451.2 [M+H]$^+$.

EtOAc saturated with HCl gas (5 mL) was added to I-S12-PD2 (0.55 g, 1.22 mmol) and stirred at RT for 10 h. Solvent was removed under reduced pressure and purified by preparative HPLC to give 425 mg (90%) of I-A1-PD18 as a colorless liquid. $^1$H NMR (300 MHz, CD$_3$OD): δ 1.52 (br s, 10H), 2.4 (s, 2H), 2.98-3.09 (m, 4H), 3.27-3.34 (m, 2H), 3.61 (s, 2H), 4.5 (t, J=6.0 Hz, 2H). MS: [ES]$^+$ m/z 351.0 [M+H]$^+$.

Example 33

Synthesis of prodrug I-A2-PD1: To a solution of levetiracetam (1.0 g, 5.87 mmol) in DCE (20 mL) and DCM (4 mL) was added oxalyl chloride (0.61 mL, 7.05 mmol), and heated at 70° C. for 8 h. Reaction mixture was cooled and added to a solution of SL-1 (1.81 g, 11.75 mmol) in DCM (15 mL) and stirred at RT overnight. After chromatographic purification, 1.13 g (41%) of I-A2-PD1 were obtained. $^1$H NMR (CDCl$_3$, 300 MHz): δ (ppm): 0.87 (t, J=7.3 Hz, 3H), 1.84-2.04 (m, 4H), 2.41 (t, J=6.9 Hz, 2H), 2.69 (bs, 1H), 2.87-2.95 (m, 4H), 3.02-3.11 (m, 1H), 3.65-3.75 (m, 1H), 3.85-3.95 (m, 2H), 4.06-4.12 (m, 1H), 4.34-4.41 (m, 2H), 8.69 (bs, 1H). MS: (ES$^+$): m/z 351.0 [M+H]$^+$; 372.9 [M+Na]$^+$.

Example 34

Synthesis of prodrug I-A3-PD1: To a solution of I-S13-PD1 (which was synthesized as described in Example 37, Step 2) (215 mg, 0.292 mmol) and triisopropylsilane (60 µL) in 0.75 mL of DCM was added 20% TFA in DCM (0.5 mL) and stirred at RT for 90 min. The mixture was concentrated and the residue purified by column chromatography to give 65 mg (46%) of I-A3-PD1. $^1$H-NMR (300 MHz, CDCl$_3$): δ 2.51 (s, 3H), 2.85-2.92 (m, 4H), 3.87 (t, 2H, J=4.5 Hz), 4.37 (t, 2H, J=6.0 Hz), 7.25-7.43 (m, 7H), 8.01 (d, 2H, J=3.0 Hz). MS (m/z): 493 [M−H]$^-$, 517 [M+Na]$^+$.

Example 35

Synthesis of prodrugs I-A3-PD3a and I-A3-PD3b: Step 1: DSC (210 mg, 0.824 mmol) and TEA (0.230 mL, 1.64 mmol) were added to a solution of methyl [(2-hydroxyethyl)dithio]acetate (100 mg, 0.549 mmol) in acetonitrile (1 mL) at 0° C. and stirred at RT for 3 h. The mixture was concentrated and the residue dissolved DCM. Usual aqueous work-up and chromatographic purification gave the crude intermediate.

Step 2: TEA (24 mg, 0.236 mmol) and DMAP (13 mg) were added to a mixture of valdecoxib (62 mg, 0.195 mmol) and the product obtained from step 1 above in THF (1 mL) and stirred at RT for 3 d. The mixture was concentrated and the residue dissolved in EtOAc. After usual aqueous work-up and chromatographic purification, 53 mg (52%) of I-A3-PD3a obtained. $^1$H-NMR (300 MHz, CDCl$_3$): δ 2.51 (s, 3H), 2.97 (t, 2H, J=6.0 Hz), 3.48 (s, 2H), 3.76 (s, 3H), 4.37 (t, 2H, J=6.0 Hz), 7.33-7.40 (m, 7H), 8.03-8.12 (m, 2H). MS (m/z): 521 [M−H]$^-$.

Step 3: The above material was converted to the corresponding mono-, and/or di-sodium salt forms I-A3-PD3b by using standard methods. Thus, to a cold solution of the above compound (150 mg, 0.287 mmol) in THF (1 mL) was added 1M LiOH solution (28 mg in 1 mL water) and stirred overnight at RT. The mixture was concentrated, the residue diluted with water, acidified with 1N HCl (~3 ml, pH ~3) and extracted with EtOAc. After usual aqueous work-up and chromatographic purification, 20 mg (13%) of product were obtained. $^1$H-NMR (300 MHz, CDCl$_3$): δ 2.49 (s, 3H), 2.70-2.89 (m, 4H), 4.23-4.33 (m, 2H), 7.28-7.38 (m, 7H), 8.01-8.03 (m, 2H).

Example 36

Synthesis of prodrug I-A3-PD4: This prodrug was synthesized as described in Scheme 13, Method B.

Step 1: Synthesis of Intermediate LI-8:

CDI (1.65 g, 10.19 mmol) was added to a solution of LI-1a (2.0 g, 10.19 mmol) in DMF (10 mL) and stirred at RT for 3 h. N,N-Dimethylethylenediamine (1.2 mL, 11.12 mmol) was added and stirred for 2 h. The mixture was concentrated and the residue taken up in EtOAc. After usual aqueous work-up and chromatographic purification, 1.3 g (41%) LI-8 were obtained. $^1$H-NMR (300 MHz, CDCl$_3$): δ 2.07 (s, 3H), 2.31 (bs, 6H), 2.51 (t, 2H, J=6.0 Hz), 2.91 (t, 4H, J=6.0 Hz), 3.31 (q, 2H, J=6.0 Hz), 4.28-4.34 (m, 4H), 5.52 (bs, 1H). MS (m/z): 333 [M+Na]$^+$.

Step 2: Synthesis of intermediate LI-9: To a solution of LI-8 (1.3 g, 4.18 mmol) in MeOH (7 mL) was added a 1.25M solution of K$_2$CO$_3$ (5 mL) and stirred at RT for 1 h. The mixture was concentrated and the residue was taken up in DCM. After usual aqueous work-up, 1.02 g (91%) of product were obtained. $^1$H-NMR (300 MHz, CDCl$_3$): δ 2.29 (s, 6H), 2.54 (t, 2H, J=6.0 Hz), 2.86-2.99 (m, 4H), 3.33 (q, 2H, J=5.0 Hz), 3.86 (t, 2H, J=6.0 Hz), 4.31 (t, 2H, J=6.0 Hz), 5.71 (bs, 1H). MS (m/z): 269 [M+H]$^+$. This product was used as such in the next step.

Step 3: Synthesis of intermediate LI-10: A solution of LI-9 (1.02 g, 3.80 mmol) in acetonitrile (10 mL) was added to a cold solution of DSC (1.46 g, 5.70 mmol) in acetonitrile (50 mL) followed by TEA (1.58 ml, 11.40 mmol), and stirred overnight at RT. The mixture was concentrated and the residue was taken up in DCM. After usual aqueous work-up, 1.33 g (85%) of LI-10 were obtained.

Step 4: Synthesis of I-A3-PD4: TEA (0.194 mL, 1.39 mmol) and DMAP (73 mg, 0.6 mmol) were added to a solution of LI-10 (1.33 g, 3.24 mmol) and valdecoxib (364 mg, 1.16 mmol) in THF (6 mL) and stirred at RT for 5 d. The mixture was concentrated and the residue was taken up in DCM. After usual aqueous work-up and chromatographic purification, 177 mg (12%) of LI-10 were obtained. $^1$H-NMR (300 MHz, CDCl$_3$): δ 2.46 (s, 3H), 2.85-2.95 (m, 10H), 3.28 (t, 2H, J=6.0 Hz), 3.65 (q, 2H, J=3.0 Hz), 4.22-4.28 (m, 4H), 7.22-7.41 (m, 7H), 7.94 (d, 2H, J=9.0 Hz). MS (m/z): 609 [M+H]$^+$. This product was converted to water-soluble hydrochloride salt form using standard methods.

Example 37

Synthesis of prodrug I-A3-PD5: This prodrug was synthesized as shown in Scheme 13, Method B.

Step 1: Synthesis of Prodrug Intermediate LI-1xy:

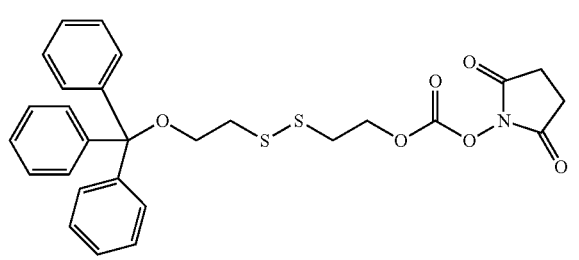

Intermediate LI-1xy

A solution of LI-1c (1.0 g, 2.52 mmol) in acetonitrile (10 mL) was added to a solution of DSC (0.96 g, 3.78 mmol) in acetonitrile (20 mL) and stirred for 10 min. After cooling to 0° C., TEA (1 ml, 7.57 mmol) was added and stirred at RT for 3.5 h. The solution was concentrated and the residue was taken up in DCM. After usual aqueous work-up, the crude product obtained was used as such in the next step.

Step 2: Synthesis of prodrug intermediate I-S13-PD1: A mixture of valdecoxib (280 mg, 0.892 mmol), DMAP (56 mg, 0.5 mmol) and TEA (150 µL, 1.06 mmol) in THF (5 mL) was stirred at RT for 4.5 d. The mixture was concentrated and the residue dissolved in EtOAc. After usual aqueous work-up and chromatographic purification, 354 mg (54%) of I-S13-PD1 were obtained. $^1$H-NMR (300 MHz, CDCl$_3$): δ 2.47 (s, 3H), 3.32-3.41 (m, 4H), 4.28 (t, 2H, J=6.0 Hz), 4.47 (t, 2H, J=6.0 Hz), 7.20-7.61 (m, 22H), 8.00 (d, 2H, J=9.0 Hz). MS (m/z): 736 [M−H]$^−$.

Step 3: Synthesis of intermediate I-A3-PD1: To a solution of I-S13-PD1 (215 mg, 0.292 mmol) and triisopropylsilane (60 µL) in 0.75 ml of DCM was added 20% TFA in DCM (0.5 mL) and stirred at RT for 90 min. The mixture was concentrated and the residue purified by column chromatography to give 65 mg (46%) of I-A3-PD1. $^1$H-NMR (300 MHz, CDCl$_3$): δ 2.51 (s, 3H), 2.85-2.92 (m, 4H), 3.87 (t, 2H, J=4.5 Hz), 4.37 (t, 2H, J=4.5 Hz), 7.25-7.43 (m, 7H), 8.01 (d, 2H, J=3.0 Hz). MS (m/z): 493 [M−H]$^−$, 517 [M+Na]$^+$.

Step 4: Synthesis of I-A3-PD5-Me-ester: CDI (40 mg, 0.243 mmol) was added to a solution of I-A3-PD1 (100 mg, 0.202 mmol) in DMF (0.5 mL) and stirred at RT for 2.5 h. To this were added a solution of dimethyl glutamate (53 mg, 0.303 mmol) in DMF (0.3 mL) and DMAP (37 mg, 0.303 mmol) and stirred overnight at RT. The mixture was dissolved in EtOAc and, after usual aqueous work-up and chromatographic purification, 110 mg (78%) of I-A3-PD5-Me-ester were obtained $^1$H-NMR (300 MHz, CDCl$_3$): δ 1.71-1.91 (m, 2H), 2.38-2.42 (m, 2H), 2.44 (s, 3H), 2.84-2.95 (m, 4H), 3.66 (s, 3H), 3.67 (s, 3H), 4.31-4.34 (m, 4H), 4.43-4.52 (m, 1H), 7.31-7.41 (m, 7H), 8.02 (d, 2H, J=9.0 Hz). MS (m/z): 694 [M−H]$^−$.

Step 5: Synthesis of prodrug I-A3-PD5: IN Lithium hydroxide (1.2 mL, 1.2 mmol) was added to a solution of I-A3-PD5-Me-ester (100 mg, 0.144 mmol) in THF (0.4 mL) at 0° C. and the mixture allowed to attain ambient temperature. After 30 min, the mixture was concentrated and the residue diluted with water. Acidification with 1N HCl, followed by extraction with EtOAc, usual aqueous work-up and chromatographic purification gave 26 mg (26%) of I-A3-PD5. $^1$H-NMR (300 MHz, CD$_3$OD): δ 1.82-1.97 (m, 1H), 2.05-2.13 (m, 1H), 2.30-2.40 (m, 2H), 2.48 (s, 3H), 2.84-2.94 (m, 4H), 4.06-4.08 (m, 1H), 4.15-4.22 (m, 4H), 7.30 (d, 2H, J=9 Hz), 7.35-7.41 (m, 5H), 7.92 (d, 2H, J=9.0 Hz). MS (m/z): 666 [M−H]$^−$.

Example 38

Synthesis of prodrug I-H1-PD1: This prodrug was synthesized as shown in Scheme 14, Method B.

Step 1: A solution of metronidazole (5.0 g, 29.22 mmol) and CDI (5.21 g, 32.2 mmol) in DCM (100 mL) was stirred overnight at RT. After usual aqueous work-up, 7.32 g of the imidazolide of metronidazole were obtained, which was used as such in the next step.

Step 2: A solution of the imidazolide of metronidazole (7.32 g) in DMF (30 mL) was added to a solution of SL-1 (6.39 g, 41.43 mmol) in DMF (10 mL) and stirred at 60° C. for 2.5 h. The mixture was concentrated and the residue was taken up in DCM. After usual aqueous work-up and chromatographic purification, 6.32 g (65%) of I-H1-PD1 were obtained. $^1$H-NMR (300 MHz, CDCl$_3$): δ 2.15 (bs, 1H), 2.52 (s, 3H), 2.83-2.92 (m, 4H), 3.84-3.92 (m, 2H), 4.34 (t, 2H, J=6.0 Hz), 4.51 (t, 2H, J=3.0 Hz), 4.53-4.62 (m, 2H), 7.96 (s, 1H).

Example 39

Synthesis of I-H1-PD14: This prodrug was synthesized as described in Scheme 14, Method C. Thus, TEA (0.915 mL, 6.56 mmol) and DMAP (cat.) were added to a solution of LI-2C.TFA (541 mg, 3.94 mmol) and the imidazolide of metronidazole (synthesis described in Example 114) (870 mg, 3.28 mmol) in DMF (2 mL) and the mixture was heated at 60° C. for 3.5 h. The mixture was concentrated and the residue, after usual aqueous work-up and chromatographic purification, gave 546 mg (48%) of I-H1-PD14. $^1$H-NMR (300 MHz, CDCl$_3$): δ 2.48 (s, 3H), 2.76-2.96 (m, 4H), 3.46 (q, 2H, J=6.0 Hz), 3.87 (t, 2H, J=6.0 Hz), 4.41 (t, 2H, J=6.0 Hz), 4.57 (t, 2H, J=4.5 Hz), 7.90 (s, 1H). MS (m/z): 351 [M+H]$^+$.

Example 40

Synthesis of prodrug I-H1-PD2: This prodrug was synthesized as described in Scheme 14, Method C. Thus, CDI (180 mg, 1.1 mmol) was added to a solution of I-H1-PD14 (350 mg, 1.0 mmol) in DMF (2 mL) and stirred at RT for 4 h. N,N-Dimethylethylenediamine (88 mg, 1.0 mmol) was added and stirred for 3 h. The mixture was concentrated and the residue purified by column chromatography to afford 175 mg (38%) of I-H1-PD2. $^1$H-NMR (300 MHz, CDCl$_3$): δ 2.28 (s, 3H), 2.49 (s, 6H), 2.51-2.55 (m, 2H), 2.81 (t, 2H, J=6.0 Hz), 2.89 (t, 2H, J=6.0 Hz), 3.27-3.33 (m, 2H), 3.46 (q, 2H, J=6.0 Hz), 4.29 (t, 2H, J=6.0 Hz), 4.40 (t, 2H, J=4.5 Hz), 4.57 (t, 2H, J=4.5 Hz), 5.55 (bs, 1H), 7.94 (s, 1H). MS (m/z): 465 [M+H]$^+$. This product was converted to water-soluble hydrochloride salt form using a standard method.

Example 41

Synthesis of prodrug I-H1-PD5: This prodrug was synthesized as described in Scheme 14, Method A.

Step 1: Synthesis of Intermediate I-S14-PD1: A solution of the imidazolide of LI-1c (1.6 g, 2.98 mmol) in acetonitrile (10 mL) was added to a solution of zudovudine (1.0 g, 3.74 mmol) in acetonitrile (20 mL) at RT, followed by DMAP (0.914 g, 7.48 mmol) and stirred for 24 h. The mixture was concentrated and the residue, after usual aqueous work-up and chromatographic purification, gave 1.62 g (79%) of intermediate I-S14-PD1. $^1$H-NMR (300 MHz, CDCl$_3$): δ 1.95 (s, 3H), 2.35-2.45 (m, 2H), 2.78 (t, 2H, J=6.6 Hz), 2.87 (t, 2H, J=6.33 Hz), 3.38 (t, 2H, J=6.33 Hz), 4.05 (m, 1H), 4.25 (m, 1H), 4.35-4.41 (m, 4H), 6.20 (t, 1H, J=6.16), 7.21-7.33 (m, 9H), 7.42-7.48 (m, 6H) and 8.49 (s, 1H). MS (m/z): 712 [M+Na]$^+$.

Step 2: Synthesis of I-H1-PD5: To a solution of I-S14-PD1 in DCM (15 mL) were added triisopropylsilane (0.446 ml, 2.17 mmol), followed by 10% TFA in DCM (15 mL) and stirred at RT for 30 min. The mixture was concentrated and purified by column chromatography to afford 0.68 g (70%) of prodrug I-H1-PD5. $^1$H-NMR (300 MHz, CDCl$_3$): δ 1.93 (s, 3H), 2.30 (bs, 1H), 2.41-2.48 (m, 2H), 2.88 (t, 2H, J=6.1 Hz), 2.96 (t, 2H, J=6.6 Hz), 3.88 (t, 2H, J=5.8 Hz), 4.05 (m, 1H), 4.29 (m, 1H), 4.30-4.48 (m, 4H), 6.18 (t, 1H, J=6.3 Hz), 7.34 (s, 1H) and 9.11 (s, 1H). MS (m/z): 448 [M+H]$^+$, 470 [M+Na]$^+$.

Example 42

Synthesis of prodrug I-S22-PD1: This prodrug was synthesized in two steps as shown in Scheme 22.

Step 1: To a solution of diphosgene (0.35 mL, 2.93 mmol) in DCM (3 mL) was added a solution of LI-1d (0.404 mg, 1.75 mmol), Hunig's base (0.765 mL, 4.39 mmol) and the resulting mixture was stirred at RT for 45 min. The mixture was concentrated, the residue dissolved in DCM (5 mL), cooled in an ice-bath and treated with a solution of paclitaxel (500 mg, 0.585 mmol), Hunig's base (0.765 mL, 4.39 mmol) and DMAP (cat.) in DCM (5 mL) over 5 min and the resulting mixture was stirred at RT for 2 h. The mixture was purified by column chromatography to give 519 mg (78%) of the protected intermediate S22-I2 as an off-white solid. $^1$H NMR (500 MHz, CDCl$_3$): δ 1.14 (s, 3H), 1.28 (s, 3H), 1.68 (s, 3H), 2.04 (s, 3H), 2.23 (s, 3H), 2.37-2.45 (m, 2H), 2.46 (s, 3H), 2.50-2.52 (m, 2H), 2.90-2.95 (m, 4H), 3.82 (d, 1H, J=7.0 Hz), 4.05 (s, 2H), 4.21 (d, 1H, J=8.5 Hz), 4.32 (d, 1H, J=8.0 Hz), 4.40-4.42 (m, 5H), 4.97 (d, 1H, J=9.5 Hz), 5.29 (s, 1H), 5.43 (d, 1H, J=2.5 Hz), 5.69 (d, 1H, J=7.0 Hz), 6.00 (dd, 1H, J=9.5 Hz, 2.5 Hz), 6.26-6.29 (m, 2H), 7.02 (d, 1H, J=9.5 Hz), 7.38-7.61 (m, 11H), 7.75 (d, 2H, J=7.5 Hz), 8.15 (d, 2H, J=7.5 Hz).

Step 2: To an ice-cold solution of S22-I2 (60 mg, 0.0532 mmol) in MeOH (1 mL) was added 2 drops of methanol saturated with ammonia gas and the resulting mixture was stirred for 1 h. The reaction mixture was purified by column chromatography to give 38 mg (69%) of I-S22-PD1 as an off white solid. $^1$H NMR (500 MHz, CDCl$_3$): δ 1.14 (s, 3H), 1.23 (s, 3H), 1.68 (s, 3H), 1.91 (s, 3H), 2.23 (s, 3H), 2.38-2.42 (m, 2H), 2.46 (s, 3H), 2.50-2.58 (m, 2H), 2.84 (t, 2H, J=5.4 Hz), 2.94 (t, 2H, J=6.5 Hz), 3.82 (t, 3H, J=6.0 Hz), 4.20 (d, 1H, J=8.5 Hz), 4.31 (d, 1H, J=8.5 Hz), 4.35-4.41 (m, 3H), 4.97 (d, 1H, J=7.5 Hz), 5.44 (d, 1H, J=2.5 Hz), 5.69 (d, 1H, 7.0 Hz), 6.0 (dd, 1H, J=9.25 Hz, 2.25 Hz), 6.22-6.29 (m, 2H), 7.08 (d, 1H, J=9.5 Hz), 7.36-7.60 (m, 11H), 7.78 (d, 2H, J=7.5 Hz), 8.14 (d, 2H, J=7.5 Hz).

Example 43

Synthesis of prodrug I-S22-PD2: To a solution of I-S22-PD1 (38 mg, 0.0367 mmol) in acetonitrile (0.6 mL) was added succinic anhydride (5 mg, 0.044 mmol) and DMAP (cat.). The resulting mixture was stirred overnight at RT and purified by column chromatography to give 12 mg (29%) of prodrug I-S22-PD2 as an off white solid. $^1$H NMR (500 MHz, CDCl$_3$): δ 1.14 (s, 3H), 1.25 (s, 3H), 1.68 (s, 3H), 1.91 (s, 3H), 2.22 (s, 3H), 2.36-2.41 (m, 1H), 2.49 (s, 3H), 2.57-2.63 (m, 5H), 2.86-2.89 (m, 2H), 2.93 (t, 2H, J=6.5 Hz), 3.79 (d, 1H, J=7.0 Hz), 4.20-4.44 (m, 7H), 4.98 (d, 1H, J=8.0 Hz), 5.53 (d, 1H, 3.0 Hz), 5.69 (d, 1H, J=7.0 Hz), 6.02 (dd, 1H, J=9.5 Hz, J=3.0 Hz), 6.26-6.29 (m, 2H), 7.20 (d, 1H, J=9.0 Hz), 7.33-7.62 (m, 11H), 7.74 (d, 2H, J=7.5 Hz), 8.14 (d, 2H, J=7.5 Hz). MS (ES$^+$) m/z: 1134.44 [M+H]$^+$; 1156.56 [M+Na]$^+$.

Water solubility: Paclitaxel and its prodrug I-S22-PD2 (2 mg each) were suspended in 1 mL water or PBS-buffer (pH 7.4). The suspensions were sonicated for 15 min and centrifuged (13,000 g) for 10 min. The supernatant was analyzed using HPLC.

HPLC: Waters RP18 column (150×3.9 mM, X-Terra); DAD-HP Agilent (Model 1100); eluent: CH$_3$CN:H$_2$O (gradient 0-100% acetonitrile in 0-15 min). The UV-detector was set at 210 nM. The concentrations were determined by measuring the relative area of paclitaxel or I-S22-PD2. It was observed that the solubility of I-S22-PD2 was 20 times more than that of paclitaxel. (i.e., ~0.2 mg/mL).

The following double/mutual prodrugs (Examples 44-80) were synthesized by the methods depicted in Schemes 17-21, using appropriate therapeutic agents and obvious modifications:

Example 44

Synthesis of Mutual Prodrug of Desloratidine and Pseudoephedrine (I-AA-MPD1)

This mutual prodrug was synthesized as depicted in Scheme 21. The compound I-AA-MPD1 was obtained as a colorless gum. $^1$H-NMR (300 MHz, CDCl$_3$): δ 1.00 (d, 3H, J=6.9 Hz), 2.27-2.51 (m, 4H), 2.74-2.97 (m, 9H), 3.28-3.41

(m, 4H), 3.79 (bs, 2H), 4.28-4.30 (m, 4H), 4.57 (m, 1H), 7.04-7.44 (m, 9H), 8.26-8.33 (m, 2H). MS (m/z): 682 [M+H]⁺.

Example 45

Synthesis of Mutual Prodrug of Amlodipine and Lisinopril (I-AA-MPD2)

Step 1: Synthesis of Diethyl Ester of Lisinopril:
To a suspension of lisinopril (10.0 g, 22.62 mmol) in ethanol (150 mL) was added $SOCl_2$ (4.95 mL, 67.94 mmol) and refluxed for 1.5 h. An additional 1 mL of $SOCl_2$ was added to the mixture every hour for 4 h. The mixture was concentrated and azeotroped with benzene. The resulting hydrochloride was basified with saturated $NaHCO_3$ and extracted with EtOAc. Usual aqueous work-up gave 12.86 g of lisinopril diethyl ester, which was used without purification. ¹H-NMR (300 MHz, $CDCl_3$): δ 1.23-1.64 (m, 10H), 1.89-2.3 (m, 6H), 2.63-2.66 (m, 2H), 2.80 (bs, 2H), 3.19 (t, 2H, J=7.5 Hz), 3.36-3.59 (m, 6H), 4.12-4.19 (m, 4H), 4.4-4.5 (m, 1H), 7.14-7.28 (m, 5H). MS [m/z]: 462.4 [M+H]⁺.

Step 2: Synthesis of I-AA-MPD2: CDI (1.23 g, 7.64 mmol) was added to a solution of I-A1-PD2 (Example 18) (3.0 g, 5.09 mmol) in DMF (10 mL) and stirred RT for 3.5 h. A solution of lisinopril diethyl ester (2.34 g, 5.09 mmol) in DMF (5 mL) was added and stirred at 65° C. for 8 h. The reaction was quenched with brine and taken up in EtOAc. After usual aqueous work-up and chromatographic purification, 2.5 g (45%) of I-AA-MPD2 were obtained. ¹H-NMR (300 MHz, $CDCl_3$): δ 1.17 (t, 3H, J=7.5 Hz), 1.24-1.30 (m, 7H), 1.45-1.80 (m, 7H), 1.90-2.30 (m, 7H), 2.36 (s, 3H), 2.70 (bs, 2H), 2.89-2.95 (m, 4H), 3.10-3.20 (bs, 3H), 3.40-3.70 (m, 9H), 4.00-4.40 (m, 10H), 4.47-4.53 (m, 1H), 4.68-4.73 (q, 2H, J=13 Hz), 5.30 (bs, 1H), 5.39 (s, 1H), 5.65 (bs, 1H), 7.15-7.36 (m, 9H). MS (m/z): 1076 [M+H]⁺, 1098 [M+Na]⁺.

Example 46

Synthesis of Mutual Prodrug of Amlodipine and Losartan (I-AA-MPD3a)

This mutual prodrug was synthesized as described in Example 34, with obvious modifications, using the appropriate amino containing therapeutic agents. The product I-AA-MPD3a was obtained as a cream color solid. ¹H-NMR (300 MHz, $CDCl_3$): δ 0.86 (t, 3H, J=6.6 Hz), 1.16 (t, 3H, J=7.1 Hz), 1.31 (m, 2H), 1.60 (m, 2H), 2.31 (s, 3H), 2.48 (t, 2H, J=7.9 Hz), 2.80-2.92 (m, 4H), 3.40 (m, 4H), 3.56 (s, 3H), 4.01 (m, 2H), 4.32 (m, 4H), 4.68 (q, 2H, J=6.5 Hz), 5.00 (s, 2H), 5.14 (s, 2H), 5.37 (s, 1H), 6.90 (d, 1H, J=7.8 Hz), 7.02-7.22 (m, 5H), 7.33-7.43 (m, 3H), 7.50-7.60 (m, 2H). MS (m/z): 1037 [M−H]⁻.

Example 47

Synthesis of Mutual Prodrug of Celecoxib and Valdecoxib (I-AA-MPD4)

This mutual prodrug was synthesized by reacting the imidazolide intermediate of I-A3-PD1 with valdecoxib according to method described in Scheme 17 with appropriate modifications. This mutual prodrug I-AA-MPD4 was obtained as a white solid. ¹H-NMR (300 MHz, $CDCl_3$): δ 2.16 (s, 3H), 2.29 (s, 3H), 2.71 (bs, 4H), 4.14 (bs, 4H), 6.69 (s, 2H), 7.02-7.33 (m, 14H), 7.97 (d, 3H, J=9.0 Hz). MS (m/z): 900 [M−H]⁻.

Example 48

Synthesis of Double Prodrug of Valdecoxib (I-AA-MPD5)

This double prodrug was synthesized by reacting I-A3-PD1 and valdecoxib using the method B described in Scheme 13. The double prodrug I-AA-MPD5 was obtained as an off white solid. ¹H-NMR (300 MHz, $CDCl_3$): δ 2.40 (s, 6H), 2.82 (bs, 4H), 4.20 (bs, 4H), 7.20-7.35 (m, 14H), 7.97 (d, 4H, J=9.0 Hz). MS (m/z): 833 [M−H]⁻.

Example 49

Synthesis of Double Prodrug of Valdecoxib (I-AA-MPD8a)

This mutual prodrug was synthesized using succinic anhydride and valdecoxib according to method B described in Scheme 13 with appropriate modifications. This double prodrug I-AA-MPD8a was obtained as an off-white solid. ¹H-NMR (300 MHz, $CDCl_3$): δ 2.46 (s, 6H), 2.58 (s, 4H), 7.25-7.37 (m, 16H), 7.95 (d, 2H, J=9.0 Hz). MS (m/z): 709 [M−H]⁻.

Example 50

Synthesis of Double Prodrug of Valdecoxib (I-AA-MPD8b)

This mutual prodrug was synthesized using glutaric anhydride and valdecoxib according to method B described in Scheme 13 with appropriate modifications. This double prodrug I-AA-MPD8b was obtained as a colorless gum. ¹H-NMR (300 MHz, $CDCl_3$+$CD_3OD$): δ 1.68-1.74 (m, 2H), 2.15 (t, 4H, J=4.5 Hz), 2.38 (s, 6H), 7.01 (bs, 1H), 7.17-7.30 (m, 14H), 7.50 (bs, 1H), 7.88 (d, 4H, J=8.58 Hz). MS (m/z): 723 [M−H]⁻.

Example 51

Synthesis of Mutual Prodrug of Olanzapine and Fluoxetine (I-AA-MPD9)

This mutual prodrug was made according to Scheme 17 with appropriate modifications. This mutual prodrug I-AA-MPD9 was obtained as a yellow gum. ¹H-NMR (300 MHz, $CDCl_3$): δ 2.05-2.20 (m, 2H), 2.40 (s, 3H), 2.44 (s, 3H), 2.50-2.90 (m, 12H), 3.30-3.80 (m, 4H), 4.10-4.50 (m, 4H), 5.20 (bs, 1H), 6.42 (s, 1H), 6.87 (d, 2H, J=8.52 Hz), 7.04-7.36 (m, 9H), 7.42 (d, 2H, J=8.67 Hz). MS (m/z): 828 [M+H]⁺.

Example 52

Synthesis of Double Prodrug of Gabapentin (I-AA-MPD10a)

This double prodrug was synthesized as described below:
Step 1: A solution of SL-1 (3.0 g, 19.4 mmol) in DMF (5 mL) was added to a suspension of CDI (9.46 g, 5.83 mmol) in DMF (15 mL) and stirred at RT for 20 h. The mixture was concentrated and the residue purified by column chromatography. The bis-imidazolide obtained was used as such in the next step.
Step 2: A solution of the bis-imidazolide (1.0 g, 2.91 mmol) in acetonitrile (3 mL) was added to a dispersion of gabapentin (1.49 g, 8.75 mmol) in 1N $NaHCO_3$ (8 mL) and stirred at RT for 3 d. The mixture was diluted with water, acidified with 2N HCl and extracted with EtOAc. After usual aqueous work-up and chromatographic purification, 1.04 g (65%) of pure I-AA-MPD10 was obtained. $^1$H-NMR (300 MHz, CDCl$_3$): δ 1.20-1.47 (m, 20H), 2.33 (s, 4H), 2.96 (t, 4H, J=5.48 Hz), 3.23 (d, 4H, J=6.5 Hz), 4.31 (t, 4H, J=6.0 Hz), 5.55 (t, 2H, J=6.6 Hz). ESI– MS (m/z): 547 [M–H]$^-$.

Example 53

Synthesis of Double Prodrug of Gabapentin Ethyl Ester (I-AA-MPD10b)

A mixture of I-A1-PD8 (2.0 g, 5.26 mmol) and Hunig's base (2.75 mL, 15.8 mmol) in DCM (8 mL) was added to a solution of diphosgene (1.27 mL, 10.53 mmol) in DCM (4 mL) at 0° C. and stirred for 30 min. The mixture was concentrated, dissolved in DCM (10 mL) and treated with a solution of gabapentin ethyl ester hydrochloride (1.86 g, 7.88 mmol) and Hunig's base (2.74 mL, 15.77 mmol) in DCM (10 mL). The mixture was stirred for 3 h. After usual aqueous work-up, the crude material was purified by preparative HPLC to afford 2.2 g (69%) of I-AA-MPD10b as a colorless oil. $^1$H-NMR (300 MHz, CDCl$_3$): δ 1.25 (t, 6H, J=6.0 Hz), 1.35-1.67 (m, 20H), 2.33 (s, 4H), 2.91 (t, 4H, J=6.0 Hz), 3.18 (d, 4H, J=6.0 Hz), 4.12 (q, 4H, J=6.0 Hz), 4.29 (t, 4H, J=6.0 Hz) 5.42 (bs, 2H). MS: ES+ m/z 605 [M+H]$^+$, 627 [M+Na]$^+$.

Example 54

Synthesis of Mutual Prodrug of Lamotrigine and Gabapentin (I-AA-MPD11)

To a solution of I-A1-PD4 (4.5 g, 10.32 mmol) in acetonitrile (40 mL) at RT was added CDI (2.0 g, 12.38 mmol) and stirred for 3 h. To this was added a solution of gabapentin (2.12 g, 12.38 mmol) in 10 ml of 1% NaHCO$_3$ solution and the mixture was stirred at RT for 24 h. After usual aqueous work-up and chromatographic purification, 2.6 g (40%) of I-AA-MPD11 was obtained as an off white solid. $^1$H NMR (CD$_3$OD, 300 MHz): δ 1.14-1.48 (m, 10H), 2.28 (s, 2H), 2.99 (t, 2H, J=6.0 Hz), 3.06 (t, 2H, J=6.3 Hz), 3.22 (s, 2H), 4.31 (t, 2H, J=6.0 Hz), 4.46 (t, 2H, J=6.3 Hz), 7.39-7.49 (m, 2H), 7.69-7.71 (m, 1H). MS: (ES+) m/z 633.1 (M+H)$^+$, 655.1 (M+Na)$^+$.

Example 55

Synthesis of Mutual Prodrug of Gabapentin Ethyl Ester and Lamotrigine (I-AA-MPD12)

To a suspension of lamotrigine (2.70 g, 10.55 mmol) and DMAP (1.28 g, 10.55 mmol) in toluene (40 mL) at 110° C. was added a solution of the imidazolide of I-A1-PD4 (4.99 g, 10.55 mmol) THF (20 mL) and stirred overnight at 110° C. The reaction mixture was purified by column chromatography to afford 0.85 g (12%) of I-AA-MPD12 as a white solid. $^1$H NMR (CDCl$_3$, 300 MHz) δ 1.24 (t, 2H, J=7.2 Hz), 1.36-1.77 (m, 10H), 2.29 (s, 2H), 2.93-3.03 (m, 4H), 3.22 (d, 2H, J=6.6 Hz), 4.11 (q, 2H, J=7.2 Hz), 4.34 (t, 2H, J=6.6 Hz), 4.47 (t, 2H, J=6.3 Hz), 5.65 (t, 1H), 7.34-7.41 (m, 2H), 7.60-7.63 (m, 1H). MS: ES+ m/z 661 (M+H)$^+$, 682 (M+Na)$^+$.

Example 56

Synthesis of Mutual Prodrug of Gabapentin Ethyl Ester and Levetiracetam (I-AA-MPD13)

To a solution of levetiracetam (1.0 g, 5.87 mmol) in DCE (25 mL) and DCM (5 mL) at RT was added oxalyl chloride (895 mg, 7.05 mmol). The reaction mixture was refluxed for 8 h, after which it was cooled to RT and a solution of I-A1-PD8 (2.67 g, 7.05 mmol) in DCE (20 mL) was added dropwise. The resulting mixture was stirred at RT for 18 h. After usual aqueous work-up and chromatographic purification, 1.63 g (48%) of I-AA-MPD13 was obtained as a yellow oil. $^1$H NMR (CDCl$_3$, 300 MHz): δ 0.87 (t, 3H, J=7.4 Hz), 1.25 (t, 3H, J=7.1 Hz), 1.34-1.52 (m, 10H), 1.82-2.01 (m, 4H), 2.28 (s, 2H), 2.40 (t, 2H, J=7.0 Hz), 2.89-2.94 (m, 4H), 3.04-3.11 (m, 1H), 3.19 (d, 2H, J=6.6 Hz), 3.66-3.75 (m, 1H), 4.07-4.16 (m, 3H), 4.27-4.35 (m, 4H), 5.48 (t, 1H, J=6.5 Hz), 8.18 (bs, 1H). MS: (ES$^+$): m/z 576.1 [M+H]$^+$; 598.1 [M+Na]$^+$. (ES$^-$): m/z 574.2 [M–H]$^-$.

Example 57

Synthesis of Mutual Prodrug of Gabapentin Ethyl Ester and Valproic Acid (I-AA-MPD14)

This mutual prodrug was synthesized according method outlined in Scheme 18. This mutual prodrug I-AA-MPD14 was obtained as oil. MS (m/z): 592 [M+H]$^+$.

Example 58

Synthesis of Mutual Prodrug of Gabapentin Ethyl Ester and Valproic Acid (I-AA-MPD15)

This mutual prodrug was synthesized according to the method outlined in Scheme 18. The mutual prodrug I-AA-MPD15 was obtained as a yellow oil. MS (m/z): 620 [M+H]$^+$.

Example 59

Synthesis of Mutual Prodrug of Gabapentin Ethyl Ester and Valproic Acid (I-AA-MPD16)

To a suspension of valpromide (750 mg, 5.24 mmol) in DCE (15 mL) at 0-5° C. was added oxalyl chloride (0.5 mL, 6.29 mmol) and refluxed overnight. The reaction mixture was cooled to RT, treated with a solution of I-A1-PD8 (2.18 g, 5.76 mmol) in DCE (2 mL) and stirred at RT for 2 h. The reaction mixture was purified by column chromatography to afford 1.61 g (51%) of I-AA-MPD16 as a colorless oil. $^1$H NMR (CDCl$_3$, 300 MHz): δ 0.89 (t, 6H, J=7.09 Hz), 1.25 (t, 3H, J=6.96 Hz), 1.31-1.69 (m, 18H), 2.29 (s, 3H), 2.89-2.99 (m, 4H), 3.20 (d, 2H, J=6.47 Hz), 4.13 (q, 2H), 4.33 (t, 2H, J=6.71 Hz), 4.40 (t, 2H, J=5.97 Hz), 5.54 (t, 1H), 8.29 (br s, 1H). MS: ES+ m/z 549 [M+H]$^+$, 571 [M+Na]$^+$.

Example 60

Synthesis of Double Prodrug of Valproic Acid (I-AA-MPD22)

To a suspension of valpromide (3.0 g, 20.95 mmol) in DCE (30 mL) at 0-5° C. was added oxalyl chloride (1.3 mL, 15.08 mmol) and refluxed overnight. The reaction mixture was cooled to RT, a solution of SL-1 (0.808 g, 5.24 mmol) in DCE (3 mL) was added and stirred overnight. After usual work-up and chromatographic purification, 1.97 g (43%) of I-AA-MPD22 were obtained as a white solid. $^1$H NMR (CDCl$_3$, 300 MHz): δ 0.89 (t, 12H, J=7.18 Hz), 1.28-1.66 (m, 16H), 2.94-2.95 (m, 2H), 3.02 (t, 6H, J=6.51 Hz), 4.42 (t, 4H, J=6.47 Hz). MS: m/z 493.2 [M+H]$^+$, 510.0 [M+NH$_4$]$^+$, 515.10 [M+Na]$^+$.

Example 61

Synthesis of Mutual Prodrug of Gabapentin Ethyl Ester and Valproic Acid (I-AA-MPD27)

Step 1: To a solution of I-A1-PD8 (4.0 g, 10.54 mmol) in THF (25 mL) was added CDI (2.22 g, 13.7 mmol) and stirred at RT for 90 min. To this was added t-butyl carbazate (1.39 g, 10.54 mmol) and DMAP (1.288 g, 10.54 mmol), and stirred overnight at RT. After usual aqueous work-up and chromatographic purification, 4.0 g (91%) of the intermediate boc-hydrazide was obtained as a colorless gummy material. $^1$H NMR (CDCl$_3$, 300 MHz): δ 1.25 (t, 3H, J=7.1 Hz), 1.43 (s, 9H), 1.31-1.74 (m, 10H), 2.30 (s, 2H), 2.90-3.01 (m, 4H), 3.20 (d, 2H, J=6.6 Hz), 4.17 (q, 2H, J=7.1 Hz), 4.32 (t, 2H, J=6.5 Hz), 4.39 (t, 2H, J=6.5 Hz), 5.42 (br s, 1H), 6.04 (br s, 1H), 6.98 (br s, 1H).

Step 2: To a solution of the above boc-hydrazide (4.0 g, 7.44 mmol) in DCM (20 mL) was added 50% TFA/DCM (10 mL) and stirred at RT for 1 h. DCM was removed under vacuum, the resulting residue triturated with diethyl ether (2×20 mL) and dried to give a colorless oil, which was dissolved in THF (20 mL). To the above solution at 0-5° C. was added TEA (2.1 mL, 14.88 mmol), valproic acid (1.18 g, 8.184 mmol), DCC (2.3 g, 11.16 mmol) and DMAP (0.909 g, 7.44 mmol) and the mixture was stirred overnight at RT. The mixture was filtered, concentrated and purified by column chromatography to afford 2.59 g (51%) of I-AA-MPD27 as a colorless gummy material. $^1$H NMR (CDCl$_3$, 300 MHz): δ 0.85 (t, 6H, J=7.2 Hz), 1.3 (t, 6H, J=7.11 Hz), 1.21-1.80 (m, 26H), 2.2-2.3 (m, 1H), 2.35 (s, 2H), 2.81-2.94 (m, 4H), 3.21 (d, 2H, J=6.6 Hz), 3.65-3.68 (m, 1H), 4.19 (q, 2H, J=7.11 Hz), 4.36 (t, 2H, J=6.51 Hz), 4.39 (t, 2H, J=6.51 Hz), 5.51 (t, 1H), 8.17 (s, 1H). MS: m/z 712 [M+Na]$^+$, 728 [M+K]$^+$, 688 [M–H]$^-$.

Example 62

Synthesis of Mutual Prodrug of Valproic Acid and Nicotinic Acid (I-CC-MPD.1)

Step 1: To a solution of nicotinyl chloride hydrochloride (3.16 g, 17.76 mmol) and LI-2c (3 g, 11.84 mmol) in THF (50 mL) was added TEA (8.3 mL, 59.2 mmol) and stirred overnight at RT. After usual aqueous work-up and chromatographic purification, 4.14 g (97%) of LI-2c-nicotinate ester was obtained as a colorless oil. $^1$H NMR (CDCl$_3$, 300 MHz): δ 1.43 (s, 9H), 2.82 (t, 2H, J=6.31 Hz), 3.42-3.48 (q, 2H), 4.62 (t, 2H, J=6.59 Hz), 7.29-7.33 (m, 1H), 8.30 (d, 1H, J=7.95 Hz), 8.78 (dd, 1H, J=4.86, 1.72 Hz), 9.23 (d, 1H, J=2.13 Hz). MS: m/z 358 [M+H]$^+$, 381 [M+Na]$^+$, 739 [2M+Na]$^+$.

Step 2: To a solution of LI-2c-nicotinate ester (0.92 g, 2.50 mmol) in DCM (5 mL) was added 50% TFA/DCM (5 mL) and stirred for 1 h. Reaction mixture was concentrated and the residual TFA salt was used as such in Step 3.

Step 3: To a solution of valproic acid (0.37 g, 2.56 mmol) in THF (5 mL) was added CDI (0.5 g, 3.08 mmol) and stirred for 2 h. This was treated with a solution of the above TFA salt, TEA (0.7 mL, 5.13 mmol) and DMAP (50 mg, 0.41 mmol) in THF (10 mL) and the mixture was stirred overnight at RT. After usual aqueous work-up and chromatographic purification, 0.7 g (71%) of I-CC-MPD1 was obtained as a white solid. $^1$H NMR (CDCl$_3$, 500 MHz): δ 0.88 (t, 6H, J=7 Hz), 1.25-1.59 (m, 8H), 2.06-2.08 (m, 1H), 2.86 (t, 2H, J=6 Hz), 3.05 (t, 2H, J=7 Hz), 3.58-3.61 (q, 2H, J=9.0 Hz), 4.63 (t, 2H, J=6.5 Hz), 7.40-7.42 (m, 1H), 8.30 (dt, 1H, J=8.0, 2.0 Hz), 8.79 (dd, 1H, J=5.0, 2.0 Hz), 9.23 (d, 1H, J=0.5 Hz). MS: m/z 385 [M+H]$^+$, 407 [M+Na]$^+$, 423 [M+K]$^+$.

Example 63

Synthesis of Mutual Prodrug of Valproic Acid and Nicotinic Acid (I-CC-MPD2)

This mutual prodrug was synthesized as described in Example 62, with obvious modifications. 0.612 g (41%) of I-CC-MPD2 was obtained as a white solid. $^1$H NMR (CDCl$_3$, 300 MHz): δ 0.89 (t, 6H, J=7.23 Hz), 1.24-1.62 (m, 8H), 2.34-2.42 (m, 1H), 2.92 (t, 2H, J=6.83 Hz), 2.98 (t, 2H, J=6.04 Hz), 3.78-3.84 (q, 2H), 4.37 (t, 2H, J=6.79 Hz), 7.36-7.41 (m, 1H), 8.15 (d, 1H, J=7.92 Hz), 8.73 (d, 1H, J=4.78 Hz), 9.02 (s, 1H). MS: m/z 385 [M+H]$^+$, 419 [M+HCl]$^+$, 383 [M–H]$^-$.

Example 64

Synthesis of Mutual Prodrug of Zidovudine and Lamivudine (I-HH-MPD1)

Step 1: Synthesis of Intermediate I-S17-PD11:

4-Nitrophenyl chloroformate (0.27 g, 1.34 mmol) was added to a solution of the I-H1-PD5 (0.4 g, 0.89 mmol) and pyridine (76 μL, 1 mmol) in DCM (10 mL) and stirred at RT for 15 h. The mixture was concentrated and the residue purified by column chromatography to give 0.29 g (53%) of I-S17-PD11. $^1$H-NMR (300 MHz, CDCl$_3$): δ 1.93 (s, 3H), 2.45 (m, 2H), 2.97-3.06 (m, 4H), 4.05 (m, 1H), 4.41 (m, 1H), 4.40-4.49 (m, 4H), 4.54 (t, 2H, J=6.5 Hz), 6.17 (t, 1H, J=6.0 Hz), 7.33 (s, 1H), 7.39 (d, 2H, J=4.8 Hz), 8.28 (d, 2H, J=4.8 Hz) and 8.50 (s, 1H). MS (m/z): 635 [M+Na]$^+$.

Step 2: Synthesis of I-HH-MPD1: Lamivudine (45 mg, 0.196 mmol) and DMAP (48 mg, 0.39 mmol) were added to a solution of I-S17-PD11 (80 mg, 0.13 mmol) in DMF (1.5 mL) and stirred at RT for 30 min. The mixture was concentrated and purified by column chromatography to give 40 mg (43%) of product I-HH-MPD1. $^1$H-NMR (300 MHz, CDCl$_3$): δ 1.90 (s, 3H), 2.45 (t, 2H, J=6.1 Hz), 3.05 (t, 4H, J=6.2 Hz), 3.20 (m, 1H), 3.53 (m, 1H), 4.08 (m, 1H), 4.30-4.80 (m, 8H), 5.45 (t, 1H, J=3.0 Hz), 5.90 (d, 1H, J=7.5 Hz), 6.17 (t, 1H), 6.30 (t, 1H), 7.55 (s, 1H) and 7.90 (d, 1H, J=7.50 Hz). MS (m/z): 725 [M+Na]$^+$.

Example 65

Synthesis of Mutual Prodrug of Zidovudine and Lamivudine (I-HH-MPD2b)

This mutual prodrug was synthesized according to the method outlined in Scheme 18. The mutual prodrug I-HH-MPD2b was obtained as a white solid. $^1$H-NMR (300 MHz, CDCl$_3$): δ 1.97 (s, 3H), 2.42 (m, 2H), 2.90-2.94 (m, 16H), 3.06 (m, 1H), 3.40-3.44 (m, 8H), 3.50-3.56 (m, 1H), 3.71-3.73 (m, 1H), 4.95 (m, 1H), 4.27-4.30 (m, 4H), 4.37-4.49 (m, 4 h), 5.32 (t, 1H, J=5.1 Hz), 5.83 (d, 1H, J=6.6 Hz), 6.07 (m, 1H), 6.33 (bs, 1H), 7.20-7.25 (m, 1H), 7.74 (m, 1H). MS (m/z): 954 [M+Na]$^+$.

Example 66

Synthesis of Mutual Prodrug of Cetirizine and Pseudoephedrine (I-CA-MPD1)

Step 1: Synthesis of Intermediate I-S17-PD11:

This intermediate was prepared by reacting I-C1-PD10 with p-nitrophenyl chloroformate by a procedure similar to that described in Example 64. The desired intermediate I-S17-PD11 was obtained as a gum. $^1$H-NMR (300 MHz, CDCl$_3$): δ 2.49-2.71 (m, 10H), 2.95 (t, 2H, J=6.6 Hz), 3.01 (t, 2H, J=6.5 Hz), 3.73 (bs, 2H), 4.13 (s, 2H), 4.22 (s, 1H), 4.41 (t, 2H, J=6.6 Hz), 4.53 (t, 2H, J=6.6 Hz), 7.18-7.40 (m, 11H), 8.28 (d, 2H, J=7.1 Hz).

Step 2: The mutual prodrug I-CA-MPD1 was synthesized by reacting intermediate I-S17-PD11 with pseudoephidrine by a procedure similar to that described in Example 64, Step 2. The desired mutual prodrug I-CA-MPD1 was obtained as a colorless gummy material. $^1$H-NMR (300 MHz, CDCl$_3$): δ 0.99-1.09 (d, 3H, J=6.6 Hz), 2.45 (bs, 4H), 2.68 (bs, 6H), 2.90 (s, 3H), 2.91-2.94 (m, 4H), 3.71 (bs, 3H), 4.11 (s, 2H), 4.18 (s, 1H), 4.26-4.41 (m, 4H), 4.56 (m, 2H), 7.17-7.35 (m, 12H). MS (m/z): 716 [M+H]$^+$.

Example 67

Synthesis of Mutual Prodrug of Gabapentin Ethyl Ester and Naproxen (I-CA-MPD5)

This mutual prodrug was synthesized by reacting I-A1-PD8 and Naproxen using Scheme 11, Method B. This mutual prodrug was obtained as colorless oil. $^1$H-NMR (300 MHz, CDCl$_3$): δ 1.25 (t, 3H, J=7.1 Hz), 1.30-1.55 (m, 10H), 1.57 (d, 3H, J=7.1 Hz), 2.27 (s, 2H), 2.84 (q, 4H, J=6.4 Hz), 3.18 (d, 2H, J=6.7 Hz), 3.80-3.88 (m, 1H), 3.91 (s, 3H), 4.12 (q, 2H, J=7.1 Hz), 4.20-4.40 (m, 4H), 5.35 (bt, 1H), 7.05-7.20 (m, 2H), 7.39 (dd, 1H, J=1.8 Hz, 8.4 Hz), 7.60-7.73 (m, 3H). MS (m/z): 592 [M+H]$^+$, 614 [M+Na]$^+$.

Example 68

Synthesis of Mutual Prodrug of Valproic Acid and Nicotinic Acid (I-CA-MPD14)

This mutual prodrug was synthesized using valpromide and nicotinyl chloride hydrochloride, according to the methods described in Scheme 13 and Scheme 17, with obvious modifications. 1.0 g of the mutual prodrug I-CA-MPD14 was obtained as a yellow oil. $^1$H NMR (CD$_3$OD, 300 MHz): δ 0.87 (t, 6H, J=6 Hz), 1.26-1.75 (m, 9H), 2.83 (s, 1H), 2.95-3.0 (m, 4H), 3.81 (t, 2H, J=6 Hz), 4.44 (t, 2H, J=6 Hz), 7.0 (s, 1H), 7.4 (bs, 1H), 7.42 (m, 1H), 8.20 (d, 1H), 8.65-8.74 (bs, 2H), 9.0 (s, 1H). MS: ES$^+$ m/z 428.1 [M+H]$^+$, 450.1 [M+Na]$^+$.

Example 69

Synthesis of Mutual Prodrug of Valproic Acid and Nicotinic Acid (I-CA-MPD15)

To a solution of I-C1-PD13 (1.5 g, 4.63 mmol) and nicotinyl chloride hydrochloride (0.99 g, 5.56 mmol) in THF (25 mL) was added TEA (2 mL, 13.89 mmol) at 0° C. and stirred for 20 h at RT. After usual aqueous work-up and chromatographic purification, 1.0 g (83%) of I-CA-MPD15 was obtained as a yellow viscous liquid. $^1$H NMR (CD$_3$OD, 500 MHz): δ 0.89 (t, 6H, J=5.0 Hz), 1.29-1.33 (m, 8H), 1.64 (bs, 2H), 3 (t, 2H, J=5.0 Hz), 3.07 (t, 2H, J=5.0 Hz), 4.42 (t, 2H, J=5.0 Hz), 4.63 (t, 2H, J=5.0 Hz), 7.41-7.43 (m, 1H), 8.31 (bs, 1H), 8.78 (bs, 1H), 9.26 (s, 1H). MS: ES$^+$ m/z 429 [M+H]$^+$, 451 [M+Na]$^+$, 467 [M+K]$^+$.

Example 70

Synthesis of Mutual Prodrug of Gabapentin Ethyl Ester and Nicotinic Acid (I-CA-MPD18)

To a solution of BOC deprotected I-S12-PD2 (synthesized as described in Scheme 12, Method C, and then deprotected using a known general BOC deprotection method) (3.76 g, 7.64 mmol) in THF (30 mL) was added nicotinyl chloride hydrochloride (1.5 g, 8.40 mmol), followed by TEA (4.26 mL, 30.56 mmol) and stirred overnight at RT. After usual aqueous work-up and chromatographic purification, 0.87 g (23%) of I-CA-MPD18 was obtained as a yellow oil. $^1$H NMR (CDCl$_3$, 300 MHz): δ 1.24 (t, 3H, J=6.0 Hz), 1.27-1.47 (m, 10H), 2.27 (s, 2H), 2.90-3.17 (m, 4H), 3.16 (d, 2H, J=6.0 Hz), 3.79 (q, 2H, J=6.0 Hz), 4.10 (q, 2H, J=6.0 Hz), 4.36 (t, 2H, J=6.0 Hz), 5.56 (bt, 1H, J=6.0 Hz), 7.32-7.38 (m, 1H), 8.17 (d, 1H, J=9.0 Hz), 8.71 (d, 1H, J=6.0 Hz), 9.07 (s, 1H). MS: (ES)$^+$ m/z 484 (M+H)$^+$, 506 (M+Na)$^+$; (ES)$^-$ m/z 482 (M−H)$^+$.

Example 71

Synthesis of Mutual Prodrug of Levetiracetam and Valproic Acid (I-CA-MPD19)

To a solution of levetiracetam (1.0 g, 5.87 mmol) in DCE (20 mL) and DCM (4 mL) was added oxalyl chloride (894 mg, 7.05 mmol) and heated at 80° C. for 7 h. The reaction mixture was cooled to RT, a solution of I-C1-PD11 (1.97 g, 7.05 mmol) in DCE (10 mL) was added and stirred at RT for 18 h. After usual aqueous work-up and chromatographic purification, 1.73 g (61%) of I-CA-MPD19 was obtained as a yellow oil. $^1$H NMR (CDCl$_3$, 300 MHz): δ 0.85-0.91 (m, 9H), 1.24-1.62 (m, 8H), 1.80-2.05 (m, 4H), 2.34-2.44 (m, 3H), 2.91 (t, 4H, J=6.0 Hz), 3.03-3.12 (m, 1H), 4.06-4.09 (m, 1H), 4.31-4.36 (m, 4H), 8.32 (bs, 1H). MS: (ES$^+$) m/z 477.1 [M+H]$^+$, 498.9 [M+Na]$^+$ (ES)$^-$ m/z 475.0 [M−H]$^-$.

Example 72

Synthesis of Mutual Prodrug of Gabapentin Ethyl Ester and Valproic Acid (I-CA-MPD21)

This mutual prodrug was synthesized by following a route depicted in Scheme 19, with obvious modifications. The mutual prodrug I-CA-MPD21 was obtained as a colorless oil. $^1$H-NMR (CDCl$_3$, 300 MHz): δ 0.81 (t, 6H, J=7.19 Hz), 1.15-1.60 (m, 21H), 2.20 (s, 2H), 2.25-2.35 (m, 1H), 2.84 (t, 4H, J=6.6 Hz), 3.11 (d, 2H, J=6.7 Hz), 4.05 (q, 2H, J=7.16 Hz and 17.3 Hz), 4.15-4.25 (m, 4H), 5.43 (bt, 1H). MS (m/z): 506 [M+H]$^+$, 528 [M+Na]$^+$.

Example 73

Synthesis of Mutual Prodrug of Gabapentin Ethyl Ester and Nicotinic Acid (I-CA-MPD22)

To a suspension of nicotinyl chloride hydrochloride (0.35 g, 1.97 mmol) in THF (3 mL) at 0° C. was added TEA (0.82 mL, 5.91 mmol). After 5 min, a solution of I-A1-PD8 (0.5 g, 1.31 mmol) and TEA (0.27 mL, 1.97 mmol) in THF (4 mL) was added and stirred overnight at RT. The mixture was purified by column chromatography to afford 0.573 g (90%) of I-CA-MPD22 as a yellow oil. $^1$H NMR (CDCl$_3$, 300 MHz): δ 1.24 (t, 3H, J=6.0 Hz), 1.27-1.47 (m, 10H), 2.27 (s, 2H), 2.94 (t, 2H, J=6.0 Hz), 3.07 (t, 2H, J=6.0 Hz), 3.19 (d, 2H, J=6.0 Hz), 4.12 (q, 2H, J=6.0 Hz), 4.32 (t, 2H, J=6.0 Hz), 4.62 (t, 2H, J=6.0 Hz), 5.29 (bs, 1H), 7.36-7.42 (m, 1H), 8.30 (t, 1H, J=3.0 Hz), 8.78 (dd, 1H, J=1.69 Hz), 9.24 (s, 1H). MS: (ES)$^+$ m/z 485 (M+H)$^+$, 507 (M+Na)$^+$.

Example 74

Synthesis of Mutual Prodrug of Lamotrigine and Valproic Acid (I-CA-MPD23)

To a suspension of lamotrigine (0.455 g, 1.78 mmol) and DMAP (0.217 g, 1.78 mmol) in toluene (10 mL) at 110° C. was added a solution of the imidazolide of I-C1-PD11 (0.665 g, 1.78 mmol) in THF (5 mL). The reaction was stirred at 110° C. overnight and purified by column chromatography to afford 0.20 g (20%) of I-CA-MPD23 as a white solid. $^1$H NMR (300 MHz, CDCl$_3$): δ 0.86-0.90 (m, 6H), 1.20-1.44 (m, 6H), 1.53-1.62 (m, 2H), 2.36-2.39 (m, 1H), 2.90-3.0 (m, 4H), 4.34 (t, 2H, J=6.3 Hz), 4.46 (t, 2H J=6.6 Hz), 7.36-7.38 (m, 2H), 7.60-7.63 (m, 1H). MS: (ES+) m/z 562 (M+H)$^+$, 585 (M+Na)$^+$.

Example 75

Synthesis of Mutual Prodrug of Lamotrigine and Nicotinic Acid (I-CA-MPD24)

A solution of I-A1-PD4 (0.5 g, 1.14 mmol) and TEA (0.5 mL, 2.87 mmol) in THF (5 mL) was added to a suspension of nicotinyl chloride (0.305 g, 1.71 mmol) and 0.5 mL TEA in THF (5 mL). The mixture was stirred at RT for 24 h. After usual aqueous work-up and chromatographic purification, 0.15 g (14%) of I-CA-MPD24 were obtained as a white solid. $^1$H NMR (CDCl$_3$, 500 MHz): δ 3.06 (t, 2H, J=6.5 Hz), 3.10 (t, 2H, J=6.5 Hz), 4.49 (t, 2H, J=6.5 Hz), 4.65 (t, 2H, J=6.5 Hz), 7.38-7.43 (m, 3H), 7.60-7.62 (m, 1H), 8.33-8.36 (m, 1H), 8.81 (m, 1H), 9.35 (bs, 1H). MS: (ES+) m/z 540.9 (M+H)$^+$.

Example 76

Synthesis of Mutual Prodrug of Lamotrigine and Nicotinic Acid (I-CA-MPD25)

This mutual prodrug was synthesized using lamotrigine and nicotinyl chloride hydrochloride, according to the methods outlined in Scheme 12 and Scheme 17. 0.8 g (44%) of I-CA-MPD25.HCl were obtained as an off white solid. $^1$H NMR (D$_2$O, 500 MHz): δ 2.93 (t, 2H, J=6.5 Hz), 3.10 (t, 2H, J=6.0 Hz), 3.69 (t, 2H, J=6.5 Hz), 4.49 (m, 2H), 7.37-7.43 (m, 3H), 7.69-7.71 (m, 1H), 8.05-8.07 (m, 1H), 8.78-8.79 (m, 1H), 9.30 (bs, 1H). MS: (ES+) m/z 539.9 (M+H)$^+$, 561.8 (M+Na)$^+$.

Example 77

Synthesis of Mutual Prodrug of Metronidazole and Norfloxacin (I-AH-MPD1)

Step 1: Synthesis of Imidazolide of I-H1-PD1:
CDI (319 mg, 1.97 mmol) was added to a solution of I-H1-PD1 (577 mg, 1.64 mmol) in DMF (8 mL) and stirred at RT for 4 h. The mixture was concentrated and the residue purified by column chromatography to give 395 mg (54%) of the imidazolide of I-H1-PD1. $^1$H-NMR (300 MHz, CDCl$_3$): δ 2.50 (s, 3H), 2.92 (t, 2H, J=6.0 Hz), 3.00-3.10 (m, 2H), 4.36 (t, 2H, J=3.0 Hz), 4.47-4.51 (m, 2H), 4.57-4.70 (m, 4H), 7.07 (s, 1H), 7.43 (s, 1H), 7.95 (s, 1H), 8.15 (s, 1H). MS (m/z): 446 [M+H]$^+$.

Step 2: Synthesis of I-AH-MPD1: A solution of the imidazolide of I-H1-PD1 (100 mg, 0.224 mmol) in DMF (1 mL) was added to a suspension of norfloxacin (86 mg, 0.269 mmol) in DMF (2 mL) and stirred at RT for 60 h. The mixture was concentrated and the residue purified by column chromatography to give 35 mg (22%) of I-AH-MPD1. $^1$H-NMR (300 MHz, CDCl$_3$): δ 1.59 (t, 3H, J=7.5 Hz), 2.53 (s, 3H), 2.86-2.97 (m, 4H), 3.27-3.30 (m, 4H), 3.72 (t, 4H, J=4.5 Hz), 4.32-4.40 (m, 6H), 4.48-4.52 (m, 2H), 4.59-4.63 (m, 2H), 6.85 (d, 1H, J=6.0 Hz), 7.96 (s, 1H), 8.09 (d, 1H, J=12.0 Hz), 8.68 (s, 1H). MS (m/z): 697 [M+H]$^+$.

The following mutual prodrugs (Examples 78-80) were obtained according to procedures similar to those described in Example 77, with the substitution of the appropriate pairs of amino-containing and hydroxyl-containing therapeutic agents:

Example 78

Synthesis of Mutual Prodrug of Metronidazole and Norfloxacin (I-AH-MPD3b)

The mutual prodrug I-AH-MPD3b was obtained as a yellow solid. $^1$H-NMR (300 MHz, CDCl$_3$): δ 1.59 (t, 3H, J=7.1 Hz), 2.49 (s, 3H), 2.82-2.98 (m, 10H), 3.30 (t, 4H, J=4.5 Hz), 3.39 (bs, 4H), 3.72 (t, 4H, J=4.8 Hz), 4.38 (dt, 8H, J=26.2, 6.4 Hz), 4.61 (t, 2H, J=4.8 Hz), 6.86 (d, 1H, J=6.4 Hz), 7.95 (s, 1H), 8.07 (bd, 1H, J=12.8 Hz), 8.67 (s, 1H), 14.9 (s, 1H). MS (m/z): 811.26 [M+H]$^+$.

Example 79

Synthesis of Mutual Prodrug of Gabapentin and Tramadol (I-AH-MPD7)

The mutual prodrug was synthesized according to the method in Scheme 15 with obvious modifications. The mutual prodrug I-AH-MPD7 was obtained as a colorless gummy material. $^1$H-NMR (300 MHz, CDCl$_3$): δ 1.25 (t, 3H, J=7.1 Hz), 1.32-2.45 (m, 30H), 2.91-2.99 (m, 4H), 3.16 (t, 2H, J=7.3 Hz), 3.80 (s, 3H), 4.08-4.15 (q, 2H, J=7.1 Hz), 4.28-4.40 (m, 4H), 5.4 (t, 1H), 6.74-6.81 (m, 3H), 7.23-7.29 (t, 1H, J=8 Hz). MS (m/z): 669.30 [M+H]$^+$.

Example 80

Synthesis of Mutual Prodrug of Venlafaxine and Paroxetine (I-AH-MPD8)

The mutual prodrug was synthesized according to the method outlined in Scheme 15 with obvious modifications. The mutual prodrug I-AH-MPD8 was obtained as a white sticky solid. $^1$H-NMR was consistent with the expected structure. MS: m/z 812 [M]$^+$.

Example 81

Synthesis of NO-Releasing Prodrug of Valproic Acid (I-C1-NOPD1)

This prodrug was synthesized as shown in Scheme 11, Method B using as reagents valproic acid (725 mg, 5.03 mmol), LI-2b (1 g, 5.03 mmol), TEA (611 mg, 6.04 mmol), DCC (1.25 g, 6.04 mmol) and DMAP (100 mg). Yield: 832 mg (51%). $^1$H-NMR (300 MHz, CDCl$_3$): δ 0.89 (t, 6H, J=7.09 Hz), 1.22-1.77 (m, 8H), 2.36-2.40 (m, 1H), 2.93-3.00 (m, 4H), 4.34 (t, 2H, J=6.8 Hz), 4.70 (t, 2H, J=6.35 Hz). MS (CI)$^+$ m/z: 326 [M+H]$^+$.

Example 82

Synthesis of NO-Releasing Prodrug of Valproic Acid (I-C1-NOPD3a)

This prodrug was prepared as shown in Scheme 13, Method A. Thus, to a stirred mixture of valproyl isocyanate, which was freshly prepared from valpromide (0.7 g, 4.90 mmol [valpromide was synthesized from valproic acid by using known methods as shown in Scheme 11, Method I) using a known method (see *J. Org. Chem.*, 1962, 27, 3742) in DCM (20 mL) at RT was added a solution of LI-2b (0.976 g, 4.90 mmol) in DCM (5 mL) drop-wise and stirred at RT for 2 h. The mixture was concentrated and the residue, after usual aqueous work-up and chromatographic purification, afforded 0.6 g (33%) of prodrug I-C1-NOPD3a. $^1$H-NMR data is consistent with the expected structure. MS: [ES]$^+$ m/z 391 [M+Na]$^+$, 407.2 [M+K]$^+$; [EI]$^+$ m/z 368 [M+H]$^+$.

Example 83

Synthesis of NO-Releasing Prodrug of Aspirin (I-C1-NOPD4)

This prodrug was synthesized as shown in Scheme 11, Method D. Thus, to a solution of aspirin (3.0 g, 16.65 mmol) in THF (30 mL) at 0° C. was added oxalyl chloride (1.86 mL, 21.64 mmol) and heated at 70° C. for 2 h. The mixture was concentrated, the residue was dissolved in THF (30 mL) and treated with a solution of LI-2a (3.61 g, 16.65 mmol), TEA (3.48 mL, 24.97 mmol) and DMAP (361 mg) in THF (20 mL). The resulting mixture was stirred at RT for 2 h and filtered through celite. The filtrate was concentrated and the residue purified by column chromatography to afford 3.06 g (48%) of the bromide S11-I1. $^1$H-NMR (300 MHz, CDCl$_3$): δ 2.35 (s, 3H), 3.01-3.12 (m, 4H), 3.61 (t, 2H, J=6.5 Hz), 4.53 (t, 2H, J=6.0 Hz), 7.11 (dd, 1H, J=8 Hz, 1 Hz), 7.32 (t, 1H, J=7.6 Hz), 7.57 (t, 1H, J=7.6 Hz), 8.03 (dd, 1H, J=7.8 Hz, 1.6 Hz). MS (ES$^+$) m/z: 403.92 (M+Na)$^+$.

To a solution of S11-I1 (2.0 g, 5.27 mmol) in acetonitrile (20 mL) at 0° C. was added AgNO$_3$ (1.07 g, 6.32 mmol) in the dark. The mixture was stirred at RT for 1.5 h, filtered through celite and concentrated. The residue, after usual aqueous work-up and chromatographic purification, afforded 0.965 g (50%) pure I-C1-NOPD4. $^1$H-NMR (300 MHz, CDCl$_3$): δ 2.36 (s, 3H), 2.98 (t, 2H, J=6.8 Hz), 3.05 (t, 2H, J=6.4 Hz), 4.54 (t, 2H, J=6.4 Hz), 4.70 (t, 2H, J=6.8 Hz), 7.12 (d, 1H, J=8 Hz), 7.33 (t, 1H, J=7.6 Hz), 7.59 (t, 1H, J=7.5 Hz), 8.03 (dd, 1H, J=7.8 Hz, 1 Hz). MS (ES)$^+$ m/z: 379.11 (M+NH$_4$)$^+$, 383.98 (M+Na)$^+$.

Example 84

Synthesis of NO-Releasing Prodrug of Aspirin (I-C1-NOPD5a)

As shown in Scheme 11, Method H, this prodrug was synthesized in three steps:

Step 1: To a suspension of aspirin (1 g, 5.55 mmol) in benzene (15 mL) and DMF (1 drop) at 0-5° C. was added a solution of oxalyl chloride (0.6 mL, 6.66 mmol) in benzene (5 mL) and stirred at 85° C. for 2 h. The reaction mixture was concentrated, and the crude acid chloride was used immediately in the next step.

Step 2: To a solution of the above acid chloride in benzene (30 mL) was added silver cyanate (998 mg, 6.66 mmol) and refluxed in the dark for 1 h. The mixture, containing 2-acetoxybenzoyl isocyanate, was cooled to RT and used in the next step.

Step 3: To the above mixture was added a solution of LI-2b (1.33 g, 6.66 mmol) in benzene (5 mL) and stirred at RT for 1 h. The mixture was filtered through celite and concentrated, and the residue was purified by column chromatography to afford 1.2 g (54%) of pure I-C1-NOPD5a. $^1$H-NMR data is consistent with the expected structure. MS (ES$^+$) m/z: 404.98 [M+H]$^+$, 426.94 [M+Na]$^+$, 442.97 [M+K]$^+$, (ES$^-$) m/z: 403.01 [M–H]$^-$.

Example 85

Synthesis of Sodium Salt of NO-Releasing Prodrug of Aspirin (I-C1-NOPD5b)

To a suspension of 60% sodium hydride (45 mg, 1.3 mmol) in THF (0.5 mL) was added solution of I-C1-NOPD5a (500 mg, 1.24 mmol) in THF (1.5 mL). After stirring for 5 min, THF was removed under vacuum, the residue was washed with dry Et$_2$O (4×3 mL) to remove unreacted starting material and dried in vacuum to afford 410 mg (78%) of I-C1-NOPD5b as an off-white solid. $^1$H NMR (D$_2$O, 500 MHz): δ 2.28 (s, 3H), 2.93-2.97 (m, 4H), 4.33 (t, 2H, J=6.0 Hz), 4.68 (t, 2H, J=7.2 Hz), 7.07 (d, 1H, J=8.0 Hz), 7.26 (t, 1H, J=7.5 Hz), 7.41 (t, 1H, J=9.0 Hz), 7.57 (d, 1H, J=7.5 Hz). MS: m/z 427.0 [M+H]$^+$, 449.0 [M+Na]$^+$.

Example 86

Synthesis of NO-Releasing Prodrug of Aspirin (I-C1-NOPD6)

This prodrug was synthesized as shown in Scheme 11, Method E. Thus, to a solution of aspirin (1.20 g, 6.70 mmol) in DCM (15 mL) at 0° C. was added oxalyl chloride (0.74 mL, 8.65 mmol) and stirred at RT for 1.5 h. The mixture was concentrated and the residual acid chloride was treated with LI-5.TFA (6.70 mmol) in DCM (14 mL), followed by drop-wise addition of TEA (3.73 mL, 26.81 mmol) at 0° C. The mixture was stirred at RT for 4 h and concentrated. The residue, after usual aqueous work-up and chromatographic purification, gave 0.822 g (34%) of I-C1-NOPD6. $^1$H-NMR (300 MHz, CDCl$_3$): δ 2.35 (s, 3H), 2.92 (t, 2H, J=6.11 Hz), 2.98 (t, 2H, J=6.0 Hz), 3.76 (q, 2H, J=6.0 Hz), 4.71 (t, 2H, J=6.0 Hz), 6.70 (bs, 1H), 7.10 (d, 1H, J=9.0 Hz), 7.31-7.33 (m, 1H), 7.48-7.50 (m, 1H), 7.78 (d, 1H, J=6.0 Hz). MS (EI)$^+$ m/z: 361 (M+H)$^+$.

Example 87

Synthesis of NO-Releasing Prodrug of Nicotinic Acid (I-C1-NOPD7)

This prodrug was synthesized as shown in Scheme 11, Method C. Thus, to a suspension of nicotinyl chloride hydrochloride (2.68 g, 15.07 mmol) in THF (10 mL) at 0° C. was added a solution of LI-2b (2.0 g, 10.05 mmol) and TEA (5.6 mL, 40.2 mmol) in THF (7 mL) and stirred at RT for 15 h. The mixture was filtered, concentrated and the residue purified by column chromatography to afford 2.23 g (73%) of pure I-C1-NOPD7. $^1$H-NMR (300 MHz, CDCl$_3$): δ 3.01 (t, 2H, J=4.75 Hz), 3.09 (t, 2H, J=6.5 Hz), 4.63 (t, 2H, J=5.25 Hz), 4.70 (t, 2H, J=4.75 Hz), 7.39-7.42 (m, 1H), 8.29-8.31 (dt, 1H, J=8 Hz, 2 Hz), 8.78-8.80 (dd, 1H, J=2 Hz), 9.23 (d, 1H, J=2 Hz). MS (ES)$^+$ m/z: 305 (M+H)$^+$.

Example 88

Synthesis of NO-Releasing Prodrug of Nicotinamide (I-C1-NOPD8a)

This prodrug was synthesized from nicotinamide (1 g, 8.18 mmol) according to the procedure described in Example 77 (see Scheme 11, Method I or Scheme 13, Method A). After usual workup, the crude product was purified by column chromatography to afford 0.1 g (3.5%) of prodrug I-C1-NOPD8a. $^1$H-NMR (300 MHz, CDCl$_3$): δ 2.97-3.0 (m, 4H), 4.51 (t, 2H, J=6.3 Hz), 4.73 (t, 2H, J=6.7 Hz), 7.38-7.48 (m, 1H), 8.16-8.22 (m, 1H), 8.71-8.79 (m, 2H), 9.04 (s, 1H). MS [ES]$^+$ m/z: 348 [M+H]$^+$, 370 [M+Na]$^+$.

Example 89

Synthesis of NO-Releasing Prodrug of Nicotinic Acid (I-C1-NOPD9)

This prodrug was synthesized as shown in Scheme 11, Method F. Thus, TEA (6.92 mL, 50.55 mmol) was added to a suspension of nicotinyl chloride hydrochloride (3.0 g, 16.85 mmol) and cysteamine hydrochloride (2.11 g, 18.53 mmol) in DCM (30 mL) at 0° C. and stirred at RT for 4 h. The mixture was concentrated and the residue dissolved in MeOH (20 mL). To this solution at 0° C. was added a solution of LI-3b (4.11 g, 16.85 mmol) in MeOH (5 mL), followed by TEA (4.61 mL, 33.70 mmol) and stirred overnight at RT. The mixture was filtered through celite, concentrated and the residue was purified by column chromatography to afford 3 g (58%) of pure I-C1-NOPD9. $^1$H-NMR (300 MHz, DMSO-d$_6$): 2.94 (t, 2H, J=6.7 Hz), 3.09 (t, 2H, J=6.3 Hz), 3.56 (q, 2H, J=6.3 Hz), 4.73 (t, 2H, J=6.3 Hz), 7.49-7.53 (m, 1H), 8.16-8.19 (m, 1H), 8.69-8.70 (m, 1H), 8.87 (br t, 1H), 8.98 (s, 1H). MS (ES$^+$) m/z: 304 (M+H)$^+$, 326 (M+Na)$^+$.

Example 90

Synthesis of NO-Releasing Prodrug of Naproxen (I-C1-NOPD10)

This prodrug was synthesized as shown in Scheme 11, Method B. Thus, to a solution of naproxen (2.23 g, 9.7 mmol) and LI-2b (1.93 g, 9.7 mmol) in THF (70 mL) at RT were added DCC (3 g, 14.55 mmol) and DMAP (1.78 g, 14.55 mmol) and stirred overnight. The mixture was filtered and concentrated, and the residue purified by column chromatography to afford 1.03 g (25%) of pure I-C1-NOPD10. $^1$H-NMR (300 MHz, CDCl$_3$): δ 1.59 (d, 3H, J=7.16 Hz), 2.81 (t, 2H, J=6.77 Hz), 2.87 (t, 2H, J=6.42 Hz), 3.85-3.88 (m, 1H), 3.91 (s, 3H), 4.33 (t, 2H, J=5.26 Hz), 4.53 (t, 2H, J=6.79 Hz), 7.10-7.16 (m, 2H), 7.41 (d, 1H, J=1.7 Hz), 7.69 (t, 3H, J=8.55 Hz).

Example 91

Synthesis of NO-Releasing Prodrug of Naproxen (I-C1-NOPD12)

This prodrug was synthesized as shown in Scheme 11, Method E. Thus, to a solution of naproxen (1.698 g, 7.37 mmol) in chloroform (20 mL) at 0-5° C. was added oxalyl chloride (0.8 mL, 8.844 mmol), followed by 2-3 drops of DMF. The mixture was stirred at RT for 90 min and concentrated. This acid chloride (~7.37 mmol) was treated with LI-5.TFA (6.7 mmol) in THF (20 mL) and cooled to 0° C. To this was added TEA (5.6 mL, 40 mmol) and stirred at RT for 3 h. The mixture was concentrated and the residue, after usual aqueous work-up and chromatographic purification, afforded 0.409 g (14%) of pure I-C1-NOPD12. $^1$H-NMR (CDCl$_3$, 300 MHz): δ 1.24 (d, 3H), 2.87 (t, 2H, J=6.5 Hz), 2.93 (t, 2H, J=6.7 Hz), 3.64 (q, 2H, 7.5 Hz), 3.76 (m, 1H), 3.88 (s, 3H), 4.70 (t, 2H, J=6.6 Hz), 4.79 (br s, 1H), 6.97-7.08 (m, 3H), 7.35-7.46 (m, 3H).

Example 92

Synthesis of NO-Releasing Prodrug of Flurbiprofen (I-C1-NOPD13)

This prodrug was synthesized as shown in Scheme 11, Method A, using as reagents flurbiprofen (4.0 g, 16.37 mmol), CDI (3.97 g, 24.56 mmol) and LI-2b (3.25 g, 16.37 mmol). Yield: 3 g (43%). $^1$H-NMR (300 MHz, CDCl$_3$): δ 1.56 (d, 3H, J=7.2 Hz), 2.80-3.0 (m, 4H, J=5.67 Hz), 3.78 (q, 1H, J=7.10 Hz), 4.36 (m, 2H), 4.66 (t, 2H, J=6.78), 7.11-7.54 (m, 8H).

Example 93

Synthesis of NO-Releasing Prodrug of Flurbiprofen (I-C1-NOPD14a)

This prodrug was synthesized as shown in Scheme 11, Method I. Thus, to a solution of flurbiprofen (5.0 g, 20.46 mmol) in benzene (50 mL), was added oxalyl chloride (3.11 g, 24.55 mmol) at 0° C. and 2 drops of DMF and stirred at RT for 20 hrs. Benzene was removed under vacuum and the residue was diluted with DCM (50 mL). The reaction mixture was cooled to 0° C. and dry ammonia was passed for 30 min. The reaction mixture was concentrated and, after usual aqueous work-up, 4.5 g of flurbiprofen amide was obtained as a white solid.

To a solution of flurbiprofen amide (3.0 g, 12.33 mmol) in DCM (70 mL) was added oxalyl chloride (1.87 g, 14.79 mmol) at 0° C. and refluxed for 16 h. Reaction mixture was cooled to RT and treated with LI-2b (2.45 g, 12.33 mmol) in DCE (10 mL) and stirred overnight. After usual aqueous work-up and chromatographic purification, 0.5 g of I-C1-NOPD14a were obtained. $^1$H NMR (CDCl$_3$, 300 MHz): δ 1.55 (d, 3H, J=6.9 Hz), 2.94-2.97 (bs, 4H), 4.38-4.47 (bs, 3H), 4.68 (t, 2H, J=6.6 Hz), 7.13-7.55 (bs, 8H) MS: ES$^+$ m/z 469.03 [M+H]$^+$, 467.16 [M−H]$^+$.

Example 94

Synthesis of NO-Releasing Prodrug of Flurbiprofen (I-C1-NOPD15b)

This prodrug was synthesized as shown in Scheme 11, Method A. Thus, to a solution of flurbiprofen (2.5 g, 10.23 mmol) in THF (30 mL) was added CDI (3.31 g, 20.46 mmol) and stirred at RT for 16 h. To this was added LI-5.TFA (3.64 g, 10.23 mmol) in THF (15 mL), followed by TEA (2.85 mL, 20.46 mmol) and stirred for 16 h. After usual work-up and chromatographic purification, 1.5 g (91%) of I-C1-NOPD15b were obtained. $^1$H NMR (CDCl$_3$, 300 MHz): δ 1.5 (d, 3H, J=6.9 Hz), 2.82 (t, 2H, J=6.3 Hz), 2.92 (t, 2H, J=6.9

Hz), 3.50 (m, 3H), 4.6 (t, 2H, J=6.6 Hz), 5.8 (s, 1H), 7.11-7.55 (bs, 8H). MS: ES+ m/z 425.21 [M+H]+, 423.11 [M−H]−.

Example 95

Synthesis of NO-Releasing Prodrug of Indomethacin (I-C1-NOPD16)

This prodrug was synthesized as shown in Scheme 11, Method A. Thus, to a solution of indomethacin (2.0 g, 5.59 mmol) in chloroform (25 mL) was added CDI (1.09 g, 6.71 mmol) and stirred for 2 h. A solution of LI-2b (1.22 g, 6.15 mmol) and DMAP (751 mg, 6.15 mmol) in chloroform (5 mL) was added, and the mixture was stirred at RT for 16 h. After usual aqueous work-up and chromatographic purification, 2.02 g (67%) of pure I-C1-NOPD16 was obtained. $^1$H-NMR (300 MHz, CDCl$_3$): δ 2.39 (s, 3H), 2.88-2.95 (m, 4H), 3.69 (s, 2H), 3.84 (s, 3H), 4.38 (t, 2H, J=6.3 Hz), 4.63 (t, 2H, J=6.6 Hz), 6.67 (dd, 1H, J=2.4, 8.7 Hz), 6.87 (d, 1H, J=8.7 Hz), 6.96 (d, 1H, J=2.1 Hz), 7.47 (d, 2H, J=8.4 Hz), 7.67 (d, 2H, J=8.4 Hz). MS (ES+) m/z: 539.2 [M+H]+, 560.79 [M+Na]+.

Example 96

Synthesis of NO-Releasing Prodrug of Indomethacin (I-C1-NOPD18)

This prodrug was synthesized as shown in Scheme 11, Method A. Thus, to a solution of indomethacin (3.01 g, 8.42 mmol) in THF (50 mL) at RT was added CDI (1.64 g, 10.10 mmol). After 1 h, LI-5.TFA (3 g, 8.42 mmol) was added at 0° C., followed by TEA (5.9 mL, 42.1 mmol) and DMAP (0.6 g, 4.91 mmol). The reaction mixture was stirred at RT for 2 d. After usual aqueous work-up and chromatographic purification, 3.16 g (70%) of I-C1-NOPD18 were obtained as yellow solid. $^1$H NMR (CDCl$_3$, 300 MHz): δ 2.38 (s, 3H), 2.79 (t, 2H, J=6.3 Hz), 2.86 (t, 2H, J=6.9 Hz), 3.54 (q, 2H, J=6.0 Hz), 3.66 (s, 2H), 3.83 (s, 3H), 4.61 (t, 2H, J=6.6 Hz), 6.01 (bs, 1H), 6.71 (dd, 1H, J=2.1, 9.0 Hz), 6.9 (dd, 2H, J=3.3, 8.1 Hz), 7.49 (d, 2H, J=8.4 Hz, 2H), 7.66 (d, 2H, J=8.4 Hz). MS: m/z 538.10 [M+H]+, 560.1 [M+Na]+.

Example 97

Synthesis of NO-Releasing Prodrug of Ketoprofen (I-C1-NOPD19)

This prodrug was synthesized as shown in Scheme 11, Method A according to the method described in Example 90, using as reagents ketoprofen (1.27 g, 5 mmol), CDI (1.21 g, 7.5 mmol) and LI-2b (1 g, 5 mmol). Yield: 0.6 g (51%). $^1$H-NMR (300 MHz, CDCl$_3$): δ 1.55 (d, 3H; J=7.0 Hz), 2.80-2.95 (m, 4H), 3.82 (q, 1H, J=6.7 Hz), 4.35 (t, 2H, J=6.1 Hz), 4.64 (t, 2H, J=6.5 Hz), 7.40-7.85 (m, 9H). MS (ES+) m/z: 436.06 [M+H]+, 458.02 [M+Na]+.

Example 98

Synthesis of NO-Releasing Prodrug of Ketoprofen (I-C1-NOPD20a)

This prodrug was synthesized as shown in Scheme 11, Method I. Thus, to a solution of the amide of ketoprofen (1.78 g, 7 mmol) in DCE (70 mL) was added oxalyl chloride (1.0 g, 8.4 mmol) at 0° C. and refluxed for 16 h. After cooling to RT, a solution of LI-2B (1.4 g, 7 mmol) in DCE (10 mL) was added and stirred for 20 h. After usual aqueous work-up and chromatographic purification, 0.6 g (17%) of I-C1-NOPD20a was obtained as a pale yellow gum. $^1$H NMR (CDCl$_3$, 300 MHz): δ 1.47 (d, 3H, J=6.96 Hz), 3.00 (bs, 4H), 4.00 (q, 1H, J=6.81 Hz), 4.39 (t, 2H, J=6.21 Hz), 4.68 (bs, 2H), 7.47-7.77 (bs, 9H). MS: ES+ m/z 478 [M+H]+, 477.15 [M−H]+.

Example 99

Synthesis of NO-Releasing Prodrug of Diclofenac (I-C1-NOPD22)

This prodrug was synthesized as shown in Scheme 11, Method B, using as reagents diclofenac (1.0 g, 3.378 mmol), LI-2b (0.68 g, 3.37 mmol), DMF (8 mL), DCC (0.835 g, 4.054 mmol) and DMAP (0.082 g, 0.675 mmol). Yield: 0.35 g (22%). $^1$H-NMR (300 MHz, CDCl$_3$): δ 2.91-3.04 (m, 4H), 3.85 (s, 2H), 4.42 (t, 2H, J=6.6 Hz), 4.72 (t, 2H, J=6.6 Hz), 6.56 (d, 1H, J=8.1 Hz), 6.82 (s, 1H), 6.94-7.03 (m, 2H), 7.12-7.27 (m, 2H), 7.35 (d, 1H, J=8.1 Hz). MS (ES+) m/z: 476.90 [M+H]+, 498.86 [M+Na]+.

Example 100

Synthesis of NO-Releasing Prodrug of Flurbiprofen (I-C1-NOPD26)

This prodrug was synthesized as outlined in Scheme 20. Thus, to a solution of S20-I1 (0.8 g, 2.90 mmol) in THF (10 mL) and DMF (10 mL) was added the cesium salt of flurbiprofen (1.2 g, 3.19 mmol) and stirred at RT for 2 h. After usual aqueous work-up and chromatographic purification, 1.13 g (80%) of I-C1-NOPD26 was obtained as a light yellow semi solid. $^1$H NMR (500 MHz, CDCl$_3$): δ 1.58 (d, 3H, J=7.5 Hz), 2.88-2.94 (m, 4H), 3.88 (q, 1H, J=7.0 Hz), 4.40 (t, 2H, J=6.5 Hz), 4.64-4.68 (m, 4H), 7.14-7.54 (m, 8H). MS: m/z 501.1 [M+NH$_4$]+, 506.1 [M+Na]+.

Example 101

Synthesis of NO-Releasing Prodrug of Gabapentin Ethyl Ester (I-A1-NOPD1)

This prodrug was synthesized as shown in Scheme 12, Method A. Thus, to a stirred solution of diphosgene (0.88 mL, 7.37 mmol) in DCM (3 mL) at 0° C. was added drop-wise a solution of LI-2a (0.80 g, 3.68 mmol) & Hunig's base (1.92 mL, 11.85 mmol) in DCM (1 mL). The mixture was stirred at 0° C. for 30 min and concentrated. The residue was dissolved in DCM (4 mL) and treated with gabapentin ethyl ester hydrochloride (0.95 g, 4.05 mmol) & Hunig's base (1.39 mL, 8.05 mmol). The mixture was stirred at RT for 3 h and concentrated. The residue, after usual aqueous work-up, gave 1.6 g (98%) of I-S12-I1. $^1$H-NMR data is consistent with the expected structure. MS (ES+) m/z: 444 [M+H]+, 465.9 [M+Na]+.

To a stirred solution of I-S12-I1 (1.3 g, 2.94 mmol) in acetonitrile (8 mL) at RT was added silver nitrate (0.6 g, 3.52 mmol) portion-wise and stirred at RT for 2.5 h. After filtration through celite, the filtrate was concentrated and the residue purified by column chromatography to afford 0.561 g (45%) of prodrug I-A1-NOPD1. $^1$H-NMR data is consistent with the expected structure. MS (ES+) m/z: 425 (M+H)+, 447 (M+Na)+.

Example 102

Synthesis of NO-Releasing Prodrug of Lamotrigine (I-A1-NOPD3a and I-A1-NOPD3b)

This prodrug was synthesized as shown in Scheme 12, Method B. Thus, to a suspension of lamotrigine (1 g, 3.90 mmol) in toluene (20 mL) at 120° C. was added drop-wise a solution of the imidazolide of LI-2b (1.4 g, 4.70 mmol) in THF (10 mL) and refluxed for 6 h. After usual aqueous work-up and chromatographic purification, 340 mg (20%) of I-A1-NOPD-3a/b was obtained. $^1$H-NMR data is consistent with the expected structure. MS (ES)$^+$ m/z: 481 (M+H)$^+$.

Example 103

Synthesis of NO-Releasing Prodrug of Nicotinic Hydrazide (I-A1-NOPD4)

This prodrug was synthesized from nicotinic hydrazide (235 mg, 1.70 mmol) according to the procedure described in Example 109 (see Scheme 13, Method B). After usual workup, the crude product was purified by column chromatography to afford 0.21 g (34%) of prodrug I-A1-NOPD4. $^1$H-NMR (300 MHz, DMSO-d$_6$): δ 3.02 (t, 2H, J=5.8 Hz), 3.10 (t, 2H, J=6.1 Hz), 4.28 (t, 2H, J=5.8 Hz), 4.76 (t, 2H, J=6.1 Hz), 7.51-7.55 (dd, 1H, J=4.8 Hz, 7.7 Hz), 8.17 (d, 1H, J=7.8 Hz), 8.74 (d, 1H, J=3.8 Hz), 8.98 (s, 1H), 9.44 (bs, 1H), 10.54 (bs, 1H). MS (EI)$^+$ m/z: 363 [M+H]$^+$.

Example 104

Synthesis of NO-Releasing Prodrug of Lisinopril Dimethyl Ester (I-A1-NOPD5)

This prodrug was synthesized from lisinopril dimethyl ester hydrochloride (1.10 g, 2.56 mmol) according to the procedure described in Example 101 (see Scheme 12, Method B). After usual workup, the crude product was purified by column chromatography to afford 0.76 g (67%) of prodrug I-A1-NOPD5. $^1$H-NMR (300 MHz, CDCl$_3$): δ 1.49-1.54 (m, 2H), 1.93-2.07 (m, 8H), 2.12-2.28 (m, 1H), 2.64-2.68 (m, 2H), 2.91-3.0 (m, 4H), 3.18-3.25 (m, 3H), 3.42-3.47 (m, 1H), 3.52-3.55 (m, 2H), 3.69 (s, 3H), 3.73 (s, 3H), 4.28 (t, J=6.3 Hz, 2H), 4.47-5.05 (m, 1H), 4.69 (t, J=6.8 Hz, 2H), 5.22 (bt, 1H), 7.14-7.19 (m, 3H), 7.23-7.28 (m, 2H). MS (EI)$^+$ m/z: 659 [M+H]$^+$.

Example 105

Synthesis of NO-Releasing Prodrug of Omeprazole (I-A1-NOPD6)

This prodrug was synthesized as shown in Scheme 12, Method B. To an ice-cold solution of diphosgene (0.3 mL, 2.48 mmol) in toluene at 0° C., was added a mixture of LI-2b (0.5 g, 2.51 mmol) and TEA (0.42 mL, 3.0 mmol) in toluene (3 mL) and stirred for 2 h. In a separate flask, omeprazole (0.867 g, 2.50 mmol) was dissolved in THF (5 mL), cooled to 0° C. and NaH (0.059 g, 2.5 mmol) was added. The mixture was stirred for 30 min, the above reaction mixture was added dropwise to it and stirred for 2 h. After usual aqueous work-up and chromatographic purification, 0.23 g (20%) of I-A1-NOPD6 was obtained as a reddish-yellow gum. MS: ES+m/z 571 (M+H)$^+$, 593 (M+Na)$^+$.

Example 106

Synthesis of NO-Releasing Prodrug of Hydralazine (I-A1-NOPD7)

This prodrug was synthesized from hydralazine hydrochloride (0.99 g, 5.01 mmol) according to the procedure described in Example 109 (see Scheme 13, Method B). After usual workup, the crude product was purified by column chromatography to afford 0.8 g (41%) of prodrug I-A1-NOPD7. $^1$H-NMR (300 MHz, CDCl$_3$): δ 2.95-3.06 (m, 4H), 4.43 (t, 2H, J=6.35 Hz), 4.69 (t, 2H, J=6.7 Hz), 7.57 (m, 1H), 7.63-7.71 (m, 2H), 8.16 (s, 1H), 8.29 (d, 1H, J=7.6 Hz). MS (ES$^+$) m/z: 386.05 (M+H)$^+$.

Example 107

Synthesis of NO-Releasing Prodrug of Amlodipine (I-A1-NOPD8)

This prodrug was synthesized from amlodipine (1.67 g, 4.09 mmol) according to the procedure described in Example 109 (see Scheme 12, Method B). After usual workup, the crude product was purified by column chromatography to afford 1.33 g (61%) of I-A1-NOPD8. $^1$H-NMR (300 MHz, CDCl$_3$): δ 1.18 (t, 3H, J=7.1 Hz), 2.36 (s, 3H), 2.93-2.99 (m, 4H), 3.47 (bs, 2H), 3.61-3.64 (m, 5H), 4.04 (q, 2H, J=7.1 Hz), 4.35 (bt, 2H), 4.68-4:74 (m, 4H), 5.0 (bs, 1H), 7.13-7.36 (m, 4H). MS (ES$^+$) m/z: 634.14 (M+H)$^+$, 656.83 (M+Na)$^+$; (ES$^-$) m/z: 631.94 (M−H)$^+$.

Example 108

Synthesis of NO-Releasing Prodrug of Levetiracetam (I-A2-NOPD1a)

This prodrug was synthesized from levetiracetam (1.0 g, 5.87 mmol) according to the procedure generally described in Example 82 (see Scheme 13, Method A). After usual workup and chromatographic purification, the product was further purified by preparative HPLC to afford 728 mg (31%) of prodrug I-A2-NOPD1a. $^1$H-NMR was consistent with the expected structure. MS (ES)$^+$ m/z: 396.1 [M+H]$^+$, 418.1 [M+Na]$^+$, (ES)$^-$ m/z: 394.1 [M−H]$^-$.

Example 109

Synthesis of NO-Releasing Prodrug of Valdecoxib (I-A3-NOPD1a)

This prodrug was synthesized as shown in Scheme 13, Method B. Thus, to a cold suspension of sodium hydride (271 mg, 6.81 mmol) in THF (7 mL) was added drop-wise a solution of valdecoxib (1.78 g, 5.68 mmol) in THF (15 mL) and stirred at RT for 2 h. A solution of the imidazolide of LI-2b (2.0 g, 6.81 mmol) in THF (15 mL) was added and stirred at room temperature for 18 h. The reaction mixture was concentrated and the residue, after usual aqueous work-up and chromatographic purification, afforded 976 mg (32%) of prodrug I-A3-NOPD1a. $^1$H-NMR data is consistent with the expected structure. MS (ES)$^-$ m/z: 538 [M−H]$^-$.

Example 110

Synthesis of NO-Releasing Prodrug of Celecoxib (I-A3-NOPD2a)

This prodrug was synthesized from celecoxib (6.62 g, 17.35 mmol) according to the procedure described in Example 109 (see Scheme 13, Method B). After usual workup, the crude product was purified by column chromatography to afford 1.55 g (15%) of prodrug I-A3-NOPD2a. $^1$H-NMR (300 MHz, CDCl$_3$): δ 2.38 (s, 3H), 2.84-2.98 (m, 4H), 4.34 (t, 2H, J=6.45 Hz), 4.63-4.71 (m, 2H), 6.74 (s, 1H), 7.09-7.25 (m, 4H), 7.51 (d, 2H, J=6.8 Hz), 8.02 (d, 2H, J=6.8 Hz). MS (ES)$^+$ m/z: 606.87 [M+H]$^+$, 628.93 [M+Na]$^+$; (ES)$^-$ m/z: 604.88 [M−H]$^-$.

Example 111

Synthesis of NO-Releasing Prodrug of Paracetamol
(I-H1-NOPD1)

This prodrug was synthesized as shown in Scheme 14, Method B. Thus, to a solution of paracetamol (2.0 g, 13.24 mmol) in THF (20 mL) was added CDI (2.36 g, 14.57 mmol) and the mixture was stirred at RT for 3 h. To this was added a solution of LI-2b (1.21 g, 6.62 mmol), followed by DMAP (0.802 g, 6.622 mmol) and stirred overnight at RT. The mixture was quenched with water and extracted with EtOAc. After usual aqueous work-up and chromatographic purification, 0.3 g (6%) of prodrug I-H1-NOPD1. $^1$H-NMR data is consistent with the expected structure. MS (CI)$^+$ m/z: 376 [M+H]$^+$.

Example 112

Synthesis of NO-Releasing Prodrug of Paracetamol
(I-H1-NOPD2a)

This prodrug was synthesized as shown in Scheme 14, Method D. Thus, to a solution of chlorocarbonyl isocyanate (0.701 g, 6.622 mmol) in benzene (5 mL) at 0° C. was added a solution of paracetamol (1 g, 6.622 mmol) and stirred at 0° C. for 1 h. To this was added a solution of LI-2b (1.21 g, 6.622 mmol) and TEA (1 mL) in THF (5 mL), and stirred overnight at RT. After usual aqueous work-up and chromatographic purification, 90 mg (3%) of prodrug I-H1-NOPD2a was obtained. $^1$H-NMR data was consistent with the expected structure. MS: (ES)$^-$ m/z: 418 [M−H]$^-$.

Example 113

Synthesis of NO-Releasing Prodrug of Paracetamol
(I-H1-NOPD3)

This prodrug was synthesized from paracetamol (2.0 g, 13.24 mmol) according to the procedure described in Example 122 (see Scheme 14, Method C). After usual workup, the crude product was purified by column chromatography to afford 1.0 g (20%) of prodrug I-H1-NOPD3. $^1$H-NMR (500 MHz, CDCl$_3$): δ 2.11 (s, 3H), 2.91 (t, 2H, J=6.5 Hz), 3.06 (t, 2H, J=6.5 Hz), 3.49 (t, 2H, J=6.5 Hz), 4.75 (t, 2H, J=6.5 Hz), 7.05 (d, 2H, J=9.0 Hz), 7.54 (d, 2H, J=9.0 Hz). MS (ES)$^+$ m/z: 376 [M+H]$^+$, 393 [M+NH$_4$]$^+$, 397 [M+K]$^+$.

Example 114

Synthesis of NO-Releasing Prodrug of
Metronidazole (I-H1-NOPD6)

This prodrug was synthesized in two steps as shown in Scheme 14, Method C.
Step 1: To a suspension of metronidazole (5 g, 29.22 mmol) in chloroform (100 mL) was added CDI (5.21 g, 32.2 mmol) and stirred overnight at RT. The reaction mixture, after usual aqueous work-up, gave 7.66 g (98%) of the imidazolide intermediate. $^1$H-NMR data was consistent with the expected structure. MS (ES)$^+$ m/z: 266.1 [M+H]$^+$.

Step 2: To a mixture of LI-5.TFA (2.68 mmol) and TEA (1.08 g, 10.72 mmol) in DCM (10 mL) at 0° C. was added the imidazolide of metronidazole (0.78 g, 2.95 mmol) and stirred at RT for 48 h. The reaction mixture was quenched with water and extracted with DCM. After usual aqueous work-up and chromatographic purification, 50 mg (4.3%) of I-H1-NOPD6 was obtained. $^1$H-NMR (500 MHz, CDCl$_3$): δ 2.50 (s, 3H), 2.80 (t, 2H, J=6.3 Hz), 2.96 (t, 2H, J=6.6 Hz), 3.47-3.50 (m, 2H), 4.41 (t, 2H, J=5.1 Hz), 4.58 (t, 2H, J=5.1 Hz), 4.70 (t, 2H, J=6.6 Hz), 7.96 (s, 1H). MS (ES)$^+$ m/z: 395.99 [M+H]$^+$.

Example 115

Synthesis of NO-Releasing Prodrug of Budesonide
(I-H1-NOPD9)

This prodrug was synthesized from budesonide (0.5 g, 1.16 mmol) according to the procedure described in Example 122 (see Scheme 14, Method C). After usual workup, the crude product was purified by column chromatography to afford 0.25 g (33%) of prodrug I-H1-NOPD9. $^1$H-NMR data was consistent with the expected structure. MS (ES)$^+$ m/z: 655 [M+H]$^+$.

Example 116

Synthesis of NO-Releasing Prodrug of
4-Hydroxy-TEMPO (I-H1-NOPD10)

A solution of LI-2b (0.20 g, 1.20 mmol) and CDI (0.195 g, 1.20 mmol) in chloroform (5 mL) was stirred at RT for 2 h, which was followed by the addition of 4-hydroxy-TEMPO (0.173 g, 1.00 mmol) and DMAP (0.122 g, 1.00 mmol). The mixture was refluxed for 2 d, then purified by column chromatography to afford 110 mg (27%) of I-H1-NOPD10 as a red oil. MS: EI+ m/z 398 [M+H]$^+$, 420 [M+Na]$^+$.

Example 117

Synthesis of NO-Releasing Prodrug of Edaravone
(I-H1-NOPD11)

To a solution of edaravone (0.87 g, 5 mmol) in acetonitrile was added KF—Al$_2$O$_3$ (66 g) and, under thorough mixing, LI-3a (2.8 g, 10 mmol) was added. The mixture was agitated for 20 h. After usual aqueous work-up and chromatographic purification, 70 mg (4%) of the intermediate bromide was obtained as a reddish-yellow oil. $^1$H NMR (CDCl$_3$, 500 MHz): δ 2.28 (s, 3H), 3.00-3.10 (m, 4H), 3.59 (t, 2H, J=8 Hz), 4.34 (t, 2H, J=6.5 Hz), 5.5 (s, 1H), 7.4 (t, 2H, J=1 Hz), 7.69 (t, 3H, J=1 Hz). MS: ES$^+$ m/z 375 [M+H]$^+$, 397.0 [M+Na]$^+$.

To a solution of the above bromide (0.05 g, 0.134 mmol) in acetonitrile (1.5 mL) was added AgNO$_3$ (0.027 g, 0.160 mmol) and stirred for 20 h. After usual aqueous workup and purification, 0.025 g (53%) of I-H1-NOPD11 was obtained as a brown gum. $^1$H NMR (CDCl$_3$, 500 MHz): δ 2.28 (s, 3H), 2.90 (t, 2H, J=6.5 Hz), 3.10 (t, 2H, J=6.5 Hz), 4.33 (t, 2H, J=6.0 Hz), 4.63 (t, 2H, J=6.5 Hz), 5.5 (s, 1H), 7.60-7.63 (bs, 2H), 7.65-7.67 (bs, 3H). MS: ES$^+$ m/z 356 [M+H]$^+$.

Biological Example 1

Screening of Prodrugs and Mutual Prodrugs of Anticonvulsants

Most of the prodrugs and mutual prodrugs of anticonvulsants described in this invention were evaluated at National Institute of Neurological Disorders and Stroke (NINDS), National Institute of Health (NIH), under their Antiepileptic Screening Program (ASP).

Test 1 is an initial screening for anticonvulsant activity in the Maximal Electroshock Test (MES) and Subcutaneous Metrazol Seizure Threshold Test (scMET) models combined with an initial assessment of toxicity (TOX) in mice via i.p. injection (see further explanation below). The data for each condition is presented as N/F, where N=number of animals protected from seizure and F=number of animals tested. For test of toxicity, N=number of animals displaying toxic effects and F=number of animals tested. Any deaths occurring during the test were recorded.

Maximal Electroshock Test (MES): The MES is a model for generalized tonic-clonic seizure and provides an indication of a compound's ability to prevent seizure spread when all neuronal circuits in the brain are maximally active. These seizures are highly reproducible and electro-physiologically consistent with human seizures. For all tests based on MES convulsions, 60 Hz of alternating current (50 mA in mice) is delivered for 2 s by corneal electrodes, which have been primed with an electrolyte solution containing an anesthetic agent (0.5% tetracaine hydrochloride). Mice were tested at various intervals following doses of 30, 100 and 300 mg/kg of test compound given by i.p. injection of a volume of 0.01 mL/g. Other doses can be used if indicated by previously known pharmacology. An animal is considered "protected" from MES-induced seizures upon abolition of the hind-limb tonic extensor component of the seizure.

Subcutaneous Metrazol Seizure Threshold Test (scMET): Subcutaneous injection of the convulsant metrazol produces clonic seizures in laboratory animals. The scMET test detects the ability of the test compound to raise the seizure threshold of an animal and thus protect it from exhibiting a clonic seizure. Animals were pretreated with various doses of the test compound given by i.p. injection. At the previously determined Time to Peak Effect (TPE) of the test compound, the dose of metrazol which will produce convulsions in 97% of animals ($CD_{97}$: 85 mg/kg in mice) was injected into a loose fold of skin in the midline of the neck. The animals were placed in isolation cages to minimize stress and observed for the next 30 minutes for the presence or absence of a seizure. An episode of clonic spasms, approximately 305 seconds, of the fore and/or hind limbs, jaws, or vibrissae is taken as the end point. Animals which do not meet this criterion were considered protected.

Acute Toxicity—Minimal Motor Impairment (MMI): To assess a compound's undesirable side effects (toxicity), animals were monitored for overt signs of impaired neurological or muscular function. In mice, the rotorod procedure is used to disclose minimal muscular or neurological impairment. When a mouse is placed on a rod that rotates at a speed of 6 rpm, the animal can maintain its equilibrium for long periods of time. The compound is considered toxic if the animal falls off this rotating rod three times during a 1-min period. In addition to MMI, animals may exhibit a circular or zigzag gait, abnormal body posture and spread of the legs, tremors, hyperactivity, lack of exploratory behavior, somnolence, stupor, catalepsy, loss of placing response and changes in muscle tone.

Compounds that were active in Test 1 (mice i.p.) were further screened in Test 2 (rat p.o.). Compounds retaining activity in Test 2 (rat p.o.) were selected for secondary evaluation (i.e., Test 3, Rat P.O. quantification) as explained below:

Secondary Evaluation: All quantitative in vivo anticonvulsant/toxicity evaluations of the active compounds were conducted at compound's time of peak pharmacodynamic activity (TPE). Groups of at least 8 rats received various doses of the candidate compound until at least two points were established between the limits of 100 percent protection or toxicity and zero percent protection or minimal toxicity. The 95 percent confidence limits, slopes of the regression lines and standard errors of the slopes were calculated for each quantitative determination. Rats received test compounds orally.

Test 1 screening results are presented in Table 1. Compound I-CA-MPD24 was active in both MES and scMET models and was shown to be non-toxic. However, some compounds were active in both MES and scMET models and were also shown to be toxic. The compounds (i.e., I-A1-PD4, I-AA-MPD12, I-CA-MPD23, I-A1-PD5, I-A1-NOPD3, I-CA-MPD24, I-A1-PD15, I-CA-MPD25, and I-AA-MPD11) that are shown to be active in MES but showed no or mild toxicity were selected for Test 2 screening and those results are presented in Table 2.

Three of the compounds (i.e., I-A1-PD4, I-AA-MPD12, and I-A1-NOPD3) were considered for secondary evaluation, where quantification of their antiepileptic activity and neurotoxicity in rats (p.o.) was carried out. This secondary evaluation determines the time to peak effect (TPE), neurotoxicity, median effective dose ($ED_{50}$) and biological response. The 95% confidence interval, the slope of the regression line, and the standard error are then calculated. The results of secondary evaluation (Test 3) are presented in Tables 3A and 3B.

TABLE 1

Primary Screening (Test 1) data for Anticonvulsant Activity and Neurotoxicity in Mice (test compound administered i.p.)

| Compd | MES[a,b] 0.5 h | MES[a,b] 4.0 h | ScMET[a,c] 0.5 h | ScMET[a,c] 4.0 h | Rotorod Toxicity[a,d] 0.5 h | Rotorod Toxicity[a,d] 4.0 h |
|---|---|---|---|---|---|---|
| I-A1-PD7 | +(1/1) | – | +(1/1)[e] | – | +(2/4)[d] | – |
| I-A1-PD8 | ++(2/3) | – | – | – | – | – |
|  | +(1/1) | +(1/1) | +(1/1) | – | +(4/4)[f] | – |
| I-A1-PD4 | – | +++(1/1) | – | – | – | – |
|  | ++(1/7) | ++(3/3) | – | – | – | – |
|  | +(2/5) | +(1/1) | – | – | – | – |
| I-AA-MPD12 | – | ++(3/3) | – | – | – | – |
|  | nd | ++(1/3)[g] | nd | nd | nd | nd |
|  | – | +(1/1) | – | – | – | – |
| I-CA-MPD23 | – | ++(1/3)[h] | – | – | – | – |
|  | – | +(1/3) | – | – | – | – |
| I-A1-PD13 | +(1/1) | – | +(1/1) | – | +(1/4) | – |
| I-A1-PD5 | +(1/1) | – | +(3/5) | – | +(3/4)[i] | – |
| I-A1-PD6 | +(1/1) | – | +(1/1) | – | +(4/4)[i] | – |
| I-A1-PD10 | – | – | – | – | ++(8/8)[j] | nd |
| I-AA-MPD13 | – | – | +(1/1) | – | +(4/4)j | – |
| I-A1-NOPD1 | ++(1/3)[k] | – | – | – | – | – |
|  | +(1/1) | – | +(1/1) | – | +(4/4)[i] | – |
| I-A1-NOPD3 | – | ++(1/3) | ++(1/1)[l] | – | +++(1/4) | – |
|  | – | +(1/1) | – | – | – | – |
| I-CA-MPD24 | – | ++(3/3) | – | – | – | – |
|  | – | ++(3/3)[h] | – | – | – | – |
|  | – | ++(3/3)[m] | – | +(1/1)[l] | – | – |
| I-A1-PD15 | +(1/1) | ++(2/3) | – | – | – | – |
|  | – | +(1/1) | – | – | – | – |
| I-CA-MPD25 | +(1/1) | ++(2/3) | – | – | – | – |
|  | – | +(1/1) | – | – | – | – |

TABLE 1-continued

Primary Screening (Test 1) data for Anticonvulsant Activity and Neurotoxicity in Mice (test compound administered i.p.)

| Compd | MES[a,b] 0.5 h | MES[a,b] 4.0 h | ScMET[a,c] 0.5 h | ScMET[a,c] 4.0 h | Rotorod Toxicity[a,d] 0.5 h | Rotorod Toxicity[a,d] 4.0 h |
|---|---|---|---|---|---|---|
| I-AA-MPD11 | – +(1/1) | ++(3/3) +(1/1) | – – | – – | – +(1/4) | – – |

[a]Key: +++ = activity or toxicity at 30. mg/kg, ++ = activity or toxicity at 100 mg/kg, + = activity or toxicity at 300 mg/kg,
– = no activity or no toxicity at 300 mg/kg.
[b]Maximal electroshock seizure test.
[c]Subcutaneous pentylenetetrazole seizure test.
[d]Neurological toxicity (number of animals exhibiting toxicity/number of animals tested).
[e](number of animal protected/number of animal tested).
nd =not determined.
[f]Loss of righting reflux.
[g]At 6 hours after dosing.
[h]At 2 hours after dosing.
[i]Unable to grasp rotorod.
[j]Death.
[k]At 0.25 hours after dosing.
[l]Myoclonic jerks.
[m]At 6 hours after dosing.

TABLE 2

Screening (Test 2) data for Anticonvulsant Activity and Neurotoxicity in Rats (test compound administered p.o.)

| Compd | Dose (mg/kg) | Time (h) | MES[a,b] | Toxicity[c,d] |
|---|---|---|---|---|
| I-A1-PD4 | 30 | 0.50 | 0/4 | 0/4 |
| | | 1.00 | 1/4 | 0/4 |
| | | 2.00 | 3/4 | 0/4 |
| | | 4.00 | 4/4 | 0/4 |
| I-AA-MPD12 | 30 | 0.50 | 0/4 | 0/4 |
| | | 1.00 | 0/4 | 0/4 |
| | | 2.00 | 1/4 | 0/4 |
| | | 4.00 | 3/4 | 0/4 |
| I-CA-MPD23 | 150 | 2.00 | 4/4 | 0/4 |
| | | 4.00 | 4/4 | 0/4 |
| | | 6.00 | 4/4 | 0/4 |
| | | 8.00 | 4/4 | 0/4 |
| I-A1-PD5 | 50 | 0.50 | 0/4 | 0/4 |
| | | 1.00 | 0/4 | 0/4 |
| | | 2.00 | 1/4 | 0/4 |
| | | 4.00 | 1/4 | 0/4 |
| I-A1-NOPD3 | 30 | 0.50 | 0/4 | 0/4 |
| | | 1.00 | 2/4 | 0/4 |
| | | 2.00 | 1/4 | 0/4 |
| | | 4.00 | 4/4 | 0/4 |
| I-CA-MPD24 | 30 | 0.50 | 0/4 | 0/4 |
| | | 1.00 | 2/4 | 0/4 |
| | | 2.00 | 3/4 | 0/4 |
| | | 4.00 | 4/4 | 0/4 |
| I-A1-PD15 | 30 | 0.50 | 0/4 | 0/4 |
| | | 1.00 | 1/4 | 0/4 |
| | | 2.00 | 3/4 | 0/4 |
| | | 4.00 | 4/4 | 0/4 |
| I-CA-MPD25 | 30 | 0.50 | 0/4 | 0/4 |
| | | 1.00 | 3/4 | 0/4 |
| | | 2.00 | 4/4 | 0/4 |
| | | 4.00 | 2/4 | 0/4 |
| I-AA-MPD11 | 30 | 0.50 | 0/4 | 0/4 |
| | | 1.00 | 2/4 | 0/4 |
| | | 2.00 | 1/4 | 0/4 |
| | | 4.00 | 4/4 | 0/4 |

[a]Maximal electroshock seizure test.
[b](number of animal protected/number of animal tested).
[c]Neurological toxicity.
[d](number of animals exhibiting toxicity (i.e., atoxia)/number of animals tested).

TABLE 3A

Screening (Test 3) data for Anticonvulsant Activity (Time to Peak Effect) and Neurotoxicity in Rats (test compound administered p.o.)

| | | | Time to Peak Effect | | |
|---|---|---|---|---|---|
| Compd | Dose (mg/kg) | Time (h) | MES[a,b] | ScMET[b,c] (50 mg/kg) | Toxicity[d,e] (mg/kg) |
| I-A1-PD4 | 10 | 4.0 | 4/4 | | |
| | | 6.0 | 3/4 | | |
| | | 8.0 | 2/4 | | |
| | | 24 | 0/4 | | |
| | 30 | 0.25 | 2/4 | 1/4[f] | 0/4 (100) |
| | | 0.5 | 2/4 | 0/4 | 0/4 (100) |
| | | 1.0 | 2/4 | 2/4 | 0/4 (100) |
| | | 2.0 | 2/4 | 1/4[g] | 0/4 (100) |
| | | 4.0 | 4/4 | 0/4 | |
| I-AA-MPD12 | 15 | 6.0 | 2/4 | | |
| | | 8.0 | 1/4 | | |
| | 30 | 0.5 | 0/4 | | |
| | | 1.0 | 0/4 | 1/4 | 0/4 (50) |
| | | 2.0 | 1/4 | 0/4 | 0/4 (50) |
| | | 4.0 | 3/4 | 0/4 | 0/4 (50) |
| | | 6.0 | 4/4 | 1/4 | 0/4 (50) |
| | | 8.0 | 4/4 | 2/4 | 0/4 (50) |
| | | 24 | 2/4 | 0/4 | 0/4 (50) |
| | | 8.0 | | | 1/8 (100)[h] |
| I-A1-NOPD3 | 30 | 0.25 | | | 0/8 (500) |
| | | 0.5 | | | 0/8 (500) |
| | | 1.0 | | | 0/8 (500) |
| | | 2.0 | 1/4 | 0/4 | 0/8 (500) |
| | | 4.0 | 3/4 | 0/4 | 0/8 (500) |
| | | 6.0 | 3/4 | 1/4 | 1/8 (500) |
| | | 8.0 | 4/4 | 3/4 | 0/8 (500) |
| | | 24 | 3/4 | 1/4 | |

[a]Maximal electroshock seizure test.
[b](number of animal protected/number of animal tested).
[c]Subcutaneous pentylenetetrazole seizure test.
[d]Neurological toxicity.
[e](number of animals exhibiting toxicity (i.e., atoxia)/number of animals tested).
[f]Death following continuous seizure.
[g]Popcorn effect and continuous seizure activity.
[h]Mild ataxia only.

TABLE 3B

Screening (Test 3) data for Anticonvulsant Activity (ED50 and Biological Response and $ED_{50}$) in Rats (test compound administered p.o.)

| | | | ED 50 Values and Biological Response | | | |
|---|---|---|---|---|---|---|
| Compd | Time (h) | Dose (mg/kg) | MES[a,b] | $ED_{50}$ | 95% Confidence Interval Low/High | Slope/Std.Er |
| I-A1-PD4 | 4 | 1.9 | 0/8 | 6.55 | 3.56/10.72 | 2.27/0.63 |
| | | 3.8 | 4/8 | | | |
| | | 7.5 | 4/8 | | | |
| | | 15 | 7/8 | | | |
| | | 30 | 7/8 | | | |
| I-AA-MPD12 | 6 | 7.5 | 0/8 | 17.1 | 9.98/25.8 | 3.2/0.95 |
| | | 15 | 5/8 | | | |
| | | 30 | 7/8 | | | |
| | | 60 | 7/8 | | | |
| I-A1-NOPD3 | 8 | 3.8 | 3/8 | | | |
| | | 7.5 | 3/8 | | | |
| | | 15 | 4/8 | 10.1 | 2.99/17.44 | 1.61/3.15 |
| | | 30 | 9/12 | | | |
| | | 60 | 8/8 | | | |

[a]Maximal electroshock seizure test.
[b](number of animal protected/number of animal tested).

I-A1-PD4 is a simple prodrug of lamotrigine. For this prodrug, $ED_{50}$ for the MES model was determined to be 6.55 mg/kg and the time to peak effect was found to be 4.0 h after drug administration at doses of 10 as well as 30 mg/kg. This compound has shown moderate protection in scMET models where one out of four animals were protected at 0.25 h and 2.0 h period and two out of four animals were protected at 1.0 h after administration of the drug at a dose of 50 mg/kg. For the toxicity analysis, none of the animals given 100 mg/kg showed signs of toxicity.

I-AA-MPD12 is a mutual prodrug of lamotrigine and gabapentin ethyl ester. For this compound, $ED_{50}$ for the MES model was found to be 17 mg/kg and the time to peak effect was found to be 6.0-8.0 h at a dose of 30 mg/kg and indicated a significant extension protection (2 out of 4 animals were still protected) at 24 h after drug administration. Surprisingly, this compound, although less potent than lamotrigine, has exhibited significant extension in the duration of protection. At 50 mg/kg, none of the animals exhibited toxicity. However, at 100 mg/kg, one of eight animals exhibited mild ataxia.

I-AH-NOPD3 is a NO-releasing prodrug of lamotrigine. For this prodrug, ED50 for the MES model was determined to be 10.1 mg/kg and the time to peak effect was found be at 8.0 h at a dose of 30 mg/kg and revealed a significant extension of protection (3 out 4 animals were still protected) even at 24 h after drug administration. Surprisingly, this prodrug, although less potent than its parent drug, has exhibited significant extension in the duration of protection. At 50 mg/kg, this compound has also exhibited significant protection (3 out of 4 animals were protected at 8 h after drug administration) in scMET rat model. For the toxicity analysis, only one in eight animals exhibited toxicity at 6.0 h time point at a dose of 500 mg/kg. At other time points (i.e., 0.25 h, 0.5 h, 1.0 h, 2.0 h, 4.0 h, 8.0 h after drug administration), none of the animals (0/8) exhibited any significant toxicity at the high dose of 500 mg/kg.

Biological Example 2

The pharmacological experiments on NO-releasing aspirin prodrugs were carried out by following the procedures described herein:

Animals and Procedures:

Male or female Sprague-Dawley rats weighing 150-200 g were used in the study. The rats were fed normal standard laboratory chow and maintained under standard conditions (room temperature of 22±2° C.; 50±10% relative humidity; artificial light 06:00 to 18:00). All experimental procedures mentioned below are approved by institutional animal research committees and were performed in accordance with standard guidelines for the treatment of animals.

Sample Preparation and Standard Curve:

HPLC: Waters Allience analytical HPLC equipped with 2996 PDA detector and Empower software were used to analyze the samples.

HPLC Column: Waters X-Terra RP-18 analytical column, 150×3.9 mm, 5µ.

HPLC Method: Flow: 1 mL/min, detector set at 210 nm and at Maxplot (210-400 nm range). Solvent A: Acetonitrile; Solvent B: 0.1% TFA in water. Elution method: A linear gradient of 0-100% A.

Plasma samples were processed by transferring 75 µl quantity of blood into a test tube containing 250 µl acetonitrile, vortex-mixed and centrifuged at 1000 g for 5 min. 200 µl of supernatant was then taken and diluted to 2 times with acetonitrile. 100 µl of the sample was injected into HPLC for analysis. Salicylate standard curves were generated using acetonitrile as solvent in the working range of 1-100 µg/ml.

Pharmacokinetic parameters were calculated using WinNonlin software (4.1 version). Cmax, Tmax, AUC 0-24, AUC 0-infinity, and $T_{1/2}$ characterized and each curve generated following oral treatment.

In Vitro Plasma Stability:

The rationale is that the prodrugs would be hydrolyzed in-vivo before, during or after absorption to release the corresponding free drugs. Therefore, we tested whether the test compounds (I-C1-NOPD6, I-C1-NOPD4, I-C1-NOPD5A) released parent drug in rat plasma at 37° C. after 30 minutes incubation. The compounds were extracted back into acetonitrile with rigorous vortex. The results suggested that all prodrugs tested except I-C1-NOPD6 were found to be converting to the expected metabolite (salicylate) of the parent drug (aspirin) as revealed by HPLC analysis. Even aspirin was completely metabolized to salicylate after 30 minutes of incubation with rat plasma indicating that all the test compounds released aspirin, which in turn converted into salicylate.

Pharmacokinetic Studies:

The oral pharmacokinetics of the test compounds, I-C1-NOPD6, I-C1-NOPD4, I-C1-NOPD5A and I-C1-NOPD5B was done in rats and the release profiles of salicylate from these compounds were analyzed by HPLC and the results were presented in FIG. 1 and Table 4. Overnight fasted rats were fed with 35 mg/kg equivalent doses of aspirin and test compounds. Blood was collected from orbital plexus of test animals at various time points up to 24 hrs. As shown in FIG. 1, the test compounds I-C1-NOPD4 and I-C1-NOPD5B indicated unexpected drug release profiles wherein the salicylate is released in a sustained and controlled manner starting from 1 hour through 12 hours. For I-C1-NOPD5B, the plasma salicylate concentration was maintained between 50 and 75 µg/ml during this extended period of over 11 hours. This kind of plasma concentrations of the drug can result in significant extension of duration of action. For I-C1-NOPD4 also, the plasma salicylate concentration was maintained between 35 and 50 µg/mL during an extended period of over 11 hours. Although aspirin absorption (FIG. 1) was highest during 0.5-6.0 hrs (during which period much of the damage to the gastrointestinal tract of the subject occurs due to high concentrations of the drug), plasma salicylate concentration for aspirin and I-C1-NOPD4 were comparable during the period from 8 through 24 hours. Such sustained release profile of active drug from the prodrug is expected to cause negligible or insignificant gastrointestinal damage as the plasma concentration of the drug never reaches to the toxic levels. Similar release profile was observed with I-C1-NOPD5A but for a shorter period of time. Unexpectedly, we have also observed as recorded in Table 4, nearly equal drug AUC values for aspirin and I-C1-NOPD5B (i.e., 923.63±182.08 for aspirin vs 951.98±11.58 for I-C1-NOPD5B) which indicates that the prodrug is as bioavailable as its parent drug, but prodrug does not cause gastric damage. Surprisingly, neither the prodrug nor the salicylate was found in the plasma of the animals fed with I-C1-NOPD6 (data not included in the graph) at any point of time tested, the reasons for which are not known.

TABLE 4

Comparison of pharmacokinetic parameters of aspirin and its nitro derivatives

| Parameters* | Aspirin | I-C1-NOPD4 | I-C1-NOPD5A | I-C1-NOPD5B |
|---|---|---|---|---|
| Cmax (µg/mL) | 98.67 ± 12.64 | 53.24 ± 6.39 | 50.14 ± 10.12 | 66.08 ± 3.31 |
| Tmax (h) | 0.50 ± 0.00 | 4.66 ± 0.57 | 3.00 ± 0.57 | 4.00 ± 0.81 |
| $AUC_{0-24\,h}$ (h · µg/ml) | 905.84 ± 173.14 | 749.36 ± 69.38 | 557.80 ± 97.65 | 922.89 ± 12.50 |

TABLE 4-continued

Comparison of pharmacokinetic parameters of aspirin and its nitro derivatives

| Parameters* | Aspirin | I-C1-NOPD4 | I-C1-NOPD5A | I-C1-NOPD5B |
|---|---|---|---|---|
| $AUC_{0-\alpha}$ (h · µg/ml) | 923.63 ± 182.08 | 772.17 ± 75.68 | 565.30 ± 96.78 | 951.98 ± 11.58 |
| $T_{1/2}$ (h) | 3.56 ± 0.42 | 3.98 ± 0.25 | 3.35 ± 0.32 | 4.14 ± 0.24 |

*The data values are mean ± SEM, n = 3-4

Ulcerogenic Activity:

Gastrointestinal ulceration is a serious side effect associated with NSAIDs. The clinical uses of potent NSAIDs are greatly limited by its gastrointestinal toxicity. We tested ulcerogenic potential of the test compounds, I-C1-NOPD6, I-C1-NOPD4, I-C1-NOPD5A, and I-C1-NOPD5B in rats. Overnight fasted rats were given orally 100 mg/kg equivalent doses of aspirin and prodrugs (in the case of I-C1-NOPD5A and I-C1-NOPD5B, 200 mg/kg equivalent doses were administered). The animals were sacrificed at 3 hours after drug administration. Stomachs of treated rats were separated, perfused with 10 ml of 2% formalin, and then cut open over the greater curvature. The severity of the mucosal damage was then assessed on the basis of size (area) of the observed ulcers under surgical microscope with a square grid as per the established procedure (Takeuchi et al., J. Pharmacol. Exp. Ther. 1998, 286 (1), 115-121). Interestingly, none of the animals treated with the test compounds showed any signs of development of ulcers. However, severe haemorrhagic lesions (Mean±S.E.M.: 2.7±0.9 mm$^2$) were seen in aspirin treated rats.

Anti-Inflammatory Activity:

Anti-inflammatory activity of test compounds was measured in carrageenan-induced rat paw edema model (Takeuchi et al., J. Pharmacol. Exp. Ther. 1998, 286 (1), 115-121). The activity of aspirin and test compounds (75 mg/kg equivalent dose of aspirin) is shown in Table 5. Aspirin at 75 mg/kg, p.o. exhibited anti-inflammatory activity from 1 hr through 6 hr with peak maximal activity at 4 hr. I-C1-NOPD4 showed significant activity during the first two hours after drug administration but its activity was not as good as that of aspirin from 2 hr through 6 hr. Surprisingly, I-C1-NOPD5A showed negligible anti-inflammatory activity at any time point tested (data not incorporated). We have not yet evaluated I-C1-NOPD5B in this efficacy test.

TABLE 5

| Compound | Rat paw edema (% inhibition) Mean ± SEM, n = 6 | | | |
|---|---|---|---|---|
| | 1 hour | 2 hour | 4 hour | 6 hour |
| Aspirin | 31.0 ± 7.2 | 52.5 ± 3.4 | 60.7 ± 6.9 | 42.8 ± 6.9 |
| I-C1-NOPD4 | 42.4 ± 13.3 | 44.9 ± 12.9 | 24.3 ± 7.7 | 8.6 ± 5.1 |

The results indicate the following:

1. Sustained release of the active drug over a period of 10-11 hours, which is good for twice daily dosage regimen, and
2. Exceptional gastrointestinal safety even at high equivalent doses of prodrugs compared to aspirin, which caused severe ulcers at equivalent doses.

I claim:

1. A compound of formula (I) or pharmaceutically acceptable salts thereof:

Formula (I)

wherein, a is 0;

B is S—S;

A is $CH_2$;

$A^1$ is $CH_2$;

$D^1$ represents a therapeutic agent comprising one or more of the functional groups selected from the group consisting of —NHR$^1$, —CONHR$^1$, —SO$_2$NHR$^1$, —OSO$_2$NHR$^1$, N(R$^1$)C(═O)NHR$^1$ and —N(R$^1$)SO$_2$NHR$^1$; wherein the N atom in said functional groups is either a part of or directly attached to L$^1$;

$D^2$ represents a therapeutic agent comprising one or more of the functional groups selected from the group consisting of —OH, —SH, and —CO$_2$H, wherein the O of —OH or the S of —SH or the C(═O) of the —C(═O)OH group is either a part of or directly attached to L$^2$;

E is $CH_2$;

$L^1$ represents NR$^1$—(CO)—O and $L^2$ represents O—(CO)—;

$R^1$ represents H or a bond to the residue of the therapeutic agent at an atom other than the atom to which N is attached.

2. The compound according to claim 1, wherein the compound is selected from:

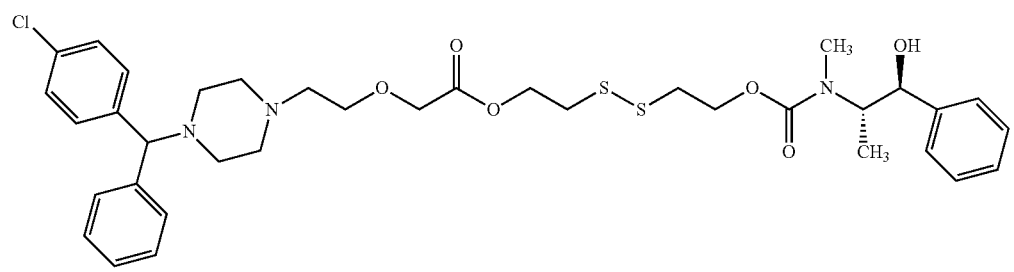

I-CA-MPD1

-continued
I-CA-MPD5
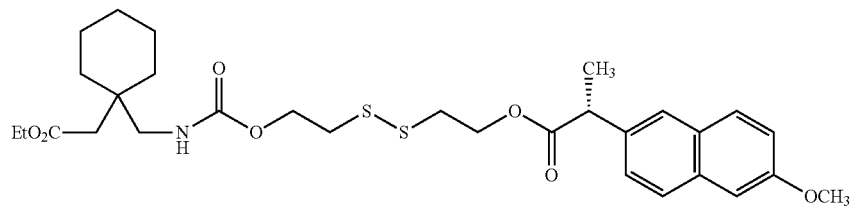
I-CA-MPD15
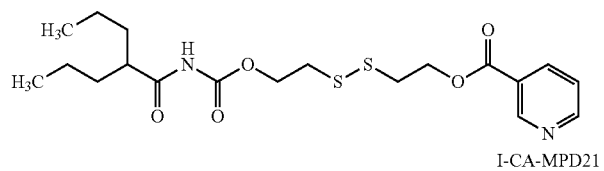
I-CA-MPD19
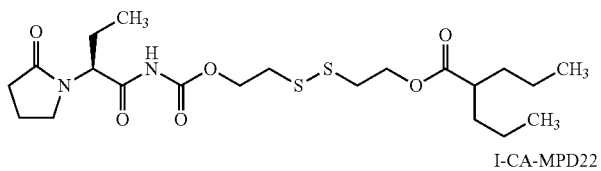
I-CA-MPD21
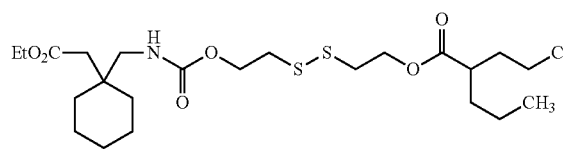
I-CA-MPD22
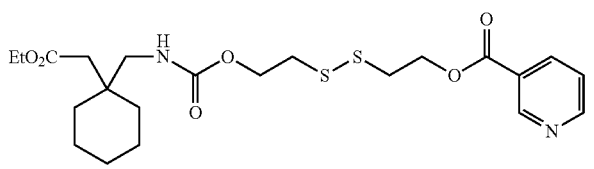
I-CA-MPD23
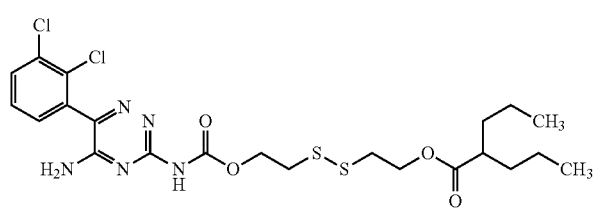
or
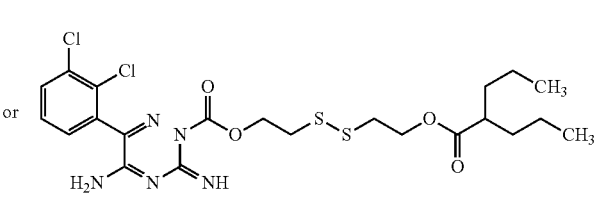
I-CA-MPD24
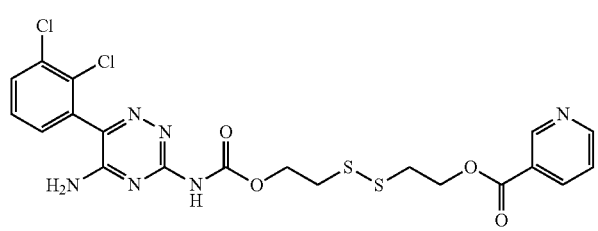
or
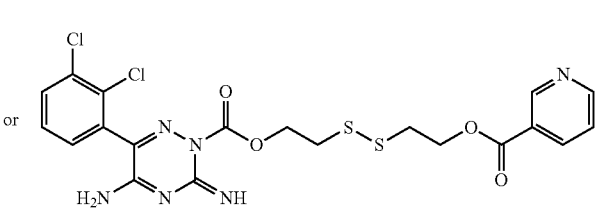
I-AH-MPD1
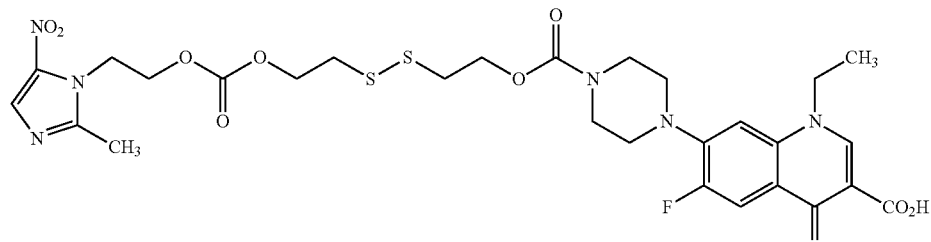
or
I-AH-MPD7
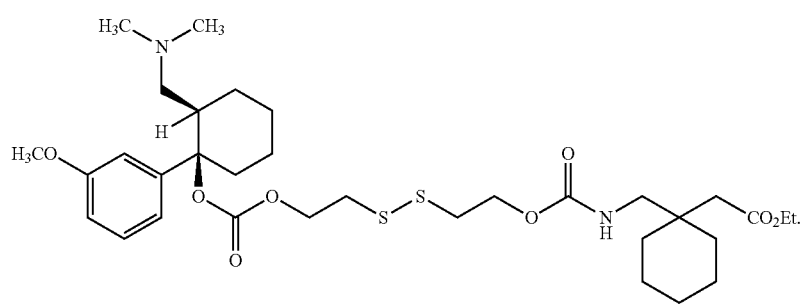

3. A pharmaceutical composition comprising a therapeutically effective amount of the compound of claim 1 or a pharmaceutically acceptable salt thereof; and one or more pharmaceutically acceptable carriers, vehicles or diluents.

4. A pharmaceutical composition comprising a therapeutically effective amount of the compound of claim 2, or a pharmaceutically acceptable salt thereof; and one or more pharmaceutically acceptable carriers, vehicles or diluents.

5. The composition of claim 3, comprising therapeutically effective amount of pairs of drugs selected from: paclitaxel and doxorubicin, paclitaxel and mitomycin C, paclitaxel and 9-aminocamptothecin, 3-aminopyridine-4-methyl-2-carboxaldehyde thiosemicarbazone (3-AMP) and paclitaxel, CC-1065 and paclitaxel, CC-1065 and doxorubicin, CC-1065 and mitomycin C; trans-resveratrol [(E)-3,4',5-trihydroxystilbene) and doxorubicin, trans-resveratrol [(E)-3,4',5-trihydroxystilbene) and mitomycin C, edatrexate and paclitaxel, cephalosporin and paclitaxel, paclitaxel and gemcitabine, amoxicillin and clavulanic acid, ampicillin and clavulanic acid, amlodipine and lovastatin, amlodipine and pravastatin, amlodipine and fluvastatin, amlodipine and atorvastatin, amlodipine and simvastatin, metformin and nateglinide, metformin and lovastatin, metformin and pravastatin, metformin and fluvastatin, metformin and atorvastatin, metformin and simvastatin, pseudoephedrine and fexofenadine, pseudoephedrine and cetirizine, salbutamol and ipratropium bromide; mometasone and formoterol, mometasone and salmeterol; fluticasone and formoterol, fluticasone and salmeterol, budesonide and formoterol, budesonide and salmeterol, diclofenac and misoprostol, diclofenac and omeprazole, diclofenac and lansoprazol, diclofenac and rabeprazole, diclofenac and leminoprazole, diclofenac and pantoprazole, acetaminophen and chlorzoxazone, acetaminophen and mephenoxalone, zidovudine and lamivudine, stavudine and lamivudine, dideoxyinosine and lamivudine, emtricitabine and penciclovir, emtricitabine and famciclovir; acyclovir and deoxycholate, and lamivudine and efavirenz.

6. The compound according to claim 1, wherein $D^1$ and $D^2$ are therapeutic agents independently selected from the group consisting of: sedatives, hypnotics, antidepressants, antipsychotics, antimanics, analgesics, antipyretics, antimigraine agents, anticonvulsants, drugs used in parkinsonism and movement disorders, drugs used for treating dementia, antiemetics, drugs used for treating vertigo, CNS stimulants activators, antiinfective eye preparations, anti-inflammatory, anti-allergic preparations, antiglucoma drugs, preparations to cure eye diseases, aural preparations, nasal preparations, oropharyngeal preparations, anti-arrhythemic drugs, antihypertensives, alfa/beta-blockers, ACE inhibitors, angiotensin II receptor antagonists, diuretics, anti-anginals, nitrates, calcium channel blockers, drugs for cardiac failure and shock, vasodilators, coagulants, anticoagulants, thrombolytics, antiplatelet drugs, respiratory stimulants, antitussives, expectorants, mucolytics, decongestants, antihistamine agents, antiasthmatics; antiulcer, antisecretory drugs, $H_2$ receptor antagonists, proton pump inhibitors, prostaglandin analogues, antacids, antispasmodics, drugs modifying intestinal motility, antidiarrhoeals, antimotility drugs, antimicrobial drugs, drugs acting on gall bladder, urinary antiinfectives, diuretics, urinary analgesics, antispasmodics, antiinfective drugs acting on urethra and vagina, drugs acting on uterus, drugs for prostatic hypertrophy, alfa blockers, antiandrogens, drugs for erectile dysfunction, spermicidals, nonhormonal contraceptives, emollients, keratolytics, topical antiinfectives, topical antifungals, topical parasiticidals, topical steroids, topical drugs for acne vulgaris, drugs for psoriasis, pigmentation disorders, and antiseborrhoeics, non steroidal anti inflammatory drugs (NSAIDs), COX-2 inhibitors, antiarthritic agents, immunosuppressants, topical analgesics, muscle relaxants, neuromuscular drugs, antianaerobics, antitubercular drugs, antileprosy drugs, antifungals, antiprotozoals, anthelminthics, antiinfective drugs, antimalarials, antivirals, anabolics, androgenic steroids, corticosteroids, oestrogens, progestogens and hormonal contraceptives, fertility agents, trophic hormones and related drugs, thyroid and antithyroid drugs, antidiabetics and hyperglycaemics, vitamins, amino acids, anti-obesity drugs, hypolipidaemic drugs, fibric acid derivatives, statins, HMG CoA reductase inhibitors, drugs used for gout, drugs affecting bone metabolism, bisphosphonates, anticancer or antineoplastic drugs, cytotoxic antibiotics, antimetabolites, topoisomerase I inhibitors, cytotoxic immunosuppressants, immunostmulants, cytoprotectives, amifostine, oestrogens, progestogens, hormone antagonists, non-sedative antihistamins, sedative histamines, histamine receptor blockers, local anaesthetics, intravenous anaesthetics, inhalation anaesthetics, and muscle relaxants.

7. The compound according to claim 1, wherein $D^1$ and $D^2$ are therapeutic agents independently selected from the group consisting of: penicillin antibiotics, cephalosporin antibiotics, quinolone, fluoroquinolone antibiotics, macrolide antibiotics, chloramphenicol, tetracyline antibiotics, sulfonamides, metronidazole, nicotinic acid drugs, alkylating agents, cytarabine, fludarabine, 5-fluorouracil, mercaptopurine, thioguanine, vinca alkaloids, etoposide, taxanes, cetirizine, desloratadine, terfenadine and fexofenadine.

8. A method of treating a disease where a chronic, sustained and selective release of the constituent therapeutic agent is beneficial; comprising administering to a mammal or a human in need of the treatment a therapeutically effective amount of the compound of claim 1.

9. A method of treating a disease in a human or mammal where a chronic, sustained and selective release of the constituent therapeutic agent is beneficial; comprising administering to said mammal a therapeutically effective amount of the pharmaceutical composition as claimed in claim 3.

10. The method of claim 8, wherein the disease is selected from the group consisting of the diseases of central nervous system, eye, ear, nose and oropharynx, cardiovascular system, respiratory system, gastrointestinal tract system, genitourinary system, skin, musculoskeletal system, endocrine system, metabolism and neoplastic disorders, infectious diseases, allergy and immunology, and for anaesthetic, analgesic and surgical needs in a mammal.

11. The method of claim 9, wherein the disease is selected from the group consisting of: the diseases of central nervous system, eye, ear, nose and oropharynx, cardiovascular system, respiratory system, gastrointestinal tract system, genitourinary system, skin, musculoskeletal system, endocrine system, metabolism and neoplastic disorders, infectious diseases, allergy and immunology, and for anaesthetic, analgesic and surgical needs in a mammal.

12. A process for the preparation of the compound according to claim 1, wherein $D^1$ and $D^2$ independently represent a therapeutic agent containing one or more functional groups selected from —OH, —SH or —$NHR^1$ provided that when $D^1$ is a therapeutic agent containing $NHR^1$, then $D^2$ is a therapeutic agent containing a hydroxyl- or sulfhydryl-group;
  wherein said process comprises the steps of:
  a) monoprotection of bis-(2-hydroxyethyl)disulphide (SL-1) with an appropriate hydroxylprotecting group (PG) to yield the corresponding monoprotected intermediate (LI-1x);

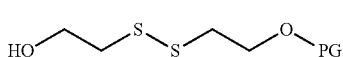
LI-1x b) converting said intermediate (LI-1x) to an activated formyl intermediate (LI-1xy) by treating with phosgene;

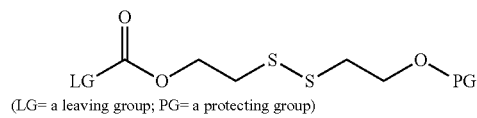
LI-1xy (LG= a leaving group; PG= a protecting group)

c) reacting the intermediate LI-1xy obtained in the step b) with an appropriate therapeutic agent ($D^1$) in the presence of a base and a solvent to obtain the intermediate compound of the following formula;

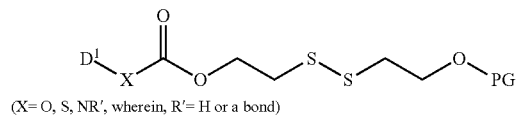

(X= O, S, NR′, wherein, R′= H or a bond)

d) subjecting the intermediate obtained in step c) above to a deprotection step to remove the hydroxyl protecting group to yield an intermediate of the following formula;

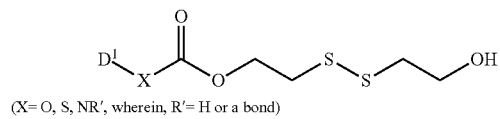

(X= O, S, NR′, wherein, R′= H or a bond)

e) converting the resulting intermediate as obtained in step d) to an activated formyl intermediate of the following formula by treating with phosgene,

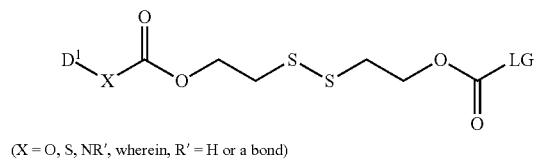

(X = O, S, NR′, wherein, R′ = H or a bond)

f) reacting said intermediate obtained in step d) with an appropriate therapeutic agent ($D^2$) in the presence of a base and a solvent to yield the compound of formula I; or said process comprises the steps of:

a) converting an appropriate therapeutic agent ($D^1$) to its isocyanate derivative or its carbamoyl derivative or its formyl derivative;

b) treating the isocyanate derivative or the carbamoyl derivative or the formyl derivative of the therapeutic agent $D^1$ with the monoprotected linker intermediate LI-1x in the presence of a base and a solvent to yield the intermediate;

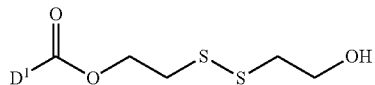

(X= O, S, NR′, wherein, R′= H or a bond)

c) subjecting the resulting intermediate of step (b) to deprotection to yield the corresponding intermediate having a free terminal hydroxyl group;

d) converting an appropriate therapeutic agent $D^2$ to its isocyanate derivative or its carbamoyl derivative or its formyl derivative under appropriate reaction conditions;

e) reacting the intermediate obtained in step (c) above with the isocyanate derivative or the carbamoyl derivative or the formyl derivative of the therapeutic agent $D^2$ as obtained in step (d) above in the presence of a base and a solvent to yield the compound of formula I; or said process comprises the steps of a) converting an appropriate therapeutic agent ($D^1$) to its isocyanate derivative or its carbamoyl derivative or its formyl derivative;

b) treating the isocyanate derivative or the carbamoyl derivative or the formyl derivative of the therapeutic agent $D^1$ as obtained in step (a) above with the disulfide linker SL-1 in the presence of a base and a solvent to yield the corresponding intermediate which on removal of the protection group (PG) to yield the corresponding intermediate having a free hydroxyl group;

c) converting an appropriate therapeutic agent $D^2$ to its isocyanate derivative or its carbamoyl derivative or its formyl derivative;

d) reacting the intermediate obtained in step (b) above with the isocyanate derivative or the carbamoyl derivative or the formyl derivative of the therapeutic agent $D^2$ obtained in step (c) above in the presence of a base and a solvent to yield compound of formula I.

13. A process for the preparation of the compound according to claim 1, wherein $D^1$ and $D^2$ independently represent a therapeutic agent containing —COOH group provided that $D^1$ and $D^2$ are different therapeutic agents; wherein said process comprises the steps of:

(a) converting both the therapeutic agents $D^1$ and $D^2$ to their corresponding acyl chloride or imidazolide derivatives by a standard known method;

(b) reacting the reactive acyl chloride or imidazolide derivatives obtained in step (a) with 1.5 to 3.0 fold excess of the disulfide linker SL-1 in the presence of a base and a solvent to yield the following intermediate containing a free terminal hydroxyl group;

(c) reacting the intermediate obtained in step (b) above with the acyl chloride or imidazolide derivative of the therapeutic agent $D^2$ in the presence of a base and a solvent to yield the compound of formula I; or said process comprises the steps of:

(a) reacting the therapeutic agent $D^1$ with 1.5 to 3.0 fold excess of the disulfide linker SL-1 in the presence of a coupling agent selected from selected from N,N′-dicyclohexylcarbodiimide (DCC), 4-dimethylaminopyridine (DMAP) or triethylamine (TEA) in a solvent to obtain the intermediate containing a free terminal hydroxyl group;

(b) reacting the intermediate obtained in step (a) with a therapeutic agent $D^2$ in the presence of a coupling agent N,N'-dicyclohexylcarbodiimide (DCC), 4-dimethylamino-pyridine (DMAP) or triethylamine (TEA) in a solvent to yield the compound of formula I; or, said process comprises the steps of:

(a) converting the therapeutic agents $D^1$ and $D^2$ into their carboxylate metal salts $(D^1\text{-}COO^-)_n$ $M^{n+}$ and $(D^2\text{-}COO^-)_n$ $M^{n+}$ (wherein, $M^+=Na^+$, $K^+$, $Cs^+$ or $Ca^{++}$; n 1-2) respectively by a known method;

(b) converting the disulfide linker SL-1 to its mono bromide (LI-2a) and dibromide (LI-3a) intermediates by a known method;

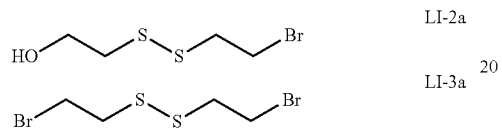

(c) reacting the carboxylate metal salt $(D^1\text{-}COO^-)_n$ $M^{n+}$ obtained in step (a) with either mono bromide LI-2a or with 1.5 to 3.0 fold excess of dibromide LI-3a in a solvent to yield the corresponding intermediate with free terminal alcohol or bromide group;

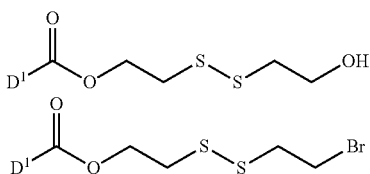

(d) reacting the carboxylate salt $(D^2\text{-}COO^-)_n$ $M^{n+}$ obtained in step (a) with the intermediate having a terminal bromide group obtained in step (c) in a suitable solvent to yield the compound of formula I.

14. A process for the preparation of the compound according to claim 1, wherein $D^1$ is a therapeutic agent containing —COOH group and $D^2$ represent a therapeutic agent containing —OH, —SH or —NHR$^1$ wherein R$^1$ as defined in claim 1; said process comprising the steps of:

(a) preparing an intermediate containing a free terminal hydroxyl group on the linker from the intermediate which is obtained by coupling of the therapeutic agent $D^1$ containing —COOH group and the disulfide linker (SL-1);

(b) reacting the intermediate obtained in step (a) with an appropriate therapeutic agent $D^2$ containing one or more of the functional group selected from —OH, —SH or —NHR$^1$ to yield the mutual prodrug compound of formula I or said process comprises the steps of:

(a) preparing an intermediate containing a free terminal hydroxyl group on the linker from the intermediate which is obtained by coupling of the therapeutic agent $D^2$ containing —OH, —SH or —NHR$^1$; wherein R$^1$ as defined in claim 1; and the disulfide linker (SL-1);

(b) reacting the intermediate obtained in step (a) with a therapeutic agent $D^1$ containing —COOH group under suitable reaction conditions to yield the mutual prodrug compound of formula I; or said process comprises the steps of:

(a) converting a therapeutic agent $D^1$ containing —COOH group into its acid chloride by reacting with thionyl chloride or oxalyl chloride and treating the resulting acid chloride derivative of $D^1$ with ammonia to yield the corresponding amide derivative ($D^1$-C(=O)NH$_2$) of the therapeutic agent;

(b) treating the amide derivative obtained in step (a) with oxalyl chloride to yield the corresponding acyl isocyanate derivative ($D^1$-C(=O)N=C=O) of $D^1$; or said acyl isocyanate derivative ($D^1$-C(=O)N=C=O) of $D^1$ can be prepared by treating the acid chloride ($D^1$-COCl) derivative of $D^1$ with silver isocyanate;

(c) reacting the resulting acyl isocyanate ($D^1$-C(=O)N=C=O) derivative with 2-3 equivalents of the disulfide linker (SL-1) to yield the following intermediate with free terminal hydroxyl group on the linker;

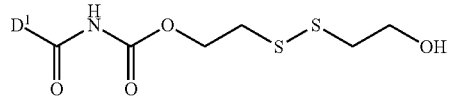

and (d) reacting the intermediate obtained in step (d) with a therapeutic agent $D^2$ containing either an —OH, —SH, —COOH or —NHR$^1$ to yield compound of formula I.

15. A process for the preparation of the compound according to claim 1, wherein $D^1$ and $D^2$ represent a therapeutic agent containing —OH wherein said $D^1$ and $D^2$ may be the same or different therapeutic agents; said process comprising the steps of:

(a) monoprotecting the compound having formula, R$^1$HNCH$_2$CH$_2$NHR$^1$ to obtain the corresponding Boc protected derivative, R$^1$HNCH$_2$CH$_2$N(Boc)R$^1$;

(b) converting a therapeutic agent $D^1$ containing —OH group to its formyl derivative [$D^1$-O—C(=O)-LG, wherein, LG=a leaving group] by treating with phosgene or its equivalent in the presence of a base and a solvent;

(c) reacting the intermediate R$^1$HNCH$_2$CH$_2$N(Boc)R$^1$ obtained in step (a) with the intermediate $D^1$-O—C(=O)-LG obtained in step (b) in the presence of a base and a solvent to yield the intermediate $D^1$-O—C(=O)—(R$^1$)NCH$_2$CH$_2$N(Boc)R$^1$;

(d) treating the resulting intermediate $D^1$-O—C(=O)—(R$^1$)NCH$_2$CH$_2$N(Boc)R$^1$ by treatment with trifluoroacetic acid (TFA) to remove the Boc group and to obtain the intermediate TFA salt [$D^1$-O—C(=O)—(R$^1$)NCH$_2$CH$_2$NHR$^1$.TFA];

(e) reacting the intermediate obtained in step (d) with a linker (LI-1xy) of the following formula;

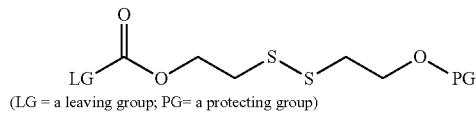

(LG = a leaving group; PG= a protecting group)

in the presence of a base and a solvent to yield an intermediate, which upon removal of the protecting group by a standard method provided an intermediate containing a free terminal hydroxyl group on the linker;

(f) reacting the intermediate obtained in step (e) above with phosgene in the presence of a base and a solvent to its corresponding formyl derivative;

(g) converting the therapeutic agent $D^2$ into an intermediate having the following formula by following the same steps (a) to (d):

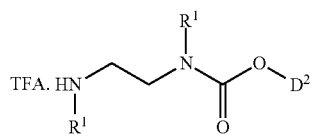

(h) reacting the intermediates obtained in steps (f) and (g) in presence of a base and a solvent to yield to compound of formula I.

16. A process for the preparation of the compound according to claim 1, wherein $D^1$ and $D^2$ represent a therapeutic agent containing —OH, —SH or —$NHR^1$ group; wherein said $D^1$ and $D^2$ may be the same or different therapeutic agents; said process comprising the steps of:

(a) converting a therapeutic agent $D^1$ to its isocyanate derivative or carbamoyl derivative or formyl derivative under suitable reaction conditions;

(b) treating the resulting isocyanate derivative or carbamoyl derivative or formyl derivative obtained in step (a) with 2-(2-aminoethyl)disulfanyl)-ethanol (SL-2) in the presence of a base and a solvent to obtain an intermediate containing a terminal free hydroxyl group;

(c) converting a therapeutic agent $D^2$ to its isocyanate derivative or carbamoyl derivative or formyl derivative under suitable reaction conditions; and (d) reacting the intermediate obtained in step (b) isocyanate derivative or carbamoyl derivative or formyl derivative of the therapeutic agent $D^2$ obtained in step (c) in the presence of a base and a solvent to yield the compound of formula I.

* * * * *

UNITED STATES PATENT AND TRADEMARK OFFICE
CERTIFICATE OF CORRECTION

PATENT NO.       : 8,357,723 B2
APPLICATION NO.  : 12/977929
DATED            : January 22, 2013
INVENTOR(S)      : Apparao Satyam It is certified that error appears in the above-identified patent and that said Letters Patent is hereby corrected as shown below:

Title Page, Item (30), Foreign Application Priority Data, "Jan. 7, 2005" should read --July 1, 2005--.

Signed and Sealed this
Seventh Day of May, 2013

Teresa Stanek Rea
*Acting Director of the United States Patent and Trademark Office*